US009493506B2

(12) United States Patent
Chen et al.

(10) Patent No.: US 9,493,506 B2
(45) Date of Patent: *Nov. 15, 2016

(54) MACROCYCLIC HEPATITIS C SERINE PROTEASE INHIBITORS

(71) Applicants: Enanta Pharmaceuticals, Inc., Watertown, MA (US); AbbVie, Inc., North Chicago, IL (US)

(72) Inventors: Hui-Ju Chen, Grayslake, IL (US); Keith F. McDaniel, Wauconda, IL (US); Brian E. Green, Wonder Lake, IL (US); Jason P. Shanley, Chicago, IL (US); Albert W. Kruger, Pleasant Prairie, WI (US); Jorge Gandarilla, North Riverside, IL (US); Dennie S. Welch, Lake Bluff, IL (US); Russell D. Cink, Grayslake, IL (US); Steven C. Cullen, Lake Villa, IL (US); Yonghua Gai, North Grafton, MA (US); Guoqiang Wang, Belmont, MA (US); Yat Sun Or, Watertown, MA (US)

(73) Assignees: AbbVie Inc., Abbott Park, IL (US); Enata Pharmacueticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/299,095

(22) Filed: Jun. 9, 2014

(65) Prior Publication Data
US 2014/0287992 A1 Sep. 25, 2014

Related U.S. Application Data

(63) Continuation of application No. 13/154,721, filed on Jun. 7, 2011, now Pat. No. 8,748,374.

(60) Provisional application No. 61/397,103, filed on Jun. 7, 2010.

(51) Int. Cl.
*C07D 487/04* (2006.01)
*C07K 5/083* (2006.01)

(52) U.S. Cl.
CPC .............. *C07K 5/081* (2013.01); *C07D 487/04* (2013.01)

(58) Field of Classification Search
None
See application file for complete search history.

(56) References Cited

U.S. PATENT DOCUMENTS

| | | |
|---|---|---|
| 2004/0266668 A1 | 12/2004 | Nakajima et al. |
| 2009/0180981 A1 | 7/2009 | Niu et al. |
| 2011/0081315 A1 | 4/2011 | Buckman et al. |
| 2012/0101031 A1 | 4/2012 | Chen et al. |

FOREIGN PATENT DOCUMENTS

| | | |
|---|---|---|
| WO | WO-0181325 A2 | 11/2001 |
| WO | WO-2004072243 A2 | 8/2004 |
| WO | WO-2005010029 A1 | 2/2005 |
| WO | WO-2007148135 A1 | 12/2007 |
| WO | WO-2008/002924 A2 | 1/2008 |
| WO | WO-2012/092409 A2 | 7/2012 |

OTHER PUBLICATIONS

Ettmayer P. et al. J. Med. Chem. (2004) 47(10), pp. 2393-2404.*
Singh, Yashveer et al, "Recent Trends in Targeted Anticancer Prodrug and Conjugate," DesignCurr Med Chem. 2008 ; 15(18): 1802-1826.*
Muller, Christa E. "Prodrug Approaches for Enhancing the Bioavailability of Drugs with Low Solubility," Chemistry & Biodiversity, vol. 6 (2009), pp. 2071-2083.*
Beaumont, et, al "Design of Ester Prodrugs to Enhance Oral Absorption of Poorly Permeable Compounds: Challenges to the Discovery Scientist," Current Drug Metabolism, 2003, 4, 461-485.*
Han, H.-K.. AAPS Pharmsci. (2000) 2(1), Article 6, pp. 1-11.*
Testa Prodrug research: futile or fertile? Biochemical Pharmacology (2004) 2097-2106.*
A.M. Faucher et al., "Synthesis of BILN 2061, an HCV NS3 Protease Inhibitor with Proven Antiviral Effect in Humans", Organic Letters, 6(17), pp. 2901-2904 (2004).
Y.S. Tsantrizos et al., "Olefin ring-closing metathesis as a powerful tool in drug discovery and development—potent macrocyclic inhibitors of the hepatitis C virus NS3 protease", Journal of Organometallic Chemistry, vol. 691, pp. 5163-5171 (2006).
N. Goudreau et al., "Potent Inhibitors of the Hepatitis C Virus NS3 Protease: Design and Synthesis of Macrocyclic Substrate-Based β-Strand Mimics", Journal of Organic Chemistry, vol. 69, pp. 6185-6201 (2004).
J.T. Randolph et al., "Synthesis, antiviral activity, and conformational studies of a P3 aza-peptide analog of a potent macrocyclic tripeptide HCV protease inhibitor", Bioorganic & Medicinal Chemistry Letters, vol. 18, pp. 2745-2750 (2008).
Extended European Search Report dated Jan. 7, 2014 in corresponding European Patent Application No. 11792997.6.

* cited by examiner

Primary Examiner — Thomas S Heard
(74) Attorney, Agent, or Firm — Dana M. Gordon; Foley Hoag LLP

(57) ABSTRACT

The present invention relates to novel macrocyclic compounds and methods of treating a hepatitis C infection in a subject in need of such therapy with said macrocyclic compounds. The present invention further relates to pharmaceutical compositions comprising the compounds of the present invention, or pharmaceutically acceptable salts, esters, or prodrugs thereof, in combination with a pharmaceutically acceptable carrier or excipient.

21 Claims, No Drawings

MACROCYCLIC HEPATITIS C SERINE PROTEASE INHIBITORS

RELATED APPLICATION

This application is a continuation of U.S. patent application Ser. No. 13/154,721, filed Jun. 7, 2011, allowed, which claims the benefit of U.S. provisional application 61/397,103, filed on Jun. 7, 2010. The contents of the foregoing applications are incorporated herein in their entirety.

JOINT RESEARCH AGREEMENT

Inventions described in this application were made by or on behalf of Abbott Laboratories and Enanta Pharmaceuticals, Inc. whom are parties to a joint research agreement, that was in effect on or before the date such inventions were made and such inventions were made as a result of activities undertaken within the scope of the joint research agreement.

TECHNICAL FIELD

The present invention relates to novel macrocycles having activity against the hepatitis C virus (HCV) and useful in the treatment of HCV infections. More particularly, the invention relates to macrocyclic compounds, compositions containing such compounds and methods for using the same, as well as processes for making such compounds.

BACKGROUND OF THE INVENTION

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantations in the western world.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which often have significant side effects.

SUMMARY OF THE INVENTION

The present invention relates to novel macrocyclic compounds and methods of treating a hepatitis C infection in a subject in need of such therapy with said macrocyclic compounds. The compounds of the present invention interfere with the life cycle of the hepatitis C virus and are useful as antiviral agents. The present invention further relates to pharmaceutical compositions comprising the compounds of the present invention, or pharmaceutically acceptable salts, esters or prodrugs thereof, in combination with a pharmaceutically acceptable carrier or excipient.

In one aspect, the invention provides a compound of Formula I:

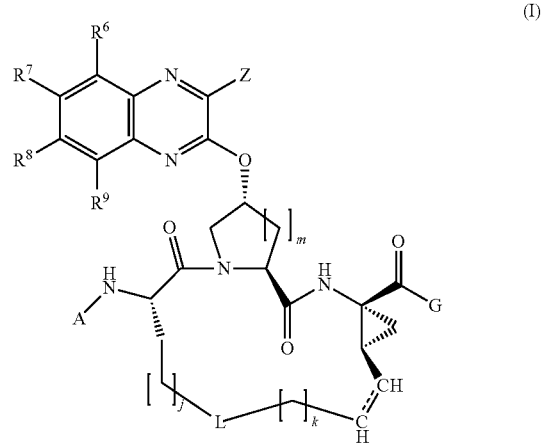

(I)

wherein
A is H, —(C=O)—O—$R^1$, —(C=O)—$R^1$, —(C=O)—N($R^1R^2$), —S(O)$_2$—$R^1$, or —S(O)$_2$—N($R^1R^2$), each $R^1$ is independently selected from the group consisting of:
  (i) H, aryl; substituted aryl; heteroaryl; substituted heteroaryl;
  (ii) heterocycloalkyl or substituted heterocycloalkyl; and
  (iii) —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; substituted —$C_1$-$C_8$ alkyl, substituted —$C_2$-$C_8$ alkenyl or substituted —$C_2$-$C_8$ alkynyl, each containing 0, 1, 2, or 3 heteroatoms independently selected from O, S and N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;

each $R^2$ is independently selected from the group consisting of:
  (i) hydrogen;
  (ii) aryl; substituted aryl; heteroaryl; substituted heteroaryl;
  (iii) heterocycloalkyl or substituted heterocycloalkyl; and
  (iv) —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; substituted —$C_1$-$C_8$ alkyl, substituted —$C_2$-$C_8$ alkenyl or substituted —$C_2$-$C_8$ alkynyl, each containing 0, 1, 2, or 3 heteroatoms independently selected from O, S and N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;

G is —NHS(O)$_2$—$R^3$, —O—$R^4$, or —NH(SO$_2$)N$R^4R^5$;
each $R_3$ is independently selected from:
  (i) $C_3$-$C_{12}$ cycloalkyl, substituted —$C_3$-$C_{12}$ cycloalkyl, aryl; substituted aryl; heteroaryl; substituted heteroaryl;
  (ii) heterocycloalkyl or substituted heterocycloalkyl; and
  (iii) —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; substituted —C$_1$-C$_8$ alkyl, substituted —C$_2$-C$_8$ alkenyl or substituted —C$_2$-C$_8$ alkynyl, each containing 0, 1, 2, or 3 heteroatoms independently selected from O, S and N; —C$_3$-C$_{12}$ cycloalkenyl, or substituted —C$_3$-C$_{12}$ cycloalkenyl; and each R$_4$ and R$_5$ is independently selected from:
(i) hydrogen;
(ii) aryl; substituted aryl; heteroaryl; substituted heteroaryl;
(iii) heterocycloalkyl or substituted heterocycloalkyl; and
(iv) —C$_1$-C$_8$ alkyl, —C$_2$-C$_8$ alkenyl or —C$_2$-C$_8$ alkynyl, each containing 0, 1, 2, or 3 heteroatoms independently selected from O, S, and N; substituted —C$_1$-C$_8$ alkyl, substituted —C$_2$-C$_8$ alkenyl or substituted —C$_2$-C$_8$ alkynyl, each containing 0, 1, 2, or 3 heteroatoms independently selected from O, S and N; —C$_3$-C$_{12}$ cycloalkyl, or substituted —C$_3$-C$_{12}$ cycloalkyl; —C$_3$-C$_{12}$ cycloalkenyl, or substituted —C$_3$-C$_{12}$ cycloalkenyl;

L is a C$_2$-C$_5$ saturated or unsaturated chain, optionally containing one to three heteroatoms independently selected from O, N, and S(O)$_n$, wherein L is optionally substituted with one or more substituents selected from halogen, hydroxy, mercapto, amino, carboxy, nitro, oxo, phosphonoxy, phosphono, thioxo, cyano, C$_1$-C$_6$alkyl, C$_2$-C$_6$alkenyl and C$_2$-C$_6$alkynyl, wherein each C$_1$-C$_6$alkyl, C$_2$-C$_6$alkenyl and C$_2$-C$_6$alkynyl, group is optionally substituted at each occurrence with one or more substituents selected from halogen, hydroxy, mercapto, amino, carboxy, nitro, oxo, phosphonoxy, phosphono, thioxo, formyl and cyano;

Z is
(i) —C$_1$-C$_8$ alkyl, —C$_2$-C$_8$ alkenyl or —C$_2$-C$_8$ alkynyl, each containing 0, 1, 2, or 3 heteroatoms independently selected from O, S, and N and optionally substituted with one or more halo; or
(ii) heteroaryl or substituted heteroaryl;
j=0, 1, 2, 3, or 4;
k=0, 1, 2, or 3;
m=0, 1, or 2;
n is 0, 1, or 2;
---- denotes a carbon-carbon single or double bond (i.e.,

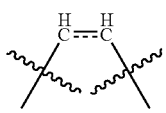

means

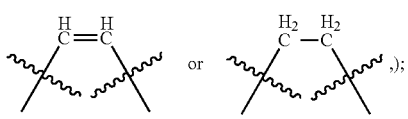

);

R$^6$ is H or halo;
R$^7$ is H or halo;
R$^8$ is H or halo;
R$^9$ is H or halo;
wherein if each of R$_6$, R$_7$, R$_8$ and R$_9$ is H, then Z is —C$_1$-C$_8$ alkyl, —C$_2$-C$_8$ alkenyl or —C$_2$-C$_8$ alkynyl, each substituted with one or more halo and each containing 0, 1, 2, or 3 heteroatoms independently selected from O, S, and N; and salts, solvates and hydrates thereof.

The present invention also features the compounds of Formula I', and salts, solvates and hydrates thereof,

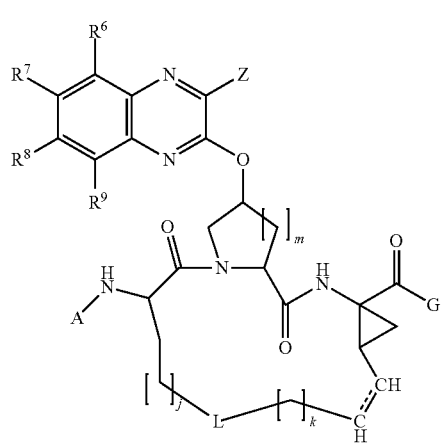

wherein A, G, L, j, k, m, Z, R$^6$, R$^7$, R$^8$ and R$^9$ are as defined in Formula I.

In another aspect, the invention provides a pharmaceutical composition comprising a compound of Formula I or I', or a pharmaceutically acceptable salt, ester, or prodrug thereof, in combination with an excipient.

In one aspect, the invention provides a method of treating a viral infection in a subject, comprising administering to the subject a therapeutically effective amount of a compound of Formula I or I', or a pharmaceutically acceptable salt, ester or prodrug thereof, or a pharmaceutical composition comprising the same.

DETAILED DESCRIPTION OF THE INVENTION

In one aspect, the invention provides a compound of Formula I:

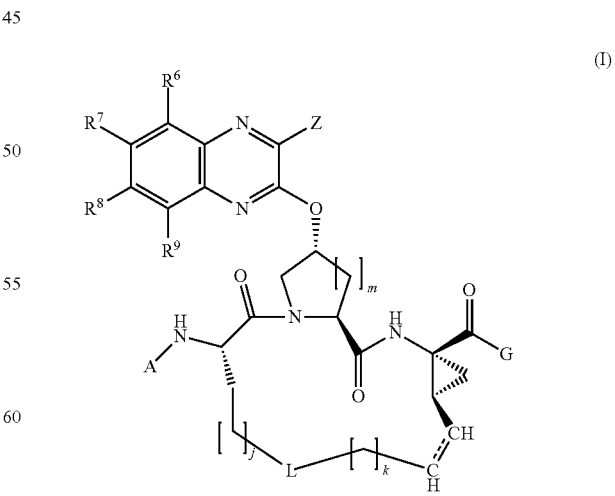

wherein
A is H, —(C=O)—O—R$^1$, —(C=O)—R$^1$, —(C=O)—N(R$^1$R$^2$), —S(O)$_2$—R$^1$, or —S(O)$_2$—N(R$^1$R$^2$), each $R^1$ is independently selected from the group consisting of:
- (i) H, aryl; substituted aryl; heteroaryl; substituted heteroaryl;
- (ii) heterocycloalkyl or substituted heterocycloalkyl; and
- (iii) —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; substituted —$C_1$-$C_8$ alkyl, substituted —$C_2$-$C_8$ alkenyl or substituted —$C_2$-$C_8$ alkynyl, each containing 0, 1, 2, or 3 heteroatoms independently selected from O, S and N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;

each $R^2$ is independently selected from the group consisting of:
- (i) hydrogen;
- (ii) aryl; substituted aryl; heteroaryl; substituted heteroaryl;
- (iii) heterocycloalkyl or substituted heterocycloalkyl; and
- (iv) —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; substituted —$C_1$-$C_8$ alkyl, substituted —$C_2$-$C_8$ alkenyl or substituted —$C_2$-$C_8$ alkynyl, each containing 0, 1, 2, or 3 heteroatoms independently selected from O, S and N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;

G is —$NHS(O)_2$—$R^3$, —O—$R^4$, or —$NH(SO_2)NR_4R^5$;
each $R_3$ is independently selected from:
- (i) $C_3$-$C_{12}$ cycloalkyl, substituted —$C_3$-$C_{12}$ cycloalkyl, aryl; substituted aryl; heteroaryl; substituted heteroaryl;
- (ii) heterocycloalkyl or substituted heterocycloalkyl; and
- (iii) —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; substituted —$C_1$-$C_8$ alkyl, substituted —$C_2$-$C_8$ alkenyl or substituted —$C_2$-$C_8$ alkynyl, each containing 0, 1, 2, or 3 heteroatoms independently selected from O, S and N; —$C_3$-$C_{12}$ cycloalkenyl, or substituted —$C_3$-$C_{12}$ cycloalkenyl; and each $R_4$ and $R_5$ is independently selected from:
- (i) hydrogen;
- (ii) aryl; substituted aryl; heteroaryl; substituted heteroaryl;
- (iii) heterocycloalkyl or substituted heterocycloalkyl; and
- (iv) —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; substituted —$C_1$-$C_8$ alkyl, substituted —$C_2$-$C_8$ alkenyl or substituted —$C_2$-$C_8$ alkynyl, each containing 0, 1, 2, or 3 heteroatoms independently selected from O, S and N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

L is a $C_2$-$C_5$ saturated or unsaturated chain, optionally containing one to three heteroatoms independently selected from O, N and $S(O)_n$, wherein L is optionally substituted with one or more substituents selected from halogen, hydroxy, mercapto, amino, carboxy, nitro, oxo, phosphonoxy, phosphono, thioxo, cyano, $C_1$-$C_6$alkyl, $C_2$-$C_6$alkenyl and $C_2$-$C_6$alkynyl, wherein each $C_1$-$C_6$alkyl, $C_2$-$C_6$alkenyl and $C_2$-$C_6$alkynyl, group is optionally substituted at each occurrence with one or more substituents selected from halogen, hydroxy, mercapto, amino, carboxy, nitro, oxo, phosphonoxy, phosphono, thioxo, formyl and cyano;

Z is
- (iii) —$C_1$-$C_8$ alkyl, —$C_2$-$C_8$ alkenyl or —$C_2$-$C_8$ alkynyl, each containing 0, 1, 2, or 3 heteroatoms independently selected from O, S, and N and optionally substituted with one or more halo; or
- (iv) heteroaryl or substituted heteroaryl;

j=0, 1, 2, 3, or 4;
k=0, 1, 2, or 3;
m=0, 1, or 2;
n is 0, 1, or 2;
----- denotes a carbon-carbon single or double bond (i.e.,

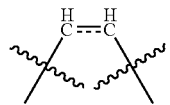

means

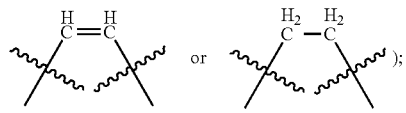

);

$R^6$ is H or halo;
$R^7$ is H or halo;
$R^8$ is H or halo;
$R^9$ is H or halo;
wherein if each of $R_6$, $R_7$, $R_8$ and $R_9$ is H, then Z is —$C_1$-$C_8$ alkyl, —$C_2$-$C_8$ alkenyl or —$C_2$-$C_8$ alkynyl, each substituted with one or more halo and each containing 0, 1, 2, or 3 heteroatoms independently selected from O, S, and N; and
salts, solvates and hydrates thereof.

The present invention also features the compounds of Formula I', and salts, solvates and hydrates thereof,

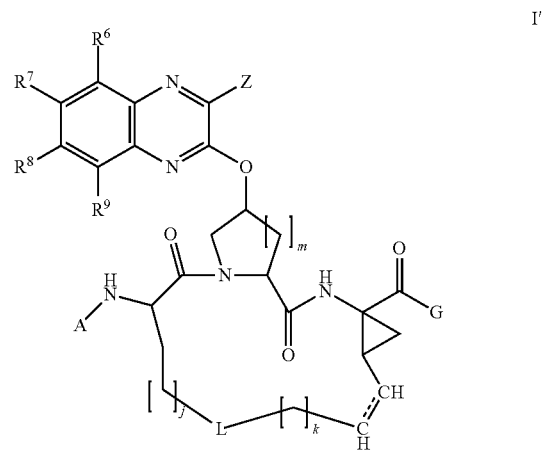

wherein A, G, L, j, k, m, Z, $R^6$, $R^7$, $R^8$ and $R^9$ are as defined in Formula I.

It is understood that the embodiments of the invention discussed below with respect to the preferred variable selections can be taken alone or in combination with one or more of the other embodiments, or preferred variable selections, of the invention, as if each combination were explicitly listed herein.

In another aspect, alternatively or additionally, k=1, j=1, and m=1.

In another aspect, each $R^1$ or $R^2$ is substituted with one, two, three or four independent $R^A$, wherein each $R^A$ is independently selected from alkyl, aryl, heteroaryl, cycloalkyl, heterocycloalkyl, halogen, hydroxy, amino, —CN, —CF$_3$, —N$_3$, —NO$_2$, —OR$^B$, —SR$^B$, —SOR$^B$, —SO$_2$R$^B$, —N(R$^B$)S(O$_2$)—R$^B$, —N(R$^B$)S(O$_2$)NR$^B$R$^B$, —NR$^B$R$^B$, —C(O)OR$^B$, —C(O)R$^B$, —C(O)NR$^B$R$^B$, or —N(R$^B$)C(O)R$^B$; wherein each $R^B$ is independently hydrogen, C$_1$-C$_6$ alkyl, C$_2$-C$_6$ alkenyl, or C$_2$-C$_6$ alkynyl.

In another aspect, the compound is of any of the formulae herein, wherein $R^3$ is independently cyclopropyl optionally substituted with C$_1$-C$_6$alkyl, C$_1$-C$_6$alkoxyC$_1$-C$_6$alkyl, —C(O)OH, —C(O)NH$_2$, or —C(O)O—C$_1$-C$_6$alkyl.

In another aspect, the compound is of any of the formulae herein, wherein A is —(C=O)—O—$R^1$.

In another aspect, the compound is of any of the formulae herein, wherein A is —(C=O)—$R^1$.

In another aspect, the compound is of any of the formulae herein, wherein $R^1$ is optionally substituted aryl.

In another aspect, the compound is of any of the formulae herein, wherein $R^1$ is optionally substituted heteroaryl.

In another aspect, the compound is of any of the formulae herein, wherein Z is C$_1$-C$_4$alkyl.

In another aspect, the compound is of any of the formulae herein, wherein Z is C$_1$-C$_4$alkyl substituted with one or more halo.

In another aspect, the compound is of any of the formulae herein, wherein Z is heteroaryl or substituted heteroaryl, preferably substituted or unsubstituted thienyl, more preferably thien-2-yl.

In another aspect, the compound is of any of the formulae herein, wherein Z is heteroaryl or substituted heteroaryl, preferably substituted or unsubstituted thienyl, more preferably thien-2-yl; and G is —NHS(O)$_2$—$R^3$, or —NH(SO$_2$)NR$_4$R$^5$.

In another aspect, the compound is of any of the formulae herein, wherein A is —(C=O)—$R^1$; and $R^1$ is optionally substituted aryl.

In another aspect, the compound is of any of the formulae herein, wherein A is —(C=O)—$R^1$; and $R^1$ is optionally substituted heteroaryl.

In another aspect, the compound is of any of the formulae herein, wherein A is —(C=O)—$R^1$; $R^1$ is optionally substituted aryl; and Z is C$_1$-C$_4$alkyl optionally substituted with one or more halo.

In another aspect, the compound is of any of the formulae herein, wherein A is —(C=O)—$R^1$; $R^1$ is optionally substituted heteroaryl; and Z is C$_1$-C$_4$alkyl optionally substituted with one or more halo.

In another aspect, the compound is of any of the formulae herein, wherein A is —(C=O)—$R^1$; $R^1$ is optionally substituted aryl; and Z is C$_1$-C$_4$alkyl substituted with one or more halo.

In another aspect, the compound is of any of the formulae herein, wherein A is —(C=O)—$R^1$; $R^1$ is optionally substituted heteroaryl; and Z is C$_1$-C$_4$alkyl substituted with one or more halo.

In another aspect, the compound is of any of the formulae herein, wherein each of $R^6$, $R^7$, $R^8$ and $R^9$ is H, and Z is C$_1$-C$_4$alkyl substituted with one or more halo.

In another aspect, the compound is of any of the formulae herein, wherein one of $R^6$, $R^7$, $R^8$ and $R^9$ is halo, and Z is C$_1$-C$_4$alkyl optionally substituted with one or more halo.

In another aspect, the compound is of any of the formulae herein, wherein two of $R^6$, $R^7$, $R^8$ and $R^9$ are halo, and Z is C$_1$-C$_4$alkyl optionally substituted with one or more halo.

In another aspect, the compound is of any of the formulae herein, wherein one of $R^7$ or $R^8$ is halo, and Z is C$_1$-C$_4$alkyl optionally substituted with one or more halo.

In another aspect, the compound is of any of the formulae herein, wherein $R^7$ is fluoro, and Z is C$_1$-C$_4$alkyl optionally substituted with one or more halo.

In another aspect, the compound is of any of the formulae herein, wherein $R^8$ is fluoro, and Z is C$_1$-C$_4$alkyl optionally substituted with one or more halo.

In another aspect, the compound is of any of the formulae herein, wherein $R^9$ is halo and Z is C$_1$-C$_4$alkyl optionally substituted with one or more halo.

In another aspect, the compound is of any of the formulae herein, wherein $R^6$ is fluoro, and Z is C$_1$-C$_4$alkyl optionally substituted with one or more halo.

In another aspect, the compound is of any of the formulae herein, wherein $R_3$ is independently cyclopropyl optionally substituted with C$_1$-C$_6$alkyl.

In another aspect, the compound is of any of the formulae herein, wherein,
G is —NHS(O)$_2$—$R^3$;
$R^3$ is independently cyclopropyl optionally substituted with C$_1$-C$_6$alkyl;
A is —(C=O)—$R^1$;
$R^1$ is independently heteroaryl, or substituted heteroaryl;
Z is C$_1$-C$_4$ alkyl (e.g., methyl or ethyl), or C$_1$-C$_4$alkyl (e.g., methyl or ethyl) substituted with one or more fluoro;
$R^7$ is fluoro; and
each of $R^6$, $R^8$ and $R^9$ is H.

In another aspect, the compound is of any of the formulae herein, wherein,
G is —NHS(O)$_2$—$R^3$;
$R^3$ is independently cyclopropyl optionally substituted with C$_1$-C$_6$alkyl;
A is —(C=O)—$R^1$;
$R^1$ is independently heteroaryl, or substituted heteroaryl;
Z is C$_1$-C$_4$ alkyl (e.g., methyl or ethyl), or C$_1$-C$_4$alkyl (e.g., methyl or ethyl) substituted with one or more fluoro;
$R^8$ is fluoro; and
each of $R^6$, $R^7$ and $R^9$ is H.

In another aspect, the compound is of any of the formulae herein, wherein,
Z is C$_1$-C$_4$ alkyl (e.g., methyl or ethyl), or C$_1$-C$_4$alkyl (e.g., methyl or ethyl) substituted with one or more fluoro;
$R^7$ is halo; and
each of $R^6$, $R^8$ and $R^9$ is H or halo.

In another aspect, the compound is of any of the formulae herein, wherein,
Z is C$_1$-C$_4$ alkyl (e.g., methyl or ethyl), or C$_1$-C$_4$alkyl (e.g., methyl or ethyl) substituted with one or more fluoro;
$R^8$ is halo; and
each of $R^6$, $R^7$ and $R^9$ is H or halo.

In a further embodiment, the invention provides a compound wherein,

G is —NHS(O)$_2$—R$^3$;
R$^3$ is independently cyclopropyl optionally substituted with C$_1$-C$_6$alkyl;
A is —(C=O)—R$^1$; and
R$^1$ is independently heteroaryl, or substituted heteroaryl.

In another further embodiment, Z is alkyl substituted with halo and in a further embodiment Z is fluoroalkyl.

In another aspect, the compound is of any of the formulae herein, wherein R$^1$ is an optionally substituted nitrogen-containing heteroaryl.

In another aspect, the compound is of any of the formulae herein, wherein R$^1$ is optionally substituted isoxazolyl, optionally substituted thiazolyl, optionally substituted pyrazolyl, optionally substituted pyrazinyl, optionally substituted pyridinyl, or optionally substituted pyrimidinyl.

In another aspect, the compound is of any of the formulae herein, wherein R$^1$ is alkyl-substituted isoxazolyl.

In another aspect, the compound is of any of the formulae herein, wherein R$^1$ is 5-methylisoxazol-3-yl.

A can be, for example, —(C=O)—R$^1$; wherein R$^1$ is selected from the following groups:

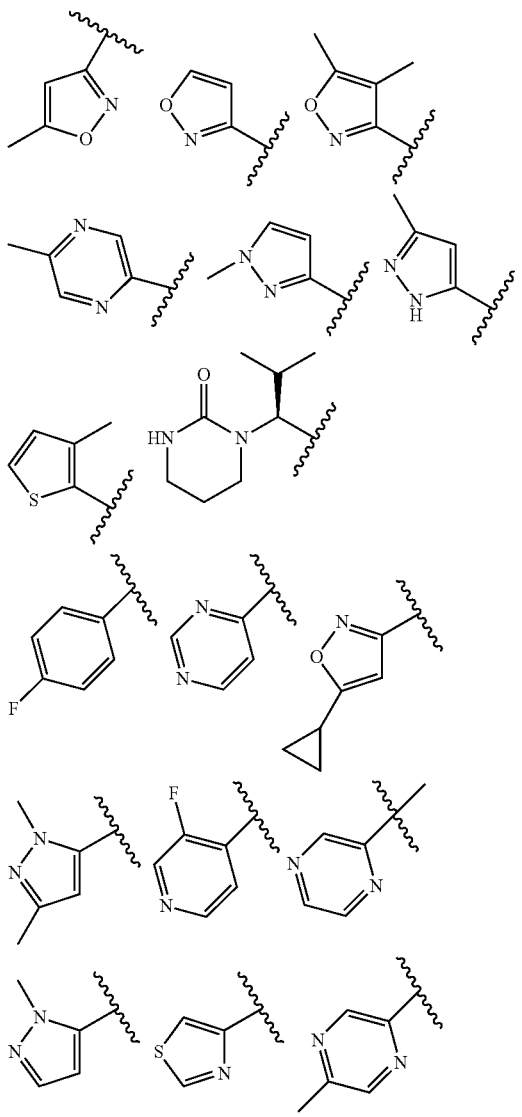

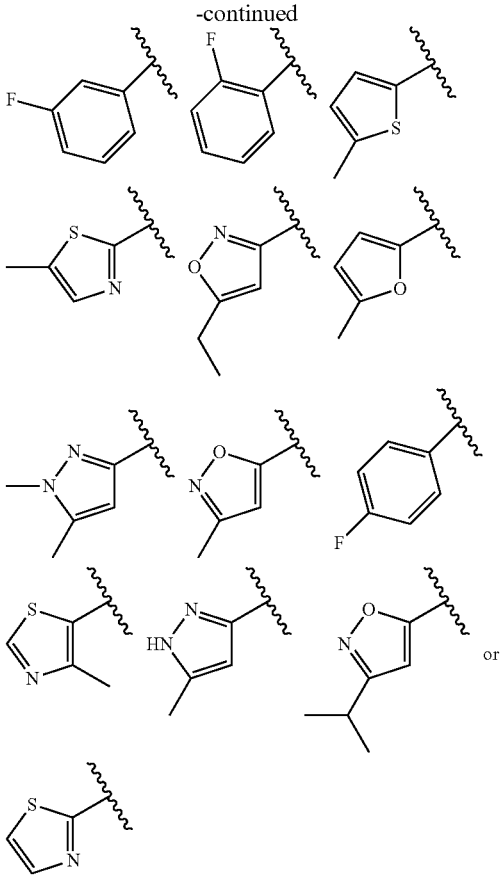

In another aspect, the present invention features compounds having Formula I' or preferably Formula I, and salts, solvates and hydrates thereof, wherein
A is —(C=O)—O—R$^1$, —(C=O)—R$^1$, —(C=O)—N(R$^1$R$^2$), —S(O)$_2$—R$^1$, or —S(O)$_2$—N(R$^1$R$^2$),
R$^1$ is selected from the group consisting of:
  (i) C$_3$-C$_{10}$-carbocycle or 5- to 10-membered heterocycle, each of which is optionally substituted with one or more R$^C$; and
  (ii) —C$_1$-C$_6$ alkyl, —C$_2$-C$_6$ alkenyl or —C$_2$-C$_6$ alkynyl, each of which is optionally substituted with one or more R$^C$;
R$^2$ is selected from the group consisting of:
  (i) hydrogen;
  (ii) C$_3$-C$_{10}$-carbocycle or 5- to 10-membered heterocycle, each of which is optionally substituted with one or more R$^C$; and
  (iii) —C$_1$-C$_6$ alkyl, —C$_2$-C$_6$ alkenyl or —C$_2$-C$_6$ alkynyl, each of which is optionally substituted with one or more R$^C$;
G is —NHS(O)$_2$—R$^3$, and R$^3$ is selected from:
  (i) C$_3$-C$_{10}$-carbocycle or 5- to 10-membered heterocycle, each of which is optionally substituted with one or more R$^C$; and
  (iii) —C$_1$-C$_6$ alkyl, —C$_2$-C$_6$ alkenyl or —C$_2$-C$_6$ alkynyl, each of which is optionally substituted with one or more R$^C$;
L is a C$_3$-C$_5$ saturated or unsaturated chain, optionally containing one to three heteroatoms independently selected from O, N or S(O)n, wherein L is optionally substituted with one more substituents R$^C$;

Z is —$C_1$-$C_4$alkyl, —$C_2$-$C_4$alkenyl or —$C_2$-$C_4$alkynyl, each of which is optionally substituted with one or more $R^D$;

j=0;
k=0;
m=1;
n is 0, 1, or 2;
$R^6$ is H or halo;
$R^7$ is H or halo;
$R^8$ is H or halo;
$R^9$ is H or halo;

each $R^C$ is independently selected at each occurrence from halogen, hydroxy, mercapto, amino, carboxy, nitro, oxo, phosphonoxy, phosphono, thioxo, cyano; or $C_1$-$C_6$alkyl, $C_2$-$C_6$alkenyl, $C_2$-$C_6$alkynyl, $C_1$-$C_6$alkyl-O—, $C_2$-$C_6$alkenyl-O— or $C_2$-$C_6$alkynyl-O—, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_{10}$-carbocycle or 5- to 10-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$alkyl-O—, $C_2$-$C_6$alkenyl-O— or $C_2$-$C_6$alkynyl-O—, $C_1$-$C_6$haloalkyl, $C_2$-$C_6$haloalkenyl, $C_2$-$C_6$haloalkynyl, $C_1$-$C_6$haloalkyl-O—, $C_2$-$C_6$haloalkenyl-O—, or $C_2$-$C_6$haloalkynyl-O—;

each $R^D$ is independently selected at each occurrence from halogen, hydroxy, mercapto, amino, carboxy, nitro, oxo, phosphonoxy, phosphono, thioxo, or cyano;

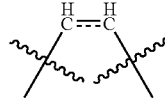 denotes a carbon-carbon single or double bond (i.e.,

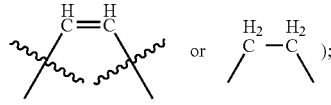

means wherein if each of $R_6$, $R_7$, $R_8$ and $R_9$ is H, then Z is —$C_1$-$C_8$ alkyl, —$C_2$-$C_8$ alkenyl or —$C_2$-$C_8$ alkynyl, each substituted with one or more halo and each containing 0, 1, 2, or 3 heteroatoms independently selected from O, S, and N.

In yet another aspect, the present invention features compounds having Formula I' or preferably Formula I, and salts, solvates and hydrates thereof, wherein A is —(C=O)—O—$R^1$ or —(C=O)—$R^1$,
$R^1$ is selected from the group consisting of:
(i) $C_3$-$C_{10}$-carbocycle or 5- to 10-membered heterocycle, each of which is optionally substituted with one or more $R^C$; and
(ii) —$C_1$-$C_6$ alkyl, —$C_2$-$C_6$ alkenyl or —$C_2$-$C_6$ alkynyl, each of which is optionally substituted with one or more $R^C$;

G is —NHS(O)$_2$—$R^3$, and $R^3$ is $C_3$-$C_6$cycloalkyl optionally substituted with one or more $R^C$;
L is a $C_4$ saturated or unsaturated chain, optionally substituted with one more substituents $R^C$;
Z is —$C_1$-$C_4$alkyl, —$C_2$-$C_4$alkenyl or —$C_2$-$C_4$alkynyl, each of which is optionally substituted with one or more halo;

j=0;
k=0;
m=1;
$R^6$ is H or halo;
$R^7$ is H or halo;
$R^8$ is H or halo;
$R^9$ is H or halo;

each $R^C$ is independently selected at each occurrence from halogen, hydroxy, mercapto, amino, carboxy, nitro, oxo, phosphonoxy, phosphono, thioxo, cyano; or $C_1$-$C_6$alkyl, $C_2$-$C_6$alkenyl, $C_2$-$C_6$alkynyl, $C_1$-$C_6$alkyl-O—, $C_2$-$C_6$alkenyl-O— or $C_2$-$C_6$alkynyl-O—, each of which is independently optionally substituted at each occurrence with one or more substituents selected from halogen, hydroxy, mercapto, amino, carboxy, nitro, oxo, phosphonoxy, phosphono, thioxo, formyl or cyano;

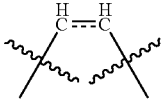 denotes a carbon-carbon single or double bond (i.e., means

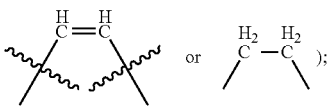

and wherein if each of $R_6$, $R_7$, $R_8$ and $R_9$ is H, then Z is —$C_1$-$C_8$ alkyl, —$C_2$-$C_8$ alkenyl or —$C_2$-$C_8$ alkynyl, each substituted with one or more halo and each containing 0, 1, 2, or 3 heteroatoms independently selected from O, S, and N.

Preferably,

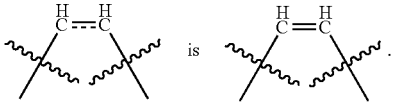

Also preferably, L is $C_4$ alkyl. $R^3$ preferably is cyclopropyl optionally substituted with one or more $R^C$.

In one embodiment of this aspect of the invention, at least one of $R^6$, $R^7$, $R^8$ or $R^9$ is halo (e.g., fluoro), and Z is $C_1$-$C_2$alkyl optionally substituted with one or more halo (e.g., fluoro).

In another embodiment of this aspect of the invention, at least one of $R^7$ or $R^8$ is halo (e.g., fluoro), and Z is $C_1$-$C_2$alkyl optionally substituted with one or more halo (e.g., fluoro).

In still another embodiment of this aspect, $R^6$ is halo (e.g., fluoro), and Z is $C_1$-$C_2$alkyl optionally substituted with one or more halo (e.g., fluoro).

In still another embodiment of this aspect, $R^7$ is halo (e.g., fluoro), and Z is $C_1$-$C_2$alkyl optionally substituted with one or more halo (e.g., fluoro).

In still another embodiment of this aspect, $R^8$ is halo (e.g., fluoro), and Z is $C_1$-$C_2$alkyl optionally substituted with one or more halo (e.g., fluoro).

In still another embodiment of this aspect, $R^9$ is halo (e.g., fluoro), and Z is $C_1$-$C_2$alkyl optionally substituted with one or more halo (e.g., fluoro).

In still another embodiment of this aspect, $R^6$ is halo (e.g., fluoro), and Z is $C_1$-$C_2$alkyl substituted with one or more halo (e.g., fluoro).

In still another embodiment of this aspect, $R^7$ is halo (e.g., fluoro), and Z is $C_1$-$C_2$alkyl substituted with one or more halo (e.g., fluoro).

In still another embodiment of this aspect, $R^8$ is halo (e.g., fluoro), and Z is $C_1$-$C_2$alkyl substituted with one or more halo (e.g., fluoro).

In still another embodiment of this aspect, $R^9$ is halo (e.g., fluoro), and Z is $C_1$-$C_2$alkyl substituted with one or more halo (e.g., fluoro).

In one embodiment of this aspect of the invention, at least one of $R^6$, $R^7$, $R^8$ or $R^9$ is halo (e.g., fluoro, bromo, chloro).

In one embodiment of this aspect of the invention, one of $R^6$, $R^7$, $R^8$ or $R^9$ is halo (e.g., fluoro, bromo, chloro).

In one embodiment of this aspect of the invention, at least two of $R^6$, $R^7$, $R^8$ or $R^9$ are halo (e.g., fluoro, bromo, chloro).

In one embodiment of this aspect of the invention, Z is $C_1$-$C_2$alkyl optionally substituted with one or more halo (e.g., fluoro).

In one embodiment of this aspect of the invention, Z is $C_1$-$C_2$alkyl substituted with one or more halo (e.g., fluoro).

Representative compounds include, but are not limited to, the following compounds:

tert-butyl (2R,6S,13aS,14aR,16aS,Z)-14a-(cyclopropylsulfonylcarbamoyl)-2-(3-(1,1-difluoroethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (Compound 1);

N-((2R,6S,13aS,14aR,16aS,Z)-14a-(cyclopropylsulfonylcarbamoyl)-2-(3-(1,1-difluoroethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 2);

N-((2R,6S,13aS,14aR,16aS,Z)-14a-(cyclopropylsulfonylcarbamoyl)-2-(3-(1,1-difluoroethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 3);

(2R,6S,13aS,14aR,16aS,Z)—N-(cyclopropylsulfonyl)-2-(3-(1,1-difluoroethyl)quinoxalin-2-yloxy)-5,16-dioxo-6-pivalamido-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 4);

N-((2R,6S,13aS,14aR,16aS,Z)-2-(3-(1,1-difluoroethyl)quinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 5);

N-((2R,6S,13aS,14aR,16aS,Z)-14a-(cyclopropylsulfonylcarbamoyl)-2-(3-(1,1-difluoroethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole-3-carboxamide (Compound 6);

N-((2R,6S,13aS,14aR,16aS,Z)-2-(3-(1,1-difluoroethyl)quinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole-3-carboxamide (Compound 7);

N-((2R,6S,13aS,14aR,16aS,Z)-2-(3-(1,1-difluoroethyl)quinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 8);

tert-butyl (2R,6S,13aS,14aR,16aS,Z)-14a-(cyclopropylsulfonylcarbamoyl)-5,16-dioxo-2-(3-(trifluoromethyl)quinoxalin-2-yloxy)-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (Compound 9);

N-((2R,6S,13aS,14aR,16aS,Z)-14a-(cyclopropylsulfonylcarbamoyl)-5,16-dioxo-2-(3-(trifluoromethyl)quinoxalin-2-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 10);

(2R,6S,13aS,14aR,16aS,Z)—N-(cyclopropylsulfonyl)-2-(3-(trifluoromethyl)quinoxalin-2-yloxy)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 11);

(2R,6S,13aS,14aR,16aS,Z)—N-(cyclopropylsulfonyl)-2-(7-fluoro-3-(trifluoromethyl)quinoxalin-2-yloxy)-6-(1-methyl-1H-pyrazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 12);

(2R,6S,13aS,14aR,16aS,Z)—N-(cyclopropylsulfonyl)-2-(7-fluoro-3-(trifluoromethyl)quinoxalin-2-yloxy)-6-(3-methyl-1H-pyrazole-5-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 13);

(2R,6S,13aS,14aR,16aS,Z)—N-(cyclopropylsulfonyl)-2-(7-fluoro-3-(trifluoromethyl)quinoxalin-2-yloxy)-6-(3-methylthiophene-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 14);

N-((2R,6S,13aS,14aR,16aS,Z)-14a-(cyclopropylsulfonylcarbamoyl)-5,16-dioxo-2-(3-(trifluoromethyl)quinoxalin-2-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 15);

N-((2R,6S,13aS,14aR,16aS,Z)-14$^a$-(cyclopropylsulfonylcarbamoyl)-5,16-dioxo-2-(3-(trifluoromethyl)quinoxalin-2-yloxy)-1,2,3,5,6,7,8,9,10,11,13$^a$,14,14$^a$,15,16,16$^a$-hexadecahydrocyclopropa[e]pyrrolo[1,2-a][1,4]diazacyclopentadecin-6-yl)-4,5-dimethylisoxazole-3-carboxamide (Compound 16);

5-methyl-N-((2R,6S,13aS,14aR,16aS,Z)-14a-(1-methylcyclopropylsulfonylcarbamoyl)-5,16-dioxo-2-(3-(trifluoromethyl)quinoxalin-2-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 17);

4,5-dimethyl-N-((2R,6S,13aS,14aR,16aS,Z)-14a-(1-methylcyclopropylsulfonylcarbamoyl)-5,16-dioxo-2-(3-(trifluoromethyl)quinoxalin-2-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 18);

(2R,6S,13aS,14aR,16aS,Z)—N-(cyclopropylsulfonyl)-6-((S)-3-methyl-2-(2-oxotetrahydropyrimidin-1(2H)-yl)butanamido)-5,16-dioxo-2-(3-(trifluoromethyl)quinoxalin-2-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 19);

tert-butyl (2R,6S,13aS,14aR,16aS,Z)-14a-(cyclopropylsulfonylcarbamoyl)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (Compound 20);

N-((2R,6S,13aS,14aR,16aS,Z)-14a-(cyclopropylsulfonylcarbamoyl)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole-3-carboxamide (Compound 21);

N-((2R,6S,13aS,14aR,16aS,Z)-14a-(cyclopropylsulfonylcarbamoyl)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 22);

N-((2R,6S,13aS,14aR,16aS,Z)-2-(7-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 23);

N-((2R,6S,13aS,14aR,16aS,Z)-2-(7-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole-3-carboxamide (Compound 24);

N-((2R,6S,13aS,14aR,16aS,Z)-2-(7-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 25);

(2R,6S,13aS,14aR,16aS,Z)—N-(cyclopropylsulfonyl)-2-(7-fluoro-3-methylquinoxalin-2-yloxy)-6-(4-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 26);

N-((2R,6S,13aS,14aR,16aS,Z)-14a-(cyclopropylsulfonylcarbamoyl)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 27);

(2R,6S,13aS,14aR,16aS,Z)—N-(cyclopropylsulfonyl)-2-(7-fluoro-3-methylquinoxalin-2-yloxy)-5,16-dioxo-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 28);

5-cyclopropyl-N-((2R,6S,13aS,14aR,16aS,Z)-14a-(cyclopropylsulfonylcarbamoyl)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 29);

(2R,6S,13aS,14aR,16aS,Z)—N-(cyclopropylsulfonyl)-6-(1,3-dimethyl-1H-pyrazole-5-carboxamido)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 30);

(2R,6S,13aS,14aR,16aS,Z)—N-(cyclopropylsulfonyl)-2-(7-fluoro-3-methylquinoxalin-2-yloxy)-6-(3-fluoroisonicotinamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 31);

(2R,6S,13aS,14aR,16aS,Z)—N-(cyclopropylsulfonyl)-2-(7-fluoro-3-methylquinoxalin-2-yloxy)-5,16-dioxo-6-(pyrazine-2-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 32);

(2R,6S,13aS,14aR,16aS,Z)—N-(cyclopropylsulfonyl)-2-(7-fluoro-3-methylquinoxalin-2-yloxy)-6-(1-methyl-1H-pyrazole-5-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 33);

N-((2R,6S,13aS,14aR,16aS,Z)-14a-(cyclopropylsulfonylcarbamoyl)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-4-carboxamide (Compound 34);

(2R,6S,13aS,14aR,16aS,Z)—N-(cyclopropylsulfonyl)-2-(7-fluoro-3-methylquinoxalin-2-yloxy)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 35);

(2R,6S,13aS,14aR,16aS,Z)—N-(cyclopropylsulfonyl)-2-(7-fluoro-3-methylquinoxalin-2-yloxy)-6-(3-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 36);

(2R,6S,13aS,14aR,16aS,Z)—N-(cyclopropylsulfonyl)-2-(7-fluoro-3-methylquinoxalin-2-yloxy)-6-(2-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 37);

(2R,6S,13aS,14aR,16aS,Z)—N-(cyclopropylsulfonyl)-2-(7-fluoro-3-methylquinoxalin-2-yloxy)-6-(5-methylthiophene-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 38);

N-((2R,6S,13aS,14aR,16aS,Z)-14a-(cyclopropylsulfonyl-carbamoyl)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylthiazole-2-carboxamide (Compound 39);

N-((2R,6S,13aS,14aR,16aS,Z)-14a-(cyclopropylsulfonyl-carbamoyl)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-ethylisoxazole-3-carboxamide (Compound 40);

(2R,6S,13aS,14aR,16aS,Z)-2-(7-fluoro-3-methylquinoxa-lin-2-yloxy)-N-(1-methylcyclopropylsulfonyl)-6-(5-methylfuran-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 41);

(2R,6S,13aS,14aR,16aS,Z)-2-(7-fluoro-3-methylquinoxa-lin-2-yloxy)-6-(1-methyl-1H-pyrazole-3-carboxamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 42);

(2R,6S,13aS,14aR,16aS,Z)—N-(1-methylcyclopropylsulfo-nyl)-2-(7-fluoro-3-methylquinoxalin-2-yloxy)-5,16-di-oxo-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 43);

5-cyclopropyl-N-((2R,6S,13aS,14aR,16aS,Z)-2-(7-fluoro-3-methylquinoxalin-2-yloxy)-14a-(1-methylcyclopropyl-sulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 44);

(2R,6S,13aS,14aR,16aS,Z)-6-(1,3-dimethyl-1H-pyrazole-5-carboxamido)-2-(7-fluoro-3-methylquinoxalin-2-yloxy)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 45);

(2R,6S,13aS,14aR,16aS,Z)-2-(7-fluoro-3-methylquinoxa-lin-2-yloxy)-6-(3-fluoroisonicotinamido)-N-(1-methylcy-clopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 46);

(2R,6S,13aS,14aR,16aS,Z)-2-(7-fluoro-3-methylquinoxa-lin-2-yloxy)-N-(1-methylcyclopropylsulfonyl)-5,16-di-oxo-6-(pyrazine-2-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 47);

N-((2R,6S,13aS,14aR,16aS,Z)-2-(7-fluoro-3-methylqui-noxalin-2-yloxy)-14a-(1-methylcyclopropylsulfonylcar-bamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-4-carboxamide (Compound 48);

(2R,6S,13aS,14aR,16aS,Z)-6-(1,5-dimethyl-1H-pyrazole-3-carboxamido)-2-(7-fluoro-3-methylquinoxalin-2-yloxy)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 49);

(2R,6S,13aS,14aR,16aS,Z)-2-(7-fluoro-3-methylquinoxa-lin-2-yloxy)-N-(1-methylcyclopropylsulfonyl)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 50);

N-((2R,6S,13aS,14aR,16aS,Z)-2-(7-fluoro-3-methylqui-noxalin-2-yloxy)-14a-(1-methylcyclopropylsulfonylcar-bamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-3-methylisoxazole-5-carboxamide (Compound 51);

(2R,6S,13aS,14aR,16aS,Z)-2-(7-fluoro-3-methylquinoxa-lin-2-yloxy)-6-(2-fluorobenzamido)-N-(1-methylcyclo-propylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 52);

N-((2R,6S,13aS,14aR,16aS,Z)-2-(7-fluoro-3-methylqui-noxalin-2-yloxy)-14a-(1-methylcyclopropylsulfonylcar-bamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylthiazole-2-carboxamide (Compound 53);

tert-butyl (2R,6S,13aS,14aR,16aS,Z)-14a-(cyclopropylsul-fonylcarbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (Compound 54);

N-((2R,6S,13aS,14aR,16aS,Z)-14a-(cyclopropylsulfonyl-carbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 55);

N-((2R,6S,13aS,14aR,16aS,Z)-14a-(cyclopropylsulfonyl-carbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 56);

N-((2R,6S,13aS,14aR,16aS,Z)-14a-(cyclopropylsulfonyl-carbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole-3-carboxamide (Compound 57);

N-((2R,6S,13aS,14aR,16aS,Z)-2-(8-fluoro-3-methylqui-noxalin-2-yloxy)-14a-(1-methylcyclopropylsulfonylcar-bamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 58);

(2R,6S,13aS,14aR,16aS,Z)—N-(cyclopropylsulfonyl)-2-(8-fluoro-3-methylquinoxalin-2-yloxy)-6-(1-methyl-1H-pyrazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 59);

(2R,6S,13aS,14aR,16aS,Z)—N-(cyclopropylsulfonyl)-2-(8-fluoro-3-methylquinoxalin-2-yloxy)-6-(4-fluoroben-zamido)-5,16-dioxo-1,2,3,5,6,7,8,9,10,11,13a,14,14a,15, 16,16a-hexadecahydrocyclopropa[e]pyrrolo[1,2-a][1,4]
diazacyclopentadecine-14a-carboxamide (Compound 60);

(2R,6S,13aS,14aR,16aS,Z)—N-(cyclopropylsulfonyl)-2-(8-fluoro-3-methylquinoxalin-2-yloxy)-5,16-dioxo-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 61);

5-cyclopropyl-N-((2R,6S,13aS,14aR,16aS,Z)-14a-(cyclopropylsulfonylcarbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 62);

(2R,6S,13aS,14aR,16aS,Z)—N-(cyclopropylsulfonyl)-6-(1,3-dimethyl-1H-pyrazole-5-carboxamido)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 63);

N-((2R,6S,13aS,14aR,16aS,Z)-14a-(cyclopropylsulfonylcarbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4-methylthiazole-5-carboxamide (Compound 64);

(2R,6S,13aS,14aR,16aS,Z)—N-(cyclopropylsulfonyl)-2-(8-fluoro-3-methylquinoxalin-2-yloxy)-6-(3-fluoroisonicotinamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 65);

(2R,6S,13aS,14aR,16aS,Z)—N-(cyclopropylsulfonyl)-2-(8-fluoro-3-methylquinoxalin-2-yloxy)-5,16-dioxo-6-(pyrazine-2-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 66);

(2R,6S,13aS,14aR,16aS,Z)—N-(cyclopropylsulfonyl)-2-(8-fluoro-3-methylquinoxalin-2-yloxy)-6-(5-methyl-1H-pyrazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 67);

(2R,6S,13aS,14aR,16aS,Z)—N-(cyclopropylsulfonyl)-2-(8-fluoro-3-methylquinoxalin-2-yloxy)-6-(1-methyl-1H-pyrazole-5-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 68);

N-((2R,6S,13aS,14aR,16aS,Z)-14a-(cyclopropylsulfonylcarbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-4-carboxamide (Compound 69);

(2R,6S,13aS,14aR,16aS,Z)—N-(cyclopropylsulfonyl)-6-(1,5-dimethyl-1H-pyrazole-3-carboxamido)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 70);

(2R,6S,13aS,14aR,16aS,Z)—N-(cyclopropylsulfonyl)-2-(8-fluoro-3-methylquinoxalin-2-yloxy)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 71);

(2R,6S,13aS,14aR,16aS,Z)—N-(cyclopropylsulfonyl)-2-(8-fluoro-3-methylquinoxalin-2-yloxy)-6-(3-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 72);

N-((2R,6S,13aS,14aR,16aS,Z)-14a-(cyclopropylsulfonylcarbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-3-methylisoxazole-5-carboxamide (Compound 73);

(2R,6S,13aS,14aR,16aS,Z)—N-(cyclopropylsulfonyl)-2-(8-fluoro-3-methylquinoxalin-2-yloxy)-6-(2-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 74);

(2R,6S,13aS,14aR,16aS,Z)—N-(cyclopropylsulfonyl)-2-(8-fluoro-3-methylquinoxalin-2-yloxy)-6-(5-methylthiophene-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 75);

N-((2R,6S,13aS,14aR,16aS,Z)-14a-(cyclopropylsulfonylcarbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-ethylisoxazole-3-carboxamide (Compound 76);

N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-3-isopropylisoxazole-5-carboxamide (Compound 77);

(2R,6S,13aS,14aR,16aS,Z)-2-(8-fluoro-3-methylquinoxalin-2-yloxy)-6-(1-methyl-1H-pyrazole-3-carboxamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 78);

(2R,6S,13aS,14aR,16aS,Z)-2-(8-fluoro-3-methylquinoxalin-2-yloxy)-6-(4-fluorobenzamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 79);

N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 80);

5-cyclopropyl-N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 81);

(2R,6S,13aS,14aR,16aS,Z)-6-(1,3-dimethyl-1H-pyrazole-5-carboxamido)-2-(8-fluoro-3-methylquinoxalin-2-yloxy)-N-(1-methylcyclopropylsulfonyl)-5,16-dioxo-1,2,3,5,6,7,8,9,10,11,13a,14,14a,15,16,16a- hexadecahydrocyclopropa[e]pyrrolo[1,2-a][1,4]
diazacyclopentadecine-14a-carboxamide (Compound 82);

N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4-methylthiazole-5-carboxamide (Compound 83);

(2R,6S,13aS,14aR,16aS,Z)-2-(8-fluoro-3-methylquinoxalin-2-yloxy)-6-(3-fluoroisonicotinamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 84);

(2R,6S,13aS,14aR,16aS,Z)-2-(8-fluoro-3-methylquinoxalin-2-yloxy)-N-(1-methylcyclopropylsulfonyl)-5,16-dioxo-6-(pyrazine-2-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 85);

(2R,6S,13aS,14aR,16aS,Z)-2-(8-fluoro-3-methylquinoxalin-2-yloxy)-6-(5-methyl-1H-pyrazole-3-carboxamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 86);

(2R,6S,13aS,14aR,16aS,Z)-2-(8-fluoro-3-methylquinoxalin-2-yloxy)-6-(1-methyl-1H-pyrazole-5-carboxamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 87);

N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-4-carboxamide (Compound 88);

(2R,6S,13aS,14aR,16aS,Z)-6-(1,5-dimethyl-1H-pyrazole-3-carboxamido)-2-(8-fluoro-3-methylquinoxalin-2-yloxy)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 89);

(2R,6S,13aS,14aR,16aS,Z)-2-(8-fluoro-3-methylquinoxalin-2-yloxy)-N-(1-methylcyclopropylsulfonyl)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 90);

(2R,6S,13aS,14aR,16aS,Z)-2-(8-fluoro-3-methylquinoxalin-2-yloxy)-6-(3-fluorobenzamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 91);

N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-3-methylisoxazole-5-carboxamide (Compound 92);

(2R,6S,13aS,14aR,16aS,Z)-2-(8-fluoro-3-methylquinoxalin-2-yloxy)-6-(2-fluorobenzamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 93);

(2R,6S,13aS,14aR,16aS,Z)-2-(8-fluoro-3-methylquinoxalin-2-yloxy)-N-(1-methylcyclopropylsulfonyl)-6-(5-methylthiophene-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 94);

N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylthiazole-2-carboxamide (Compound 95);

5-ethyl-N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 96);

tert-butyl (2R,6S,13aS,14aR,16aS,Z)-2-(5-bromo-7-fluoro-3-methylquinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (Compound 97);

N-((2R,6S,13aS,14aR,16aS,Z)-2-(5-bromo-7-fluoro-3-methylquinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 98);

N-((2R,6S,13aS,14aR,16aS,Z)-2-(5-bromo-7-fluoro-3-methylquinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole-3-carboxamide (Compound 99);

N-((2R,6S,13aS,14aR,16aS,Z)-2-(5-bromo-7-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 100);

N-((2R,6S,13aS,14aR,16aS,Z)-2-(5-bromo-7-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 101);

N-((2R,6S,13aS,14aR,16aS,Z)-2-(5-bromo-7-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole-3-carboxamide (Compound 102);

(2R,6S,13aS,14aR,16aS,Z)-2-(5-bromo-7-fluoro-3-methylquinoxalin-2-yloxy)-N-(1-methylcyclopropylsulfonyl)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 103);

(2R,6S,13aS,14aR,16aS,Z)-2-(5-bromo-7-fluoro-3-methylquinoxalin-2-yloxy)-6-(4-fluorobenzamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 104);

(2R,6S,13aS,14aR,16aS,Z)-2-(5-bromo-7-fluoro-3-methylquinoxalin-2-yloxy)-N-(1-methylcyclopropylsulfonyl)-6-(5-methylthiophene-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 105);

tert-butyl (2R,6S,13aS,14aR,16aS,Z)-14a-(cyclopropylsulfonylcarbamoyl)-2-(7-fluoro-3-(trifluoromethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (Compound 106);

N-((2R,6S,13aS,14aR,16aS,Z)-14a-(cyclopropylsulfonylcarbamoyl)-2-(7-fluoro-3-(trifluoromethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 107);

N-((2R,6S,13aS,14aR,16aS,Z)-2-(7-fluoro-3-(trifluoromethyl)quinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole-3-carboxamide (Compound 108);

N-((2R,6S,13aS,14aR,16aS,Z)-2-(7-fluoro-3-(trifluoromethyl)quinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 109);

tert-butyl (2R,6S,13aS,14aR,16aS,Z)-2-(7-fluoro-3-(trifluoromethyl)quinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (Compound 110);

N-((2R,6S,13aS,14aR,16aS,Z)-2-(7-fluoro-3-(trifluoromethyl)quinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 111);

tert-butyl (2R,6S,13aS,14aR,16aS,Z)-14a-(cyclopropylsulfonylcarbamoyl)-2-(8-fluoro-3-(trifluoromethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (Compound 112);

N-((2R,6S,13aS,14aR,16aS,Z)-14a-(cyclopropylsulfonylcarbamoyl)-2-(8-fluoro-3-(trifluoromethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 113);

tert-butyl (2R,6S,13aS,14aR,16aS,Z)-2-(8-fluoro-3-(trifluoromethyl)quinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (Compound 114);

N-((2R,6S,13aS,14aR,16aS,Z)-2-(8-fluoro-3-(trifluoromethyl)quinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 115);

tert-butyl (2R,6S,13aS,14aR,16aS,Z)-14a-(cyclopropylsulfonylcarbamoyl)-2-(3-(1,1-difluoroethyl)-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (Compound 116);

N-((2R,6S,13aS,14aR,16aS,Z)-14a-(cyclopropylsulfonylcarbamoyl)-2-(3-(1,1-difluoroethyl)-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 117);

tert-butyl (2R,6S,13aS,14aR,16aS,Z)-2-(3-(1,1-difluoroethyl)-7-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (Compound 118);

N-((2R,6S,13aS,14aR,16aS,Z)-2-(3-(1,1-difluoroethyl)-7-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 119);

N-((2R,6S,13aS,14aR,16aS,Z)-2-(3-(1,1-difluoroethyl)-7-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-methylisoxazole-3-carboxamide (Compound 120);

tert-butyl (2R,6S,13aS,14aR,16aS,Z)-14a-(cyclopropylsulfonylcarbamoyl)-2-(3-ethyl-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (Compound 121);

N-((2R,6S,13aS,14aR,16aS,Z)-14a-(cyclopropylsulfonylcarbamoyl)-2-(3-ethyl-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 122);

N-((2R,6S,13aS,14aR,16aS,Z)-14a-(cyclopropylsulfonylcarbamoyl)-2-(3-ethyl-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole-3-carboxamide (Compound 123);

N-((2R,6S,13aS,14aR,16aS,Z)-14a-(cyclopropylsulfonylcarbamoyl)-2-(3-ethyl-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 124);

tert-butyl (2R,6S,13aS,14aR,16aS,Z)-2-(3-ethyl-7-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (Compound 125);

N-((2R,6S,13aS,14aR,16aS,Z)-2-(3-ethyl-7-fluoroquinoxalin-2-yloxy)-14a-(1-methylcyclopropylsulfonylcarbamoyl)-5,16-dioxo-1,2,3,5,6,7,8,9,10,11,13a,14,14a,15,16, 16a-hexadecahydrocyclopropa[e]pyrrolo[1,2-a][1,4]
diazacyclopentadecin-6-yl)isoxazole-3-carboxamide
(Compound 126);

N-((2R,6S,13aS,14aR,16aS,Z)-2-(3-ethyl-7-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 127);

(2R,6S,13aS,14aR,16aS,Z)-2-(3-ethyl-7-fluoroquinoxalin-2-yloxy)-N-(1-methylcyclopropylsulfonyl)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 128);

N-((2R,6S,13aS,14aR,16aS,Z)-14a-(cyclopropylsulfonylcarbamoyl)-2-(3-ethyl-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-3-isopropylisoxazole-5-carboxamide (Compound 129);

(2R,6S,13aS,14aR,16aS,Z)—N-(cyclopropylsulfonyl)-2-(3-ethyl-7-fluoroquinoxalin-2-yloxy)-6-(5-methylfuran-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 130);

(2R,6S,13aS,14aR,16aS,Z)—N-(cyclopropylsulfonyl)-2-(3-ethyl-7-fluoroquinoxalin-2-yloxy)-6-(1-methyl-1H-pyrazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 131);

(2R,6S,13aS,14aR,16aS,Z)—N-(cyclopropylsulfonyl)-2-(3-ethyl-7-fluoroquinoxalin-2-yloxy)-6-(4-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 132);

(2R,6S,13aS,14aR,16aS,Z)—N-(cyclopropylsulfonyl)-2-(3-ethyl-7-fluoroquinoxalin-2-yloxy)-5,16-dioxo-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 133);

5-cyclopropyl-N-((2R,6S,13aS,14aR,16aS,Z)-14a-(cyclopropylsulfonylcarbamoyl)-2-(3-ethyl-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 134);

(2R,6S,13aS,14aR,16aS,Z)—N-(cyclopropylsulfonyl)-6-(1,3-dimethyl-1H-pyrazole-5-carboxamido)-2-(3-ethyl-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 135);

N-((2R,6S,13aS,14aR,16aS,Z)-14a-(cyclopropylsulfonylcarbamoyl)-2-(3-ethyl-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4-methylthiazole-5-carboxamide (Compound 136);

(2R,6S,13aS,14aR,16aS,Z)—N-(cyclopropylsulfonyl)-2-(3-ethyl-7-fluoroquinoxalin-2-yloxy)-6-(3-fluoroisonicotinamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 137);

(2R,6S,13aS,14aR,16aS,Z)—N-(cyclopropylsulfonyl)-2-(3-ethyl-7-fluoroquinoxalin-2-yloxy)-5,16-dioxo-6-(pyrazine-2-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 138);

(2R,6S,13aS,14aR,16aS,Z)—N-(cyclopropylsulfonyl)-2-(3-ethyl-7-fluoroquinoxalin-2-yloxy)-6-(5-methyl-1H-pyrazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 139);

(2R,6S,13aS,14aR,16aS,Z)—N-(cyclopropylsulfonyl)-2-(3-ethyl-7-fluoroquinoxalin-2-yloxy)-6-(1-methyl-1H-pyrazole-5-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 140);

(2R,6S,13aS,14aR,16aS,Z)-6-(1,5-dimethyl-1H-pyrazole-3-carboxamido)-2-(3-ethyl-7-fluoroquinoxalin-2-yloxy)-N-(cyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 141);

(2R,6S,13aS,14aR,16aS,Z)—N-(cyclopropylsulfonyl)-2-(3-ethyl-7-fluoroquinoxalin-2-yloxy)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 142);

(2R,6S,13aS,14aR,16aS,Z)—N-(cyclopropylsulfonyl)-2-(3-ethyl-7-fluoroquinoxalin-2-yloxy)-6-(3-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 143);

N-((2R,6S,13aS,14aR,16aS,Z)-2-(3-ethyl-7-fluoroquinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-3-methylisoxazole-5-carboxamide (Compound 144);

(2R,6S,13aS,14aR,16aS,Z)—N-(cyclopropylsulfonyl)-2-(3-ethyl-7-fluoroquinoxalin-2-yloxy)-6-(2-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 145);

(2R,6S,13aS,14aR,16aS,Z)-2-(3-ethyl-7-fluoroquinoxalin-2-yloxy)-N-(cyclopropylsulfonyl)-6-(5-methylthiophene-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 146);

N-((2R,6S,13aS,14aR,16aS,Z)-2-(3-ethyl-7-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-4-carboxamide (Compound 147);

N-((2R,6S,13aS,14aR,16aS,Z)-2-(3-ethyl-7-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]

diazacyclopentadecin-6-yl)-3-isopropylisoxazole-5-carboxamide (Compound 148);

(2R,6S,13aS,14aR,16aS,Z)-2-(3-ethyl-7-fluoroquinoxalin-2-yloxy)-6-(1-methyl-1H-pyrazole-3-carboxamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 149);

(2R,6S,13aS,14aR,16aS,Z)-2-(3-ethyl-7-fluoroquinoxalin-2-yloxy)-N-(1-methylcyclopropylsulfonyl)-5,16-dioxo-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 150);

5-cyclopropyl-N-((2R,6S,13aS,14aR,16aS,Z)-2-(3-ethyl-7-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 151);

N-((2R,6S,13aS,14aR,16aS,Z)-2-(3-ethyl-7-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4-methylthiazole-5-carboxamide (Compound 152);

(2R,6S,13aS,14aR,16aS,Z)-2-(3-ethyl-7-fluoroquinoxalin-2-yloxy)-N-(1-methylcyclopropylsulfonyl)-5,16-dioxo-6-(pyrazine-2-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 153);

(2R,6S,13aS,14aR,16aS,Z)-2-(3-ethyl-7-fluoroquinoxalin-2-yloxy)-6-(5-methyl-1H-pyrazole-3-carboxamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 154);

(2R,6S,13aS,14aR,16aS,Z)-2-(3-ethyl-7-fluoroquinoxalin-2-yloxy)-6-(1-methyl-1H-pyrazole-5-carboxamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 155);

N-((2R,6S,13aS,14aR,16aS,Z)-2-(3-ethyl-7-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-3-methylisoxazole-5-carboxamide (Compound 156);

(2R,6S,13aS,14aR,16aS,Z)-2-(3-ethyl-7-fluoroquinoxalin-2-yloxy)-6-(2-fluorobenzamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 157);

N-((2R,6S,13aS,14aR,16aS,Z)-2-(3-ethyl-7-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylthiazole-2-carboxamide (Compound 158);

5-ethyl-N-((2R,6S,13aS,14aR,16aS,Z)-2-(3-ethyl-7-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 159);

tert-butyl (2R,6S,13aS,14aR,16aS,Z)-14a-(cyclopropylsulfonylcarbamoyl)-2-(3-ethyl-8-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (Compound 160);

N-((2R,6S,13aS,14aR,16aS,Z)-14a-(cyclopropylsulfonylcarbamoyl)-2-(3-ethyl-8-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 161);

N-((2R,6S,13aS,14aR,16aS,Z)-14a-(cyclopropylsulfonylcarbamoyl)-2-(3-ethyl-8-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide (Compound 162);

N-((2R,6S,13aS,14aR,16aS,Z)-14a-(cyclopropylsulfonylcarbamoyl)-2-(3-ethyl-8-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole isoxazole-3-carboxamide (Compound 163);

tert-butyl (2R,6S,13aS,14aR,16aS,Z)-2-(3-ethyl-8-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (Compound 164);

(2R,6S,13aS,14aR,16aS,Z)—N-(cyclopropylsulfonyl)-2-(3-ethyl-8-fluoroquinoxalin-2-yloxy)-6-(5-methylthiophene-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 165);

(2R,6S,13aS,14aR,16aS,Z)—N-(cyclopropylsulfonyl)-2-(3-ethyl-8-fluoroquinoxalin-2-yloxy)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 166);

N-((2R,6S,13aS,14aR,16aS,Z)-14a-(cyclopropylsulfonylcarbamoyl)-2-(3-ethyl-8-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-2-carboxamide (Compound (167);

(2R,6S,13aS,14aR,16aS,Z)-2-(3-ethyl-8-fluoroquinoxalin-2-yloxy)-6-(5-methyl-1H-pyrazole-3-carboxamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 168);

N-((2R,6S,13aS,14aR,16aS,Z)-2-(3-ethyl-8-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 169);

(2R,6S,13aS,14aR,16aS,Z)-6-(1,5-dimethyl-1H-pyrazole-3-carboxamido)-2-(3-ethyl-8-fluoroquinoxalin-2-yloxy)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 170);

(2R,6S,13aS,14aR,16aS,Z)-2-(3-ethyl-8-fluoroquinoxalin-2-yloxy)-6-(1-methyl-1H-pyrazole-5-carboxamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 171);

(2R,6S,13aS,14aR,16aS,Z)-2-(3-ethyl-8-fluoroquinoxalin-2-yloxy)-N-(1-methylcyclopropylsulfonyl)-5,16-dioxo-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 172);

(2R,6S,13aS,14aR,16aS,Z)-2-(3-ethyl-8-fluoroquinoxalin-2-yloxy)-6-(4-fluorobenzamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 173);

(2R,6S,13aS,14aR,16aS,Z)-2-(3-ethyl-8-fluoroquinoxalin-2-yloxy)-6-(3-fluoroisonicotinamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 174);

(2R,6S,13aS,14aR,16aS,Z)-2-(3-ethyl-8-fluoroquinoxalin-2-yloxy)-6-(2-fluorobenzamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 175);

5-cyclopropyl-N-((2R,6S,13aS,14aR,16aS,Z)-2-(3-ethyl-8-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 176);

(2R,6S,13aS,14aR,16aS,Z)-2-(3-ethyl-8-fluoroquinoxalin-2-yloxy)-6-(1-methyl-1H-pyrazole-3-carboxamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 177);

(2R,6S,13aS,14aR,16aS,Z)-2-(3-ethyl-8-fluoroquinoxalin-2-yloxy)-N-(1-methylcyclopropylsulfonyl)-5,16-dioxo-6-(pyrazine-2-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 178);

5-ethyl-N-((2R,6S,13aS,14aR,16aS,Z)-2-(3-ethyl-8-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide (Compound 179);

N-((2R,6S,13aS,14aR,16aS,Z)-2-(3-ethyl-8-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylthiazole-2-carboxamide (Compound 180);

N-((2R,6S,13aS,14aR,16aS,Z)-2-(3-ethyl-8-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4-methylthiazole-5-carboxamide (Compound 181);

N-((2R,6S,13aS,14aR,16aS,Z)-2-(3-ethyl-8-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-2-carboxamide (Compound 182);

(2R,6S,13aS,14aR,16aS,Z)-2-(3-ethyl-8-fluoroquinoxalin-2-yloxy)-N-(1-methylcyclopropylsulfonyl)-6-(5-methylthiophene-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 183);

(2R,6S,13aS,14aR,16aS,Z)-2-(3-ethyl-8-fluoroquinoxalin-2-yloxy)-N-(1-methylcyclopropylsulfonyl)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 184); and (2R,6S,13aS,14aR,16aS,Z)-2-(3-ethyl-8-fluoroquinoxalin-2-yloxy)-N-(1-methylcyclopropylsulfonyl)-6-(5-methylfuran-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (Compound 185).

In another aspect, the invention provides a pharmaceutical composition comprising a therapeutically effective amount of a compound of formula I or I' described herein, or an embodiment or example described herein, or a pharmaceutically acceptable salt, ester, or prodrug thereof, in combination with a pharmaceutically acceptable carrier or excipient.

According to another embodiment, the pharmaceutical compositions of the present invention may further contain one or more other anti-HCV agents. Examples of anti-HCV agents include, but are not limited to, α-interferon; β-interferon; pegylated interferon-α; pegylated interferon-lambda; ribavirin; viramidine; R-5158; nitazoxanide; amantadine; Debio-025, NIM-811; HCV polymerase inhibitors such as R7128, R1626, R4048, T-1106, PSI-7851, PF-00868554, ANA-598, IDX184, IDX102, IDX375, GS-9190, VCH-759, VCH-916, MK-3281, BCX-4678, MK-3281, VBY708, ANA598, GL59728 or GL60667; BMS-790052; BMS-791325; BMS-650032; HCV entry, helicase or internal ribosome entry site inhibitors; HCV NS5A inhibitors; or other HCV replication inhibitors such as GS-9132, ACH-1095, AP-HOO5, A-831, A-689, AZD2836. For further details see S. Tan, A. Pause, Y. Shi, N. Sonenberg, Hepatitis C Therapeutics: Current Status and Emerging Strategies, *Nature Rev. Drug Discov.*, 1, 867-881 (2002); WO 00/59929 (2000); WO 99/07733 (1999); WO 00/09543 (2000); WO 99/50230 (1999); U.S. Pat. No. 5,861,297 (1999); and US2002/0037998 (2002).

According to an additional embodiment, the pharmaceutical compositions of the present invention may further contain another HCV protease inhibitor, such as telaprevir, boceprevir, ITMN-191, BI-201335, TMC-435, MK-7009, VBY-376, VX-500, VX-813, PHX-B, ACH-1625, IDX136, or IDX316.

In other embodiments, the invention provides a pharmaceutical composition further comprising pegylated interferon, another anti-viral, anti-bacterial, anti-fungal or anti-cancer agent, or an immune modulator, and/or further comprising a cytochrome P450 monooxygenase inhibitor or a pharmaceutically acceptable salt thereof. In certain embodiments, the cytochrome P450 monooxygenase inhibitor is ritonavir.

In another aspect, the invention provides for the use of a compound of the invention to manufacture an agent for preventing or treating viral infection. In another aspect, the invention provides for the use of a compound of the invention to manufacture an agent for preventing or treating hepatitis C viral infection. The present invention also contemplates the use of a solvate (e.g., hydrate) of a compound of the invention to manufacture pharmaceutical compositions for preventing or treating hepatitis C infection. As used herein, "solvate" refers to the physical association of a compound of the invention with one or more solvent molecule, whether organic or inorganic. This physical association often includes hydrogen bonding. In certain instances, the solvate is capable of isolation, for example, when one or more solvate molecules are incorporated in the crystal lattice of the crystalline solid.

In another embodiment, the compounds or pharmaceutical compositions of the invention are administered with ritonavir, either simultaneously or sequentially. In certain embodiments, a compound or a pharmaceutical composition of the invention is administered in the same composition as ritonavir. In another embodiment, a compound or a pharmaceutical composition thereof of the invention is administered in a different composition than ritonavir.

According to yet another embodiment, the pharmaceutical compositions of the present invention may further comprise inhibitor(s) of other targets in the HCV life cycle, including, but not limited to, helicase, polymerase, metalloprotease, CD81, NS5A, cyclophilin, and internal ribosome entry site (IRES).

In one aspect, the invention provides a method of treating a viral infection in a subject, comprising administering to the subject a therapeutically effective amount of a compound of formula I or I' described herein, or a pharmaceutically acceptable salt, ester or prodrug thereof, or a pharmaceutical composition comprising the same.

According to a further embodiment, the present invention includes methods of treating hepatitis C infections in a subject in need of such treatment by administering to said subject an anti-HCV virally effective amount or an inhibitory amount of the compounds or pharmaceutical compositions of the present invention.

According to another embodiment, the present invention includes methods of treating hepatitis C infections in a subject in need of such treatment by administering to said subject a compound or a pharmaceutical composition of the present invention. The methods can further include administration of an additional therapeutic agent, including another antiviral agent or an anti-HCV agent as described hereinabove. The additional agent can be co-administered (such as concurrently administered or sequentially administered) with a compound (a pharmaceutically acceptable salt, ester or prodrug thereof) or a pharmaceutical composition of the present invention. The additional agent(s) and a compound (or a pharmaceutically acceptable salt, ester or prodrug thereof) of the present invention can be formulated in the same composition, or in different compositions but co-administered concurrently or sequentially. The methods herein can further include the step of identifying that the subject is in need of treatment for hepatitis C infection. The identification can be by subjective (e.g., health care provider determination) or objective (e.g., diagnostic test) means.

In one aspect, the invention provides a method of inhibiting the replication of hepatitis C virus, the method comprising contacting a hepatitis C virus with an effective amount of a compound or pharmaceutical composition of the invention.

In another embodiment, the invention provides a method as described above, further comprising administering an additional anti-hepatitis C virus agent. Examples of anti-hepatitis C virus agents include, but are not limited to, α-interferon; β-interferon; pegylated interferon-α; pegylated interferon-lambda; ribavirin; viramidine; R-5158; nitazoxanide; amantadine; Debio-025, NIM-811; HCV polymerase inhibitors such as R7128, R1626, R4048, T-1106, PSI-7851, PF-00868554, ANA-598, IDX184, IDX102, IDX375, GS-9190, VCH-759, VCH-916, MK-3281, BCX-4678, MK-3281, VBY708, ANA598, GL59728 or GL60667; BMS-790052; BMS-791325; BMS-650032; HCV entry, helicase or internal ribosome entry site inhibitors; or other HCV replication inhibitors such as GS-9132, ACH-1095, AP-HOO5, A-831, A-689, AZD2836. For further details see S. Tan, A. Pause, Y. Shi, N. Sonenberg, Hepatitis C Therapeutics: Current Status and Emerging Strategies, *Nature Rev. Drug Discov.*, 1, 867-881 (2002); WO 00/59929 (2000); WO 99/07733 (1999); WO 00/09543 (2000); WO 99/50230 (1999); U.S. Pat. No. 5,861,297 (1999); and US2002/0037998 (2002). Preferably, a compound or a pharmaceutical composition of the present invention is co-administered with, or used in combination with, pegylated interferon (e.g., pegylated interferon alpha-2a or 2b) and ribavirin. Ritonavir or another cytochrome P450 monooxygenase inhibitor can also be used to enhance the pharmacokinetics of the compound of the present invention. The patient being treated is preferably infected with HCV genotype-1 (e.g., genotype 1a or 1b). Patients infected with other HCV genotypes, such as genotypes 2, 3, 4, 5 or 6, can also be treated with a compound or a pharmaceutical composition of the present invention.

In another embodiment, the invention provides a method as described above, further comprising administering another HCV protease inhibitor, an HCV polymerase inhibitor, an HCV helicase inhibitor, or an internal ribosome entry site (IRES) inhibitor, such as telaprevir, boceprevir, ITMN-191, BI-201335, TMC-435, MK-7009, VBY-376, VX-500, VX-813, PHX-B, ACH-1625, IDX136, IDX316, pegylated interferon, another anti-viral, anti-bacterial, anti-fungal or anti-cancer agent, or an immune modulator, and/or further comprising a cytochrome P450 monooxygenase inhibitor or a pharmaceutically acceptable salt thereof. In certain embodiments, the cytochrome P450 monooxygenase inhibitor is ritonavir.

An additional embodiment of the present invention includes methods of treating biological samples by contacting the biological samples with the compounds of the present invention.

Yet another aspect of the present invention is a process of making any of the compounds delineated herein employing any of the synthetic means delineated herein.

DEFINITIONS

Listed below are definitions of various terms used to describe this invention. These definitions apply to the terms as they are used throughout this specification and claims, unless otherwise limited in specific instances, either individually or as part of a larger group. The number of carbon atoms in a hydrocarbyl substituent can be indicated by the prefix "$C_x$-$C_y$," where x is the minimum and y is the maximum number of carbon atoms in the substituent. Likewise, a $C_x$ chain means a hydrocarbyl chain containing x carbon atoms.

The prefix "halo" indicates that the substituent to which the prefix is attached is substituted with one or more independently selected halogen radicals. For example, "$C_1$-$C_6$haloalkyl" means a $C_1$-$C_6$alkyl substituent wherein at least one hydrogen radical is replaced with a halogen radical.

If a linking element in a depicted structure is "absent", then the left element in the depicted structure is directly linked to the right element in the depicted structure. For example, if a chemical structure is depicted as X-(L)$_n$-Y wherein L is absent or n is 0, then the chemical structure is X—Y.

The term "alkyl" as used herein, refers to a saturated, straight- or branched-chain hydrocarbon radical. For example, "$C_1$-$C_8$ alkyl" contains from one to eight carbon atoms. Examples of alkyl radicals include, but are not limited to, methyl, ethyl, propyl, isopropyl, n-butyl, tert-butyl, neopentyl, n-hexyl, heptyl, octyl radicals and the like.

The term "alkenyl" as used herein, denotes a straight- or branched-chain hydrocarbon radical containing one or more double bonds. For example, "$C_2$-$C_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" as used herein, denotes a straight- or branched-chain hydrocarbon radical containing one or more triple bonds. For example, "$C_2$-$C_8$alkynyl" contains from two to eight carbon atoms. Representative alkynyl groups include, but are not limited to, for example, ethynyl, 1-propynyl, 1-butynyl, heptynyl, octynyl and the like.

The term "cycloalkyl" denotes a monovalent group derived from a monocyclic or polycyclic saturated carbocyclic ring compound. Examples of cycloalkyl include, but not limited to, cyclopropyl, cyclobutyl, cyclopentyl, cyclohexyl, bicyclo [2.2.1]heptyl, and bicyclo [2.2.2]octyl and the like.

The terms "carbocycle" or "carbocyclic" or "carbocyclyl" refer to a saturated (e.g., "cycloalkyl"), partially saturated (e.g., "cycloalkenyl" or "cycloalkynyl") or completely unsaturated (e.g., "aryl") ring system containing zero heteroatom ring atom. A carbocyclyl may be, without limitation, a single ring, or two or more fused rings, or bridged or spiro rings. A carbocyclyl may contain, for example, from 3 to 10 ring members (i.e., $C_3$-$C_{10}$-carbocyclyl, such as $C_3$-$C_{10}$cycloalkyl). A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydro-indenyl, cyclohexenyl, phenyl, naphthyl, fluorenyl, indanyl, 1,2,3,4-tetrahydro-naphthyl, indenyl, isoindenyl, bicyclodecanyl, anthracenyl, phenanthrene, benzonaphthenyl (also known as "phenalenyl"), decalinyl, and norpinanyl and the like. A carbocyclyl group can be attached to the parent molecular moiety through any substitutable carbon atom of the group.

The term "aryl" refers to an aromatic carbocyclyl containing from 6 to 14 carbon ring atoms. Non-limiting examples of aryls include phenyl, naphthalenyl, anthracenyl, and indenyl and the like. An aryl group can be connected to the parent molecular moiety through any substitutable carbon atom of the group.

The term "heteroaryl" means an aromatic heterocyclyl typically containing from 5 to 18 ring atoms. A heteroaryl may be a single ring, or two or more fused rings. Non-limiting examples of five-membered heteroaryls include imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3,4-oxadiazolyl; and isothiazolyl. Non-limiting examples of six-membered heteroaryls include pyridinyl; pyrazinyl; pyrimidinyl; pyridazinyl; and 1,3,5-, 1,2,4-, and 1,2,3-triazinyl. Non-limiting examples of 6/5-membered fused ring heteroaryls include benzothiofuranyl, isobenzothiofuranyl, benzisoxazolyl, benzoxazolyl, purinyl, and anthranilyl. Non-limiting examples of 6/6-membered fused ring heteroaryls include quinolinyl; isoquinolinyl; and benzoxazinyl (including cinnolinyl and quinazolinyl).

The term "heterocycloalkyl" refers to a non-aromatic 3-, 4-, 5-, 6- or 7-membered ring or a bi- or tri-cyclic group fused system, where at least one of the ring atoms is a heteroatom, and where (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl and the like.

The terms "heterocyclic" or "heterocycle" or "heterocyclyl" refer to a saturated (e.g., "heterocycloalkyl"), partially unsaturated (e.g., "heterocycloalkenyl" or "heterocycloalkynyl") or completely unsaturated (e.g., "heteroaryl") ring system, where at least one of the ring atoms is a heteroatom (i.e., nitrogen, oxygen or sulfur), with the remaining ring atoms being independently selected from the group consisting of carbon, nitrogen, oxygen and sulfur. A heterocyclyl group can be linked to the parent molecular moiety via any substitutable carbon or nitrogen atom in the group, provided that a stable molecule results. A heterocyclyl may be, without limitation, a single ring. Non-limiting examples of single-ring heterocyclyls include furanyl, dihydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazoly, pyranyl, dihydropyranyl, pyridinyl, piperidinyl, pyridazinyl, pyrimidinyl, pyrazinyl, piperazinyl, triazinyl, isoxazinyl, oxazolidinyl, isoxazolidinyl, oxathiazinyl, oxadiazinyl, morpholinyl, azepinyl, oxepinyl, thiepinyl, or diazepinyl. A heterocyclyl may also include, without limitation, two or more rings fused together, such as, for example, naphthyridinyl, thiazolpyrimidinyl, thienopyrimidinyl, pyrimidopyrimidinyl, or pyridopyrimidinyl. A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

The terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I,

—OH, protected hydroxy, alkoxy, oxo, thiooxo,

—$NO_2$, —CN, $CF_3$, $N_3$,

—NH$_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-cycloalkyl, —C(O)-aryl, —C(O)-heteroaryl, —C(O)-heterocycloalkyl, —CONH$_2$, —CONH-alkyl, —CONH-alkenyl, —CONH-alkynyl, —CONH-cycloalkyl, —CONH-aryl, —CONH-heteroaryl, —CONH-heterocycloalkyl, —OCO$_2$-alkyl, —OCO$_2$-alkenyl, —OCO$_2$-alkynyl, —OCO$_2$-cycloalkyl, —OCO$_2$-aryl, —OCO$_2$-heteroaryl, —OCO$_2$-heterocycloalkyl, —OCONH$_2$, —OCONH-alkyl, —OCONH-alkenyl, —OCONH-alkynyl, —OCONH-cycloalkyl, —OCONH-aryl, —OCONH-heteroaryl, —OCONH-heterocycloalkyl, —NHC(O)-alkyl, —NHC(O)-alkenyl, —NHC(O)-alkynyl, —NHC(O)-cycloalkyl, —NHC(O)-aryl, —NHC(O)-heteroaryl, —NHC(O)-heterocycloalkyl, —NHCO$_2$-alkyl, —NHCO$_2$-alkenyl, —NHCO$_2$-alkynyl, —NHCO$_2$-cycloalkyl, —NHCO$_2$-aryl, —NHCO$_2$-heteroaryl, —NHCO$_2$-heterocycloalkyl, —NHC(O)NH$_2$, —NHC(O)NH-alkyl, —NHC(O)NH-alkenyl, —NHC(O)NH-alkenyl, —NHC(O)NH-cycloalkyl, —NHC(O)NH-aryl, —NHC(O)NH-heteroaryl, —NHC(O)NH-heterocycloalkyl, NHC(S)NH$_2$, —NHC(S)NH-alkyl, —NHC(S)NH-alkenyl, —NHC(S)NH-alkynyl, —NHC(S)NH-cycloalkyl, —NHC(S)NH-aryl, —NHC(S)NH-heteroaryl, —NHC(S)NH-heterocycloalkyl, —NHC(NH)NH$_2$, —NHC(NH)NH-alkyl, —NHC(NH)NH-alkenyl, —NHC(NH)NH-alkenyl, —NHC(NH)NH-cycloalkyl, —NHC(NH)NH-aryl, —NHC(NH)NH-heteroaryl, —NHC(NH)NH-heterocycloalkyl, —NHC(NH)-alkyl, —NHC(NH)-alkenyl, —NHC(NH)-alkenyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)-alkynyl, —S(O)-cycloalkyl, —S(O)-aryl, —S(O)-heteroaryl, —S(O)-heterocycloalkyl —SO$_2$NH$_2$, —SO$_2$NH-alkyl, —SO$_2$NH-alkenyl, —SO$_2$NH-alkynyl, —SO$_2$NH-cycloalkyl, —SO$_2$NH-aryl, —SO$_2$NH-heteroaryl, —SO$_2$NH-heterocycloalkyl, —NHSO$_2$-alkyl, —NHSO$_2$-alkenyl, —NHSO$_2$-alkynyl, —NHSO$_2$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S-alkyl, —S-alkenyl, —S-alkynyl, —S-cycloalkyl, —S-aryl, —S-heteroaryl, —S-heterocycloalkyl, or methylthiomethyl.

It is understood that the aryls, heteroaryls, carbocycles, heterocycles, alkyls, and the like can be further substituted.

The terms "halo" and "halogen," as used herein, refer to an atom selected from fluorine, chlorine, bromine and iodine.

The term "subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

The term "hydroxy activating group", as used herein, refers to a labile chemical moiety which is known in the art to activate a hydroxy group so that it will depart during synthetic procedures such as in a substitution or elimination reactions. Examples of hydroxy activating group include, but not limited to, mesylate, tosylate, triflate, p-nitrobenzoate, phosphonate and the like.

The term "leaving group," or "LG", as used herein, refers to any group that leaves in the course of a chemical reaction involving the group and includes but is not limited to halogen, brosylate, mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, Protective Groups in Organic Synthesis, 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, Protective Groups in Organic Synthesis, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "alkylamino" refers to a group having the structure —N(R$_a$R$_b$), where R$_a$ and R$_b$ are independent H or alkyl.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups, and elixirs. In addition to the active compounds, the liquid dosage forms may contain inert diluents commonly used in the art such as, for example, water, alcohol or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, polysorbate, dimethylformamide, oils (in particular, cottonseed, groundnut, corn, germ, olive, castor, and sesame oils), mono- or diglycerides, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, antioxidants, sweetening, flavoring, and perfuming agents. The liquid dosage form can also be encapsulated in a gelatin capsule, wherein a compound of the present invention can be dissolved in a pharmaceutically acceptable carrier containing, for example, one or more solubilizating agents (e.g., polysorbate 80 and mono and diglycerides), and other suitable excipients (e.g., an antioxidants such as ascorbyl palmitate, or a sweetening or flavoring agent).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Immediate release forms are also contemplated by the present invention.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Preferably, a compound of the invention is formulated in a solid dispersion, where the compound can be molecularly dispersed in a matrix which comprises a pharmaceutically acceptable, hydrophilic polymer. The matrix may also contain a pharmaceutically acceptable surfactant. Suitable solid dispersion technology for formulating a compound of the invention includes, but is not limited to, melt extrusion, spray drying, or solvent evaporation.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, viral infections are treated or prevented in a subject, such as a human or another animal, by administering to the subject a therapeutically effective amount of a compound of the invention (or a pharmaceutically acceptable salt, ester or prodrug thereof), in such amounts and for such time as is necessary to achieve the desired result. The term "therapeutically effective amount" of a compound of the invention, as used herein, means a sufficient amount of the compound so as to decrease the viral load in a subject and/or decrease the subject's HCV symptoms. As is well understood in the medical arts a therapeutically effective amount of a compound of this invention will be at a reasonable benefit/risk ratio applicable to any medical treatment.

Antiviral Activity

An inhibitory amount or dose of the compounds of the present invention may range from about 0.1 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a subject such as a human or lower mammal by administering to the subject an anti-hepatitis C virally effective amount or an inhibitory amount of a compound of the present invention, in such amounts and for such time as is necessary to achieve the desired result. An additional method of the present invention is the treatment of biological samples with an inhibitory amount of a compound of composition of the present invention in such amounts and for such time as is necessary to achieve the desired result.

The term "anti-hepatitis C virally effective amount" of a compound of the invention, as used herein, means a sufficient amount of the compound so as to decrease the viral load in a biological sample or in a subject. As well understood in the medical arts, an anti-hepatitis C virally effective amount of a compound of this invention will be at a reasonable benefit/risk ratio applicable to any medical treatment.

The term "inhibitory amount" of a compound of the present invention means a sufficient amount to decrease the hepatitis C viral load in a biological sample or a subject. It is understood that when said inhibitory amount of a compound of the present invention is administered to a subject it will be at a reasonable benefit/risk ratio applicable to any medical treatment as determined by a physician. The term "biological sample(s)," as used herein, means a substance of biological origin, which may be intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof; or stem cells. Thus, another embodiment of the present invention is a method of treating a biological sample by contacting said biological sample with an inhibitory amount of a compound or pharmaceutical composition of the present invention.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In one embodiment, treatment regimens according to the present invention comprise administration to a patient in need of such treatment from about 10 mg to about 1000 mg of the compound(s) of this invention per day in single or multiple doses. In another embodiment, the treatment regimen comprises administration to a patient in need of such treatment from about 25 mg to about 6000 mg of a compound(s) of this invention per day in single or multiple doses, either with or without a cytochrome P450 monooxygenase inhibitor such as ritonavir. The suitable daily dose for the co-administered cytochrome P450 monooxygenase inhibitor (e.g., ritonavir) can range, without limitation, from 10 to 200 mg. Preferably, a compound(s) of the present invention, or a combination of a compound(s) of the invention and ritonavir, is administered once daily or twice daily to achieve the desired daily dose amount. For instance, when used without ritonavir, a compound of the present invention can be administered to a patient twice a day with a total daily dose of 4000, 4200, 4400, 4600, 4800 or 5000 mg. For another instance, when used in combination with ritonavir, a compound of the present invention can be administered to a patient once or twice a day with a total daily dose of 200, 400, 600 or 800 mg, where the amount of ritonavir can be 25, 50 or 100 mg per administration.

Synthetic Methods

The compounds and processes of the present invention will be better understood in connection with the following synthetic schemes that illustrate the methods by which the compounds of the invention may be prepared.

Definitions of variables in the structures in the schemes herein are commensurate with those of corresponding positions in the formulae delineated herein.

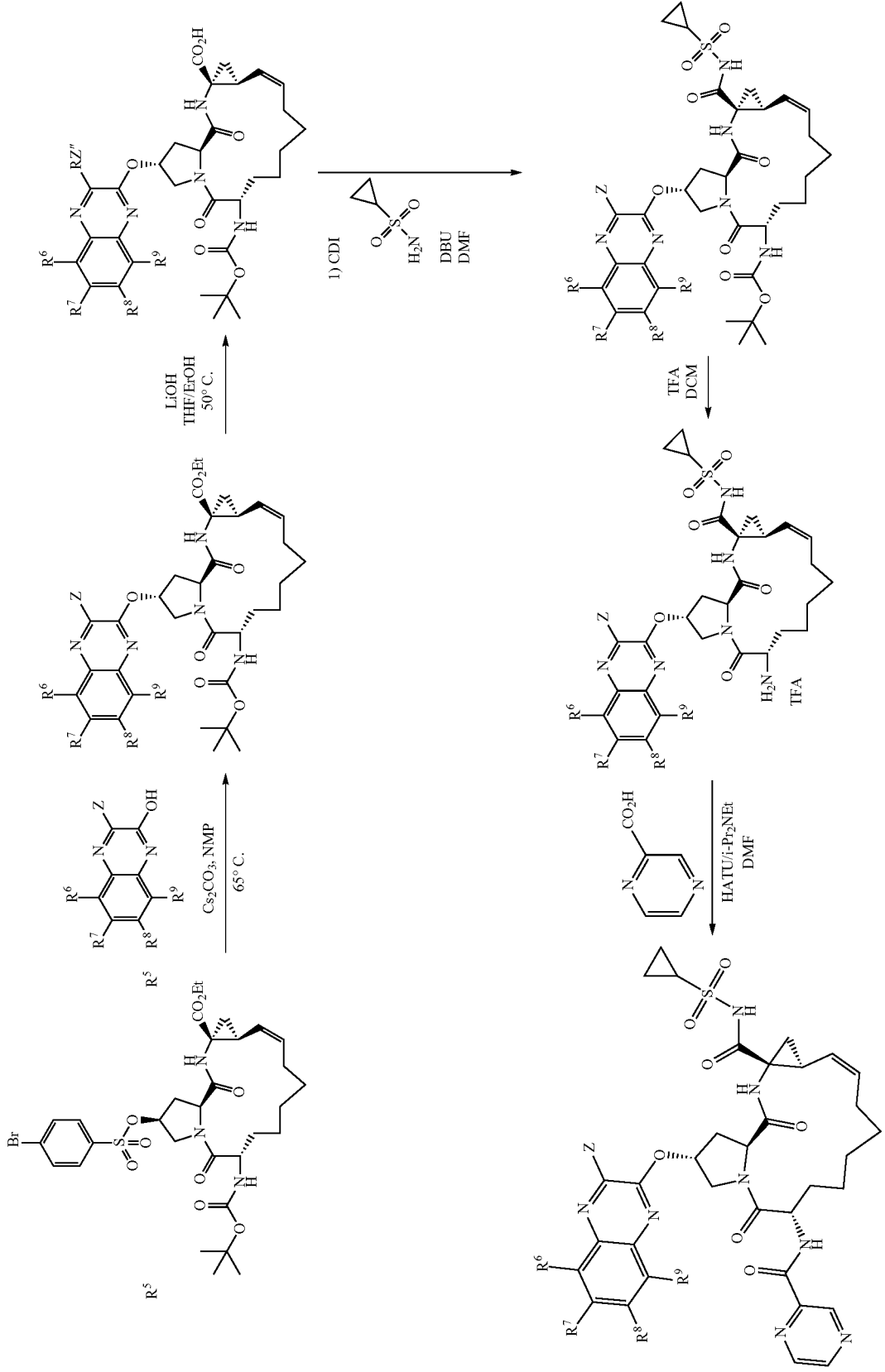

Scheme 1 describes the synthesis of various compounds of the invention. The starting material was displaced at the leaving groups by reaction with a nucleophile to provide a nucleophile substituted macrocycle. Base hydrolysis of the ester to the acid was followed by coupling of a sulfonamide derivative. The protected nitrogen was then deprotected and substituted with another group.

In one aspect, the invention provides a method of producing a compound of formula I, comprising the step of reacting a compound of formula II:

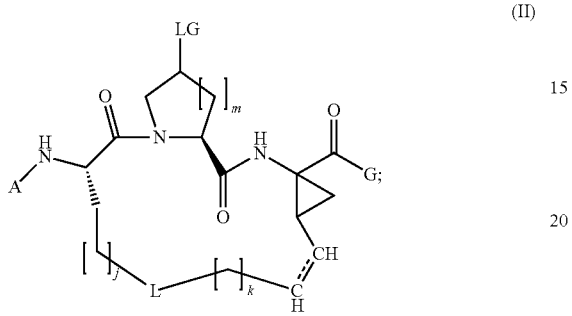

(II)

wherein,
the respective variables are as defined in formulae (I) and (I'); and
LG is a leaving group;
with a compound of formula III:

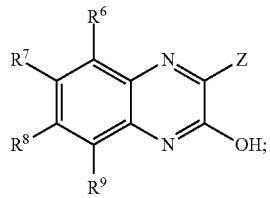

(III)

wherein,
the respective variables are as defined in formulae (I) and (I').

The compounds of the invention were also synthesized according to the synthetic steps provided in Scheme 2.

Scheme 2

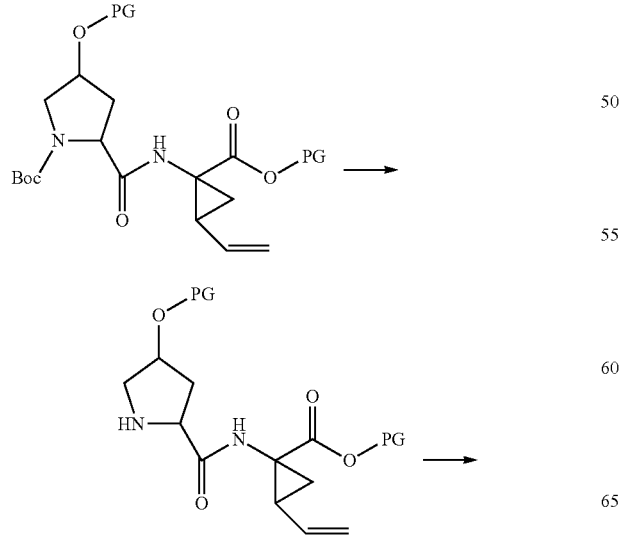

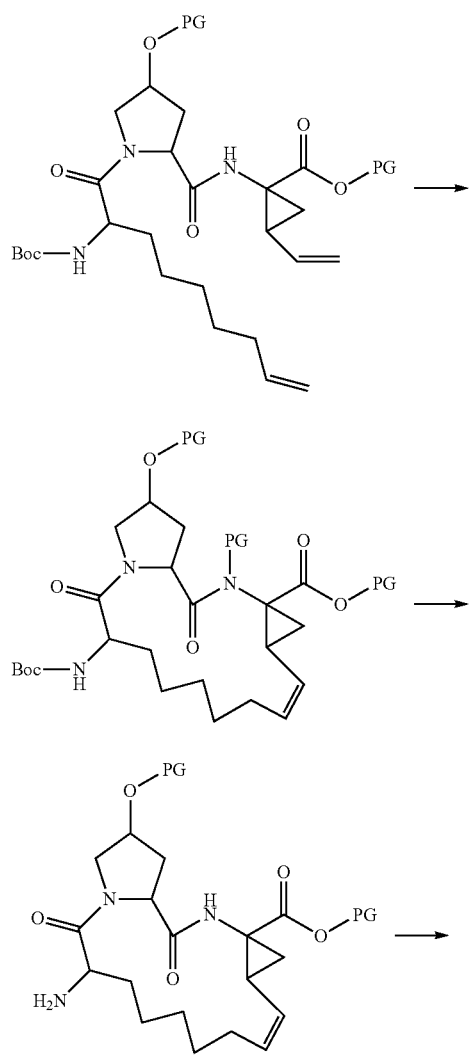

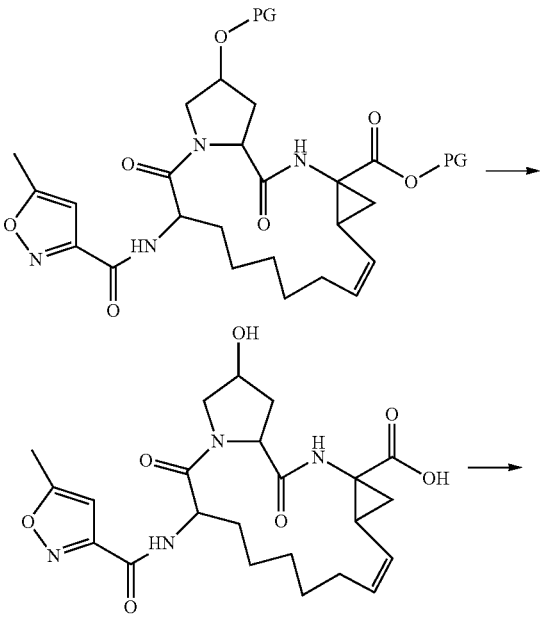

-continued

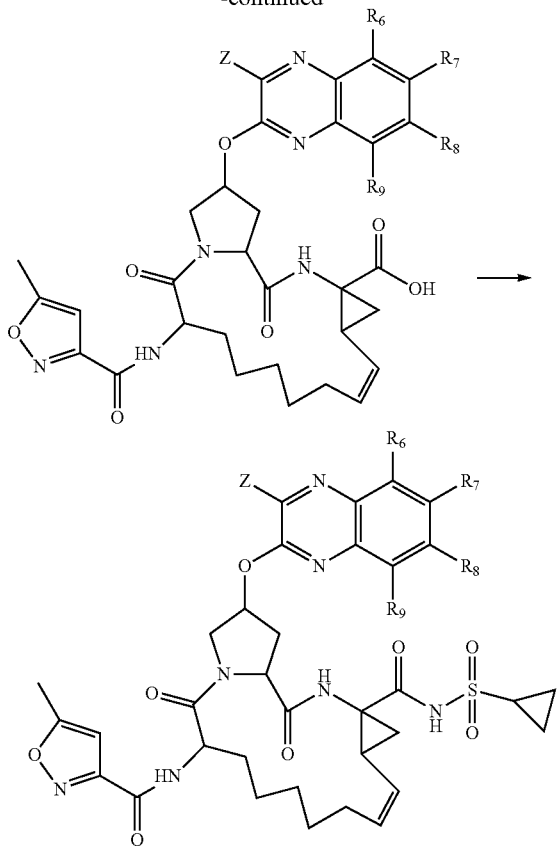

The starting material pyrrolidine ring was Boc-deprotected and was followed by carbon chain elongation. Ring closing metathesis provided a macrocyclic core. Various protecting groups (PG) were deprotected and the primary amine was further functionalized. Additional deprotection steps provided a macrocycle with a free acid and a free alcohol, which were further functionalized to arrive at the compounds of the invention.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

EXAMPLES

The compounds and processes of the present invention will be better understood in connection with the following examples, which are intended as an illustration only and not to limit the scope of the invention. The following examples can be prepared according to either Scheme 1 or Scheme 2 as described above, or according to the synthetic steps as described below. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

The chemical structures herein contain certain —NH—, —NH$_2$ (amino) and —OH (hydroxyl) groups where the corresponding hydrogen atom(s) may not explicitly appear; however they are to be read as —NH—, —NH$_2$ or —OH as the case may be.

Those of ordinary skill in the art are aware of the biological assays utililized to test the compounds of the invention. Regarding bioavailability data (F values), a more thorough explanation can be found in Rowland, M and

Example 1

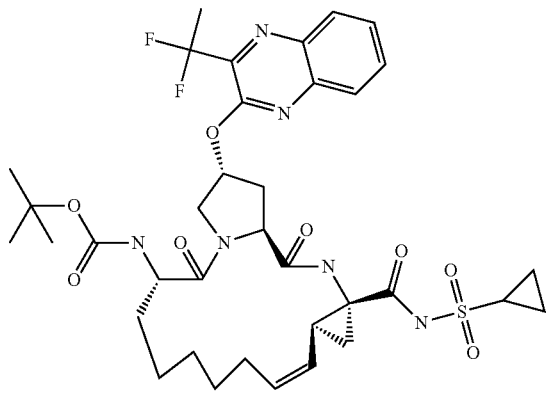 [SMILES: CC(C)(C)OC(=O)N[C@H]1CCCCC/C=C\[C@@H]2C[C@@]2(C(=O)NS(=O)(=O)C2CC2)NC(=O)[C@@H]2C[C@@H](Oc3nc4ccccc4nc3C(C)(F)F)CN2C1=O]

tert-butyl (2R,6S,13aS,14aR,16aS,Z)-14a-(cyclopropylsulfonylcarbamoyl)-2-(3-(1,1-difluoroethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

Example 1a

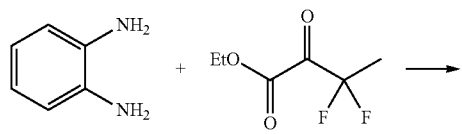

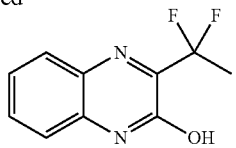

3-(1,1-difluoroethyl)quinoxalin-2-ol

A mixture of benzene-1,2-diamine (56.6 mg, 0.524 mmol) and ethyl 3,3-difluoro-2-oxobutanoate (87 mg, 0.524 mmol, prepared according to the procedure reported by Melchiorre F. Parisi, *J. Org. Chem.* 1995, 60(16), 5174-5179) in ethanol (1 mL) was heated at 76° C. for 16 h. The reaction mixture was concentrated under reduced pressure and the residue purified by flash chromatography on silica gel, eluting with a hexane/ethyl acetate gradient to provide the title compound 1a (66 mg, 60% yield) as a white solid.

Example 1b

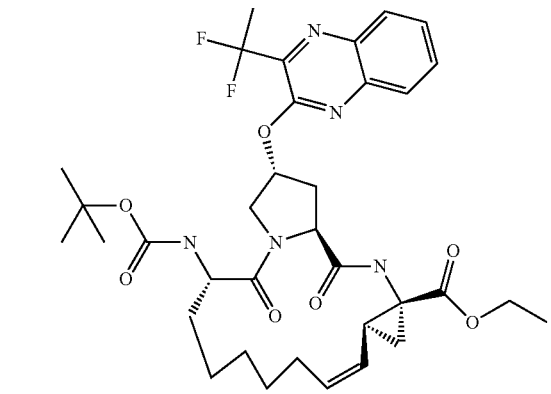 [SMILES: CCOC(=O)[C@@]12C[C@H]1/C=C\CCCCC[C@H](NC(=O)OC(C)(C)C)C(=O)N1C[C@H](Oc3nc4ccccc4nc3C(C)(F)F)C[C@H]1C(=O)N2]

(2R,6S,13aS,14aR,16aS,Z)-ethyl 6-(tert-butoxycarbonylamino)-2-(3-(1,1-difluoroethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate

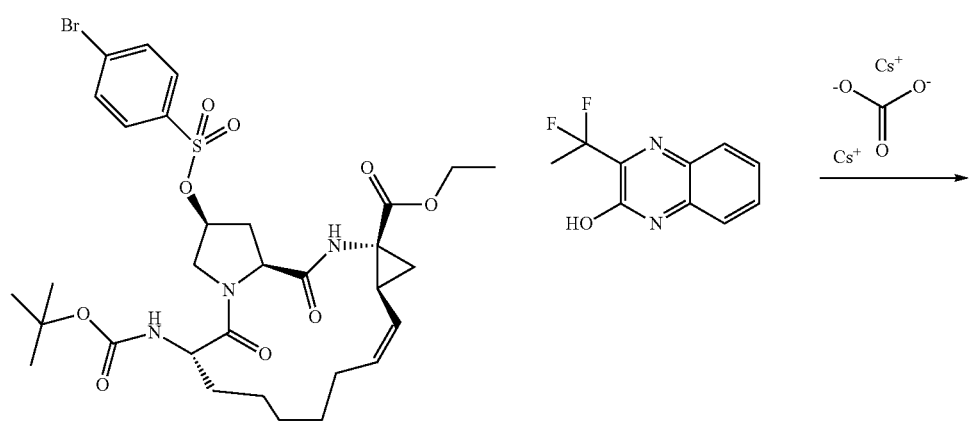

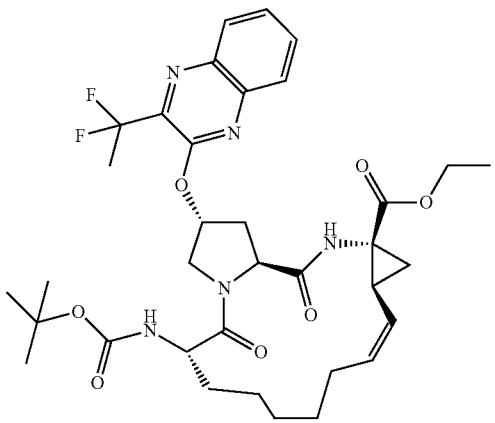

To a solution of (2S,6S,13aS,14aR,16aS,Z)-ethyl 2-(4-bromophenylsulfonyloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (0.806 g, 1.1 mmol) and 3-(1,1-difluoroethyl)quinoxalin-2-ol (0.261 g, 1.2 mmol) in DMF (3.2 ml) was added cesium carbonate (0.37 g, 1.1 mmol). The mixture was stirred at 60° C. for 16 h, diluted with dichloromethane, and filtered. The filtrate was concentrated and purified by chromatography (SNAP-HP100, 0-10% acetone/dichloromethane) to provide the title compound 1b (490.1 mg, 0.715 mmol, 63.2% yield) as a white solid.

Example 1c

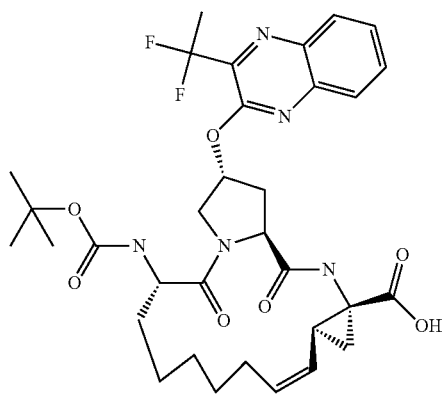 [SMILES: CC(C)(C)OC(=O)N[C@H]1CCCCC/C=C\[C@@H]2C[C@@]2(C(=O)O)NC(=O)[C@@H]2C[C@@H](Oc3nc4ccccc4nc3C(C)(F)F)CN2C1=O]

(2R,6S,13aS,14aR,16aS,Z)-6-(tert-butoxycarbonylamino)-2-(3-(1,1-difluoroethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid

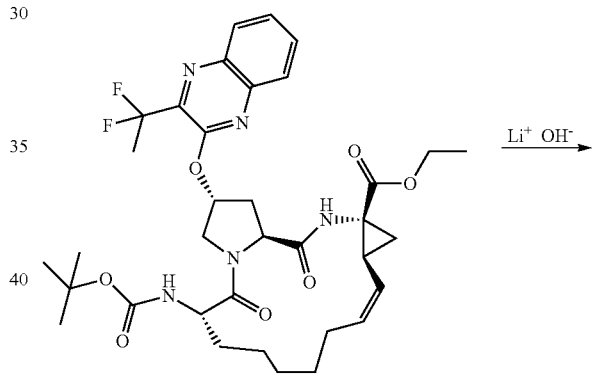

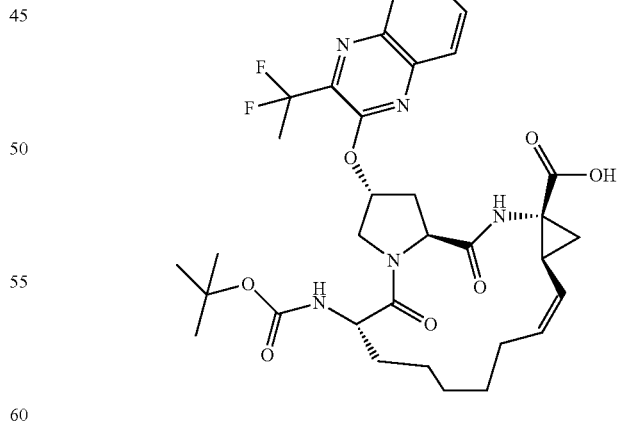

To a solution of (2R,6S,13aS,14aR,16aS,Z)-ethyl 6-(tert-butoxycarbonylamino)-2-(3-(1,1-difluoroethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (490 mg, 0.715 mmol) in THF (2.4 ml), Methanol (1.2 ml) and Water (1.2 ml) was added lithium hydroxide monohydrate (123 mg, 2.93 mmol). The mixture was stirred 16 h, diluted with water and neutralized slowly with HCl (1 N, 3 ml). A solid appeared, and the mixture was cooled to 0° C. and filtered and the solid rinsed with water. The solid was dissolved in methanol and concentrated, azeotroped with methanol and chloroform, and dried under high vacuum to give the title compound 1c as a white solid.

Example 1

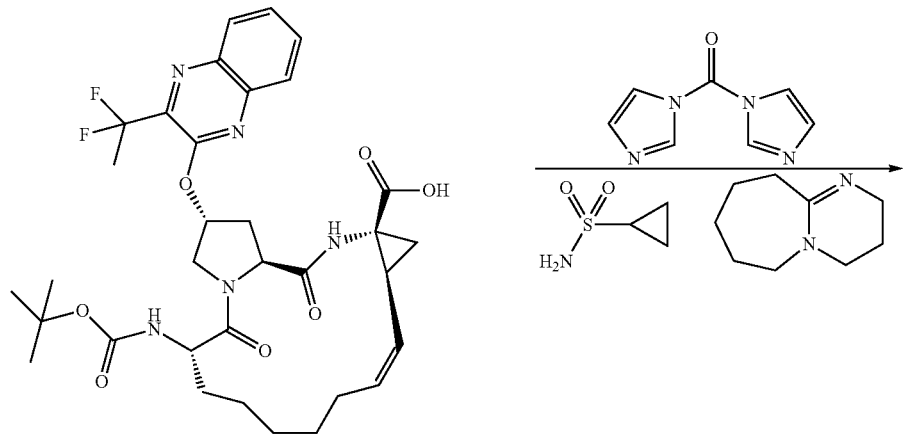

To (2R,6S,13aS,14aR,16aS,Z)-6-(tert-butoxycarbonylamino)-2-(3-(1,1-difluoroethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (83.2 mg, 0.127 mmol) was added molecular sieves and dichloroethane (1.3 ml) followed by carbonyldiimidazole (40.9 mg, 0.25 mmol). The mixture was stirred at 40° C. for 2 h, cooled to rt, and cyclopropanesulfonamide (39.43 mg, 0.32 mmol) was added followed by DBU (45 µl, 0.3 mmol). The mixture was stirred at rt for 16 h, cooled to 0° C., quenched with HCl (4 N, 0.2 ml) and filtered. The filtrate was concentrated and purified by reverse phase HPLC (C18, $CH_3CN/H_2O$ (0.1% TFA)=50/50-85/15, 15 min) to give the title compound 1 (67.97 mg, 0.089 mmol, 70.6% yield). MS (ESI): m/z=761.3 [M+H].

Example 1 provided an $EC_{50}$ of between 3-20 nM in transient replicon assay with a D168E mutation in a 1a-H77 background, an $EC_{50}$ of between 50-250 nM in a transient replicon assay with a D168V mutation in a 1a-H77 background, and an $EC_{50}$ of <1 nM in a transient replicon assay with a R155K mutation in 1a-H77 background.

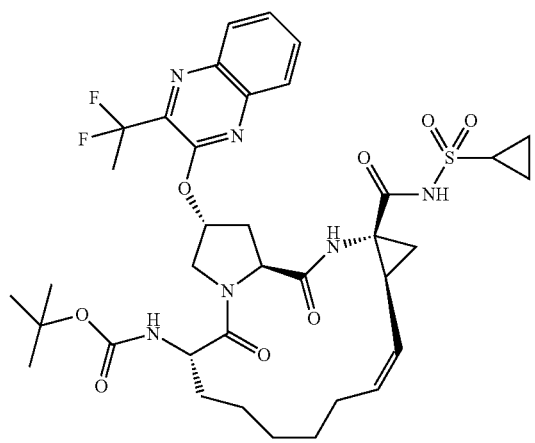

Example 2

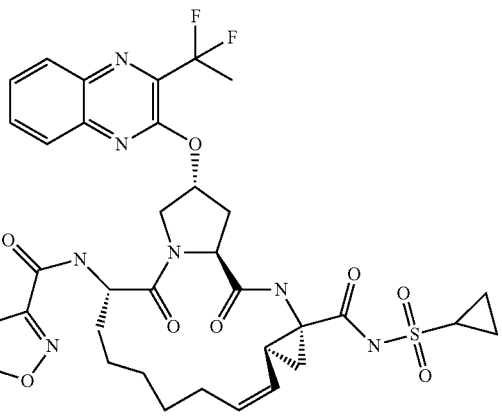

55

N-((2R,6S,13aS,14aR,16aS,Z)-14a-(cyclopropylsulfonylcarbamoyl)-2-(3-(1,1-difluoroethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide Example 2a

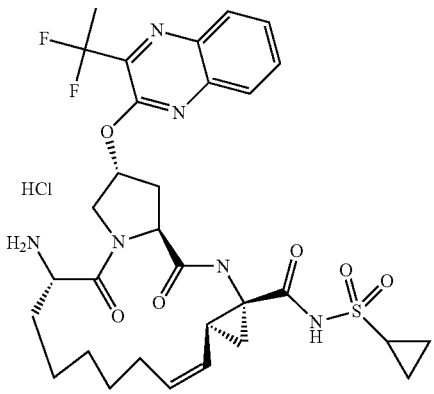 [SMILES: Cl ; CC(F)(F)c1nc2ccccc2nc1O[C@@H]1C[C@H]2C(=O)N[C@]3(C(=O)NS(=O)(=O)C4CC4)C[C@H]3/C=C\CCCCC[C@H](N)C(=O)N2C1]

56

(2R,6S,13aS,14aR,16aS,Z)-6-amino-N-(cyclopropylsulfonyl)-2-(3-(1,1-difluoroethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride To a solution of tert-butyl (2R,6S,13aS,14aR,16aS,Z)-14a-(cyclopropylsulfonylcarbamoyl)-2-(3-(1,1-difluoroethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (163.17 mg, 0.214 mmol) in dioxane (1.1 ml) was added HCl (4 N in dioxane, 1.1 ml, 36.2 mmol). The solution was stirred at rt 16 h, and a white solid appeared. LC/MS showed small amount of SM. More HCl (4 N in dioxane, 1 ml) was added. The mixture was stirred an additional and then concentrated to give the title compound 2a as a white solid.

Example 2

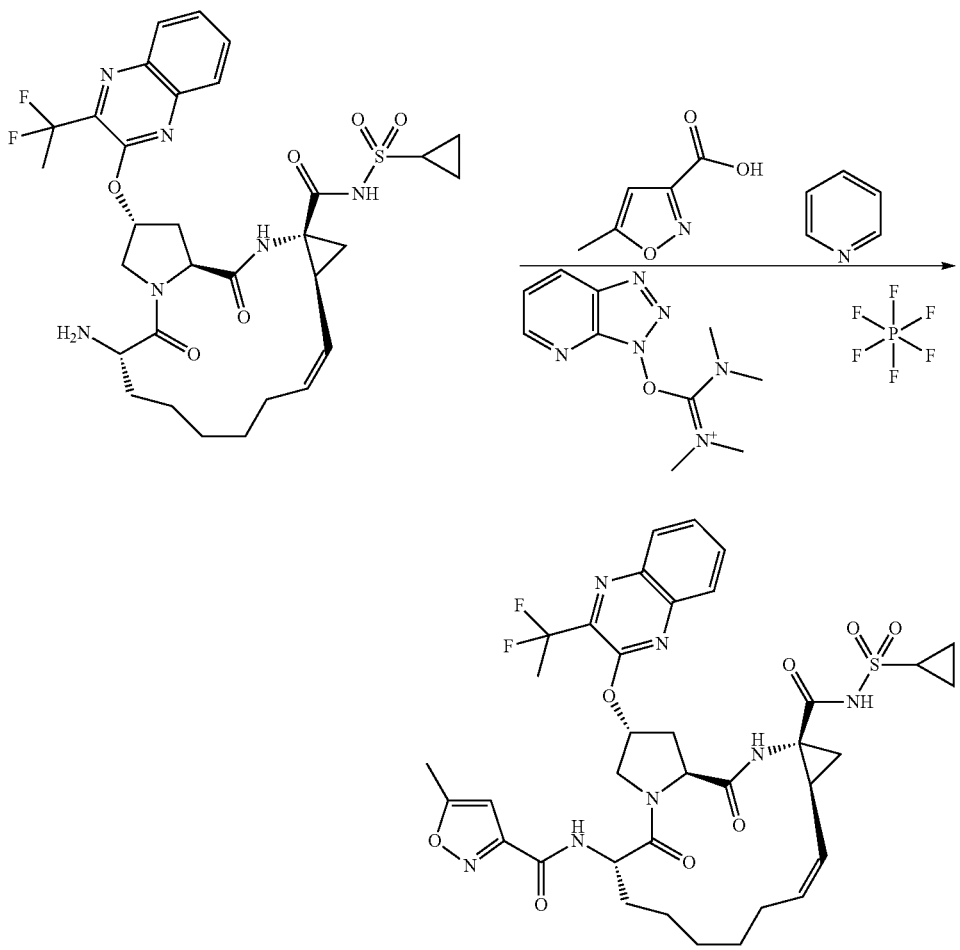

To (2R,6S,13aS,14aR,16aS,Z)-6-amino-N-(cyclopropylsulfonyl)-2-(3-(1,1-difluoroethyl) quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide, hydrochloric acid (422 mg, 0.605 mmol) was added 5-methylisoxazole-3-carboxylic acid (92 mg, 0.726 mmol) and DMF (6 ml) followed by pyridine (0.490 ml, 6.05 mmol). The reaction mixture was cooled to 0° C., and HATU (345 mg, 0.908 mmol) was added. The solution was stirred at rt 16 h, concentrated under reduced pressure, and the resulting oil was dissolved in dichloromethane (100 ml) and washed with HCl (1 N, 3×20 ml) and water (20 ml). The organic layer was dried (Na$_2$SO$_4$) and concentrated. The residue was purified by chromatography (SNAP100, acetone/dichloromethane=0-20%) to provide the title compound 2 (282.77 mg, 99.7% pure by HPLC). MS (ESI): m/z=770.3 [M+H].

Example 2 provided an EC$_{50}$ of <3 nM in a transient replicon assay with a D168E mutation in a 1a-H77 background, an EC$_{50}$ of between 25-50 nM in a transient replicon assay with a D168V mutation in a 1a-H77 background, and an EC$_{50}$ of <1 nM in a transient replicon assay with a R155K mutation in a 1a-H77 background. Example 2 also provided an AUC value of 4.5 μg*hr/mL when dose at 3 mg/kg, and F value of >100 in a dog PK experiment.

Example 3

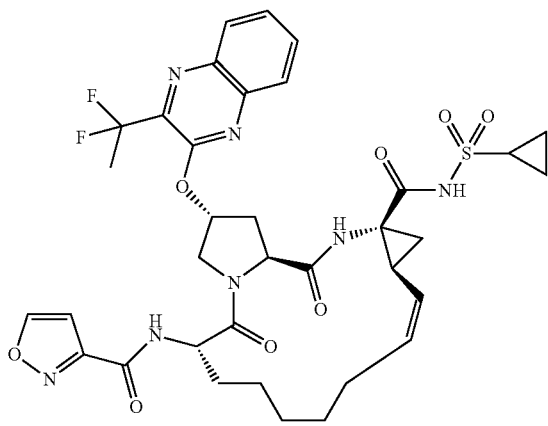 [SMILES: CC(F)(F)c1nc2ccccc2nc1O[C@@H]1C[C@H]2C(=O)N[C@]3(C(=O)NS(=O)(=O)C4CC4)C[C@H]3/C=C\CCCCC[C@H](NC(=O)c3ccon3)C(=O)N2C1]

N-((2R,6S,13aS,14aR,16aS,Z)-14a-(cyclopropylsulfonylcarbamoyl)-2-(3-(1,1-difluoroethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 3 was prepared according to the procedure used for Example 2, replacing 5-methylisoxazole-3-carboxylic acid with isoxazole-3-carboxylic acid. MS (ESI): m/z=756.7 [M+H].

Example 3 provided an EC$_{50}$ of <3 nM in a transient replicon assay with a D168E mutation in a 1a-H77 background, an EC$_{50}$ of between 50-250 nM in a transient replicon assay with a D168V mutation in a 1a-H77 background, and an EC$_{50}$ of <1 nM in a transient replicon assay with a R155K mutation in a 1a-H77 background.

Example 4

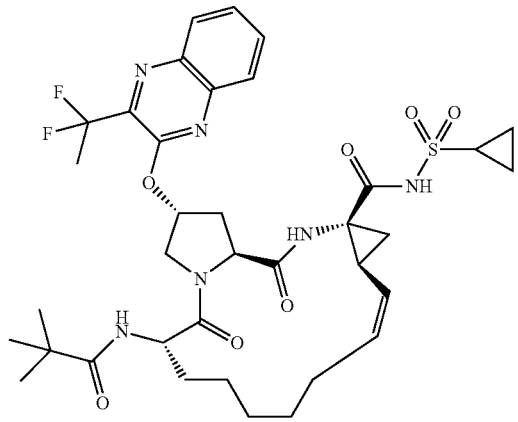 [SMILES: CC(C)(C)C(=O)N[C@H]1CCCCC/C=C\[C@@H]2C[C@@]2(C(=O)NS(=O)(=O)C2CC2)NC(=O)[C@@H]2C[C@@H](Oc3nc4ccccc4nc3C(C)(F)F)CN2C1=O]

(2R,6S,13aS,14aR,16aS,Z)—N-(cyclopropylsulfonyl)-2-(3-(1,1-difluoroethyl)quinoxalin-2-yloxy)-5,16-dioxo-6-pivalamido-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 4 was prepared according to the procedure used for Example 2, replacing 5-methylisoxazole-3-carboxylic acid with pivalic acid. MS (ESI): m/z=745.7 [M+H].

Example 4 provided an EC$_{50}$ of between 3-20 nM in a transient replicon assay with a D168E mutation in a 1a-H77 background, an EC$_{50}$ of between 50-250 nM in a transient replicon assay with a D168V mutation in a 1a-H77 background, and an EC$_{50}$ of between 1-10 nM in a transient replicon assay with a R155K mutation in a 1a-H77 background.

Example 5

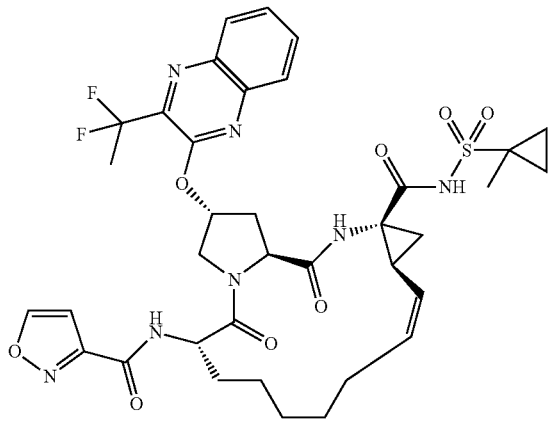 [SMILES: CC(F)(F)c1nc2ccccc2nc1O[C@@H]1C[C@H]2C(=O)N[C@]3(C(=O)NS(=O)(=O)C4(C)CC4)C[C@H]3/C=C\CCCCC[C@H](NC(=O)c3ccon3)C(=O)N2C1]

N-((2R,6S,13aS,14aR,16aS,Z)-2-(3-(1,1-difluoro-ethyl)quinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide Example 5a

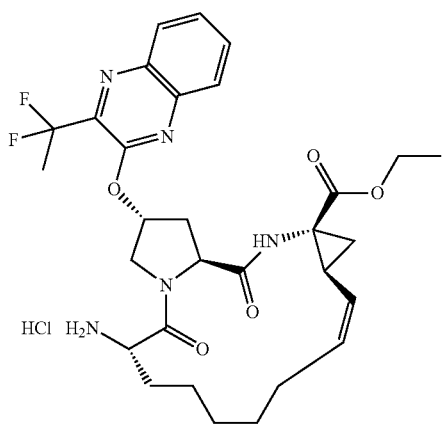 [SMILES: CCOC(=O)[C@@]12C[C@H]1/C=C\CCCCC[C@H](N)C(=O)N1C[C@H](Oc3nc4ccccc4nc3C(C)(F)F)C[C@H]1C(=O)N2 ; Cl]

(2R,6S,13aS,14aR,16aS,Z)-ethyl 6-amino-2-(3-(1,1-difluoroethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate, Hydrochloric Acid

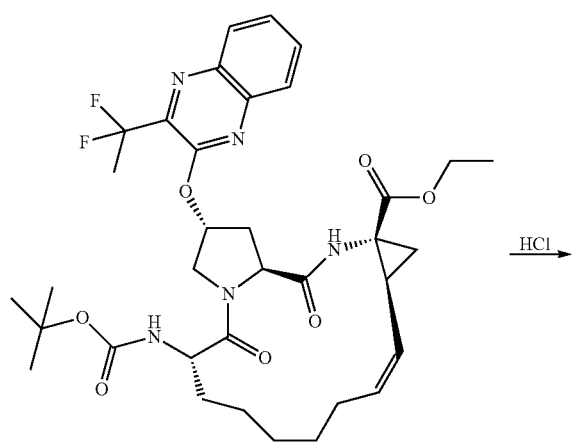

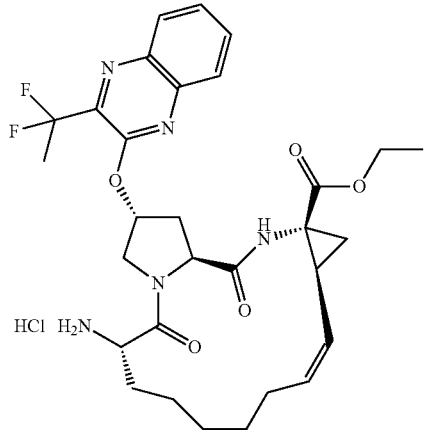

The title compound 5a was prepared according to the procedure used for Example 2a, replacing the product of Example 1 with the product of Example 1b.

Example 5b

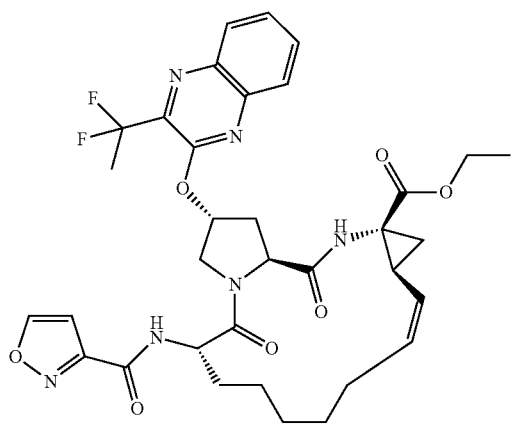 [SMILES: CCOC(=O)[C@@]12C[C@H]1/C=C\CCCCC[C@H](NC(=O)c1ccon1)C(=O)N1C[C@H](Oc3nc4ccccc4nc3C(C)(F)F)C[C@H]1C(=O)N2]

(2R,6S,13aS,14aR,16aS,Z)-ethyl 2-(3-(1,1-difluoro-
ethyl)quinoxalin-2-yloxy)-6-(isoxazole-3-carbox-
amido)-5,16-dioxo-1,2,3,5,6,7,8,9,10,11,13a,14,14a,
15,16,16a-hexadecahydrocyclopropa[e]pyrrolo[1,2-
a][1,4]diazacyclopentadecine-14a-carboxylate

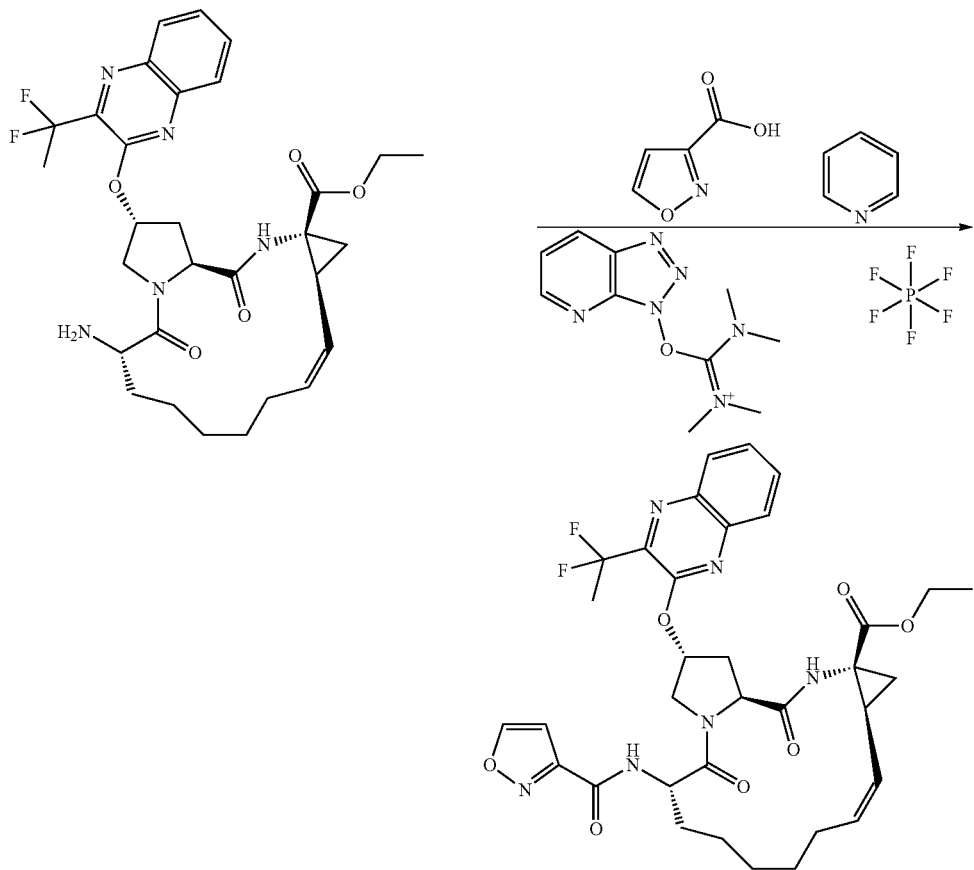

Example 5c

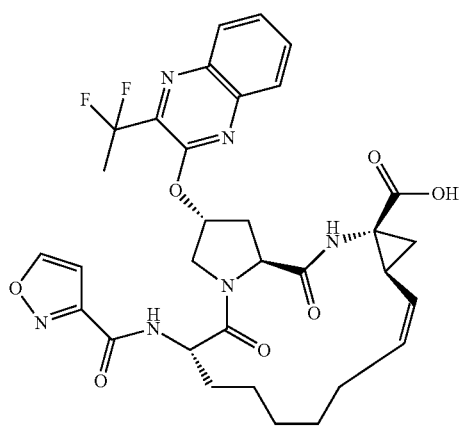 [SMILES: CC(F)(F)c1nc2ccccc2nc1O[C@@H]1C[C@H]2C(=O)N[C@]3(C(=O)O)C[C@H]3/C=C\CCCCC[C@H](NC(=O)c3ccon3)C(=O)N2C1]

To (2R,6S,13aS,14aR,16aS,Z)-ethyl 6-amino-2-(3-(1,1-difluoroethyl)quinoxalin-2-yloxy)-5,16-dioxo-1,2,3,5,6,7,8,9,10,11,13a,14,14a,15,16,16a-hexaecahydrocyclopropa[e]pyrrolo[1,2-a][1,4]diazacyclopentadecine-14a-carboxylate, hydrochloric acid (585.7 mg, 0.941 mmol) was added isoxazole-3-carboxylic acid (128 g, 1.132 ol) and DMF (9.4 m). The reaction mixture was cooled to 0° C., and pyridine (0.761 m, 9.41 mmol) then HATU (537.5 g, 1.414 mmol) were added. The solution was stirred at rt 16 h, and LC/MS showed a small amount of SM remained. More isoxazole-3-carboxylic acid (52.3 mg) pyridine (0.2 ml) and HATU (179 mg) were added. The reaction mixture was stirred for an additional 16 h and LC/MS showed completion. The reaction mixture was concentrated under reduced pressure, and the oil was dissolved in dichloromethane (100 ml) and washed with HCl (1 N, 2×15 ml) and $Na_2CO_3$ (1 N, 4×20 ml). The combined $Na_2CO_3$ layer was back-extracted with dichloromethane (2×10 ml). The organic layers were combined, dried ($MgSO_4$) and concentrated, and purified by chromatography (SNAP50, acetonitrile/$CHCl_3$=0-17%) to provide the title compound 5b (577 mg, 0.847 mmol, 90% yield).

(2R,6S,13aS,14aR,16aS,Z)-2-(3-(1,1-difluoroethyl)
quinoxalin-2-yloxy)-6-(isoxazole-3-carboxamido)-5,
16-dioxo-1,2,3,5,6,7,8,9,10,11,13a,14,14a,15,16,16a-
hexadecahydrocyclopropa[e]pyrrolo[1,2-a][1,4]
diazacyclopentadecine-14a-carboxylic acid
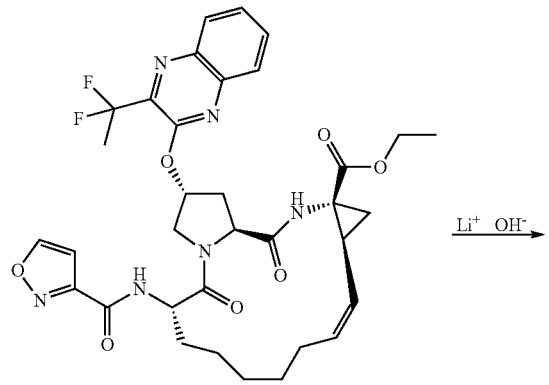
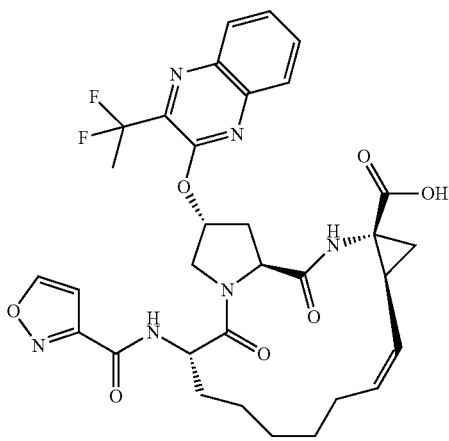
The title compound 5c was prepared according to the procedure used for Example 1c, replacing the product of Example 1b with the product of Example 5b.
Example 5
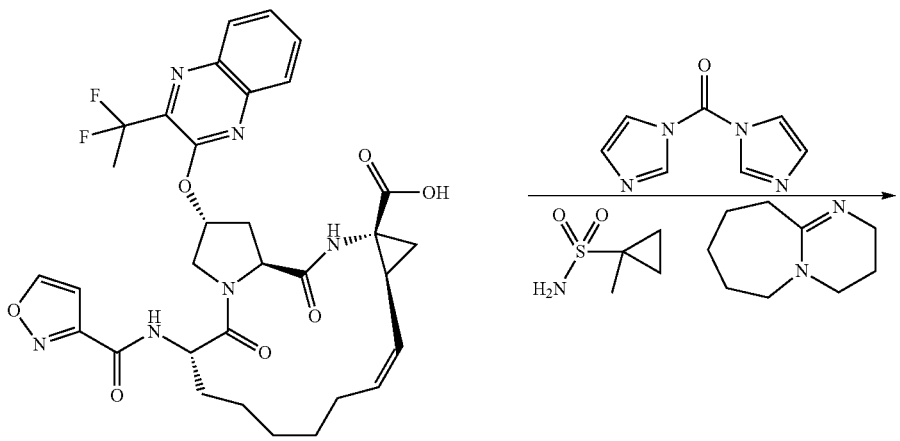
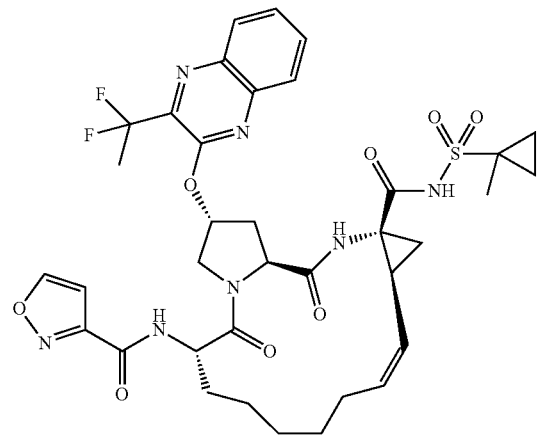

The title compound 5 was prepared according to the procedure used for Example 1, replacing the product of Example 1c with the product of Example 5c and replacing cyclopropanesulfonamide with methylcyclopropanesulfonamide.

MS (ESI): m/z=770.8 [M+H].

Example 5 provided an $EC_{50}$ of <3 nM in a transient replicon assay with a D168E mutation in a 1a-H77 background, an $EC_{50}$ of <25 nM in a transient replicon assay with a D168V mutation in a 1a-H77 background, and an $EC_{50}$ of <1 nM in a transient replicon assay with a R155K mutation in a 1a-H77 background.

Example 6

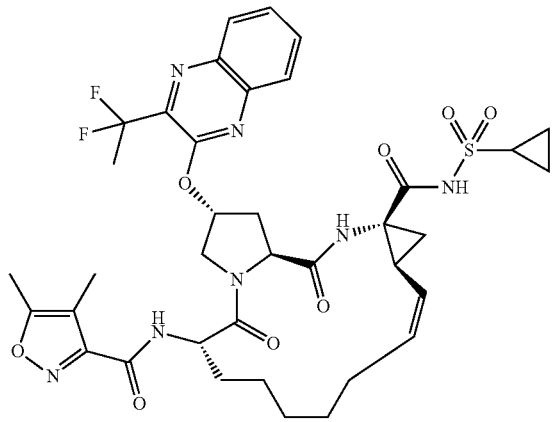 [SMILES: Cc1onc(C(=O)N[C@H]2CCCCC/C=C\[C@@H]3C[C@@]3(C(=O)NS(=O)(=O)C3CC3)NC(=O)[C@@H]3C[C@@H](Oc4nc5ccccc5nc4C(C)(F)F)CN3C2=O)c1C]

N-((2R,6S,13aS,14aR,16aS,Z)-14a-(cyclopropylsulfonylcarbamoyl)-2-(3-(1,1-difluoroethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole-3-carboxamide The title compound 6 was prepared according to the procedures used for Example 5, replacing isoxazole-3-carboxylic acid with 4,5-dimethylisoxazole-3-carboxylic acid and replacing methylcyclopropanesulfonamide with cyclopropanesulfonamide. MS (ESI): m/z=784.6 [M+H].

Example 6 provided an $EC_{50}$ of <3 nM in a transient replicon assay with a D168E mutation in a 1a-H77 background, an $EC_{50}$ of between 50-250 nM in a transient replicon assay with a D168V mutation in a 1a-H77 background, and an $EC_{50}$ of between 1-10 nM in a transient replicon assay with a R155K mutation in a 1a-H77 background.

Example 7

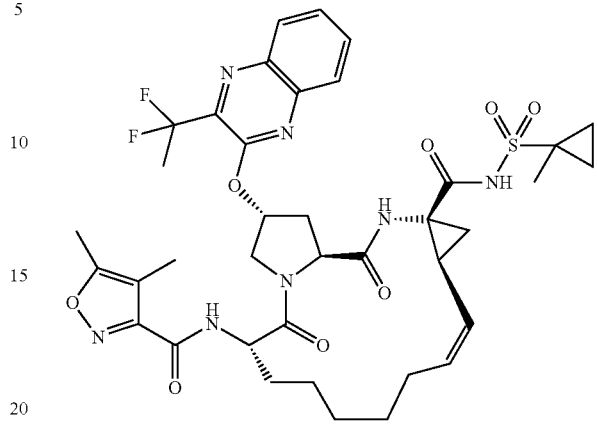

N-((2R,6S,13aS,14aR,16aS,Z)-2-(3-(1,1-difluoroethyl)quinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole-3-carboxamide The title compound 7 was prepared according to the procedures used for Example 5, replacing isoxazole-3-carboxylic acid with 4,5-dimethylisoxazole-3-carboxylic acid. MS (ESI): m/z=798.6 [M+H].

Example 7 provided an $EC_{50}$ of <3 nM in a transient replicon assay with a D168E mutation in a 1a-H77 background, an $EC_{50}$ of between 25-50 nM in a transient replicon assay with a D168V mutation in a 1a-H77 background, and an $EC_{50}$ of between 1-10 nM in a transient replicon assay with a R155K mutation in a 1a-H77 background.

Example 8

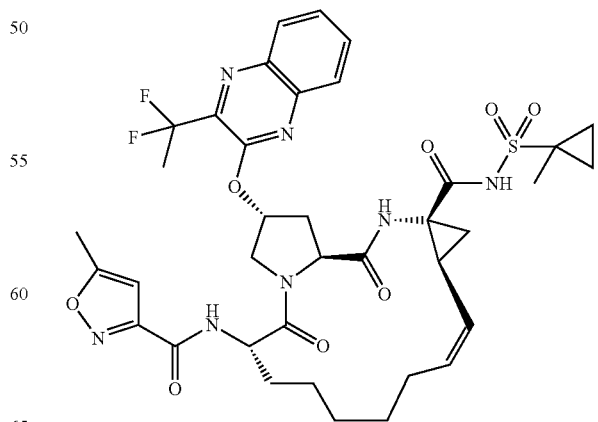

N-((2R,6S,13aS,14aR,16aS,Z)-2-(3-(1,1-difluoro-
ethyl)quinoxalin-2-yloxy)-14a-(1-methylcyclopro-
pylsulfonylcarbamoyl)-5,16-dioxo-1,2,3,5,6,7,8,9,
10,11,13a,14,14a,15,16,16a-
hexadecahydrocyclopropa[e]pyrrolo[1,2-a][1,4]
diazacyclopentadecin-6-yl)-5-methylisoxazole-3-
carboxamide The title compound 8 was prepared according to the procedures used for Example 5, replacing isoxazole-3-carboxylic acid with 5-dimethylisoxazole-3-carboxylic acid.
MS (ESI): m/z=784.2 [M+H].

Example 9

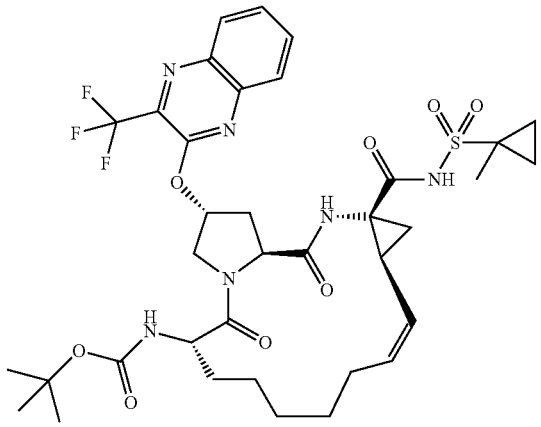

tert-butyl (2R,6S,13aS,14aR,16aS,Z)-14a-(cyclopro-
pylsulfonylcarbamoyl)-5,16-dioxo-2-(3-(trifluorom-
ethyl)quinoxalin-2-yloxy)-1,2,3,5,6,7,8,9,10,11,13a,
14,14a,15,16,16a-hexadecahydrocyclopropa[e]
pyrrolo[1,2-a][1,4]diazacyclopentadecin-6-
ylcarbamate Example 9a

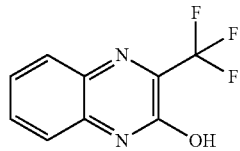 [SMILES: Oc1nc2ccccc2nc1C(F)(F)F]

3-(trifluoromethyl)quinoxalin-2-ol

In a procedure modified from the one reported by M. Patel, et. al., *Bioorg. Med. Chem. Lett.* 2000, 10, 1729-1731, hexafluoropropylene oxide (7.68 g, 46.2 mmol) was bubbled into a solution of sodium bicarbonate (38.8 g, 462 mmol) and benzene-1,2-diamine (5.0 g, 46.2 mmol) in diethyl ether at −78° C. After the addition, the reaction mixture was stirred and allowed to warm to rt over 16 h. The ether solution was cooled in an ice bath and then filtered to remove the product and sodium bicarbonate. The solids were washed with a small amount of diethyl ether and then taken up in water and stirred for several hours. The product was filtered from the aqueous layer and dried under high vacuum to give the title compound 9a (9.0 g, 91% yield) as a white solid.

Example 9b

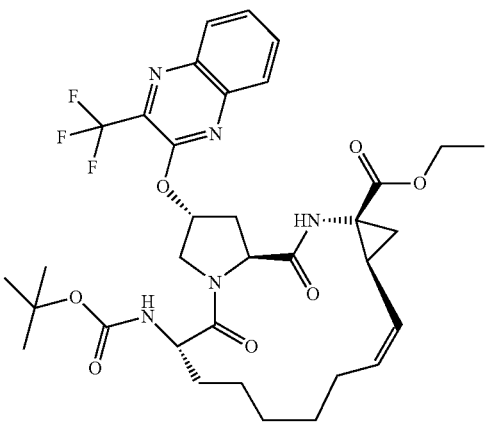

(2R,6S,13aS,14aR,16aS,Z)-ethyl 6-(tert-butoxycar-
bonylamino)-5,16-dioxo-2-(3-(trifluoromethyl)qui-
noxalin-2-yloxy)-1,2,3,5,6,7,8,9,10,11,13a,14,14a,
15,16,16a-hexadecahydrocyclopropa[e]pyrrolo[1,2-
a][1,4]diazacyclopentadecine-14a-carboxylate The title compound 9b was prepared according to the procedure used for Example 1b, replacing 3-(1,1-difluoro-ethyl)quinoxalin-2-ol with the product of Example 9a.

Example 9c

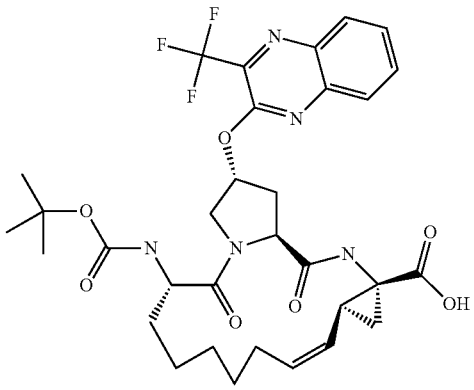 [SMILES: CC(C)(C)OC(=O)N[C@H]1CCCCC/C=C\[C@@H]2C[C@@]2(C(=O)O)NC(=O)[C@@H]2C[C@@H](Oc3nc4ccccc4nc3C(F)(F)F)CN2C1=O]

(2R,6S,13aS,14aR,16aS,Z)-6-(tert-butoxycarbo-
nylamino)-5,16-dioxo-2-(3-(trifluoromethyl)qui-
noxalin-2-yloxy)-1,2,3,5,6,7,8,9,10,11,13a,14,14a,
15,16,16a-hexadecahydrocyclopropa[e]pyrrolo[1,2-
a][1,4]diazacyclopentadecine-14a-carboxylic acid The title compound 9c was prepared according to the procedure used for Example 1c, replacing the product of Example 1b with the product of Example 9b.

Example 9

The title compound 9 was prepared according to the procedure used for Example 1, replacing the product of Example 1c with the product of Example 9b. MS (ESI): m/z=650.0 [M+H].

Example 10

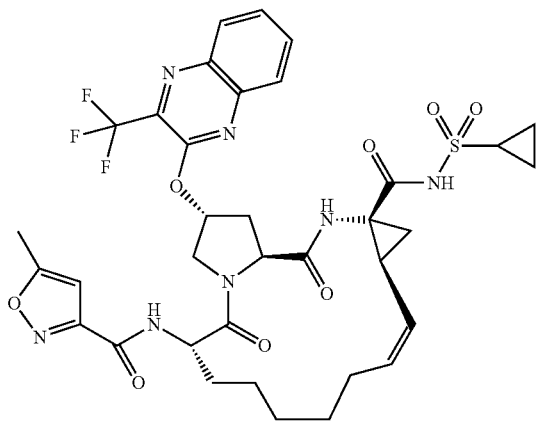

N-((2R,6S,13aS,14aR,16aS,Z)-14a-(cyclopropylsulfonylcarbamoyl)-5,16-dioxo-2-(3-(trifluoromethyl)quinoxalin-2-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide The title compound 10 was prepared according to the procedures used for Example 2, replacing the product of Example 1 with the product of Example 9, and replacing pyridine with diisopropylethylamine. MS (ESI): m/z=774.2 [M+H].

Example 10 provided an $EC_{50}$ of <3 nM in a transient replicon assay with a D168E mutation in a 1a-H77 background, an $EC_{50}$ of between 25-50 nM in a transient replicon assay with a D168V mutation in a 1a-H77 background, and an $EC_{50}$ of <1 nM in a transient replicon assay with a R155K mutation in a 1a-H77 background. Example 10 also provided an AUC value of 27 μg*hr/mL when dosed at 3 mg/kg, and F value of >100 in a dog PK experiment.

Example 11

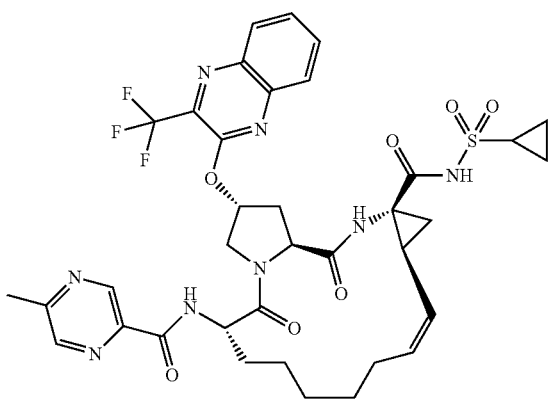 [SMILES: Cc1cnc(C(=O)N[C@H]2CCCCC/C=C\[C@@H]3C[C@@]3(C(=O)NS(=O)(=O)C3CC3)NC(=O)[C@@H]3C[C@@H](Oc4nc5ccccc5nc4C(F)(F)F)CN3C2=O)cn1]

(2R,6S,13aS,14aR,16aS,Z)—N-(cyclopropylsulfonyl)-2-(3-(trifluoromethyl)quinoxalin-2-yloxy)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 11 was prepared according to the procedure used for Example 2, replacing the product of Example 1 with the product of Example 9, replacing 5-methylisoxazole-3-carboxylic acid with 5-methylpyrazine-2-carboxylic acid and replacing pyridine with diisopropylethylamine. MS (ESI): m/z=785.2 [M+H].

Example 11 provided an $EC_{50}$ of >100 nM in a transient replicon assay with a D168E mutation in a 1a-H77 background, an $EC_{50}$ of between 50-250 nM in a transient replicon assay with a D168V mutation in a 1a-H77 background, and an $EC_{50}$ of between 10-25 nM in a transient replicon assay with a R155K mutation in a 1a-H77 background.

Example 12

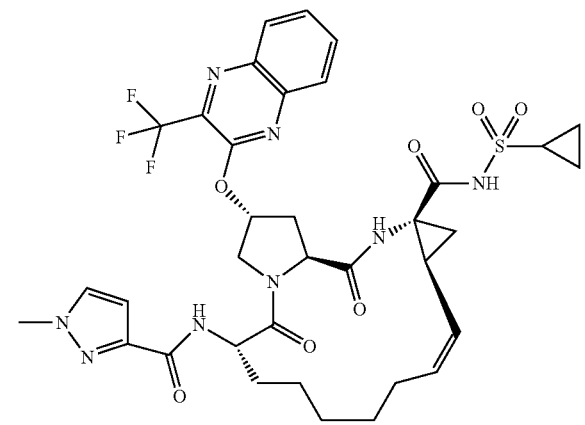 [SMILES: Cn1ccc(C(=O)N[C@H]2CCCCC/C=C\[C@@H]3C[C@@]3(C(=O)NS(=O)(=O)C3CC3)NC(=O)[C@@H]3C[C@@H](Oc4nc5ccccc5nc4C(F)(F)F)CN3C2=O)n1]

(2R,6S,13aS,14aR,16aS,Z)—N-(cyclopropylsulfonyl)-2-(7-fluoro-3-(trifluoromethyl)quinoxalin-2-yloxy)-6-(1-methyl-1H-pyrazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 12 was prepared according to the procedure used for Example 2, replacing the product of Example 1 with the product of Example 9, replacing 5-methylisoxazole-3-carboxylic acid with 1-methyl-1H-pyrazole-3-carboxylic acid and replacing pyridine with diisopropylethylamine. MS (ESI): m/z=773.3 [M+H].

Example 12 provided an $EC_{50}$ of between 50-100 nM in a transient replicon assay with a D168E mutation in a 1a-H77 background, an $EC_{50}$ of between 250-1000 nM in a transient replicon assay with a D168V mutation in a 1a-H77 background, and an $EC_{50}$ of between 10-25 nM in transient replicon assay with a R155K mutation in a 1a-H77 background.

Example 13

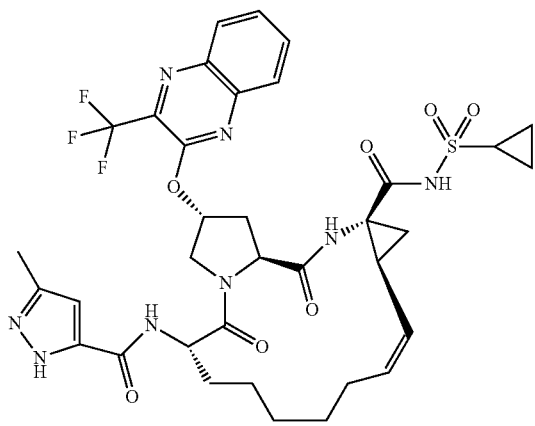 [SMILES: Cc1cc(C(=O)N[C@H]2CCCCC/C=C\[C@@H]3C[C@@]3(C(=O)NS(=O)(=O)C3CC3)NC(=O)[C@@H]3C[C@@H](Oc4nc5ccccc5nc4C(F)(F)F)CN3C2=O)[nH]n1]

(2R,6S,13aS,14aR,16aS,Z)—N-(cyclopropylsulfonyl)-2-(7-fluoro-3-(trifluoromethyl)quinoxalin-2-yloxy)-6-(3-methyl-1H-pyrazole-5-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 13 was prepared according to the procedures used for Example 2, replacing the product of Example 1 with the product of Example 9, replacing 5-methylisoxazole-3-carboxylic acid with 3-methyl-1H-pyrazole-5-carboxylic acid and replacing pyridine with diisopropylethylamine. MS (ESI): m/z=773.3 [M+H].

Example 13 provided an $EC_{50}$ of >100 nM in a transient replicon assay with a D168E mutation in a 1a-H77 background, an $EC_{50}$ of between 250-1000 nM in a transient replicon assay with a D168V mutation in a 1a-H77 background, and an $EC_{50}$ of between 10-25 nM in a transient replicon assay with a R155K mutation in a 1a-H77 background.

Example 14

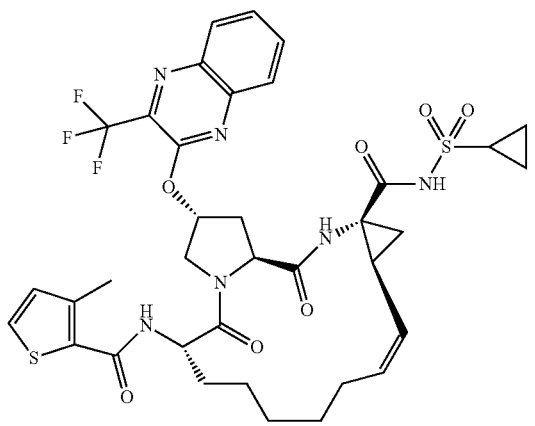 [SMILES: Cc1ccsc1C(=O)N[C@H]1CCCCC/C=C\[C@@H]2C[C@@]2(C(=O)NS(=O)(=O)C2CC2)NC(=O)[C@@H]2C[C@@H](Oc3nc4ccccc4nc3C(F)(F)F)CN2C1=O]

(2R,6S,13aS,14aR,16aS,Z)—N-(cyclopropylsulfonyl)-2-(7-fluoro-3-(trifluoromethyl)quinoxalin-2-yloxy)-6-(3-methylthiophene-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 14 was prepared according to the procedures used for Example 2, replacing the product of Example 1 with the product of Example 9, replacing 5-methylisoxazole-3-carboxylic acid with 3-methylthiophene-2-carboxylic acid and replacing pyridine with diisopropylethylamine. MS (ESI): m/z=789.2 [M+H].

Example 14 provided an $EC_{50}$ of between 3-20 nM in transient replicon assay with a D168E mutation in a 1a-H77 background, an $EC_{50}$ of between 25-50 nM in a transient replicon assay with a D168V mutation in a 1a-H77 background, and an $EC_{50}$ of <1 nM in transient replicon assay with a R155K mutation in a 1a-H77 background.

Example 15

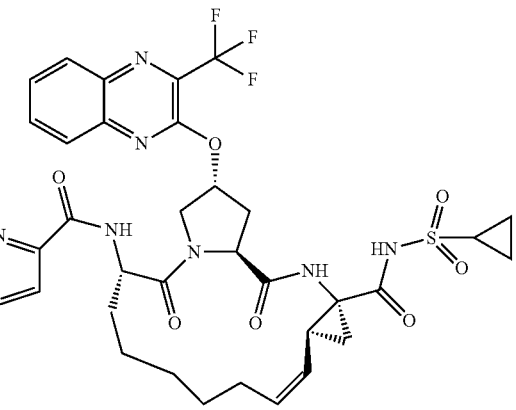

N-((2R,6S,13aS,14aR,16aS,Z)-14a-(cyclopropylsulfonylcarbamoyl)-5,16-dioxo-2-(3-(trifluoromethyl)quinoxalin-2-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 15 was prepared according to the procedure used for Example 2, replacing the product of Example 1 with the product of Example 9, replacing 5-methylisoxazole-3-carboxylic acid with isoxazole-3-carboxylic and replacing pyridine with diisopropylethylamine.

MS (ESI): m/z=760.6 [M+H].

Example 15 provided an AUC value of 3.3 µg*hr/mL when dosed at 3 mg/kg and F value of >100 in a dog PK experiment.

Example 16

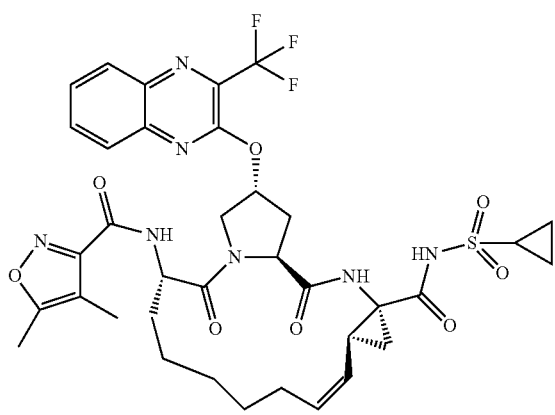 [SMILES: Cc1onc(C(=O)N[C@H]2CCCCC/C=C\[C@@H]3C[C@@]3(C(=O)NS(=O)(=O)C3CC3)NC(=O)[C@@H]3C[C@@H](Oc4nc5ccccc5nc4C(F)(F)F)CN3C2=O)c1C]

N-((2R,6S,13aS,14aR,16aS,Z)-14a-(cyclopropylsulfonylcarbamoyl)-5,16-dioxo-2-(3-(trifluoromethyl)quinoxalin-2-yloxy)-1,2,3,5,6,7,8,9,10,11,13a,14,14a,15,16,16-hexadecahydrocyclopropa[e]pyrrolo[1,2-a][1,4]diazacyclopentadecin-6-yl)-4,5-dimethylisoxazole-3-carboxamide The title compound 16 was prepared according to the procedure used for Example 2, replacing the product of Example 1 with the product of Example 9, replacing 5-methylisoxazole-3-carboxylic acid with 4,5-dimethylisoxazole-3-carboxylic and replacing pyridine with diisopropylethylamine. MS (ESI): m/z=788.5 [M+H].

Example 16 provided an $EC_{50}$ of <3 nM in a transient replicon assay with a D168E mutation in a 1a-H77 background, an $EC_{50}$ of <25 nM in a transient replicon assay with a D168V mutation in a 1a-H77 background, and an $EC_{50}$ of <1 nM in a transient replicon assay with a R155K mutation in a 1a-H77 background. Example 16 also provided an AUC value of 2.1 μg*hr/mL when dosed at 3 mg/kg and F value of 66 in a dog PK experiment.

Example 17

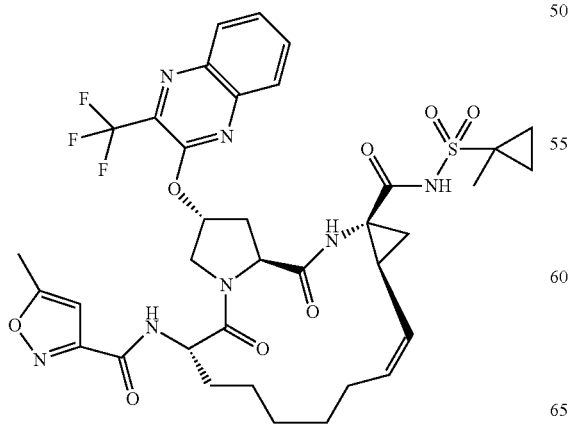

5-methyl-N-((2R,6S,13aS,14aR,16aS,Z)-14a-(1-methylcyclopropylsulfonylcarbamoyl)-5,16-dioxo-2-(3-(trifluoromethyl)quinoxalin-2-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 17 was prepared according to the procedures used for Example 2, replacing the product of Example 1c with the product of Example 9b, replacing methylcyclopropanesulfonamide with cyclopropanesulfonamide and replacing pyridine with diisopropylethylamine. MS (ESI): m/z=788.4 [M+H].

Example 17 provided an $EC_{50}$ of between 3-20 nM in a transient replicon assay with a D168E mutation in a 1a-H77 background, an $EC_{50}$ of between 25-50 nM in a transient replicon assay with a D168V mutation in a 1a-H77 background, and an $EC_{50}$ of <1 nM in a transient replicon assay with a R155K mutation in a 1a-H77 background.

Example 18

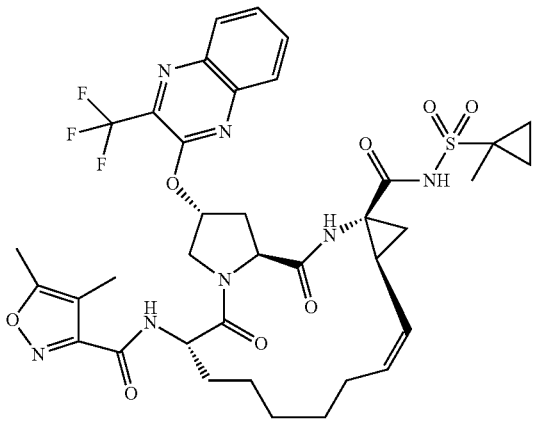 [SMILES: Cc1onc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5ccccc5nc4C(F)(F)F)CN3C2=O)c1C]

4,5-dimethyl-N-((2R,6S,13aS,14aR,16aS,Z)-14a-(1-methylcyclopropylsulfonylcarbamoyl)-5,16-dioxo-2-(3-(trifluoromethyl)quinoxalin-2-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 18 was prepared according to the procedures used for Example 2, replacing the product of Example 1c with the product of Example 9b, replacing methylcyclopropane sulfonamide with cyclopropanesulfonamide, replacing pyridine with diisopropylethylamine and 5-methylisoxazole-3-carboxylic acid with 4,5-dimethylisoxazole-3-carboxylic acid. MS (ESI): m/z=802.2 [M+H].

Example 19

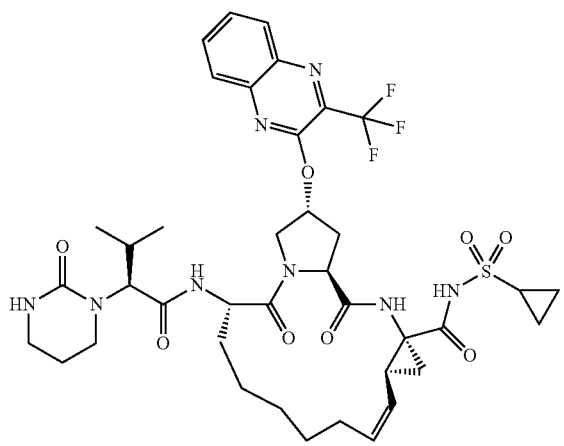 [SMILES: CC(C)[C@@H](C(=O)N[C@H]1CCCCC/C=C\[C@@H]2C[C@@]2(C(=O)NS(=O)(=O)C2CC2)NC(=O)[C@@H]2C[C@@H](Oc3nc4ccccc4nc3C(F)(F)F)CN2C1=O)N1CCCNC1=O]

(2R,6S,13aS,14aR,16aS,Z)—N-(cyclopropylsulfonyl)-6-((S)-3-methyl-2-(2-oxotetrahydropyrimidin-1(2H)-yl)butanamido)-5,16-dioxo-2-(3-(trifluoromethyl)quinoxalin-2-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 19 was prepared according to the procedures used for Example 2 replacing the product of Example 1 with the product of Example 9, replacing pyridine with diisopropylethylamine and 5-methylisoxazole-3-carboxylic acid with (S)-3-methyl-2-(2-oxotetrahydropyrimidin-1(2H)-yl)butanoic acid. MS (ESI): m/z=847.6 [M+H].

Example 19 provided an $EC_{50}$ of >100 nM in a transient replicon assay with a D168E mutation in a 1a-H77 background, an $EC_{50}$ of >1000 nM in a transient replicon assay with a D168V mutation in a 1a-H77 background, and an $EC_{50}$ of between >50 nM in a transient replicon assay with a R155K mutation in a 1a-H77 background.

Example 20

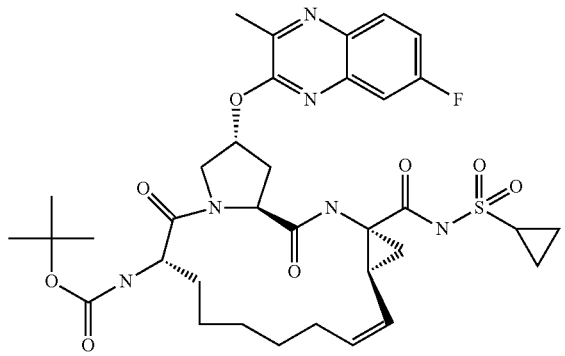 [SMILES: Cc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)OC(C)(C)C)C(=O)N2C1]

tert-butyl (2R,6S,13aS,14aR,16aS,Z)-14a-(cyclopropylsulfonylcarbamoyl)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

Example 20a

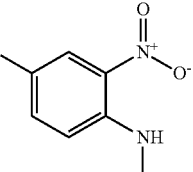

ethyl 2-(3-fluoro-2-nitrophenylamino)propanoate

To a solution of 1,3-difluoro-2-nitrobenzene (4.7 g, 29.5 mmol) in DMA (98 ml) was added ethyl 2-aminopropanoate (3.46 g, 29.5 mmol) and diisopropylethylamine (25.8 ml, 148 mmol). The reaction was heated at 110° C. 16 h, cooled to rt, diluted with 2N HCl and extracted with isopropyl acetate two times. The organic layers were combined and washed with water 3 times and brine once, dried (anh. $Na_2SO_4$) and concentrated. The residue was purified by chromatography on silica gel (100 g) eluting ethyl acetate in hexane in a gradient of 0-30% to give the title compound 20a (5.8 g, 77% yield)

Example 20b

7-fluoro-3-methyl-3,4-dihydroquinoxalin-2(1H)-one

Ethyl 2-(3-fluoro-2-nitrophenylamino)propanoate (4.6 g, 17.95 mmol) was dissolved in methanol (90 ml) and the flask was evacuated and back filled with $N_2$ three times. Palladium on carbon (0.191 g, 1.795 mmol) was then added and a hydrogen filled balloon was placed on the reaction mixture. The reaction mixture was evacuated and backfilled with hydrogen three times. The mixture was stirred at room temperature 16 h. Pd/C was removed by filtration and rinsed with methanol three times. The filtrate was concentrated to give the title compound 20b (2.52 g, 78% yield) which was used in the next step without purification.

Example 20c

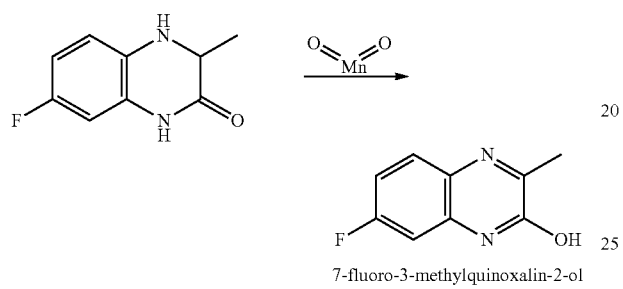

7-fluoro-3-methylquinoxalin-2-ol

To a solution of 7-fluoro-3-methyl-3,4-dihydroquinoxalin-2(1H)-one (5.0 g, 27.8 mmol) in acetone (55.5 ml) was added manganese dioxide (12.06 g, 139 mmol). The mixture was stirred at room temperature 16 h. Manganese dioxide was removed by filtration and washed with methanol, and the filtrate concentrated under reduced pressure. The crude material was dissolved in methanol and filtered through a plug of silica (50 G) using acetone as eluent to give the title compound 20c (2.6 g, 52% yield)

Example 20d

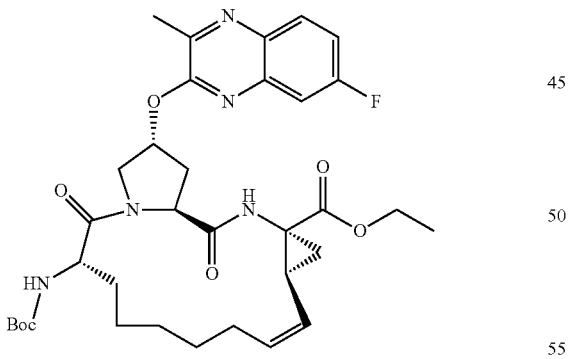

(2R,6S,13aS,14aR,16aS,Z)-ethyl 6-(tert-butoxycarbonylamino)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate The title compound 20d was prepared according to the procedures used for Example 1b, replacing the product of Example 1a with the product of Example 20c. The reaction mixture was cooled to room temperature and diluted with aq. HCl (2 N) and extracted with isopropyl acetate twice. The combined organic layer was washed with water and brine, dried ($Na_2SO_4$), filtered and evaporated under reduced pressure. The crude oil was purified on 100 G of silica using a gradient of acetone in hexane from 0-40% to afford the title compound 20d (3.03 g, 60% yield)

Example 20

The title compound 20 was prepared according to the procedures used for Example 1, replacing the product of Example 1b with the product of Example 20d. MS (ESI): m/z=729.0 [M+H]. Example 20 provided an $EC_{50}$ of between 3-20 nM in a transient replicon assay with a D168E mutation in a 1a-H77 background, an $EC_{50}$ of between 25-50 nM in a transient replicon assay with a D168V mutation in a 1a-H77 background, and an $EC_{50}$ of <1 nM in a transient replicon assay with a R155K mutation in a 1a-H77 background.

Example 21

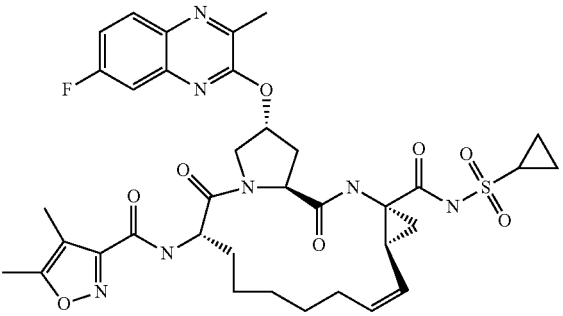 [SMILES: Cc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)c3noc(C)c3C)C(=O)N2C1]

N-((2R,6S,13aS,14aR,16aS,Z)-14a-(cyclopropylsulfonylcarbamoyl)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole-3-carboxamide Example 21a

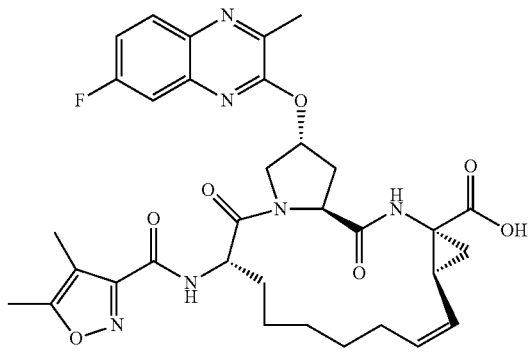 [SMILES: Cc1nc2ccc(F)cc2nc1O[C@@H]1C[C@H]2C(=O)N[C@]3(C(=O)O)C[C@H]3/C=C\CCCCC[C@H](NC(=O)c3noc(C)c3C)C(=O)N2C1]

(2R,6S,13aS,14aR,16aS,Z)-6-(4,5-dimethylisox-azole-3-carboxamido)-2-(7-fluoro-3-methylquinoxa-lin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid The title compound was prepared similarly to the procedures used for Example 5c, replacing the product of Example 1b with the product of Example 20d and replacing isoxazole-3-carboxylic acid with 4,5-dimethylisoxazole-3-carboxylic acid. The reaction mixture was diluted with aq. HCl (2 N) and extracted with dichloromethane. The combined organic layers were dried (Na$_2$SO$_4$) and concentrated. The crude oil was azeotroped with toluene and CHCl$_3$ and dried on the high vacuum for 16 h to give the title compound 21a (110 mg, 87% yield) as an off-white foam.

Example 21

The title compound 21 was prepared according to the procedure used for Example 5, replacing the product of Example 5c with the product of Example 21a and replacing methylcyclopropanesulfonamide with cyclopropanesulfonamide. MS (ESI): m/z=752.2 [M+H].

Example 21 provided an EC$_{50}$ of <3 nM in a transient replicon assay with a D168E mutation in a 1a-H77 background, an EC$_{50}$ of <25 nM in a transient replicon assay with a D168V mutation in a 1a-H77 background, and an EC$_{50}$ of <1 nM in a transient replicon assay with a R155K mutation in a 1a-H77 background.

Example 22

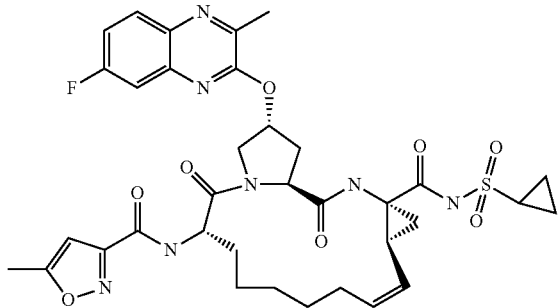 [SMILES: Cc1cc(C(=O)N[C@H]2CCCCC/C=C\[C@@H]3C[C@@]3(C(=O)NS(=O)(=O)C3CC3)NC(=O)[C@@H]3C[C@@H](Oc4nc5cc(F)ccc5nc4C)CN3C2=O)no1]

N-((2R,6S,13aS,14aR,16aS,Z)-14a-(cyclopropylsul-fonylcarbamoyl)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide The title compound 22 was prepared according to the procedures used for Example 21, replacing 4,5-dimethyl-isoxazole-3-carboxylic acid with 5-dimethylisoxazole-3-carboxylic acid. MS (ESI): m/z=737.9 [M+H].

Example 22 provided an EC$_{50}$ of between 3-20 nM in a transient replicon assay with a D168E mutation in a 1a-H77 background, an EC$_{50}$ of between 25-50 nM in a transient replicon assay with a D168V mutation in a 1a-H77 background, and an EC$_{50}$ of between 1-10 nM in a transient replicon assay with a R155K mutation in a 1a-H77 background. Example 22 also provided an AUC value of 54 μg*hr/mL when dosed at 3 mg/kg and F value of >100 in a dog PK experiment.

Example 23

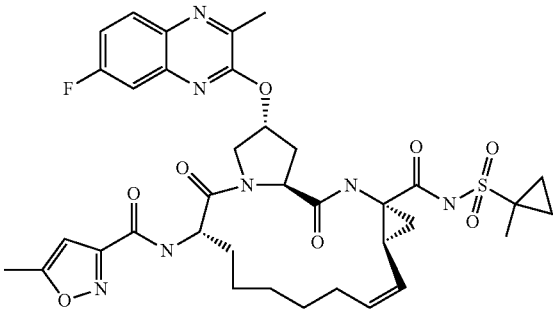 [SMILES: Cc1cc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5cc(F)ccc5nc4C)CN3C2=O)no1]

N-((2R,6S,13aS,14aR,16aS,Z)-2-(7-fluoro-3-meth-ylquinoxalin-2-yloxy)-14a-(1-methylcyclopropylsul-fonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide The title compound 23 was prepared according to the procedure used for Example 21, replacing 4,5-dimethylisox-azole-3-carboxylic acid with 5-dimethylisoxazole-3-carboxylic acid and replacing cyclopropanesulfonamide with methylcyclopropanesulfonamide. MS (ESI): m/z=752.2 [M+H].

Example 23 provided an EC$_{50}$ of between 3-20 nM in a transient replicon assay with a D168E mutation in a 1a-H77 background, an EC$_{50}$ of <25 nM in a transient replicon assay with a D168V mutation in a 1a-H77 background, and an EC$_{50}$ of between 1-10 nM in a transient replicon assay with a R155K mutation in a 1a-H77 background. Example 23 also provided an AUC value of 201 μg*hr/mL when dosed at 3 mg/kg and F value of 86 in a dog PK experiment.

Example 24

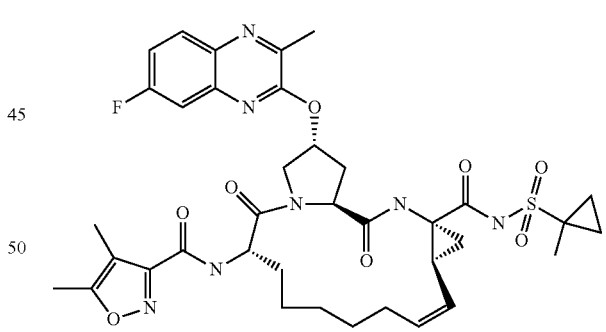

N-((2R,6S,13aS,14aR,16aS,Z)-2-(7-fluoro-3-meth-ylquinoxalin-2-yloxy)-14a-(1-methylcyclopropylsul-fonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole-3-carboxamide The title compound 24 was prepared according to the procedure used for Example 2, replacing the product of Example 1b with the product of Example 20d, using 2 eq. of LiOH—H2O, replacing cyclopropanesulfonamide with methylcyclopropanesulfonamide and replacing 5-methylisoxazole-3-carboxylic acid with 4,5-dimethylisoxazole-3-carboxylic acid. MS (ESI): m/z=766.2 [M+H].

Example 24 provided an $EC_{50}$ of <3 nM in a transient replicon assay with a D168E mutation in a 1a-H77 background, an $EC_{50}$ of <25 nM in a transient replicon assay with a D168V mutation in a 1a-H77 background, and an $EC_{50}$ of <1 nM in a transient replicon assay with a R155K mutation in a 1a-H77 background.

Example 25

Example 25a

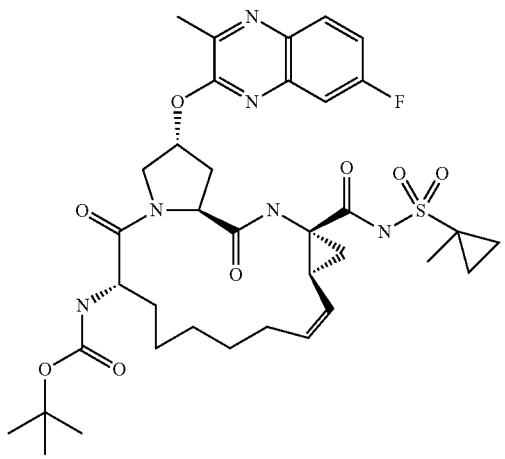 [SMILES: Cc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](NC(=O)OC(C)(C)C)C(=O)N2C1]

tert-butyl (2R,6S,13aS,14aR,16aS,Z)-2-(7-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate The title compound 25a was prepared according to the procedures used for Example 1, replacing the product of Example 1b with the product of Example 20d and replacing cyclopropanesulfonamide with methylcyclopropanesulfonamide. MS (ESI): m/z=743.1 [M+H].

Example 25

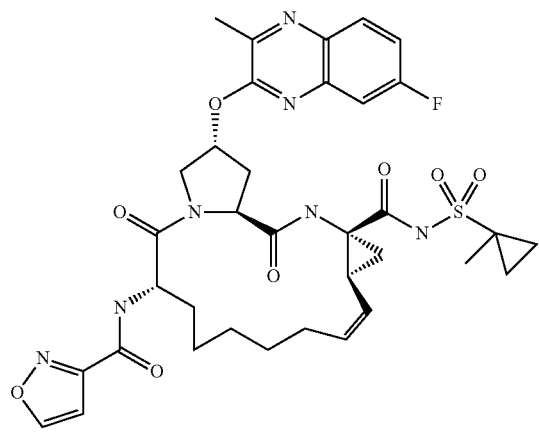 [SMILES: Cc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](NC(=O)c3ccon3)C(=O)N2C1]

N-((2R,6S,13aS,14aR,16aS,Z)-2-(7-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 25 was prepared similarly to the procedure used for Example 3, replacing the product of Example 1 with the product of Example 25a and using 2 eq. of LiOH—$H_2O$. MS (ESI): m/z=738.3 [M+H].

Example 26-40

Example 26a

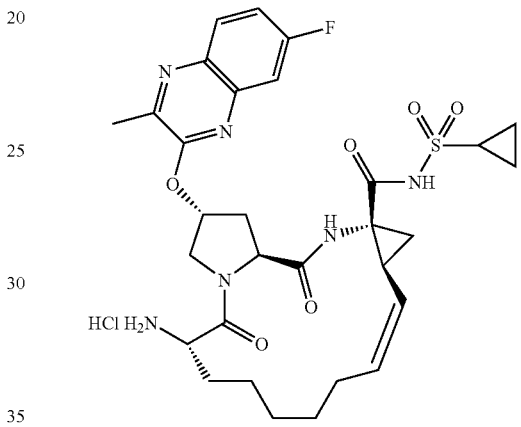

(2R,6S,13aS,14aR,16aS,Z)-6-amino-N-(cyclopropylsulfonyl)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride The title compound 26a was prepared according to the procedure used for Example 2a, replacing the product of Example 1 with the product of Example 20.

General Procedures for Example 26-40

To a solution of 26a (13 mg, 0.02 mmol) in DMA in a 4 ml vial was the acid monomer (0.025 mmol) dissolved in DMA, followed by a solution of HATU (0.025 mmol) in DMA and then triethylamine (0.4 mmol) neat. The vial was capped and microwaved at 150° C. for 30 minutes. The reaction was concentrated to dryness, the residue was dissolved in Methanol:DMSO (1:1 v:v, 1.5 ml) and purified by reverse phase HPLC.

HPLC condition: Samples were purified by preparative HPLC on a Phenomenex Luna C8(2) 5 um 100 Å AXIA column (30 mm×75 mm). A gradient of methanol (A) and 0.1% trifluoroacetic acid in water (B) was used, at a flow rate of 50 mL/min (0-0.5 min 20% A, 0.5-6.0 min linear gradient 20-100% A, 6.0-7.0 min 100% A, 7.0-8.0 min linear gradient 100-10% A).

Example 26

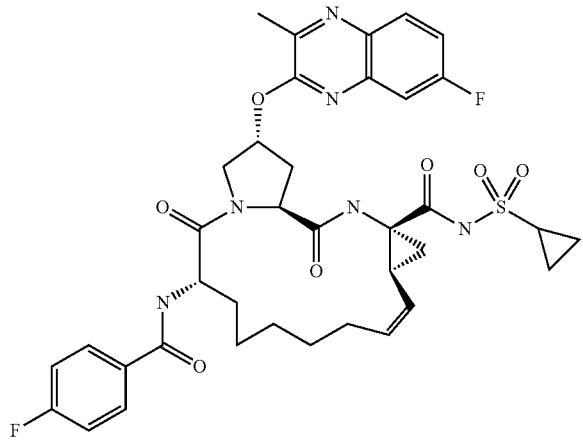 [SMILES: Cc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)c3ccc(F)cc3)C(=O)N2C1]

(2R,6S,13aS,14aR,16aS,Z)—N-(cyclopropylsulfonyl)-2-(7-fluoro-3-methylquinoxalin-2-yloxy)-6-(4-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 26 was prepared according to the general procedure used for Example 26-40, using 4-fluorobenzoic acid as the acid monomer. MS (ESI): m/z=751.2 [M+H].

Example 27

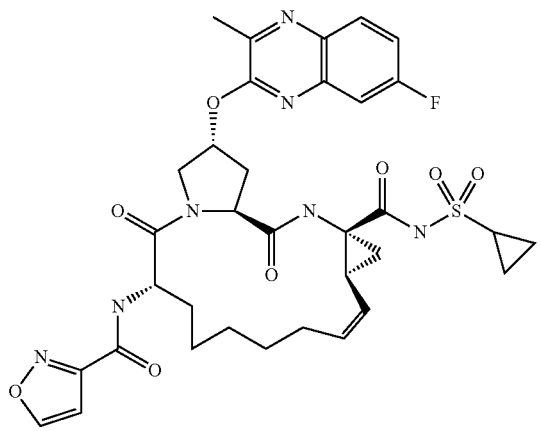 [SMILES: Cc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)c3ccon3)C(=O)N2C1]

N-((2R,6S,13aS,14aR,16aS,Z)-14a-(cyclopropylsulfonylcarbamoyl)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 27 was prepared according to the general procedure used for Example 26-40, using isoxazole-3-carboxylic acid as the acid monomer. MS (ESI): m/z=724.1 [M+H].

Example 28

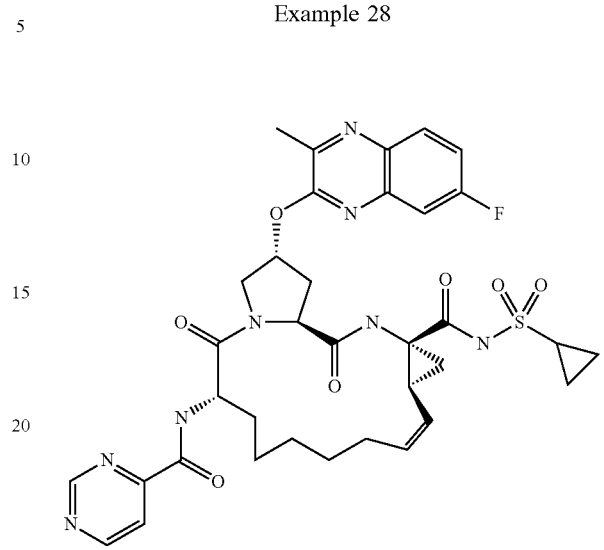

(2R,6S,13aS,14aR,16aS,Z)—N-(cyclopropylsulfonyl)-2-(7-fluoro-3-methylquinoxalin-2-yloxy)-5,16-dioxo-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 28 was prepared according to the general procedure used for Example 26-40 using pyrimidine-4-carboxylic acid as the acid monomer. MS (ESI): m/z=735.2 [M+H].

Example 29

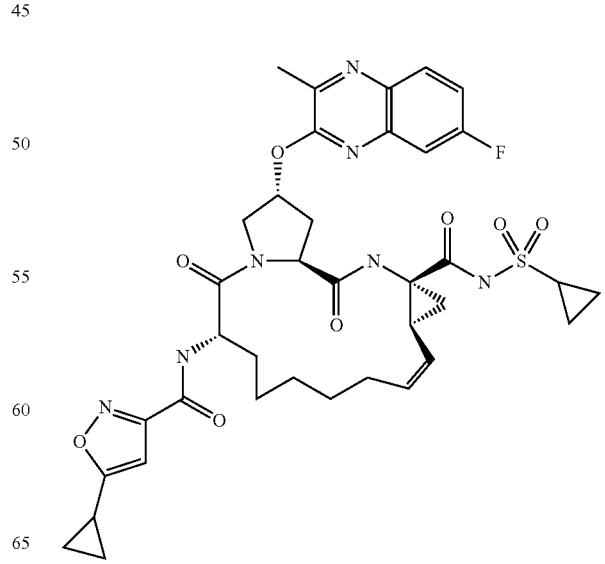

5-cyclopropyl-N-((2R,6S,13aS,14aR,16aS,Z)-14a-(cyclopropylsulfonylcarbamoyl)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 29 was prepared according to the general procedure used for Example 26-40 using 5-cyclopropylisoxazole-3-carboxylic acid as the acid monomer. MS (ESI): m/z=764.2 [M+H].

Example 30

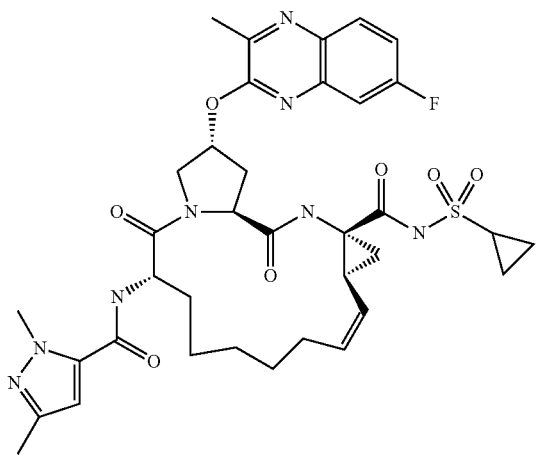 [SMILES: Cc1cc(C(=O)N[C@H]2CCCCC/C=C\[C@@H]3C[C@@]3(C(=O)NS(=O)(=O)C3CC3)NC(=O)[C@@H]3C[C@@H](Oc4nc5cc(F)ccc5nc4C)CN3C2=O)n(C)n1]

(2R,6S,13aS,14aR,16aS,Z)—N-(cyclopropylsulfonyl)-6-(1,3-dimethyl-1H-pyrazole-5-carboxamido)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 30 was prepared according to the general procedure used for Example 26-40 using 1,3-dimethyl-1H-pyrazole-5-carboxylic acid as the acid monomer. MS (ESI): m/z=751.2 [M+H].

Example 31

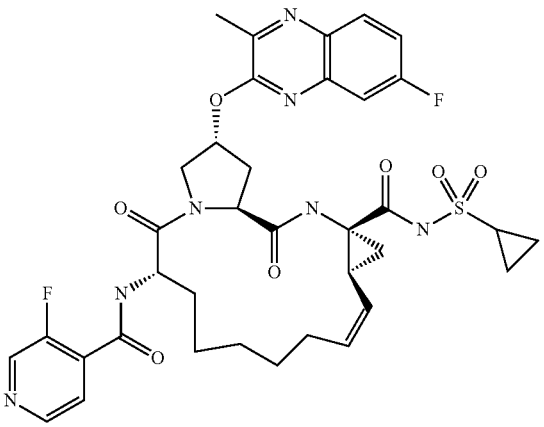 [SMILES: Cc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)c3ccncc3F)C(=O)N2C1]

(2R,6S,13aS,14aR,16aS,Z)—N-(cyclopropylsulfonyl)-2-(7-fluoro-3-methylquinoxalin-2-yloxy)-6-(3-fluoroisonicotinamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 31 was prepared according to the general procedure used for Example 26-40 using 3-fluoroisonicotinic acid as the acid monomer. MS (ESI): m/z=752.2 [M+H].

Example 32

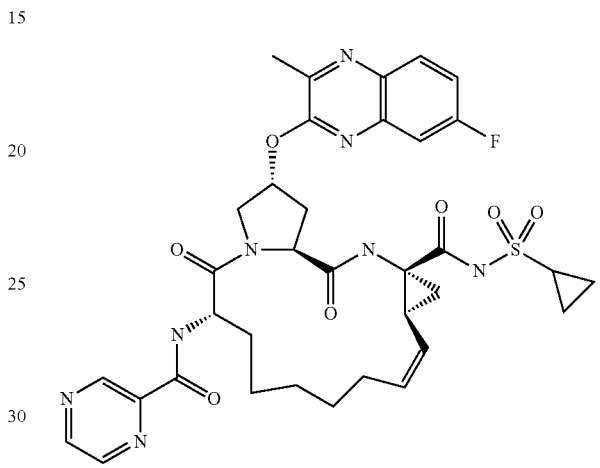

(2R,6S,13aS,14aR,16aS,Z)—N-(cyclopropylsulfonyl)-2-(7-fluoro-3-methylquinoxalin-2-yloxy)-5,16-dioxo-6-(pyrazine-2-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 32 was prepared according to the general procedure used for Example 26-40 using pyrazine-2-carboxylic acid as the acid monomer. MS (ESI): m/z=735.1 [M+H].

Example 33

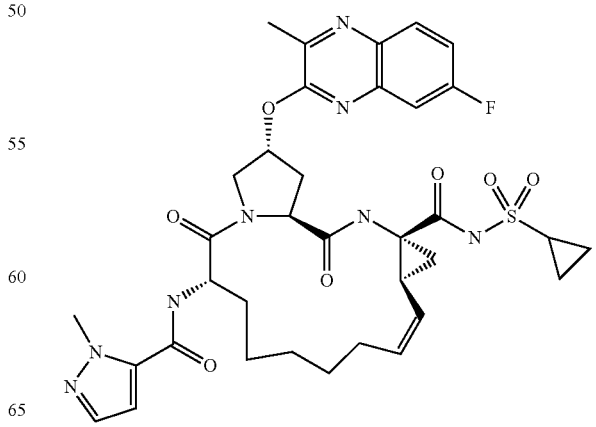

87

(2R,6S,13aS,14aR,16aS,Z)—N-(cyclopropylsulfonyl)-2-(7-fluoro-3-methylquinoxalin-2-yloxy)-6-(1-methyl-1H-pyrazole-5-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 33 was prepared according to the general procedure used for Example 26-40 using 1-methyl-1H-pyrazole-5-carboxylic acid as the acid monomer. MS (ESI): m/z=737.2 [M+H].

Example 34

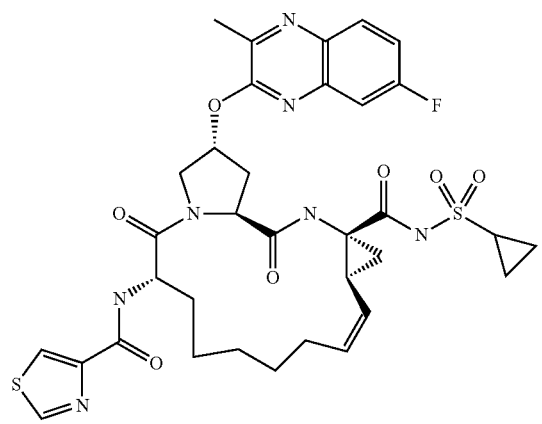 [SMILES: Cc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)c3cscn3)C(=O)N2C1]

N-((2R,6S,13aS,14aR,16aS,Z)-14a-(cyclopropylsulfonylcarbamoyl)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-4-carboxamide The title compound 34 was prepared according to the general procedure used for Example 26-40 using thiazole-2-carboxylic acid as the acid monomer. MS (ESI): m/z=740.1 [M+H].

Example 35

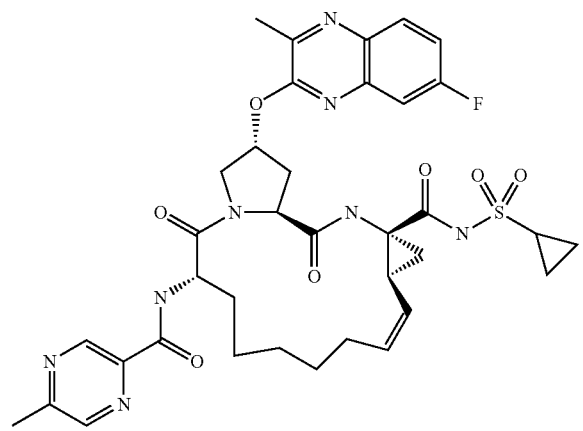 [SMILES: Cc1cnc(C(=O)N[C@H]2CCCCC/C=C\[C@@H]3C[C@@]3(C(=O)NS(=O)(=O)C3CC3)NC(=O)[C@@H]3C[C@@H](Oc4nc5cc(F)ccc5nc4C)CN3C2=O)cn1]

88

(2R,6S,13aS,14aR,16aS,Z)—N-(cyclopropylsulfonyl)-2-(7-fluoro-3-methylquinoxalin-2-yloxy)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 35 was prepared according to the general procedure used for Example 26-40 using 5-methylpyrazine-2-carboxylic acid as the acid monomer. MS (ESI): m/z=749.2 [M+H].

Example 36

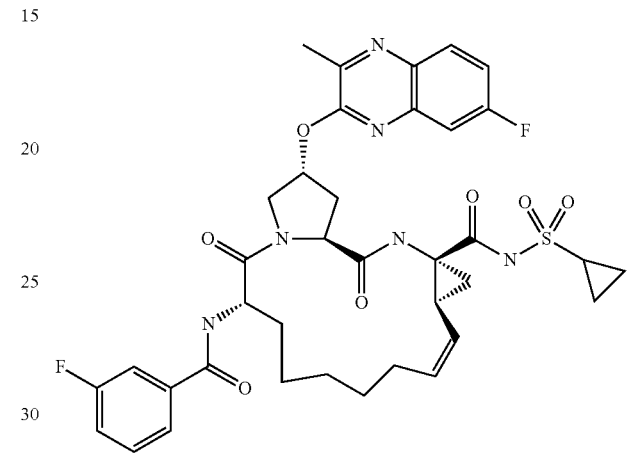

(2R,6S,13aS,14aR,16aS,Z)—N-(cyclopropylsulfonyl)-2-(7-fluoro-3-methylquinoxalin-2-yloxy)-6-(3-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 36 was prepared according to the general procedure used for Example 26-40 using 3-fluorobenzoic acid as the acid monomer. MS (ESI): m/z=751.2 [M+H].

Example 37

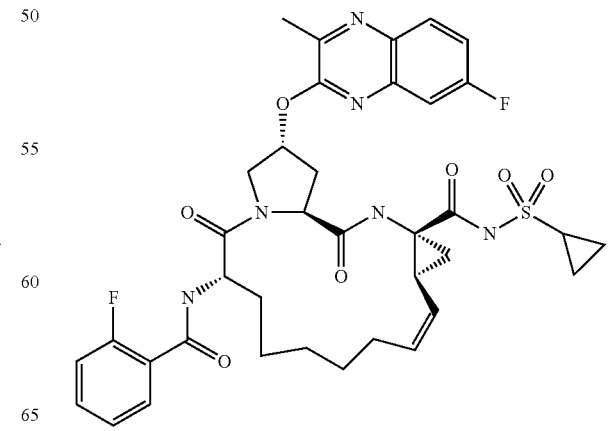

(2R,6S,13aS,14aR,16aS,Z)—N-(cyclopropylsulfo-nyl)-2-(7-fluoro-3-methylquinoxalin-2-yloxy)-6-(2-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 37 was prepared according to the general procedure used for Example 26-40 using 2-fluorobenzoic acid as the acid monomer. MS (ESI): m/z=751.2 [M+H].

Example 38

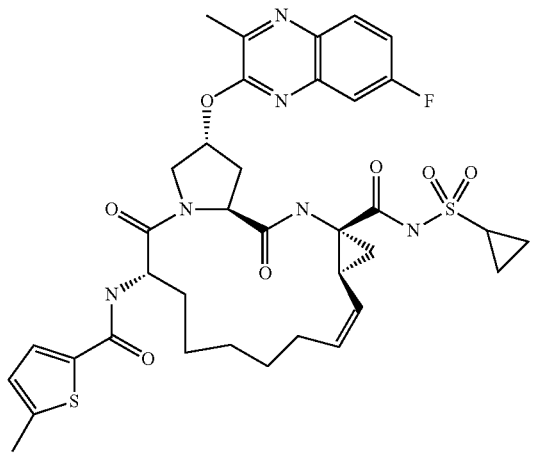 [SMILES: Cc1ccc(C(=O)N[C@H]2CCCCC/C=C\[C@@H]3C[C@@]3(C(=O)NS(=O)(=O)C3CC3)NC(=O)[C@@H]3C[C@@H](Oc4nc5cc(F)ccc5nc4C)CN3C2=O)s1]

(2R,6S,13aS,14aR,16aS,Z)—N-(cyclopropylsulfo-nyl)-2-(7-fluoro-3-methylquinoxalin-2-yloxy)-6-(5-methylthiophene-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 38 was prepared according to the general procedure used for Example 26-40 using 5-methylthiophene-2-carboxylic acid as the acid monomer. MS (ESI): m/z=753.2 [M+H].

Example 39

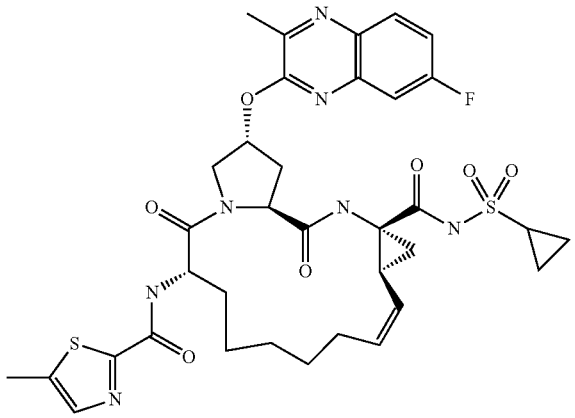 [SMILES: Cc1cnc(C(=O)N[C@H]2CCCCC/C=C\[C@@H]3C[C@@]3(C(=O)NS(=O)(=O)C3CC3)NC(=O)[C@@H]3C[C@@H](Oc4nc5cc(F)ccc5nc4C)CN3C2=O)s1]

N-((2R,6S,13aS,14aR,16aS,Z)-14a-(cyclopropylsul-fonylcarbamoyl)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylthiazole-2-carboxamide The title compound 39 was prepared according to the general procedure used for Example 26-40 using 5-methylthiazole-2-carboxylic acid as the acid monomer. MS (ESI): m/z=754.2 [M+H].

Example 40

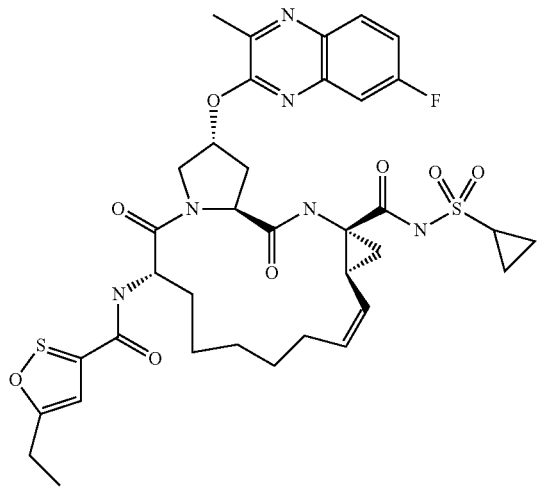

N-((2R,6S,13aS,14aR,16aS,Z)-14a-(cyclopropylsul-fonylcarbamoyl)-2-(7-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-ethylisoxazole-3-carboxamide The title compound 40 was prepared according to the general procedure used for Example 26-40 using 5-ethyl-isoxazole-3-carboxylic acid as the acid monomer. MS (ESI): m/z=752.2 [M+H].

Example 41-53

Example 41a

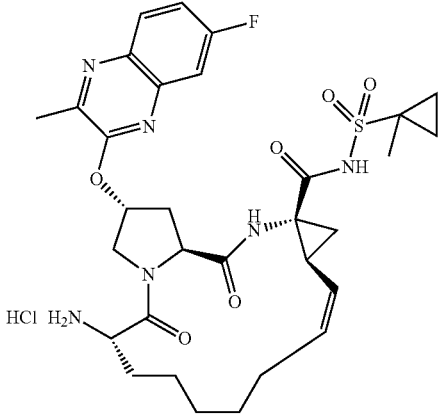 [SMILES: Cl ; Cc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](N)C(=O)N2C1]

(2R,6S,13aS,14aR,16aS,Z)-6-amino-2-(7-fluoro-3-methylquinoxalin-2-yloxy)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide, Hydrochloric Acid The title compound 41a was prepared according to the procedure used for Example 26a, replacing the product of Example 20 with the product of Example 25a.

General Procedures for Example 41-53

To a solution of 41a (13 mg, 0.02 mmol) in DMA in a 4 ml vial was added the acid monomer (0.025 mmol) dissolved in DMA followed by a solution of HATU (0.025 mmol) in DMA and then triethylamine (0.4 mmol) neat. The vial was capped and microwaved at 150° C. for 30 minutes. The reaction was checked by LC/MS and concentrated to dryness. The residue was dissolved in Methanol:DMSO (1:1 v:v, 1.5 ml) and purified by reverse phase HPLC. HPLC condition: Samples were purified by preparative HPLC on a Phenomenex Luna C8(2) 5 um 100 Å AXIA column (30 mm×75 mm). A gradient of methanol (A) and 0.1% trifluoroacetic acid in water (B) was used, at a flow rate of 50 mL/min (0-0.5 min 20% A, 0.5-6.0 min linear gradient 20-100% A, 6.0-7.0 min 100% A, 7.0-8.0 min linear gradient 100-10% A).

Example 41

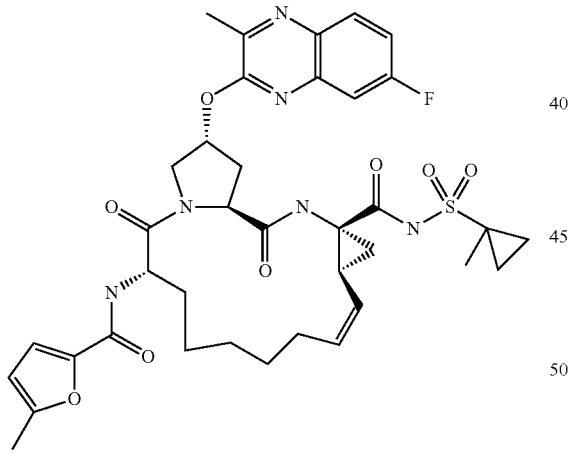

(2R,6S,13aS,14aR,16aS,Z)-2-(7-fluoro-3-methylquinoxalin-2-yloxy)-N-(1-methylcyclopropylsulfonyl)-6-(5-methylfuran-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 41 was prepared according to the general procedure used for Example 41-53 using 5-methylfuran-2-carboxylic acid as the acid monomer. MS (ESI): m/z=751.2 [M+H].

Example 42

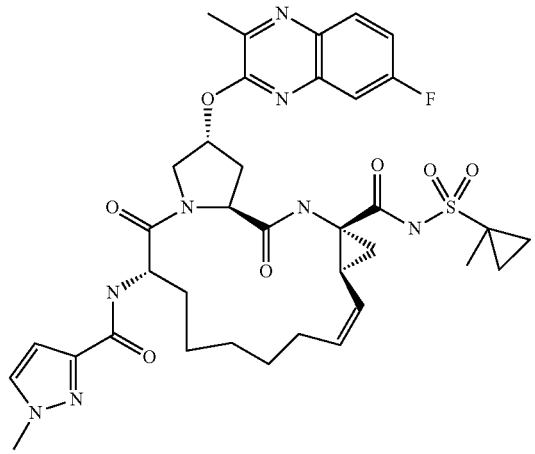 [SMILES: Cc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](NC(=O)c3ccn(C)n3)C(=O)N2C1]

(2R,6S,13aS,14aR,16aS,Z)-2-(7-fluoro-3-methylquinoxalin-2-yloxy)-6-(1-methyl-1H-pyrazole-3-carboxamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 42 was prepared according to the general procedure used for Example 41-53 using 1-methyl-1H-pyrazole-3-carboxylic acid as the acid monomer. MS (ESI): m/z=751.2 [M+H].

Example 43

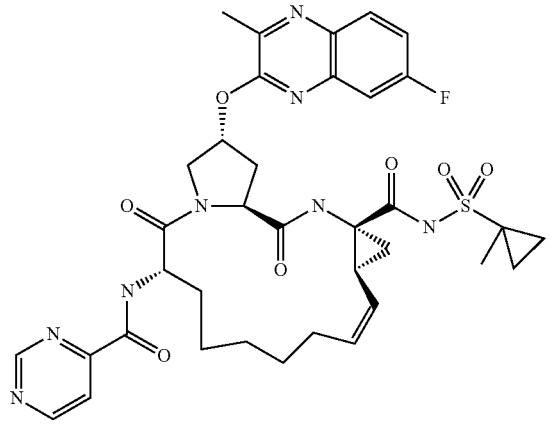 [SMILES: Cc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](NC(=O)c3ccncn3)C(=O)N2C1]

(2R,6S,13aS,14aR,16aS,Z)—N-(1-methylcyclopropylsulfonyl)-2-(7-fluoro-3-methylquinoxalin-2-yloxy)-5,16-dioxo-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 43 was prepared according to the general procedure used for Example 41-53 using pyrimidine-4-carboxylic acid as the acid monomer. MS (ESI): m/z=749.2 [M+H].

Example 44

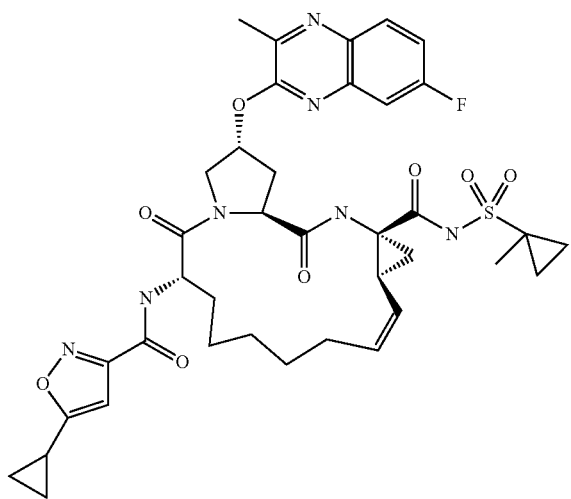 [SMILES: Cc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](NC(=O)c3cc(C4CC4)on3)C(=O)N2C1]

5-cyclopropyl-N-((2R,6S,13aS,14aR,16aS,Z)-2-(7-fluoro-3-methylquinoxalin-2-yloxy)-14a-(1-methyl-cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 44 was prepared according to the general procedure used for Example 41-53 using 5-cyclopropylisoxazole-3-carboxylic acid as the acid monomer. MS (ESI): m/z=778.2 [M+H].

Example 45

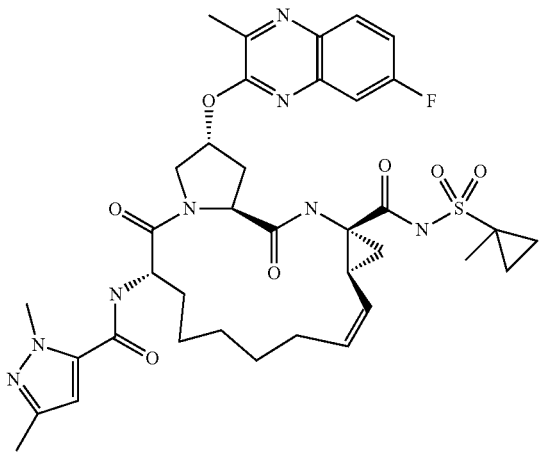 [SMILES: Cc1cc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5cc(F)ccc5nc4C)CN3C2=O)n(C)n1]

(2R,6S,13aS,14aR,16aS,Z)-6-(1,3-dimethyl-1H-pyrazole-5-carboxamido)-2-(7-fluoro-3-methylquinoxalin-2-yloxy)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 45 was prepared according to the general procedure used for Example 41-53 using 1,3-dimethyl-1H-pyrazole-5-carboxylic acid as the acid monomer. MS (ESI): m/z=765.2 [M+H].

Example 46

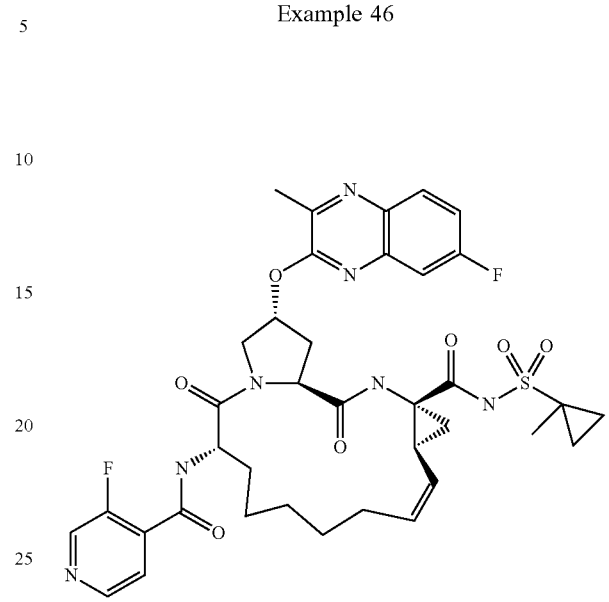

(2R,6S,13aS,14aR,16aS,Z)-2-(7-fluoro-3-methylquinoxalin-2-yloxy)-6-(3-fluoroisonicotinamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 46 was prepared according to the general procedure used for Example 41-53 using 3-fluoroisonicotinic acid as the acid monomer. MS (ESI): m/z=766.2 [M+H].

Example 47

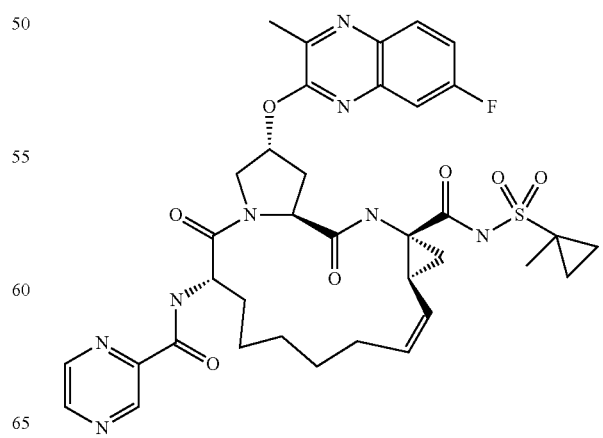

(2R,6S,13aS,14aR,16aS,Z)-2-(7-fluoro-3-methylquinoxalin-2-yloxy)-N-(1-methylcyclopropylsulfonyl)-5,16-dioxo-6-(pyrazine-2-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 47 was prepared according to the general procedure used for Example 41-53 using pyrazine-2-carboxylic acid as the acid monomer. MS (ESI): m/z=749.2 [M+H].

Example 48

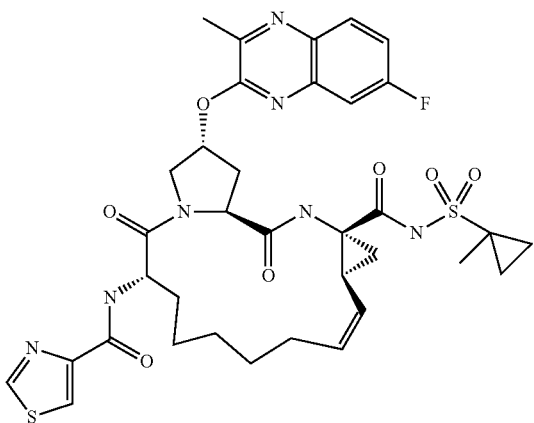 [SMILES: Cc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](NC(=O)c3cscn3)C(=O)N2C1]

N-((2R,6S,13aS,14aR,16aS,Z)-2-(7-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-4-carboxamide The title compound 48 was prepared according to the general procedure used for Example 41-53 using thiazole-2-carboxylic acid as the acid monomer. MS (ESI): m/z=754.2 [M+H].

Example 49

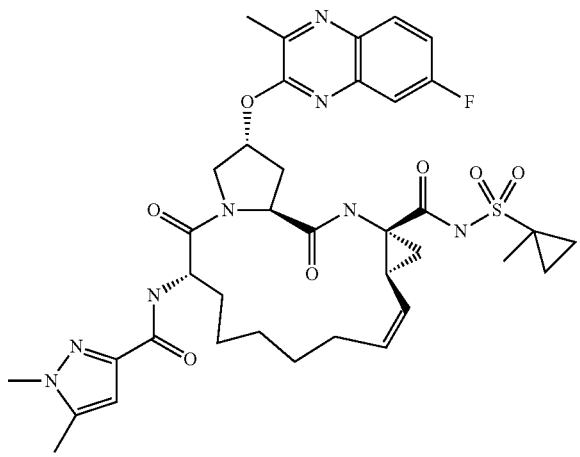 [SMILES: Cc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](NC(=O)c3cc(C)n(C)n3)C(=O)N2C1]

(2R,6S,13aS,14aR,16aS,Z)-6-(1,5-dimethyl-1H-pyrazole-3-carboxamido)-2-(7-fluoro-3-methylquinoxalin-2-yloxy)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 49 was prepared according to the general procedure used for Example 41-53 using 1-methyl-1H-pyrazole-3-carboxylic acid as the acid monomer. MS (ESI): m/z=765.2 [M+H].

Example 50

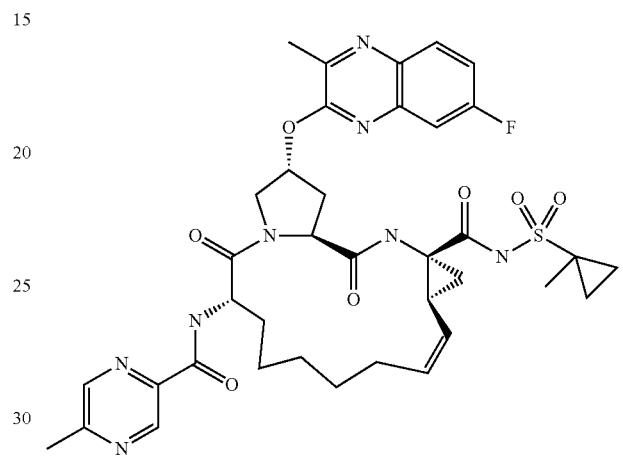

(2R,6S,13aS,14aR,16aS,Z)-2-(7-fluoro-3-methylquinoxalin-2-yloxy)-N-(1-methylcyclopropylsulfonyl)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 50 was prepared according to the general procedure used for Example 41-53 using 5-methylpyrazine-2-carboxylic acid as the acid monomer. MS (ESI): m/z=763.2 [M+H].

Example 51

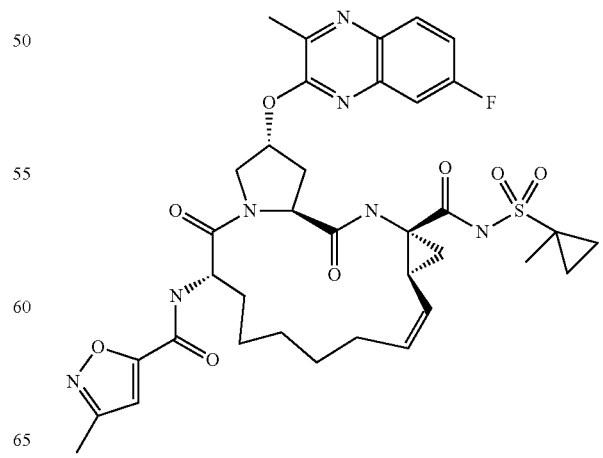

N-((2R,6S,13aS,14aR,16aS,Z)-2-(7-fluoro-3-meth-
ylquinoxalin-2-yloxy)-14a-(1-methylcyclopropylsul-
fonylcarbamoyl)-5,16-dioxo-1,2,3,5,6,7,8,9,10,11,
13a,14,14a,15,16,16a-hexadecahydrocyclopropa[e]
pyrrolo[1,2-a][1,4]diazacyclopentadecin-6-yl)-3-
methylisoxazole-5-carboxamide The title compound 51 was prepared according to the general procedure used for Example 41-53 using 3-methylisoxazole-5-carboxylic acid as the acid monomer. MS (ESI): m/z=752.2 [M+H].

Example 52

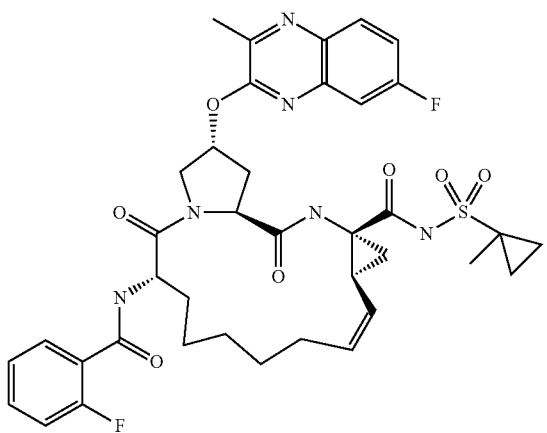 [SMILES: Cc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](NC(=O)c3ccccc3F)C(=O)N2C1]

(2R,6S,13aS,14aR,16aS,Z)-2-(7-fluoro-3-methylqui-
noxalin-2-yloxy)-6-(2-fluorobenzamido)-N-(1-meth-
ylcyclopropylsulfonyl)-5,16-dioxo-1,2,3,5,6,7,8,9,
10,11,13a,14,14a,15,16,16a-
hexadecahydrocyclopropa[e]pyrrolo[1,2-a][1,4]
diazacyclopentadecine-14a-carboxamide The title compound 52 was prepared according to the general procedure used for Example 41-53 using 2-fluorobenzoic acid as the acid monomer. MS (ESI): m/z=765.2 [M+H].

Example 53

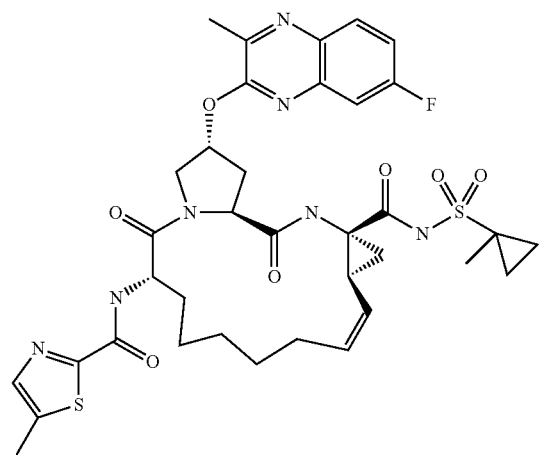 [SMILES: Cc1cnc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5cc(F)ccc5nc4C)CN3C2=O)s1]

N-((2R,6S,13aS,14aR,16aS,Z)-2-(7-fluoro-3-meth-
ylquinoxalin-2-yloxy)-14a-(1-methylcyclopropylsul-
fonylcarbamoyl)-5,16-dioxo-1,2,3,5,6,7,8,9,10,11,
13a,14,14a,15,16,16a-hexadecahydrocyclopropa[e]
pyrrolo[1,2-a][1,4]diazacyclopentadecin-6-yl)-5-
methylthiazole-2-carboxamide The title compound 53 was prepared according to the general procedure used for Example 41-53 using 5-methylthiazole-2-carboxylic acid as the acid monomer. MS (ESI): m/z=768.2 [M+H].

Example 54

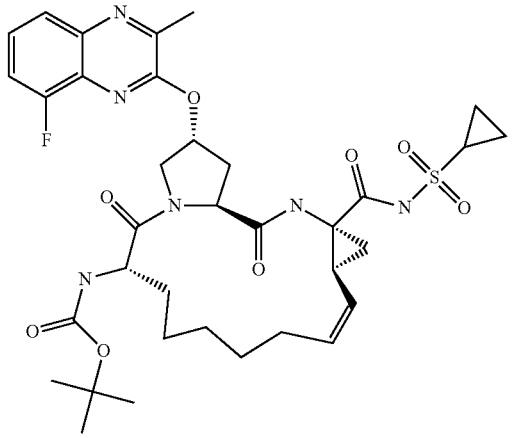 [SMILES: Cc1nc2cccc(F)c2nc1O[C@@H]1C[C@H]2C(=O)N[C@]3(C(=O)NS(=O)(=O)C4CC4)C[C@H]3/C=C\CCCCC[C@H](NC(=O)OC(C)(C)C)C(=O)N2C1]

tert-butyl (2R,6S,13aS,14aR,16aS,Z)-14a-(cyclopro-
pylsulfonylcarbamoyl)-2-(8-fluoro-3-methylqui-
noxalin-2-yloxy)-5,16-dioxo-1,2,3,5,6,7,8,9,10,11,
13a,14,14a,15,16,16a-hexadecahydrocyclopropa[e]
pyrrolo[1,2-a][1,4]diazacyclopentadecin-6-
ylcarbamate Example 54a

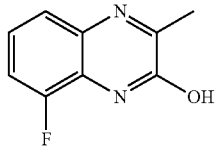

8-fluoro-3-methylquinoxalin-2-ol

The title compound 54a was prepared according to the procedures used for Examples 20a, 20b and 20c, replacing 1,3-difluoro-2-nitrobenzene with 1,2-difluoro-3-nitrobenzene.

Example 54b

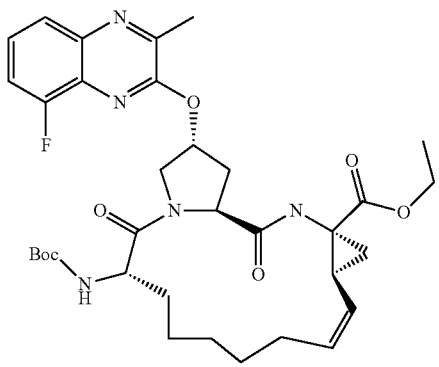 [SMILES: CCOC(=O)[C@@]12C[C@H]1/C=C\CCCCC[C@H](NC(=O)OC(C)(C)C)C(=O)N1C[C@H](Oc3nc4c(F)cccc4nc3C)C[C@H]1C(=O)N2]

(2R,6S,13aS,14aR,16aS,Z)-ethyl 6-(tert-butoxycarbonylamino)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate The title compound 54b was prepared similarly to the procedures used for Example 20d, replacing the product of Example 20c with the product of Example 54a.

Example 54

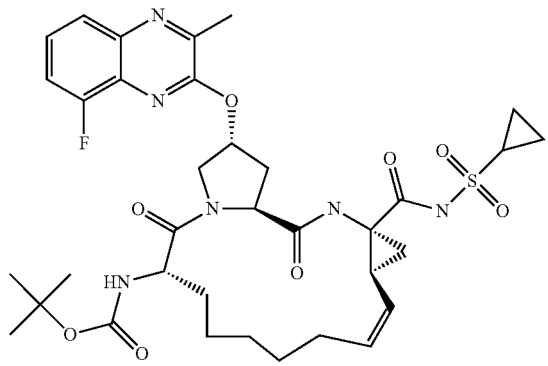 [SMILES: Cc1nc2cccc(F)c2nc1O[C@@H]1C[C@H]2C(=O)N[C@]3(C(=O)NS(=O)(=O)C4CC4)C[C@H]3/C=C\CCCCC[C@H](NC(=O)OC(C)(C)C)C(=O)N2C1]

tert-butyl (2R,6S,13aS,14aR,16aS,Z)-14a-(cyclopropylsulfonylcarbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate The title compound 54 was prepared according to the procedures used for Example 1, replacing the product of Example 1b with the product of Example 54b. MS (ESI): m/z=746.1 [M+NH4]. Example 54 provided an $EC_{50}$ of between 20-50 nM in a transient replicon assay with a D168E mutation in a 1a-H77 background, an $EC_{50}$ of between 50-250 nM in a transient replicon assay with a D168V mutation in a 1a-H77 background, and an $EC_{50}$ of between 1-10 nM in a transient replicon assay with a R155K mutation in a 1a-H77 background.

Example 55

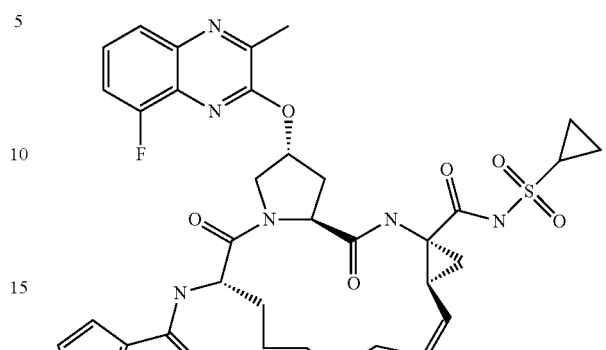

N-((2R,6S,13aS,14aR,16aS,Z)-14a-(cyclopropylsulfonylcarbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 55 was prepared according to the procedures used for Example 2, replacing the product of Example 1b with the product of Example 54b, replacing 5-methylisoxazole-3-carboxylic acid with isoxazole-3-carboxylic acid. MS (ESI): m/z=724.2 [M+H].

Example 55 provided an $EC_{50}$ of between 20-50 nM in a transient replicon assay with a D168E mutation in a 1a-H77 background, an $EC_{50}$ of between 50-250 nM in a transient replicon assay with a D168V mutation in a 1a-H77 background, and an $EC_{50}$ of between 1-10 nM in a transient replicon assay with a R155K mutation in a 1a-H77 background.

Example 56

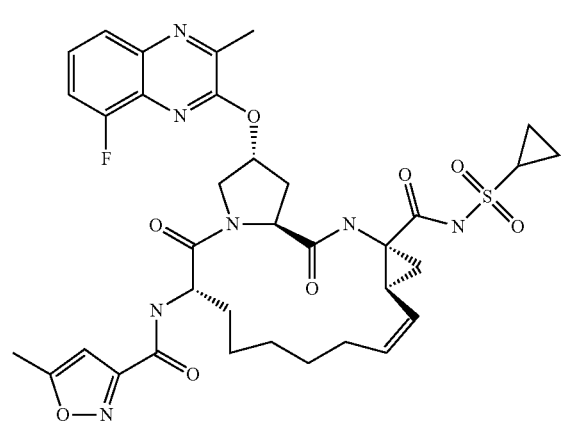 [SMILES: Cc1cc(C(=O)N[C@H]2CCCCC/C=C\[C@@H]3C[C@@]3(C(=O)NS(=O)(=O)C3CC3)NC(=O)[C@@H]3C[C@@H](Oc4nc5c(F)cccc5nc4C)CN3C2=O)no1]

N-((2R,6S,13aS,14aR,16aS,Z)-14a-(cyclopropylsulfonylcarbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide The title compound 56 was prepared according to the procedures used for Example 2, replacing the product of Example 1b with the product of Example 54b. MS (ESI): m/z=738.3 [M+H]. Example 56 provided an $EC_{50}$ of between 20-50 nM in a transient replicon assay with a D168E mutation in a 1a-H77 background, an $EC_{50}$ of between 50-250 nM in a transient replicon assay with a D168V mutation in a 1a-H77 background, and an $EC_{50}$ of between 1-10 nM in a transient replicon assay with a R155K mutation in a 1a-H77 background. Example 56 also provided an AUC value of 10.8 μg*hr/mL when dosed at 3 mg/kg and F value of >100 in a dog PK experiment.

Example 57

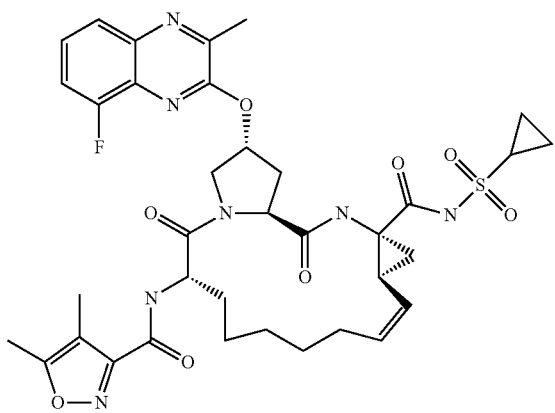 [SMILES: Cc1nc2cccc(F)c2nc1O[C@@H]1C[C@H]2C(=O)N[C@]3(C(=O)NS(=O)(=O)C4CC4)C[C@H]3/C=C\CCCCC[C@H](NC(=O)c3noc(C)c3C)C(=O)N2C1]

N-((2R,6S,13aS,14aR,16aS,Z)-14a-(cyclopropylsulfonylcarbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole-3-carboxamide The title compound 57 was prepared according to the procedures used for Example 2, replacing the product of Example 1b with the product of Example 54b, replacing 5-methylisoxazole-3-carboxylic acid with 4,5-dimethylisoxazole-3-carboxylic acid. MS (ESI): m/z=752.3 [M+H]. Example 57 provided an $EC_{50}$ of between 3-20 nM in a transient replicon assay with a D168E mutation in a 1a-H77 background, an $EC_{50}$ of <25 nM in a transient replicon assay with a D168V mutation in a 1a-H77 background, and an $EC_{50}$ of <1 nM in a transient replicon assay with a R155K mutation in a 1a-H77 background.

Example 58

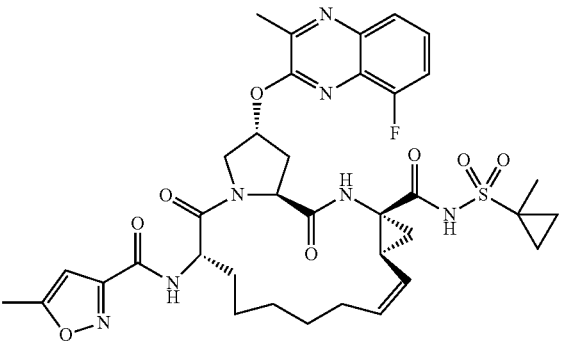 [SMILES: Cc1cc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5c(F)cccc5nc4C)CN3C2=O)no1]

N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide Example 58a

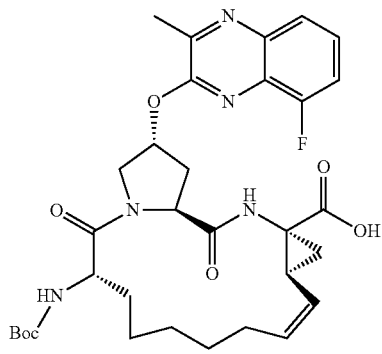 [SMILES: Cc1nc2cccc(F)c2nc1O[C@@H]1C[C@H]2C(=O)N[C@]3(C(=O)O)C[C@H]3/C=C\CCCCC[C@H](NC(=O)OC(C)(C)C)C(=O)N2C1]

(2R,6S,13aS,14aR,16aS,Z)-6-(tert-butoxycarbonylamino)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid The title compound was prepared similarly to the procedure used for Example 1c, replacing the product of Example 1b with the product of Example 54b. Water was added to the reaction and the pH was adjusted to 2 with aq. HCl (1 N). The volume was reduced by two-thirds and extracted with dichloromethane. The combined organic layers were dried over sodium sulfate and dried under high vacuum to give the title compound 58a (2.59 g, 94% yield).

Example 58b

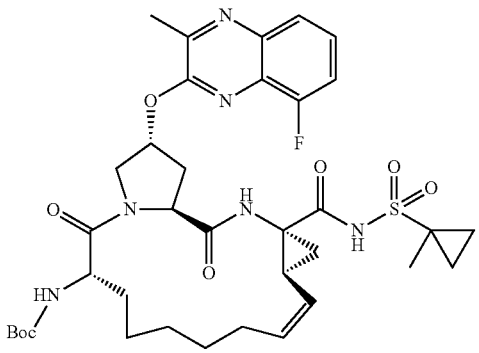 [SMILES: Cc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)OC(C)(C)C)C(=O)N2C1]

tert-butyl (2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate The title compound 58b was prepared similarly to the procedures used for Example 25a, replacing the product of Example 1b with the product of Example 58a. MS (ESI): m/z=760.1 [M+NH4].

Example 58

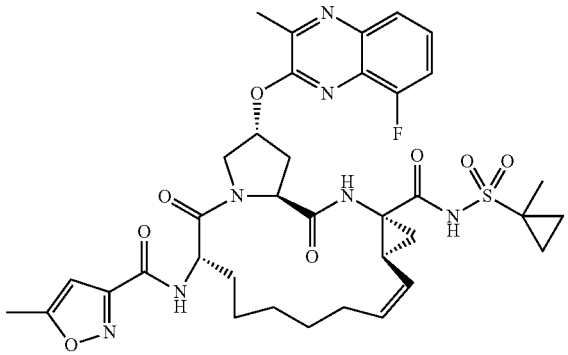 [SMILES: Cc1cc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5c(F)cccc5nc4C)CN3C2=O)no1]

N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide The title compound was prepared similarly to the procedures used for Example 2, replacing the product of Example 1 with the product of Example 58b and replacing cyclopropanesulfonamide with methylcyclopropanesulfonamide. The residue was purified by flash column chromatography on silica gel using a gradient of 0-50% acetone/hexane to give the title compound 58 (380 mg, 98% yield). MS (ESI): m/z=752.0 [M+H].

Example 58 provided an $EC_{50}$ of between 3-20 nM in a transient replicon assay with a D168E mutation in a 1a-H77 background, an $EC_{50}$ of <25 nM in a transient replicon assay with a D168V mutation in a 1a-H77 background, and an $EC_{50}$ of <1 nM in a transient replicon assay with a R155K mutation in a 1a-H77 background.

Example 59-76

Example 59a

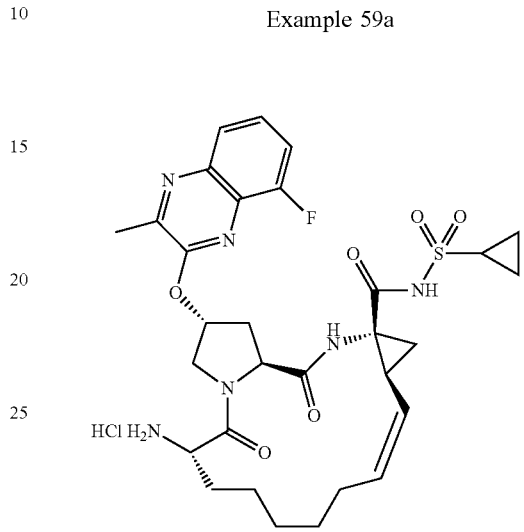

(2R,6S,13aS,14aR,16aS,Z)-6-amino-N-(cyclopropylsulfonyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide, Hydrochloric Acid The title compound 59a was prepared according to the procedure used for Example 2a, replacing the product of Example 1 with the product of Example 54.

General Procedures for Example 59-76

A 4 mL scintillation vial was charged with a stir bar, a solution of 59a (12.22 mg, 0.018 mmol) dissolved in 1 mL of N,N-dimethylacetamide, a solution of carboxylic acid monomer (1.20 eq, 0.022 mmol) dissolved in 2.0 mL of N,N-dimethylacetamide, a solution of HATU (8.36 mg, 1.20 eq, 0.022 mmol) dissolved in 500 µL of N,N-dimethylacetamide, and triethylamine (5.14 µL, 2.0 eq, 0.036 mmol). The vial was capped using inserts followed by Synthos caps. The vials were placed in Synthos Anton-Parr microwave optimizer at 150° C. for 30 minutes. The crude mixture was checked via LCMS for completion and concentrated to dryness. The residue was then dissolved in 1.4 mL of DMSO/Methanol (1/1 v:v) and purified through reverse phase HPLC to afford pure products recovering between 25-59% yield.

HPLC condition: Samples were purified by preparative HPLC on a Phenomenex Luna C8(2) 5 um 100 Å AXIA column (30 mm×75 mm). A gradient of methanol (A) and 0.1% trifluoroacetic acid in water (B) was used, at a flow rate of 50 mL/min (0-0.5 min 20% A, 0.5-6.0 min linear gradient 20-100% A, 6.0-7.0 min 100% A, 7.0-8.0 min linear gradient 100-10% A).

Example 59

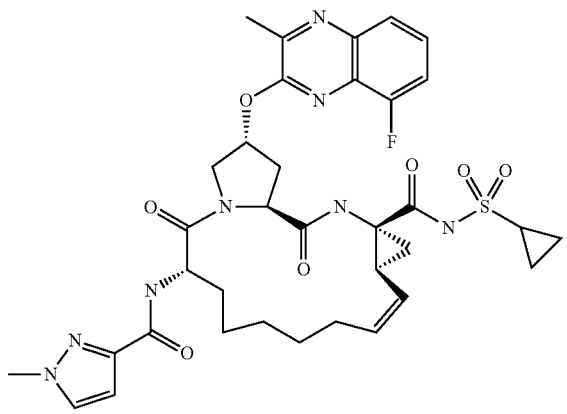 [SMILES: Cc1nc2cccc(F)c2nc1O[C@@H]1C[C@H]2C(=O)N[C@]3(C(=O)NS(=O)(=O)C4CC4)C[C@H]3/C=C\CCCCC[C@H](NC(=O)c3ccn(C)n3)C(=O)N2C1]

(2R,6S,13aS,14aR,16aS,Z)—N-(cyclopropylsulfonyl)-2-(8-fluoro-3-methylquinoxalin-2-yloxy)-6-(1-methyl-1H-pyrazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 59 was prepared according to the general procedure used for Example 59-76 using 1-methyl-1H-pyrazole-3-carboxylic acid as the carboxylic acid monomer. MS (ESI): m/z=737.2 [M+H].

Example 60

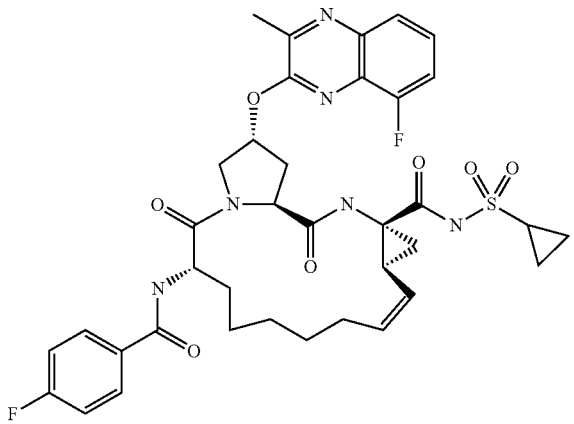 [SMILES: Cc1nc2cccc(F)c2nc1O[C@@H]1C[C@H]2C(=O)N[C@]3(C(=O)NS(=O)(=O)C4CC4)C[C@H]3/C=C\CCCCC[C@H](NC(=O)c3ccc(F)cc3)C(=O)N2C1]

(2R,6S,13aS,14aR,16aS,Z)—N-(cyclopropylsulfonyl)-2-(8-fluoro-3-methylquinoxalin-2-yloxy)-6-(4-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 60 was prepared according to the general procedure used for Example 59-76 using 4-fluorobenzoic acid as the carboxylic acid monomer. MS (ESI): m/z=751.2 [M+H].

Example 61

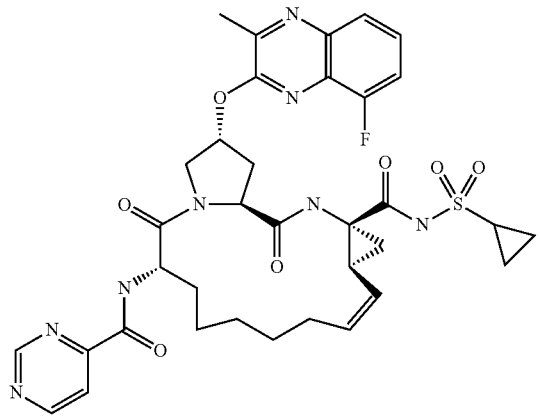 [SMILES: Cc1nc2cccc(F)c2nc1O[C@@H]1C[C@H]2C(=O)N[C@]3(C(=O)NS(=O)(=O)C4CC4)C[C@H]3/C=C\CCCCC[C@H](NC(=O)c3ccncn3)C(=O)N2C1]

(2R,6S,13aS,14aR,16aS,Z)—N-(cyclopropylsulfonyl)-2-(8-fluoro-3-methylquinoxalin-2-yloxy)-5,16-dioxo-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 61 was prepared according to the general procedure used for Example 59-76 using pyrimidine-4-carboxylic acid as the carboxylic acid monomer. MS (ESI): m/z=735.2 [M+H].

Example 62

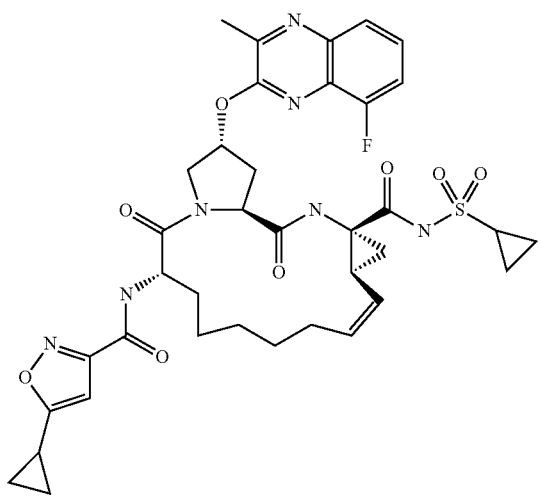 [SMILES: Cc1nc2cccc(F)c2nc1O[C@@H]1C[C@H]2C(=O)N[C@]3(C(=O)NS(=O)(=O)C4CC4)C[C@H]3/C=C\CCCCC[C@H](NC(=O)c3cc(C4CC4)on3)C(=O)N2C1]

5-cyclopropyl-N-((2R,6S,13aS,14aR,16aS,Z)-14a-(cyclopropylsulfonylcarbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 62 was prepared according to the general procedure used for Example 59-76 using 5-cyclopropylisoxazole-3-carboxylic acid as the carboxylic acid monomer. MS (ESI): m/z=764.2 [M+H].

Example 63

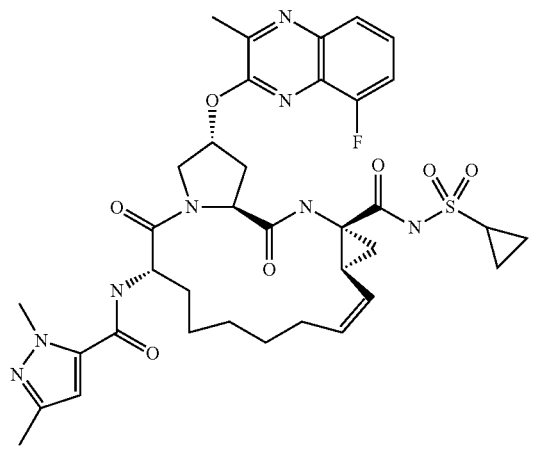 [SMILES: Cc1cc(C(=O)N[C@H]2CCCCC/C=C\[C@@H]3C[C@@]3(C(=O)NS(=O)(=O)C3CC3)NC(=O)[C@@H]3C[C@@H](Oc4nc5c(F)cccc5nc4C)CN3C2=O)n(C)n1]

(2R,6S,13aS,14aR,16aS,Z)—N-(cyclopropylsulfonyl)-6-(1,3-dimethyl-1H-pyrazole-5-carboxamido)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 63 was prepared according to the general procedure used for Example 59-76 using 1,3-dimethyl-1H-pyrazole-5-carboxylic acid as the carboxylic acid monomer. MS (ESI): m/z=751.2 [M+H].

Example 64

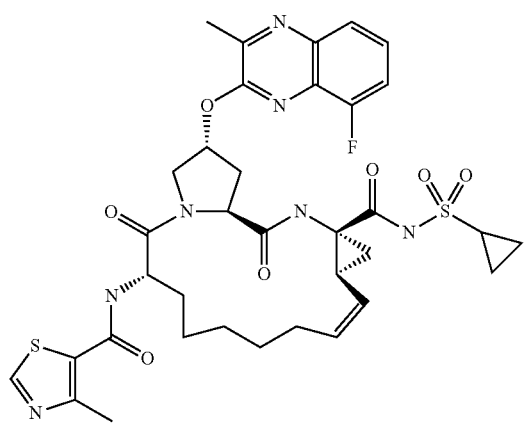 [SMILES: Cc1nc2cccc(F)c2nc1O[C@@H]1C[C@H]2C(=O)N[C@]3(C(=O)NS(=O)(=O)C4CC4)C[C@H]3/C=C\CCCCC[C@H](NC(=O)c3scnc3C)C(=O)N2C1]

N-((2R,6S,13aS,14aR,16aS,Z)-14a-(cyclopropylsulfonylcarbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4-methylthiazole-5-carboxamide The title compound 64 was prepared according to the general procedure used for Example 59-76 using 4-methylthiazole-5-carboxylic acid as the carboxylic acid monomer. MS (ESI): m/z=754.2 [M+H].

Example 65

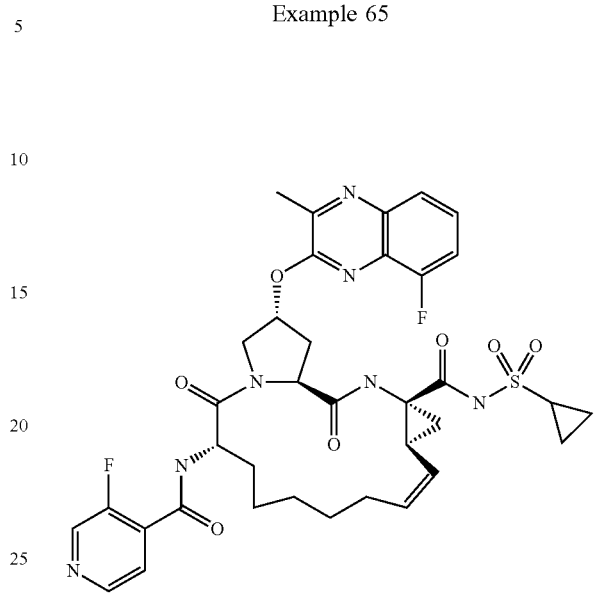

(2R,6S,13aS,14aR,16aS,Z)—N-(cyclopropylsulfonyl)-2-(8-fluoro-3-methylquinoxalin-2-yloxy)-6-(3-fluoroisonicotinamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 65 was prepared according to the general procedure used for Example 59-76 using 3-fluoroisonicotinic acid as the carboxylic acid monomer. MS (ESI): m/z=752.2 [M+H].

Example 66

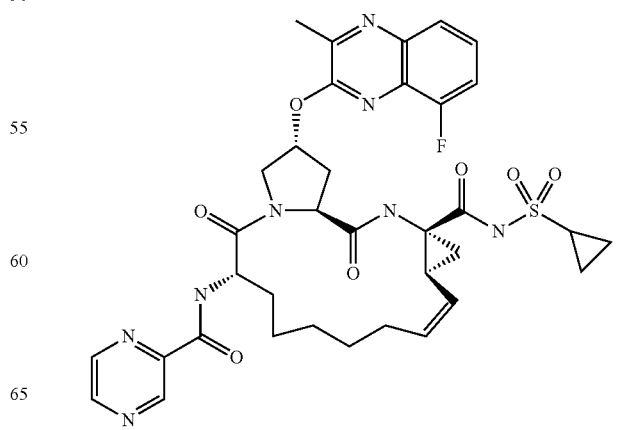

(2R,6S,13aS,14aR,16aS,Z)-N-(cyclopropylsulfonyl)-2-(8-fluoro-3-methylquinoxalin-2-yloxy)-5,16-dioxo-6-(pyrazine-2-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 66 was prepared according to the general procedure used for Example 59-76 using pyrazine-2-carboxylic acid as the carboxylic acid monomer. MS (ESI): m/z=735.2 [M+H].

Example 67

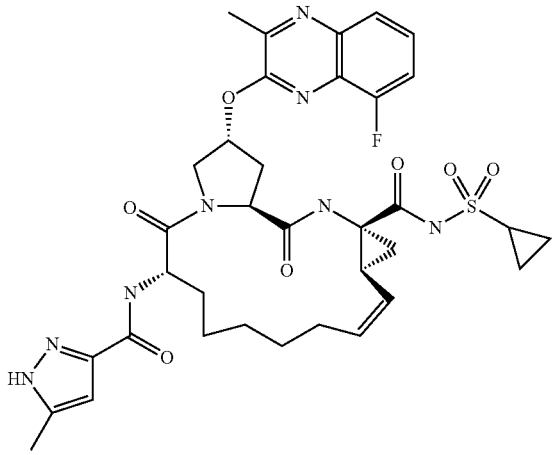 [SMILES: Cc1cc(C(=O)N[C@H]2CCCCC/C=C\[C@@H]3C[C@@]3(C(=O)NS(=O)(=O)C3CC3)NC(=O)[C@@H]3C[C@@H](Oc4nc5c(F)cccc5nc4C)CN3C2=O)n[nH]1]

(2R,6S,13aS,14aR,16aS,Z)-N-(cyclopropylsulfonyl)-2-(8-fluoro-3-methylquinoxalin-2-yloxy)-6-(5-methyl-1H-pyrazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 67 was prepared according to the general procedure used for Example 59-76 using 3-methyl-1H-pyrazole-5-carboxylic acid as the carboxylic acid monomer. MS (ESI): m/z=737.2 [M+H].

Example 68

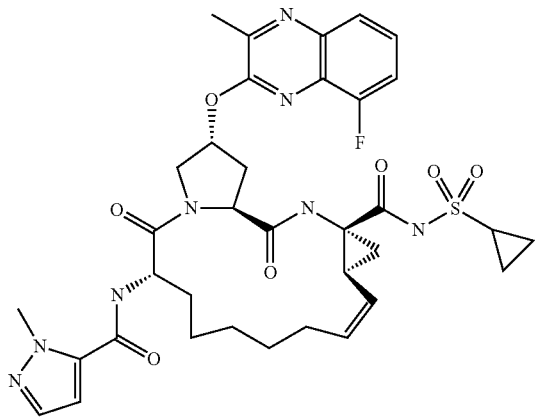 [SMILES: Cc1nc2cccc(F)c2nc1O[C@@H]1C[C@H]2C(=O)N[C@]3(C(=O)NS(=O)(=O)C4CC4)C[C@H]3/C=C\CCCCC[C@H](NC(=O)c3ccnn3C)C(=O)N2C1]

(2R,6S,13aS,14aR,16aS,Z)-N-(cyclopropylsulfonyl)-2-(8-fluoro-3-methylquinoxalin-2-yloxy)-6-(1-methyl-1H-pyrazole-5-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 68 was prepared according to the general procedure used for Example 59-76 using 1-methyl-1H-pyrazole-5-carboxylic acid as the carboxylic acid monomer. MS (ESI): m/z=737.2 [M+H].

Example 69

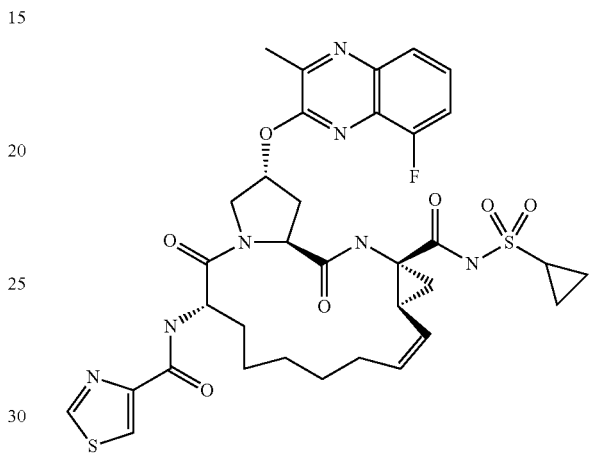

N-((2R,6S,13aS,14aR,16aS,Z)-14a-(cyclopropylsulfonylcarbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-4-carboxamide The title compound 69 was prepared according to the general procedure used for Example 59-76 using thiazole-4-carboxylic acid as the carboxylic acid monomer. MS (ESI): m/z=740.1 [M+H].

Example 70

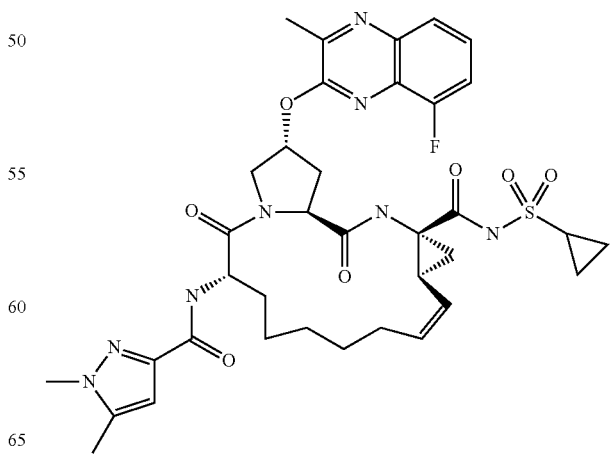

111

(2R,6S,13aS,14aR,16aS,Z)—N-(cyclopropylsulfonyl)-6-(1,5-dimethyl-1H-pyrazole-3-carboxamido)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 70 was prepared according to the general procedure used for Example 59-76 using 1,5-dimethyl-1H-pyrazole-3-carboxylic acid as the carboxylic acid monomer. MS (ESI): m/z=751.2 [M+H].

Example 71

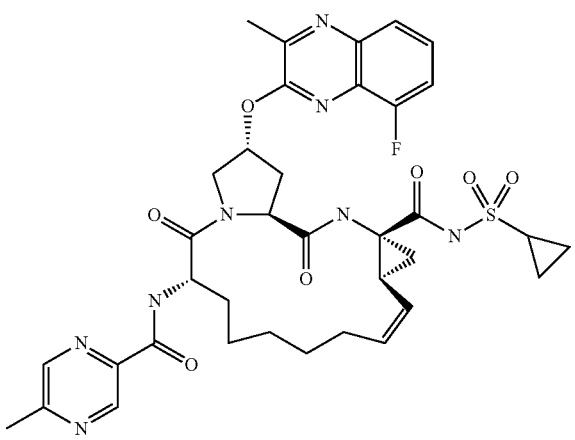 [SMILES: Cc1cnc(C(=O)N[C@H]2CCCCC/C=C\[C@@H]3C[C@@]3(C(=O)NS(=O)(=O)C3CC3)NC(=O)[C@@H]3C[C@@H](Oc4nc5c(F)cccc5nc4C)CN3C2=O)cn1]

(2R,6S,13aS,14aR,16aS,Z)—N-(cyclopropylsulfonyl)-2-(8-fluoro-3-methylquinoxalin-2-yloxy)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 71 was prepared according to the general procedure used for Example 59-76 using 5-methylpyrazine-2-carboxylic acid as the carboxylic acid monomer. MS (ESI): m/z=749.2 [M+H].

Example 72

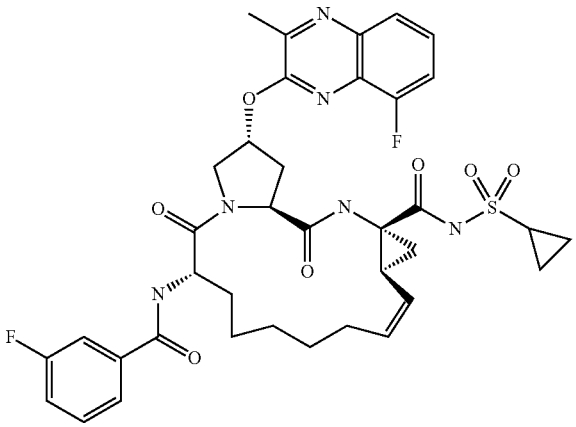 [SMILES: Cc1nc2cccc(F)c2nc1O[C@@H]1C[C@H]2C(=O)N[C@]3(C(=O)NS(=O)(=O)C4CC4)C[C@H]3/C=C\CCCCC[C@H](NC(=O)c3cccc(F)c3)C(=O)N2C1]

112

(2R,6S,13aS,14aR,16aS,Z)—N-(cyclopropylsulfonyl)-2-(8-fluoro-3-methylquinoxalin-2-yloxy)-6-(3-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 72 was prepared according to the general procedure used for Example 59-76 using 3-fluorobenzoic acid as the carboxylic acid monomer. MS (ESI): m/z=751.2 [M+H].

Example 73

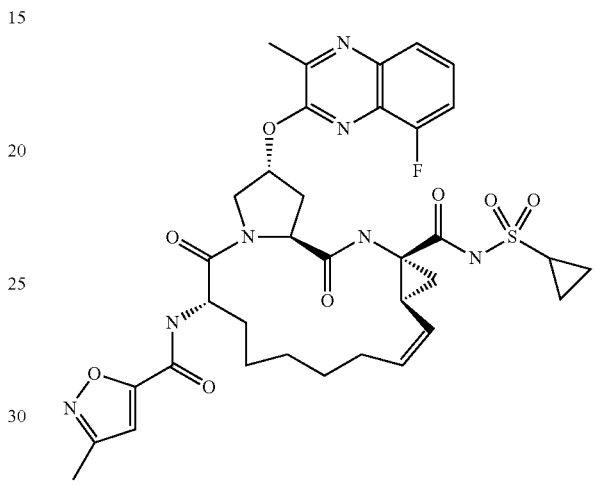

N-((2R,6S,13aS,14aR,16aS,Z)-14a-(cyclopropylsulfonylcarbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-3-methylisoxazole-5-carboxamide The title compound 73 was prepared according to the general procedure used for Example 59-76 using 3-methylisoxazole-5-carboxylic acid as the carboxylic acid monomer. MS (ESI): m/z=738.2 [M+H].

Example 74

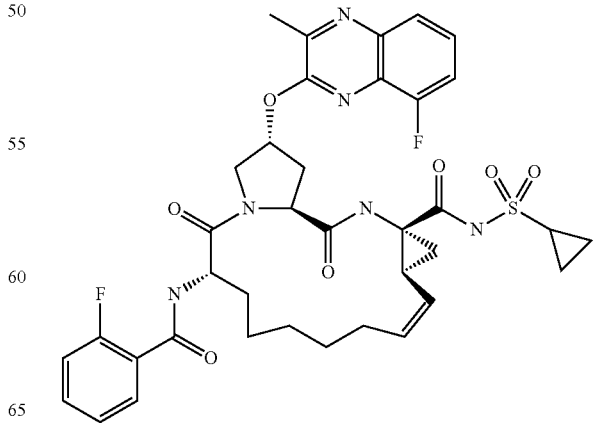

(2R,6S,13aS,14aR,16aS,Z)—N-(cyclopropylsulfonyl)-2-(8-fluoro-3-methylquinoxalin-2-yloxy)-6-(2-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 74 was prepared according to the general procedure used for Example 59-76 using 2-fluorobenzoic acid as the carboxylic acid monomer. MS (ESI): m/z=751.2 [M+H].

Example 75

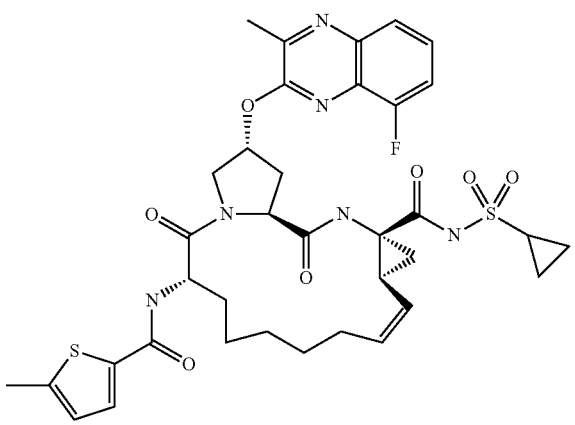 [SMILES: Cc1ccc(C(=O)N[C@H]2CCCCC/C=C\[C@@H]3C[C@@]3(C(=O)NS(=O)(=O)C3CC3)NC(=O)[C@@H]3C[C@@H](Oc4nc5c(F)cccc5nc4C)CN3C2=O)s1]

(2R,6S,13aS,14aR,16aS,Z)—N-(cyclopropylsulfonyl)-2-(8-fluoro-3-methylquinoxalin-2-yloxy)-6-(5-methylthiophene-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 75 was prepared according to the general procedure used for Example 59-76 using 5-methylthiophene-2-carboxylic acid as the carboxylic acid monomer. MS (ESI): m/z=753.2 [M+H].

Example 76

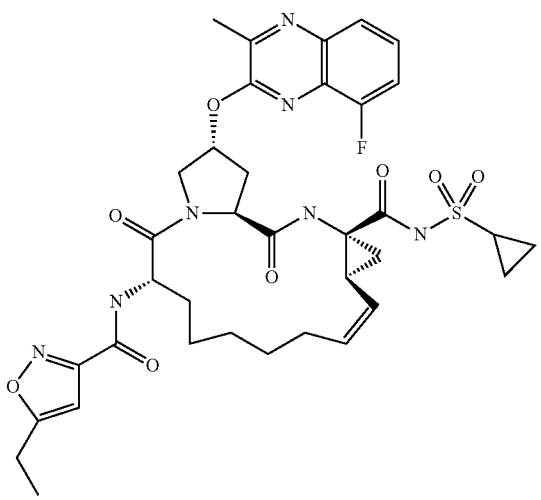 [SMILES: CCc1cc(C(=O)N[C@H]2CCCCC/C=C\[C@@H]3C[C@@]3(C(=O)NS(=O)(=O)C3CC3)NC(=O)[C@@H]3C[C@@H](Oc4nc5c(F)cccc5nc4C)CN3C2=O)no1]

N-((2R,6S,13aS,14aR,16aS,Z)-14a-(cyclopropylsulfonylcarbamoyl)-2-(8-fluoro-3-methylquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-ethylisoxazole-3-carboxamide The title compound 76 was prepared according to the general procedure used for Example 59-76 using 5-ethylisoxazole-3-carboxylic acid as the carboxylic acid monomer. MS (ESI): m/z=752.2 [M+H].

Example 77-96

Example 77a

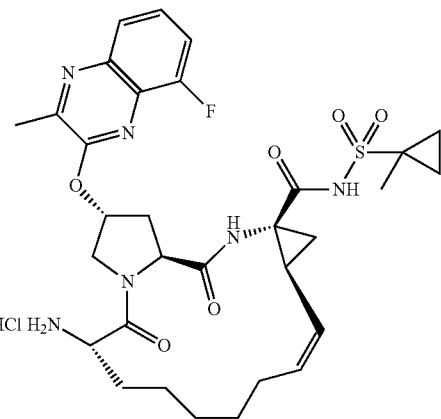

(2R,6S,13aS,14aR,16aS,Z)-6-amino-2-(8-fluoro-3-methylquinoxalin-2-yloxy)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide, Hydrochloric Acid The title compound 77a was prepared according to the procedure used for Example 59a, replacing the product of Example 1 with the product of Example 58b.

General Procedures for Example 77-96

A 4 mL scintillation vial was charged with a stir bar, a solution of 77a (11.11 mg, 0.017 mmol) dissolved in 1 mL of N,N-dimethylacetamide, a solution of carboxylic acid monomer (1.20 eq, 0.021 mmol) dissolved in 2.0 mL of N,N-dimethylacetamide, a solution of HATU (8.36 mg, 1.20 eq, 0.021 mmol) dissolved in 500 µL of N,N-dimethylacetamide, and triethylamine (5.14 µL, 2.0 eq, 0.035 mmol). The vial was capped using inserts followed by Synthos caps. The vials were placed in Synthos Anton-Parr microwave optimizer at 150° C. for 30 minutes. The crude mixture was checked via LCMS for completion and concentrated to dryness. The residue was then dissolved in 1.4 mL of DMSO/Methanol (1/1 v:v) and purified through reverse phase HPLC to afford pure products recovering between 8-46% yield. HPLC condition: Samples were purified by preparative HPLC on a Phenomenex Luna C8(2) 5 um 100 Å AXIA column (30 mm×75 mm). A gradient of methanol (A) and 0.1% trifluoroacetic acid in water (B) was used, at a flow rate of 50 mL/min (0-0.5 min 20% A, 0.5-6.0 min linear gradient 20-100% A, 6.0-7.0 min 100% A, 7.0-8.0 min linear gradient 100-10% A).

Example 77

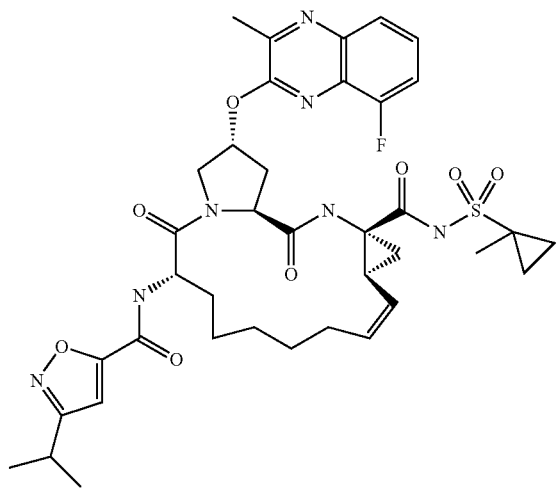 [SMILES: Cc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3cc(C(C)C)no3)C(=O)N2C1]

N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-3-isopropylisoxazole-5-carboxamide The title compound 77 was prepared according to the general procedure used for Example 77-96 using 3-isopropylisoxazole-5-carboxylic acid as the carboxylic acid monomer. MS (ESI): m/z=780.2 [M+H].

Example 78

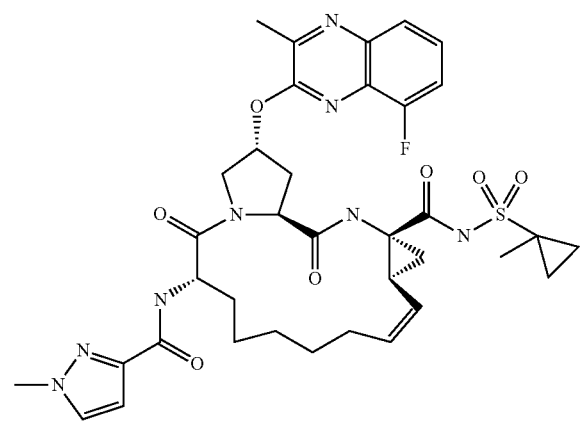 [SMILES: Cc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3ccn(C)n3)C(=O)N2C1]

(2R,6S,13aS,14aR,16aS,Z)-2-(8-fluoro-3-methylquinoxalin-2-yloxy)-6-(1-methyl-1H-pyrazole-3-carboxamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 78 was prepared according to the general procedure used for Example 77-96 using 1-methyl-1H-pyrazole-3-carboxylic acid as the carboxylic acid monomer. MS (ESI): m/z=751.2 [M+H].

Example 79

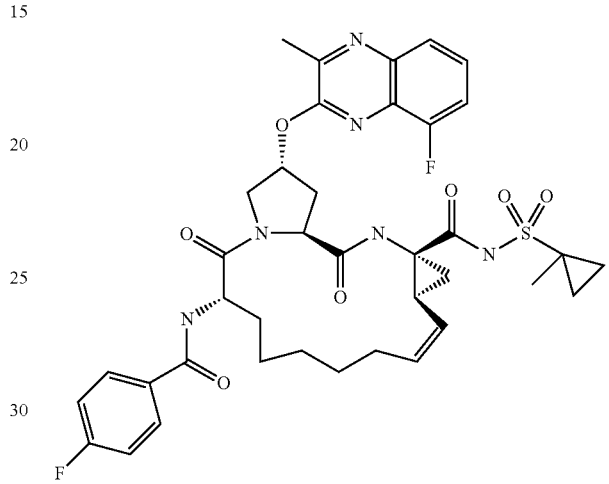

(2R,6S,13aS,14aR,16aS,Z)-2-(8-fluoro-3-methylquinoxalin-2-yloxy)-6-(4-fluorobenzamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 79 was prepared according to the general procedure used for Example 77-96 using 4-fluorobenzoic acid as the carboxylic acid monomer. MS (ESI): m/z=765.2 [M+H].

Example 80

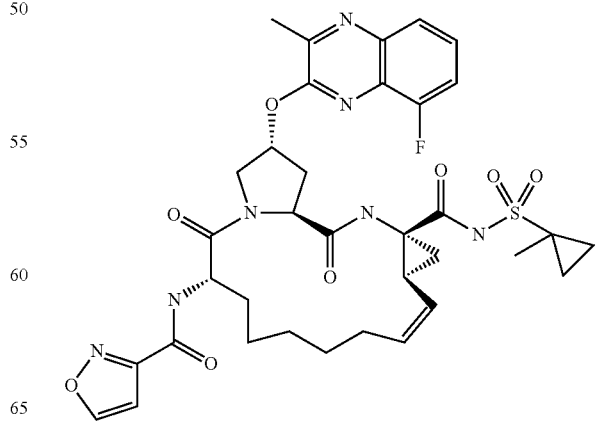

N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 80 was prepared according to the general procedure used for Example 77-96 using isoxazole-3-carboxylic acid as the carboxylic acid monomer. MS (ESI): m/z=738.2 [M+H].

Example 81

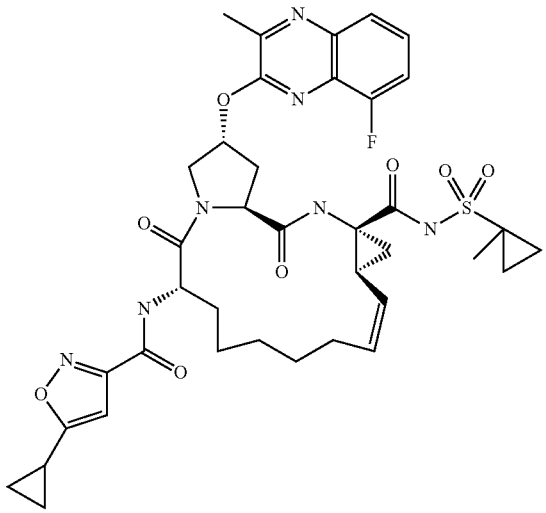 [SMILES: Cc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3cc(C4CC4)on3)C(=O)N2C1]

5-cyclopropyl-N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 81 was prepared according to the general procedure used for Example 77-96 using 5-cyclopropylisoxazole-3-carboxylic acid as the carboxylic acid monomer. MS (ESI): m/z=778.2 [M+H].

Example 82

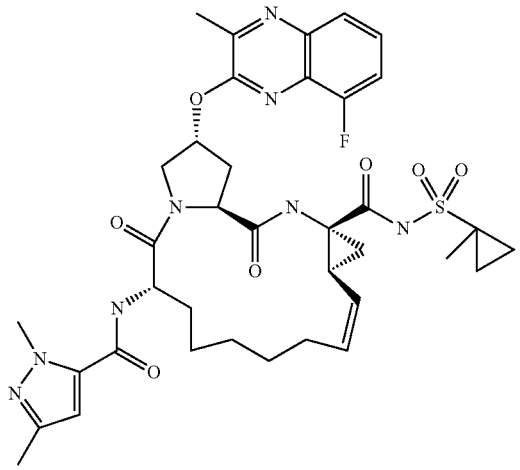 [SMILES: Cc1cc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5c(F)cccc5nc4C)CN3C2=O)n(C)n1]

(2R,6S,13aS,14aR,16aS,Z)-6-(1,3-dimethyl-1H-pyrazole-5-carboxamido)-2-(8-fluoro-3-methylquinoxalin-2-yloxy)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 82 was prepared according to the general procedure used for Example 77-96 using 1,3-dimethyl-1H-pyrazole-5-carboxylic acid as the carboxylic acid monomer. MS (ESI): m/z=765.2 [M+H].

Example 83

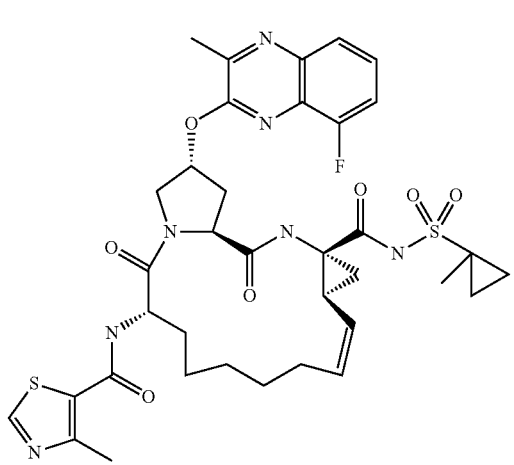 [SMILES: Cc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3scnc3C)C(=O)N2C1]

N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4-methylthiazole-5-carboxamide The title compound 83 was prepared according to the general procedure used for Example 77-96 using 4-methylthiazole-5-carboxylic acid as the carboxylic acid monomer. MS (ESI): m/z=768.2 [M+H].

Example 84

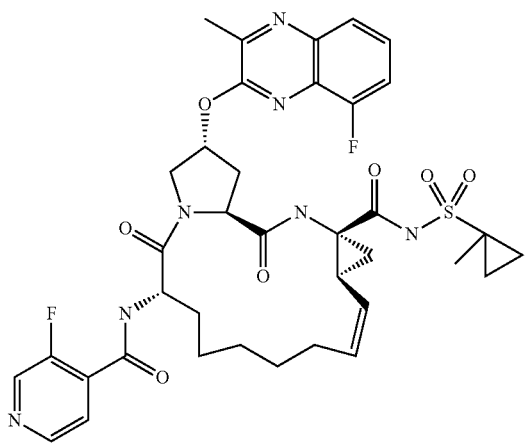 [SMILES: Cc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3ccncc3F)C(=O)N2C1]

(2R,6S,13aS,14aR,16aS,Z)-2-(8-fluoro-3-methylqui-
noxalin-2-yloxy)-6-(3-fluoroisonicotinamido)-N-(1-
methylcyclopropylsulfonyl)-5,16-dioxo-1,2,3,5,6,7,
8,9,10,11,13a,14,14a,15,16,16a-
hexadecahydrocyclopropa[e]pyrrolo[1,2-a][1,4]
diazacyclopentadecine-14a-carboxamide The title compound 84 was prepared according to the general procedure used for Example 77-96 using 3-fluoroisonicotinic acid as the carboxylic acid monomer. MS (ESI): m/z=766.1 [M+H].

Example 85

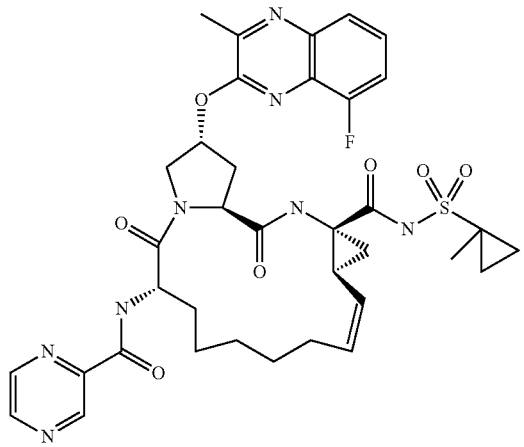 [SMILES: Cc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3cnccn3)C(=O)N2C1]

(2R,6S,13aS,14aR,16aS,Z)-2-(8-fluoro-3-methylqui-
noxalin-2-yloxy)-N-(1-methylcyclopropylsulfonyl)-
5,16-dioxo-6-(pyrazine-2-carboxamido)-1,2,3,5,6,7,
8,9,10,11,13a,14,14a,15,16,16a-
hexadecahydrocyclopropa[e]pyrrolo[1,2-a][1,4]
diazacyclopentadecine-14a-carboxamide The title compound 85 was prepared according to the general procedure used for Example 77-96 using pyrazine-2-carboxylic acid as the carboxylic acid monomer. MS (ESI): m/z=749.2 [M+H].

Example 86

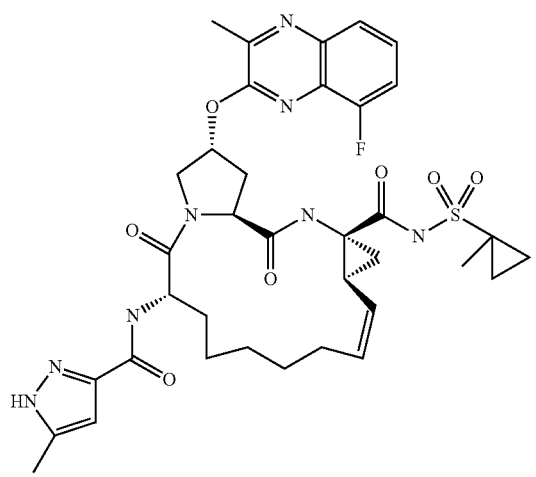 [SMILES: Cc1cc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5c(F)cccc5nc4C)CN3C2=O)n[nH]1]

(2R,6S,13aS,14aR,16aS,Z)-2-(8-fluoro-3-methylqui-
noxalin-2-yloxy)-6-(5-methyl-1H-pyrazole-3-car-
boxamido)-N-(1-methylcyclopropylsulfonyl)-5,16-
dioxo-1,2,3,5,6,7,8,9,10,11,13a,14,14a,15,16,16a-
hexadecahydrocyclopropa[e]pyrrolo[1,2-a][1,4]
diazacyclopentadecine-14a-carboxamide The title compound 86 was prepared according to the general procedure used for Example 77-96 using 5-methyl-1H-pyrazole-3-carboxylic acid as the carboxylic acid monomer. MS (ESI): m/z=751.2 [M+H].

Example 87

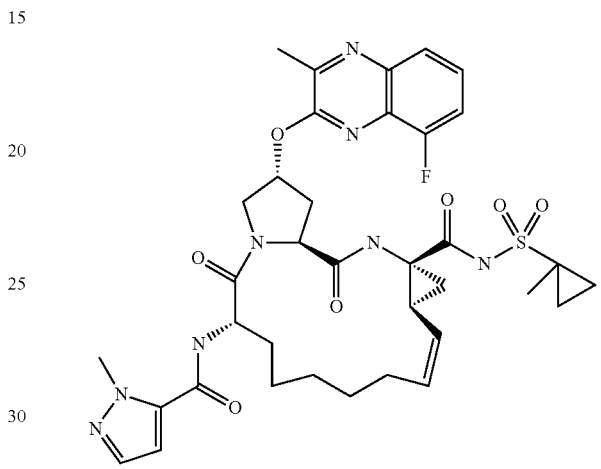

(2R,6S,13aS,14aR,16aS,Z)-2-(8-fluoro-3-methylqui-
noxalin-2-yloxy)-6-(1-methyl-1H-pyrazole-5-car-
boxamido)-N-(1-methylcyclopropylsulfonyl)-5,16-
dioxo-1,2,3,5,6,7,8,9,10,11,13a,14,14a,15,16,16a-
hexadecahydrocyclopropa[e]pyrrolo[1,2-a][1,4]
diazacyclopentadecine-14a-carboxamide The title compound 87 was prepared according to the general procedure used for Example 77-96 using 1-methyl-1H-pyrazole-5-carboxylic acid as the carboxylic acid monomer. MS (ESI): m/z=751.2 [M+H].

Example 88

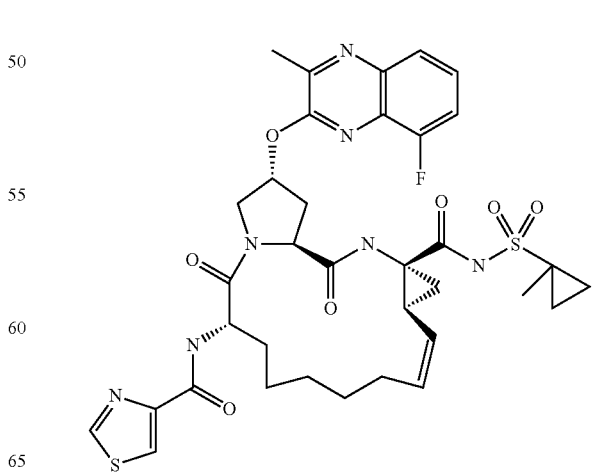

121

N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-4-carboxamide The title compound 88 was prepared according to the general procedure used for Example 77-96 using thiazole-4-carboxylic acid as the carboxylic acid monomer. MS (ESI): m/z=754.2 [M+H].

Example 89

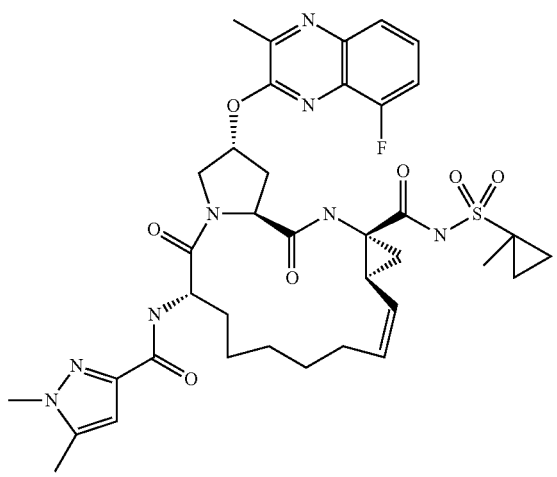 [SMILES: Cc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3cc(C)n(C)n3)C(=O)N2C1]

(2R,6S,13aS,14aR,16aS,Z)-6-(1,5-dimethyl-11H-pyrazole-3-carboxamido)-2-(8-fluoro-3-methylquinoxalin-2-yloxy)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 89 was prepared according to the general procedure used for Example 77-96 using 1,5-dimethyl-1H-pyrazole-3-carboxylic acid as the carboxylic acid monomer. MS (ESI): m/z=765.2 [M+H].

Example 90

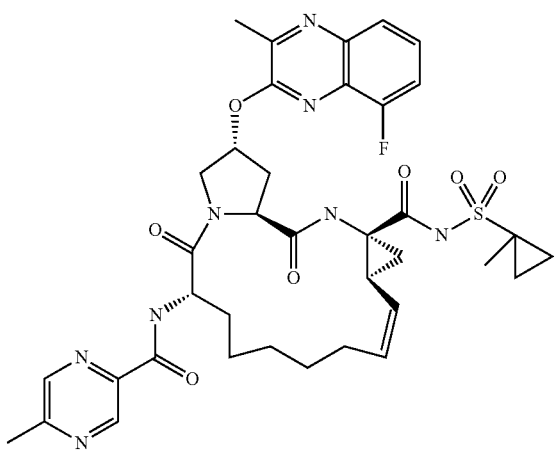 [SMILES: Cc1cnc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5c(F)cccc5nc4C)CN3C2=O)cn1]

122

(2R,6S,13aS,14aR,16aS,Z)-2-(8-fluoro-3-methylquinoxalin-2-yloxy)-N-(1-methylcyclopropylsulfonyl)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 90 was prepared according to the general procedure used for Example 77-96 using 5-methylpyrazine-2-carboxylic acid as the carboxylic acid monomer. MS (ESI): m/z=763.2 [M+H].

Example 91

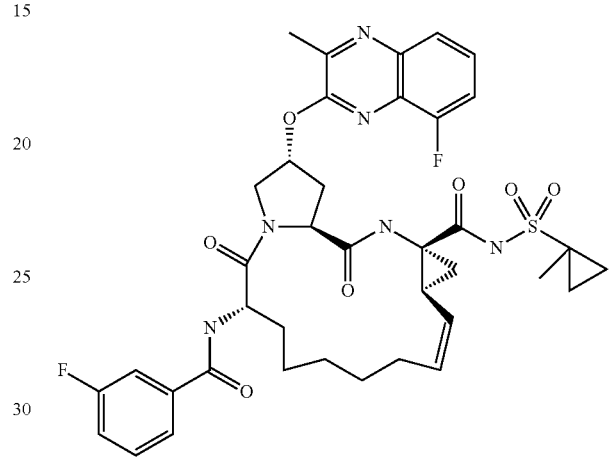

(2R,6S,13aS,14aR,16aS,Z)-2-(8-fluoro-3-methylquinoxalin-2-yloxy)-6-(3-fluorobenzamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 91 was prepared according to the general procedure used for Example 77-96 using 3-fluorobenzoic acid as the carboxylic acid monomer. MS (ESI): m/z=765.2 [M+H].

Example 92

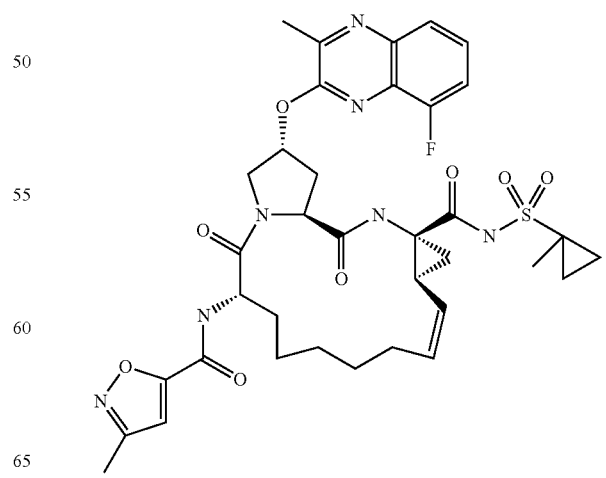

123

N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-3-methylisoxazole-5-carboxamide The title compound 92 was prepared according to the general procedure used for Example 77-96 using 3-methylisoxazole-5-carboxylic acid as the carboxylic acid monomer. MS (ESI): m/z=752.2 [M+H].

Example 93

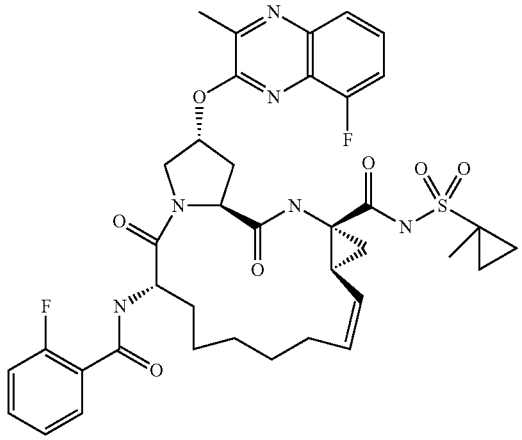 [SMILES: Cc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3ccccc3F)C(=O)N2C1]

(2R,6S,13aS,14aR,16aS,Z)-2-(8-fluoro-3-methylquinoxalin-2-yloxy)-6-(2-fluorobenzamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 93 was prepared according to the general procedure used for Example 77-96 using 2-fluorobenzoic acid as the carboxylic acid monomer. MS (ESI): m/z=765.2 [M+H].

Example 94

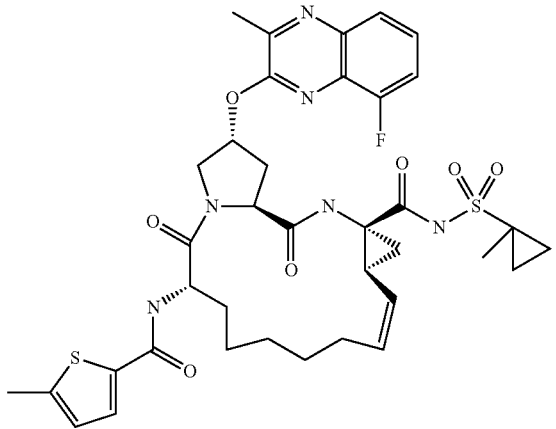 [SMILES: Cc1ccc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5c(F)cccc5nc4C)CN3C2=O)s1]

124

(2R,6S,13aS,14aR,16aS,Z)-2-(8-fluoro-3-methylquinoxalin-2-yloxy)-N-(1-methylcyclopropylsulfonyl)-6-(5-methylthiophene-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 94 was prepared according to the general procedure used for Example 77-96 using 5-methylthiophene-2-carboxylic acid as the carboxylic acid monomer. MS (ESI): m/z=767.2 [M+H].

Example 95

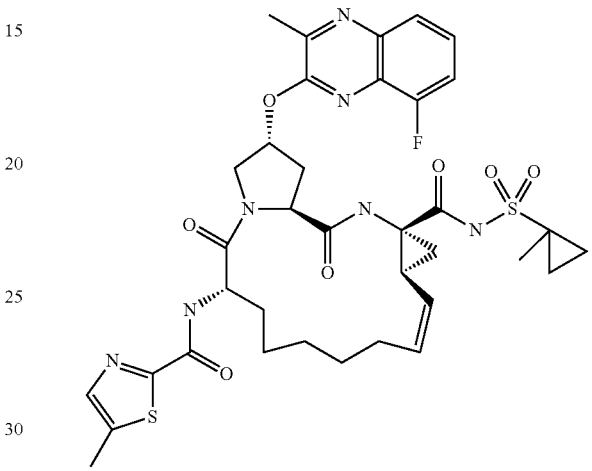

N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylthiazole-2-carboxamide The title compound 95 was prepared according to the general procedure used for Example 77-96 using 5-methylthiazole-2-carboxylic acid as the carboxylic acid monomer. MS (ESI): m/z=768.5 [M+H].

Example 96

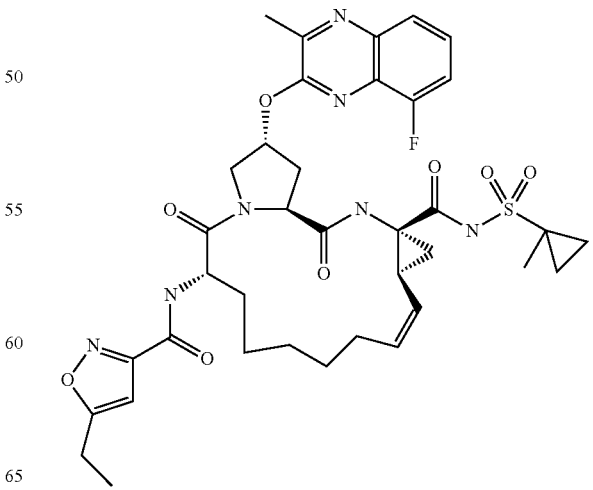

125

5-ethyl-N-((2R,6S,13aS,14aR,16aS,Z)-2-(8-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 96 was prepared according to the general procedure used for Example 77-96 using 5-ethyl-isoxazole-3-carboxylic acid as the carboxylic acid monomer. MS (ESI): m/z=766.2 [M+H].

Example 97

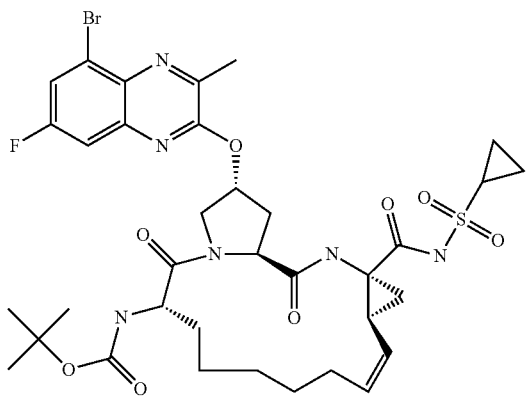 [SMILES: Cc1nc2c(Br)cc(F)cc2nc1O[C@@H]1C[C@H]2C(=O)N[C@]3(C(=O)NS(=O)(=O)C4CC4)C[C@H]3/C=C\CCCCC[C@H](NC(=O)OC(C)(C)C)C(=O)N2C1]

tert-butyl (2R,6S,13aS,14aR,16aS,Z)-2-(5-bromo-7-fluoro-3-methylquinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate Example 97a

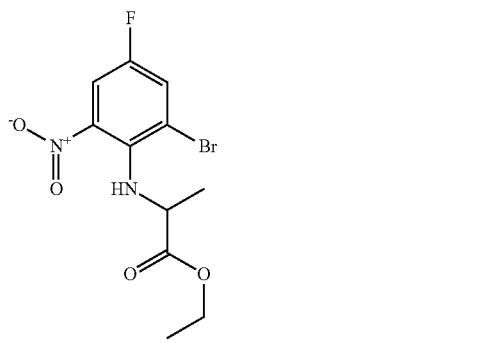

ethyl 2-(2-bromo-4-fluoro-6-nitrophenylamino)propanoate

The title compound 97a was prepared according to the procedures used for Examples 20a, replacing 1,3-difluoro-2-nitrobenzene with 1-bromo-2,5-difluoro-3-nitrobenzene.

126

Example 97b

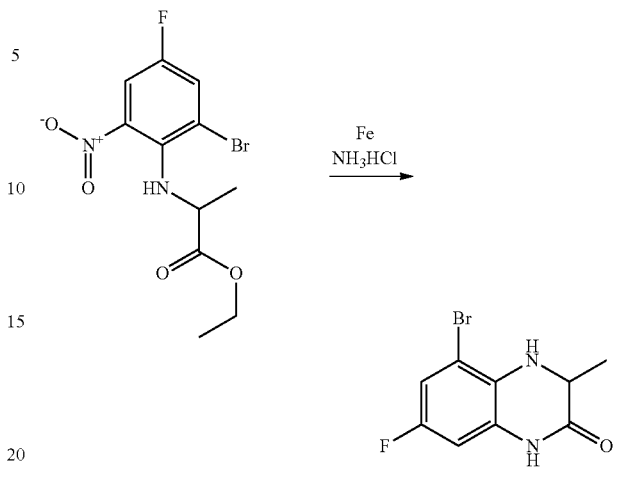

5-bromo-7-fluoro-3-methyl-3,4-dihydroquinoxalin-2(1H)-one

To a solution of ethyl 2-(2-bromo-4-fluoro-6-nitrophenylamino)propanoate (0.320 g, 0.955 mmol) in THF (6.37 ml), ethanol (1.06 ml) and Water (2.12 ml) was added iron powder (0.267 g, 4.77 mmol) and the reaction mixture was heated to 60° C. for 1 hr. Iron was removed by filtration through celite and rinsed with ethanol. The volatiles were removed under reduced pressure. The residual aqueous layer was then extracted with ethyl acetate. The combined organic layers were dried (anh. Na$_2$SO$_4$), filtered and concentrated to give the title compound 97b (0.247 g, quantitative yield).

Example 97c

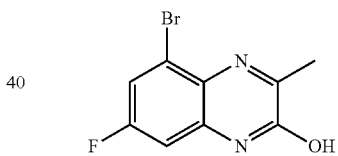

5-bromo-7-fluoro-3-methylquinoxalin-2-ol

The title compound 97a was prepared according to the procedures used for Example 20c, replacing the product of Example 20b with the product of Example 97b.

Example 97d

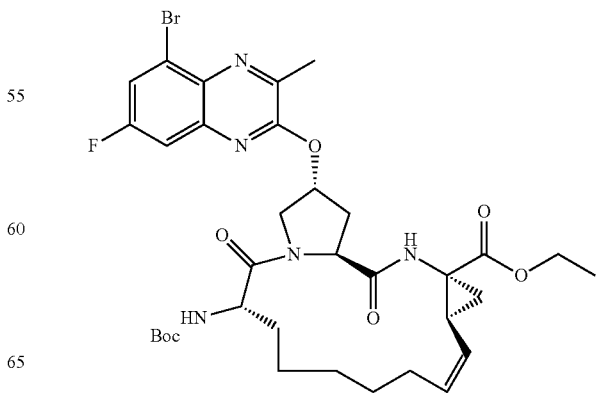

127

(2R,6S,13aS,14aR,16aS,Z)-ethyl 2-(5-bromo-7-fluoro-3-methylquinoxalin-2-yloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate The title compound 97d was prepared according to the procedures used for Example 20d, replacing the product of Example 20c with the product of Example 97c.

Example 97e

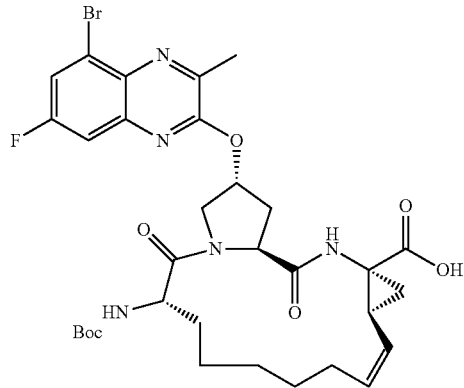 [SMILES: Cc1nc2c(Br)cc(F)cc2nc1O[C@@H]1C[C@H]2C(=O)N[C@]3(C(=O)O)C[C@H]3/C=C\CCCCC[C@H](N)C(=O)N2C1]

(2R,6S,13aS,14aR,16aS,Z)-2-(5-bromo-7-fluoro-3-methylquinoxalin-2-yloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid

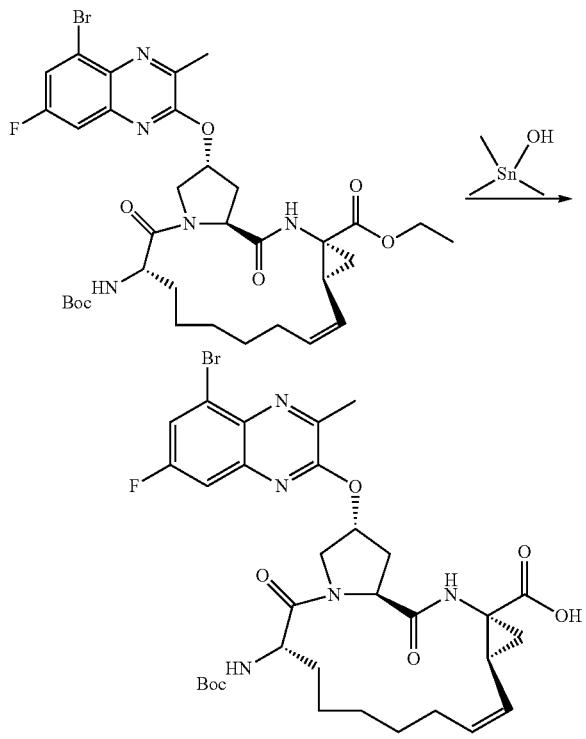

128

To a solution of (2R,6S,13aS,14aR,16aS,Z)-ethyl 2-(5-bromo-7-fluoro-3-methylquinoxalin-2-yloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (0.402 g, 0.549 mmol) in dichloroethane (5.49 ml) was added trimethyltin hydroxide (0.496 g, 2.74 mmol) and the reaction mixture was heated to 110° C. for 5 hrs. Lc/ms at this time showed about 15% conversion based on integration of the lc/ms peaks. Another charge of trimethyltin hydroxide (0.496 g, 2.74 mmol) was added and the reaction was heated at 110° C. for 63 hrs. lc/ms integration showed about 30% conversion. The mixture was cooled to room temperature, diluted with a 3:1 mixture of dichloromethane:dimethylformamide, and washed with aq. HCl (2 N) twice. The combined organic layers were dried (anh. NaSO$_4$), filtered, and concentrated. The resulting crude oil was purified by flash chromatography on silica gel using a gradient of 0-30% ethyl acetate with 0.5% acetic acid in hexane to give the title compound 97e (160 mg, 41% yield).

Example 97

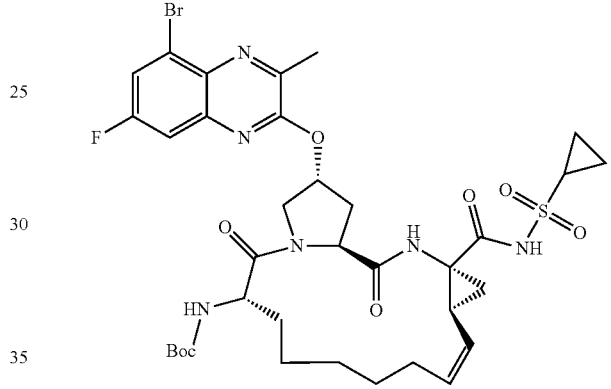

tert-butyl (2R,6S,13aS,14aR,16aS,Z)-2-(5-bromo-7-fluoro-3-methylquinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate The title compound 97 was prepared according to the procedures used for Example 1, replacing the product of Example 1c with the product of Example 97e. MS (ESI): m/z=809.0 [M+H].

Example 98

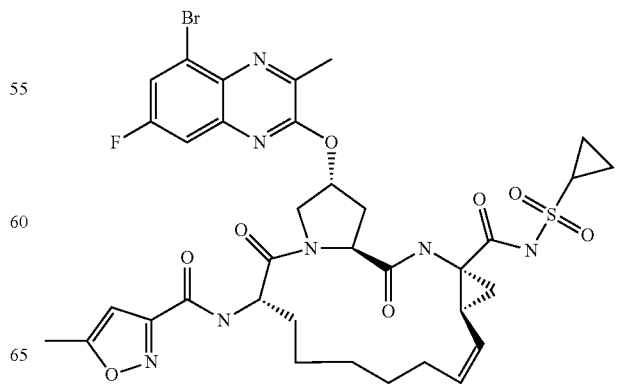

N-((2R,6S,13aS,14aR,16aS,Z)-2-(5-bromo-7-fluoro-3-methylquinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide The title compound 98 was prepared according to the procedures used for Example 2, replacing the product of Example 1 with the product of Example 97. MS (ESI): m/z=818 [M+H]

Example 98 provided an $EC_{50}$ of between 3-20 nM in a transient replicon assay with a D168E mutation in a 1a-H77 background, an $EC_{50}$ of <25 nM in a transient replicon assay with a D168V mutation in a 1a-H77 background, and an $EC_{50}$ of between 1-10 nM in a transient replicon assay with a R155K mutation in a 1a-H77 background.

Example 99

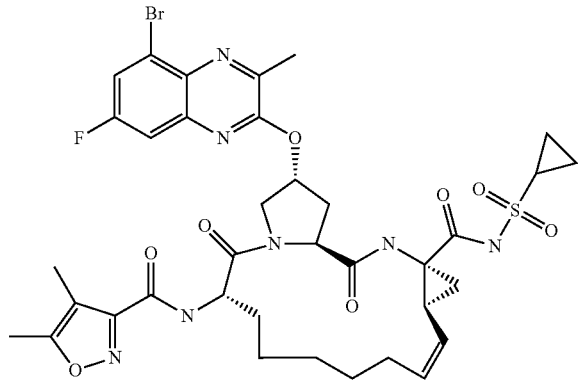 [SMILES: Cc1nc2c(Br)cc(F)cc2nc1O[C@@H]1C[C@H]2C(=O)N[C@]3(C(=O)NS(=O)(=O)C4CC4)C[C@H]3/C=C\CCCCC[C@H](NC(=O)c3noc(C)c3C)C(=O)N2C1]

N-((2R,6S,13aS,14aR,16aS,Z)-2-(5-bromo-7-fluoro-3-methylquinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole-3-carboxamide The title compound 99 was prepared according to the procedure used for Example 98, replacing 5-methylisoxazole-3-carboxylic acid with 4,5-dimethylisoxazole-3-carboxylic acid. MS (ESI): m/z=832.1 [M+H].

Example 100

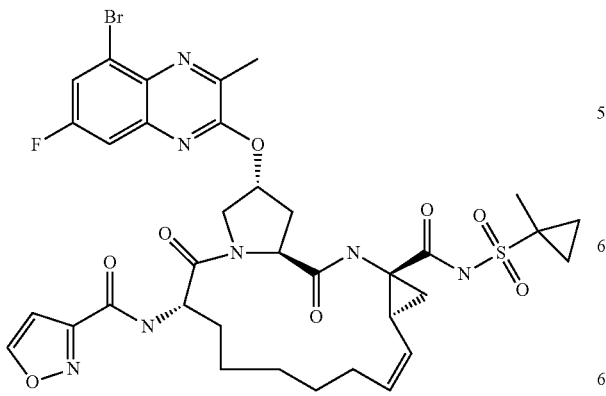

N-((2R,6S,13aS,14aR,16aS,Z)-2-(5-bromo-7-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide

Example 100a

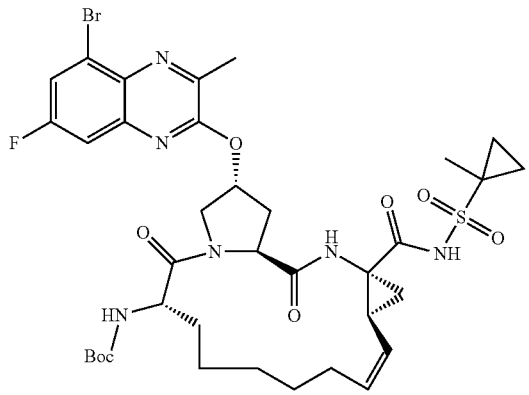 [SMILES: Cc1nc2c(Br)cc(F)cc2nc1O[C@@H]1C[C@H]2C(=O)N[C@]3(C(=O)NS(=O)(=O)C4(C)CC4)C[C@H]3/C=C\CCCCC[C@H](NC(=O)OC(C)(C)C)C(=O)N2C1]

tert-butyl (2R,6S,13aS,14aR,16aS,Z)-2-(5-bromo-7-fluoro-3-methylquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate The title compound 100a was prepared according to the procedures used for Example 97, replacing cyclopropanesulfonamide with 1-methylcyclopropane-1-sulfonamide. MS (ESI): m/z=823.0 [M+H].

Example 100

The title compound 100 was prepared according to the procedures used for Example 3, replacing the product of Example 1 with the product of Example 100a. MS (ESI): m/z=818.2 [M+H]. Example 100 provided an $EC_{50}$ of between 3-20 nM in a transient replicon assay with a D168E mutation in a 1a-H77 background, an $EC_{50}$ of <25 nM in a transient replicon assay with a D168V mutation in a 1a-H77 background, and an $EC_{50}$ of <1 nM in a transient replicon assay with a R155K mutation in a 1a-H77 background.

Example 101

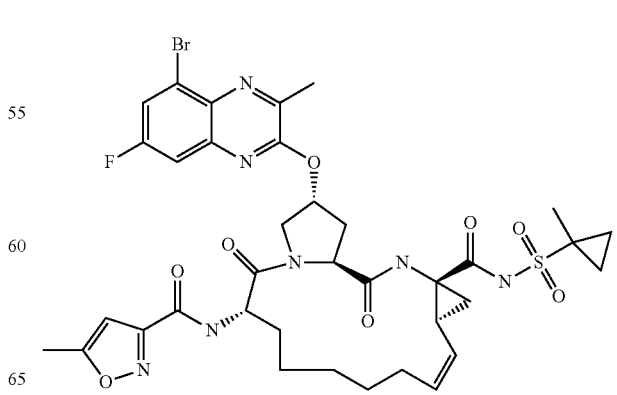

N-((2R,6S,13aS,14aR,16aS,Z)-2-(5-bromo-7-fluoro-
3-methylquinoxalin-2-yloxy)-14a-(1-methylcyclo-
propylsulfonylcarbamoyl)-5,16-dioxo-1,2,3,5,6,7,8,
9,10,11,13a,14,14a,15,16,16a-
hexadecahydrocyclopropa[e]pyrrolo[1,2-a][1,4]
diazacyclopentadecin-6-yl)-5-methylisoxazole-3-
carboxamide The title compound 101 was prepared according to the procedures used for Example 100, replacing isoxazole-3-carboxylic acid with 5-methylisoxazole-3-carboxylic acid. MS (ESI): m/z=832.1 [M+H].

Example 101 provided an $EC_{50}$ of between 3-20 nM in a transient replicon assay with a D168E mutation in a 1a-H77 background, an $EC_{50}$ of <25 nM in a transient replicon assay with a D168V mutation in a 1a-H77 background, and an $EC_{50}$ of <1 nM in a transient replicon assay with a R155K mutation in a 1a-H77 background. Example 101 also provided an AUC value of 84 μg*hr/mL when dosed with 3 mg/kg and F value of >100 in a dog PK experiment.

Example 102

N-((2R,6S,13aS,14aR,16aS,Z)-2-(5-bromo-7-fluoro-
3-methylquinoxalin-2-yloxy)-14a-(1-methylcyclo-
propylsulfonylcarbamoyl)-5,16-dioxo-1,2,3,5,6,7,8,
9,10,11,13a,14,14a,15,16,16a-
hexadecahydrocyclopropa[e]pyrrolo[1,2-a][1,4]
diazacyclopentadecin-6-yl)-4,5-dimethylisoxazole-3-
carboxamide The title compound 102 was prepared according to the procedures used for Example 100, replacing isoxazole-3-carboxylic acid with 4,5-dimethylisoxazole-3-carboxylic acid. MS (ESI): m/z=844.2 [M+H].

Example 102 provided an $EC_{50}$ of between 3-20 nM in a transient replicon assay with a D168E mutation in a 1a-H77 background, an $EC_{50}$ of <25 nM in a transient replicon assay with a D168V mutation in a 1a-H77 background, and an $EC_{50}$ of <1 nM in a transient replicon assay with a R155K mutation in a 1a-H77 background.

Example 103

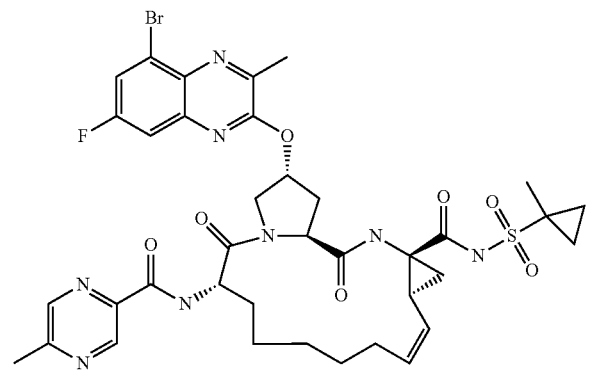 [SMILES: Cc1cnc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5cc(F)cc(Br)c5nc4C)CN3C2=O)cn1]

(2R,6S,13aS,14aR,16aS,Z)-2-(5-bromo-7-fluoro-3-
methylquinoxalin-2-yloxy)-N-(1-methylcyclopropyl-
sulfonyl)-6-(5-methylpyrazine-2-carboxamido)-5,16-
dioxo-1,2,3,5,6,7,8,9,10,11,13a,14,14a,15,16,16a-
hexadecahydrocyclopropa[e]pyrrolo[1,2-a][1,4]
diazacyclopentadecine-14a-carboxamide The title compound 103 was prepared according to the procedures used for Example 100, replacing isoxazole-3-carboxylic acid with 5-methylpyrazine-2 carboxylic acid. MS (ESI): m/z=841.2 [M+H].

Example 104

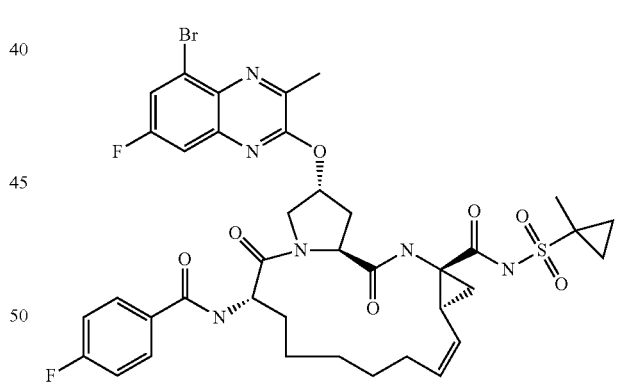

(2R,6S,13aS,14aR,16aS,Z)-2-(5-bromo-7-fluoro-3-
methylquinoxalin-2-yloxy)-6-(4-fluorobenzamido)-
N-(1-methylcyclopropylsulfonyl)-5,16-dioxo-1,2,3,
5,6,7,8,9,10,11,13a,14,14a,15,16,16a-
hexadecahydrocyclopropa[e]pyrrolo[1,2-a][1,4]
diazacyclopentadecine-14a-carboxamide The title compound 104 was prepared according to the procedures used for Example 100, replacing isoxazole-3-carboxylic acid with 4-fluorobenzoic acid. MS (ESI): m/z=845.2 [M+H].

Example 105

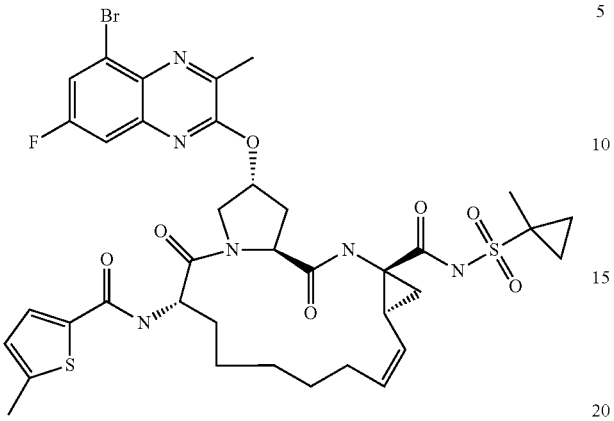

(2R,6S,13aS,14aR,16aS,Z)-2-(5-bromo-7-fluoro-3-methylquinoxalin-2-yloxy)-N-(1-methylcyclopropyl-sulfonyl)-6-(5-methylthiophene-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 105 was prepared according to the procedures used for Example 100, replacing isoxazole-3-carboxylic acid with 5-methylthiophene-2-carboxylic acid. MS (ESI): m/z=847.1 [M+H].

Example 106

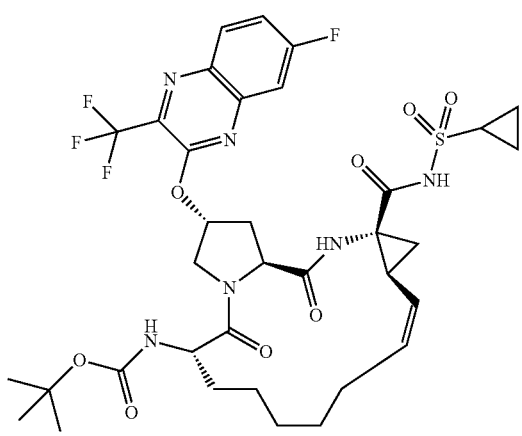

tert-butyl (2R,6S,13aS,14aR,16aS,Z)-14a-(cyclopropylsulfonylcarbamoyl)-2-(7-fluoro-3-(trifluoromethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

Example 106a

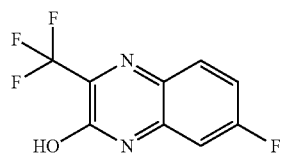

7-fluoro-3-(trifluoromethyl)quinoxalin-2-ol

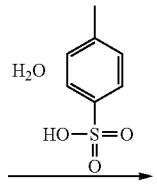

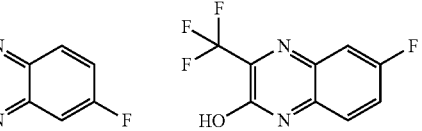

To a pressure tube was added 1,2-diamino-4-fluorobenzene (5.0567 g, 40.1 mmol) and p-toluenesulfonic acid (7.63 g, 40.1 mmol) followed by dichloroethane (40.1 ml). The suspension was stirred for a few minutes and ethyl trifluoropyruvate (5.11 ml, 42.1 mmol) was added. The tube was capped and the suspension was stirred at 80° C. and the solid dissolved. The stirring continued overnight and then the solution was cooled to rt, diluted with dichloromethane/dimethylformamide (4/1, 250 ml) and washed with NaHCO₃ (1 N, 2×100 ml) and water (100 ml). The combined aq. layers was back-extracted with dichloromethane/dimethylformamide (4/1, 2×50 ml). The combined organic layer was dried (anh. Na₂SO₄), filtered, and concentrated to give a dark mixture of solid and oil. This residue was diluted with dichloromethane and hexane and concentrated to give a solid (7 g). The ratio of isomers (6-F/7-F) was 2/1 based on ¹H NMR integration of the crude material. The solid was dissolved in acetone and silica gel (140 g) was added. The mixture was concentrated, and the solid mixture was loaded on a silica gel column. The column was eluted with ethyl acetate/hexane=1/6 to 1/3 and then the 6F-isomer was flushed out with ethyl acetate/hexane=2/1) to give the title compound 106a.

Example 106b

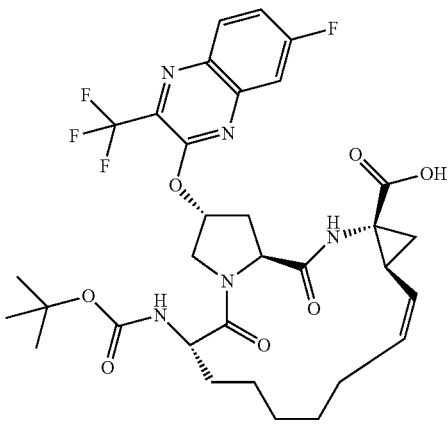 [SMILES: CC(C)(C)OC(=O)N[C@H]1CCCCC/C=C\[C@@H]2C[C@@]2(C(=O)O)NC(=O)[C@@H]2C[C@@H](Oc3nc4cc(F)ccc4nc3C(F)(F)F)CN2C1=O]

(2R,6S,13aS,14aR,16aS,Z)-6-(tert-butoxycarbonylamino)-2-(7-fluoro-3-(trifluoromethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid The title compound 106b was prepared similarly to the procedures used for Example 97d and 97e, replacing the product of Example 97c with the product of Example 106a. 10 eq. of trimethyltin hydroxide was used. The solution was refluxed at 90° C. for 72 hrs.

Example 106

The title compound 106 was prepared according to the procedures used for Example 1, replacing the product of Example 1c with the product of Example 106b. MS (ESI): m/z=783.0 [M+H] Example 106 provided an $EC_{50}$ of between 3-20 nM in a transient replicon assay with a D168E mutation in a 1a-H77 background, an $EC_{50}$ of between 50-250 nM in a transient replicon assay with a D168V mutation in a 1a-H77 background, and an $EC_{50}$ of <1 nM in a transient replicon assay with a R155K mutation in a 1a-H77 background.

Example 107

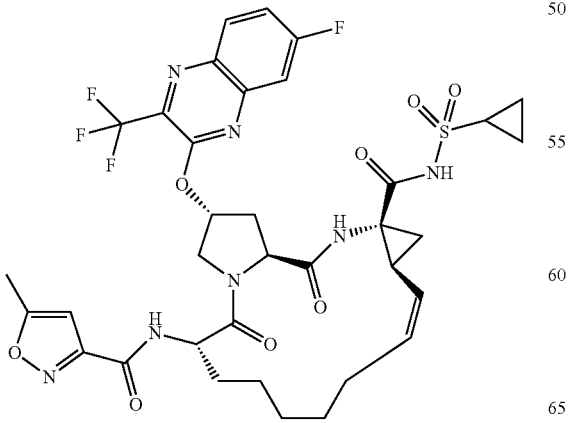

N-((2R,6S,13aS,14aR,16aS,Z)-14a-(cyclopropylsulfonylcarbamoyl)-2-(7-fluoro-3-(trifluoromethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide The title compound 107 was prepared according to the procedures used for Example 2, replacing the product of Example 1 with the product of Example 106. MS (ESI): m/z=792.1 [M+H]. Example 107 provided an $EC_{50}$ of <3 nM in a transient replicon assay with a D168E mutation in a 1a-H77 background, an $EC_{50}$ of <25 nM in a transient replicon assay with a D168V mutation in a 1a-H77 background, and an $EC_{50}$ of <1 nM in a transient replicon assay with a R155K mutation in a 1a-H77 background. Example 107 also provided an AUC value of 54 μg*hr/mL when dosed at 3 mg/kg and F value of 74 in a dog PK experiment.

Example 108

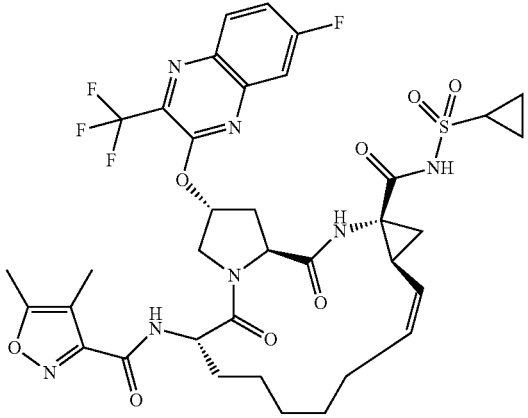 [SMILES: Cc1onc(C(=O)N[C@H]2CCCCC/C=C\[C@@H]3C[C@@]3(C(=O)NS(=O)(=O)C3CC3)NC(=O)[C@@H]3C[C@@H](Oc4nc5cc(F)ccc5nc4C(F)(F)F)CN3C2=O)c1C]

N-((2R,6S,13aS,14aR,16aS,Z)-2-(7-fluoro-3-(trifluoromethyl)quinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole-3-carboxamide The title compound 108 was prepared according to the procedures used for Example 107, replacing 5-methylisoxazole-3-carboxylic acid with 4,5-dimethylisoxazole-3-carboxylic acid. MS (ESI): m/z=836.9 [M+NH4].

Example 108 provided an $EC_{50}$ of <3 nM in a transient replicon assay with a D168E mutation in a 1a-H77 background, an $EC_{50}$ of <25 nM in a transient replicon assay with a D168V mutation in a 1a-H77 background, and an $EC_{50}$ of <1 nM in a transient replicon assay with a R155K mutation in a 1a-H77 background.

Example 109

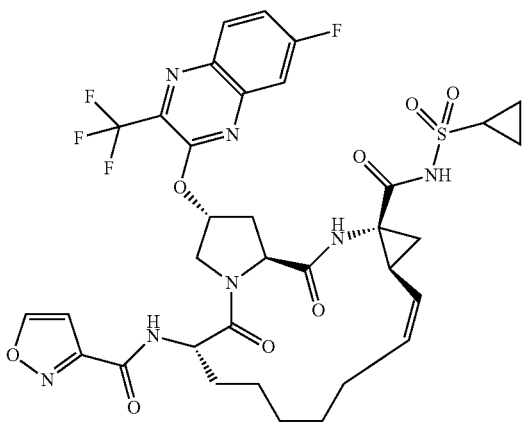 [SMILES: O=C(N[C@H]1CCCCC/C=C\[C@@H]2C[C@@]2(C(=O)NS(=O)(=O)C2CC2)NC(=O)[C@@H]2C[C@@H](Oc3nc4cc(F)ccc4nc3C(F)(F)F)CN2C1=O)c1ccon1]

N-((2R,6S,13aS,14aR,16aS,Z)-2-(7-fluoro-3-(trifluoromethyl)quinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 109 was prepared according to the procedures used for Example 107, replacing 5-methylisoxazole-3-carboxylic acid with isoxazole-3-carboxylic acid. MS (ESI): m/z=809.0 [M+NH4].

Example 109 provided an $EC_{50}$ of <3 nM in a transient replicon assay with a D168E mutation in a 1a-H77 background, an $EC_{50}$ of <25 nM in a transient replicon assay with a D168V mutation in a 1a-H77 background, and an $EC_{50}$ of <1 nM in a transient replicon assay with a R155K mutation in a 1a-H77 background.

Example 110

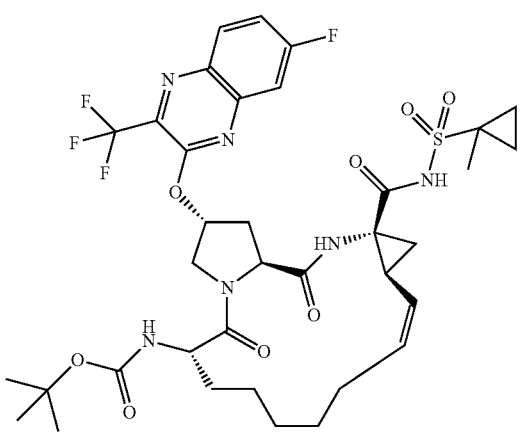 [SMILES: CC(C)(C)OC(=O)N[C@H]1CCCCC/C=C\[C@@H]2C[C@@]2(C(=O)NS(=O)(=O)C2(C)CC2)NC(=O)[C@@H]2C[C@@H](Oc3nc4cc(F)ccc4nc3C(F)(F)F)CN2C1=O]

tert-butyl (2R,6S,13aS,14aR,16aS,Z)-2-(7-fluoro-3-(trifluoromethyl)quinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate The title compound 110 was prepared according to the procedures used for Example 106, replacing the cyclopropanesulfonamide with 1-methylcyclopropane-1-sulfonamide. MS (ESI): m/z=814.0 [M+NH4].

Example 110 provided an $EC_{50}$ of between 3-20 nM in a transient replicon assay with a D168E mutation in a 1a-H77 background, an $EC_{50}$ of between 25-50 nM in a transient replicon assay with a D168V mutation in a 1a-H77 background, and an $EC_{50}$ of <1 nM in a transient replicon assay with a R155K mutation in a 1a-H77 background.

Example 111

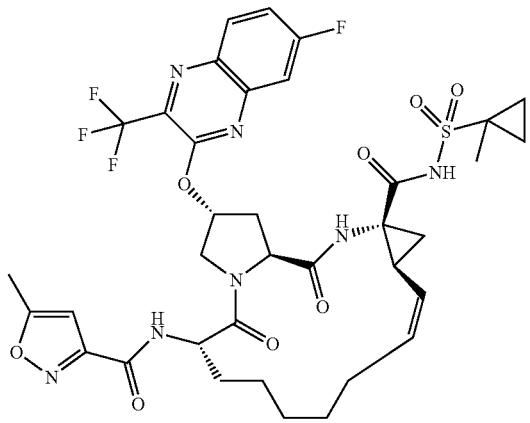 [SMILES: Cc1cc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5cc(F)ccc5nc4C(F)(F)F)CN3C2=O)no1]

N-((2R,6S,13aS,14aR,16aS,Z)-2-(7-fluoro-3-(trifluoromethyl)quinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide The title compound 111 was prepared according to the procedures used for Example 107, replacing the product of Example 1 with the product of Example 110. MS (ESI): m/z=823.0 [M+NH4].

Example 111 provided an $EC_{50}$ of <3 nM in a transient replicon assay with a D168E mutation in a 1a-H77 background, an $EC_{50}$ of <25 nM in a transient replicon assay with a D168V mutation in a 1a-H77 background, and an $EC_{50}$ of <1 nM in a transient replicon assay with a R155K mutation in a 1a-H77 background. Example 111 also provided an AUC value of 141 μg*hr/mL when dosed at 3 mg/kg and F value of 88 in a dog PK experiment.

Example 112

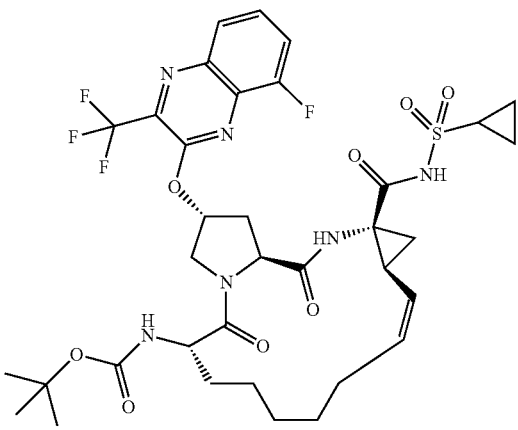 [SMILES: CC(C)(C)OC(=O)N[C@H]1CCCCC/C=C\[C@@H]2C[C@@]2(C(=O)NS(=O)(=O)C2CC2)NC(=O)[C@@H]2C[C@@H](Oc3nc4c(F)cccc4nc3C(F)(F)F)CN2C1=O]

tert-butyl (2R,6S,13aS,14aR,16aS,Z)-14a-(cyclopropylsulfonylcarbamoyl)-2-(8-fluoro-3-(trifluoromethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

Example 112a

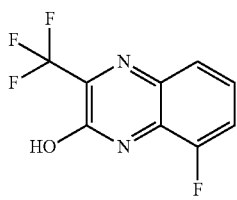 [SMILES: Oc1nc2c(F)cccc2nc1C(F)(F)F]

8-fluoro-3-(trifluoromethyl)quinoxalin-2-ol

To an ACE sealable tube was added 3-fluorobenzene-1,2-diamine (475.99 mg, 3.77 mmol), ethanol (5 ml) and ethyl trifluoropyruvate (0.500 ml, 3.77 mmol) at rt. The tube was sealed and placed in an oil bath at 90° C. The mixture was stirred at 90° C. for 3 hr, cooled to rt and the LC/MS showed starting diamines and three new peaks. More ethyl trifluoropyruvaate (0.2 ml) was added and the mixture was stirred at 90° C. overnight. The reaction mixture was cooled to rt and LC/MS showed no diamines, and two of the three new peaks remained. The reaction mixture was concentrated to give a dark solid, diluted with dichloromethane/dimethylformamide (3/1, 60 ml) and washed with HCl (1 N, 2×20 ml) and an aquious solution of sodium thiosulfate (0.1 M, 2×20 ml). The combined aq. layers were back-extracted with dichloromethane/dimethylformamide (3/1, 2×20 ml). The combined organic layers were washed with water and concentrated to give a dark solid (1.72 g). The solid was dissolved in acetone and silica gel (46 g) was added. The mixture was dried in vacuo, loaded on a silica gel column and purified by flash chromatography ($CH_3CN/CHCl_3$=1/8, 1/6 then 1/4) to give the title compound 112a (474.9 mg, 2.046 mmol, 54.2% yield).

Example 112

The title compound 112 was prepared according to the procedures used for Example 106, replacing the product of Example 106a with the product of Example 110a. MS (ESI): m/z=800.0 [M+NH$_4$].

Example 112 provided an $EC_{50}$ of between 3-20 nM in a transient replicon assay with a D168E mutation in a 1a-H77 background, an $EC_{50}$ of between 25-50 nM in a transient replicon assay with a D168V mutation in a 1a-H77 background, and an $EC_{50}$ of <1 nM in a transient replicon assay with a R155K mutation in a 1a-H77 background.

Example 113

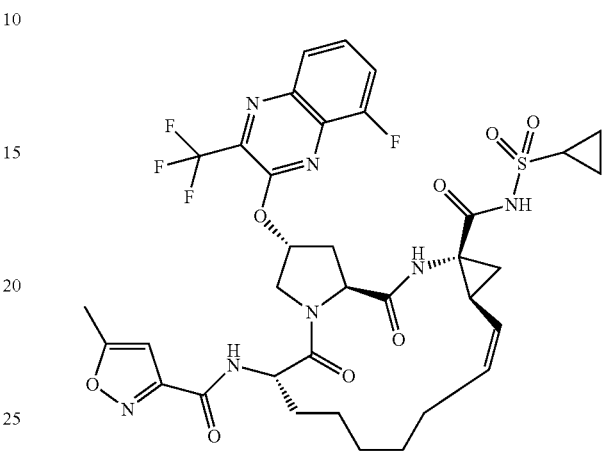

N-((2R,6S,13aS,14aR,16aS,Z)-14a-(cyclopropylsulfonylcarbamoyl)-2-(8-fluoro-3-(trifluoromethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide The title compound 113 was prepared according to the procedures used for Example 107, replacing the product of Example 106 with the product of Example 112. MS (ESI): m/z=809.0 [M+NH4].

Example 113 provided an $EC_{50}$ of <3 nM in a transient replicon assay with a D168E mutation in a 1a-H77 background, an $EC_{50}$ of <25 nM in a transient replicon assay with a D168V mutation in a 1a-H77 background, and an a $EC_{50}$ of <1 nM in a transient replicon assay with a R155K mutation in a 1a-H77 background.

Example 114

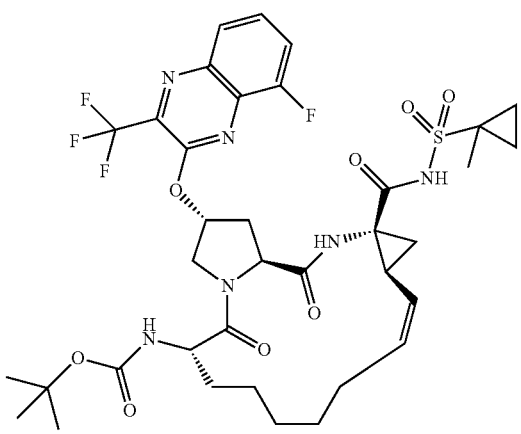 [SMILES: CC(C)(C)OC(=O)N[C@H]1CCCCC/C=C\[C@@H]2C[C@@]2(C(=O)NS(=O)(=O)C2(C)CC2)NC(=O)[C@@H]2C[C@@H](Oc3nc4c(F)cccc4nc3C(F)(F)F)CN2C1=O]

141 tert-butyl (2R,6S,13aS,14aR,16aS,Z)-2-(8-fluoro-3-(trifluoromethyl)quinoxalin-2-yloxy)-14a-(1-methyl-cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate The title compound 114 was prepared according to the procedures used for Example 112, replacing cyclopropanesulfonamide with 1-methylcyclopropane-1-sulfonamide. MS (ESI): m/z=814.0 [M+NH4].

Example 114 provided an EC$_{50}$ of between 3-20 nM in a transient replicon assay with a D168E mutation in a 1a-H77 background, an EC$_{50}$ of between 50-250 nM in a transient replicon assay with a D168V mutation in a 1a-H77 background, and an EC$_{50}$ of <1 nM in a transient replicon assay with a R155K mutation in a 1a-H77 background.

Example 115

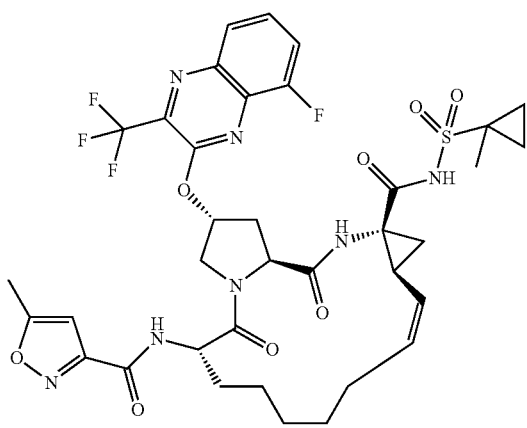 [SMILES: Cc1cc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5c(F)cccc5nc4C(F)(F)F)CN3C2=O)no1]

N-((2R,6S,13aS,14aR,16aS,Z)-2-(8-fluoro-3-(trifluoromethyl)quinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide The title compound 115 was prepared according to the procedures used for Example 113, replacing the product of Example 112 with the product of Example 114. MS (ESI): m/z=806.2 [M+H].

Example 115 provided an EC$_{50}$ of <3 nM in a transient replicon assay with a D168E mutation in a 1a-H77 background, an EC$_{50}$ of <25 nM in a transient replicon assay with a D168V mutation in a 1a-H77 background, and an EC$_{50}$ of <1 nM in a transient replicon assay with a R155K mutation in a 1a-H77 background.

Example 116

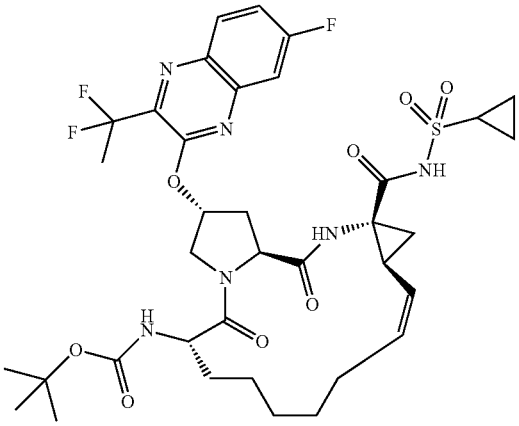 [SMILES: CC(C)(C)OC(=O)N[C@H]1CCCCC/C=C\[C@@H]2C[C@@]2(C(=O)NS(=O)(=O)C2CC2)NC(=O)[C@@H]2C[C@@H](Oc3nc4cc(F)ccc4nc3C(C)(F)F)CN2C1=O]

tert-butyl (2R,6S,13aS,14aR,16aS,Z)-14a-(cyclopropylsulfonylcarbamoyl)-2-(3-(1,1-difluoroethyl)-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate Example 116a

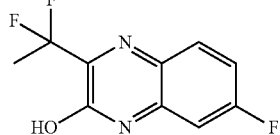

3-(1,1-difluoroethyl)-7-fluoroquinoxalin-2-ol

The title compound 116a was prepared according to the procedures used for Example 106a, replacing ethyl trifluoropyruvate with ethyl 3,3-difluoro-2-oxobutanoate.

Example 116

The title compound 116 was prepared according to the procedures used for Example 106, replacing the product of Example 106a with the product of Example 116a. MS (ESI): m/z=795.9 [M+NH4].

Example 116 provided an EC$_{50}$ of between 3-20 nM in a transient replicon assay with a D168E mutation in a 1a-H77 background, an EC$_{50}$ of between 25-50 nM in a transient replicon assay with a D168V mutation in a 1a-H77 background, and an EC$_{50}$ of <1 nM in a transient replicon assay with a R155K mutation in a 1a-H77 background.

Example 117

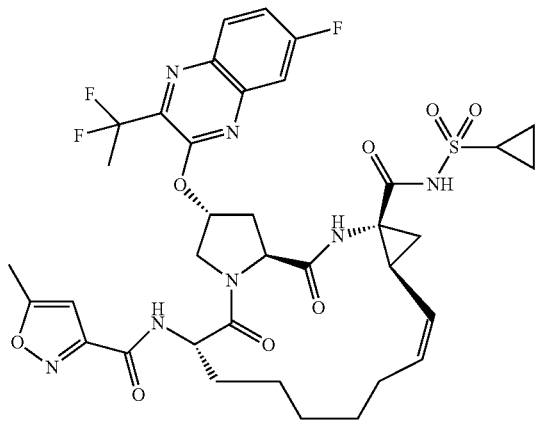 [SMILES: Cc1cc(C(=O)N[C@H]2CCCCC/C=C\[C@@H]3C[C@@]3(C(=O)NS(=O)(=O)C3CC3)NC(=O)[C@@H]3C[C@@H](Oc4nc5cc(F)ccc5nc4C(C)(F)F)CN3C2=O)no1]

N-((2R,6S,13aS,14aR,16aS,Z)-14a-(cyclopropylsulfonylcarbamoyl)-2-(3-(1,1-difluoroethyl)-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide The title compound 117 was prepared according to the procedures used for Example 107, replacing the product of Example 106 with the product of Example 116. MS (ESI): m/z=805.0 [M+NH4].

Example 117 provided an $EC_{50}$ of <3 nM in a transient replicon assay with a D168E mutation in a 1a-H77 background, an $EC_{50}$ of <25 nM in a transient replicon assay with a D168V mutation in a 1a-H77 background, and an $EC_{50}$ of <1 nM in a transient replicon assay with a R155K mutation in a 1a-H77 background. Example 117 also provided an AUC value of 63 μg*hr/mL when dosed at 3 mg/kg and F value of 63 in a dog PK experiment.

Example 118

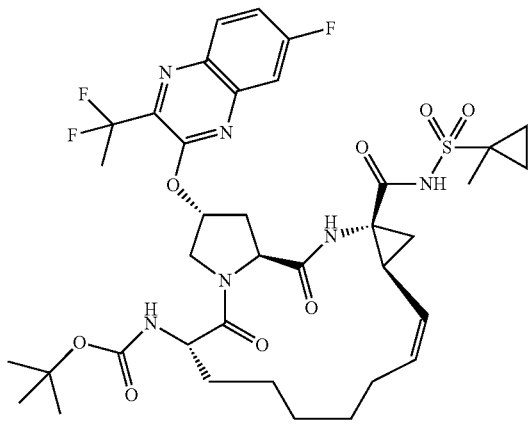 [SMILES: CC(C)(C)OC(=O)N[C@H]1CCCCC/C=C\[C@@H]2C[C@@]2(C(=O)NS(=O)(=O)C2(C)CC2)NC(=O)[C@@H]2C[C@@H](Oc3nc4cc(F)ccc4nc3C(C)(F)F)CN2C1=O]

tert-butyl (2R,6S,13aS,14aR,16aS,Z)-2-(3-(1,1-difluoroethyl)-7-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate The title compound 118 was prepared according to the procedures used for Example 110, replacing the product of Example 106a with the product of Example 116a. MS (ESI): m/z=909.9 [M+NH4].

Example 118 provided an $EC_{50}$ of >100 nM in a transient replicon assay with a D168E mutation in a 1a-H77 background, an $EC_{50}$ of between 250-1000 nM in a transient replicon assay with a D168V mutation in a 1a-H77 background, and an $EC_{50}$ of between 1-10 nM in a transient replicon assay with a R155K mutation in a 1a-H77 background.

Example 119

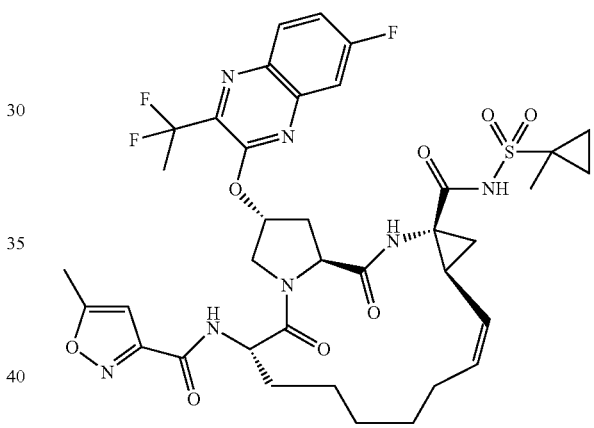

N-((2R,6S,13aS,14aR,16aS,Z)-2-(3-(1,1-difluoroethyl)-7-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide The title compound 119 was prepared according to the procedures used for Example 111, replacing the product of Example 110 with the product of Example 118. MS (ESI): m/z=802.2 [M+H].

Example 119 provided an $EC_{50}$ of <3 nM in a transient replicon assay with a D168E mutation in a 1a-H77 background, an $EC_{50}$ of <25 nM in a transient replicon assay with a D168V mutation in a 1a-H77 background, and an $EC_{50}$ of <1 nM in a transient replicon assay with a R155K mutation in a 1a-H77 background. Example 119 also provided an AUC value of 30 μg*hr/mL when dosed at 3 mg/kg and F value of 64 in a dog PK experiment.

Example 120

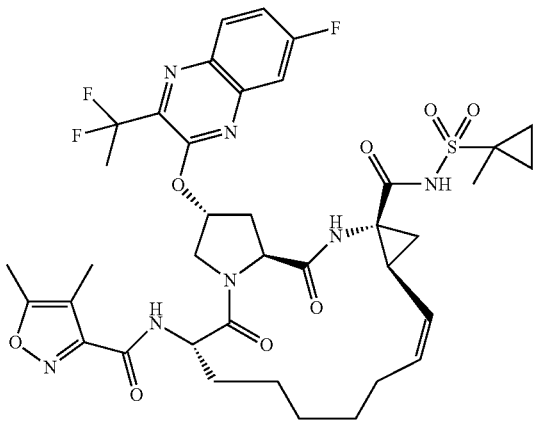 [SMILES: Cc1onc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5cc(F)ccc5nc4C(C)(F)F)CN3C2=O)c1C]

N-((2R,6S,13aS,14aR,16aS,Z)-2-(3-(1,1-difluoro-ethyl)-7-fluoroquinoxalin-2-yloxy)-14a-(1-methylcy-clopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-methylisoxazole-3-carboxamide The title compound 120 was prepared according to the procedures used for Example 119, replacing 5-methylisoxazole-3-carboxylic acid with 4,5-methylisoxazole-3-carboxylic acid. MS (ESI): m/z=816.3 [M+H].

Example 120 provided an $EC_{50}$ of <3 nM in a transient replicon assay with a D168E mutation in a 1a-H77 background, an $EC_{50}$ of <25 nM in a transient replicon assay with a D168V mutation in a 1a-H77 background, and an $EC_{50}$ of <1 nM in a transient replicon assay with a R155K mutation in a 1a-H77 background.

Example 121

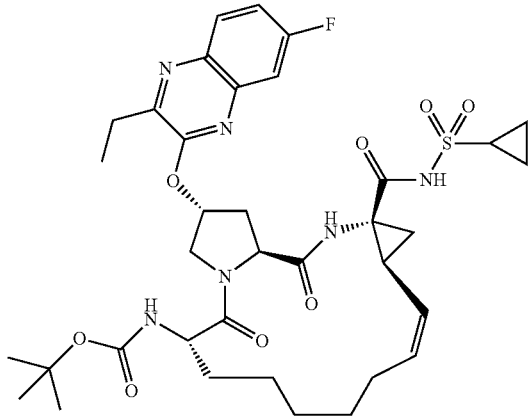 [SMILES: CCc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)OC(C)(C)C)C(=O)N2C1]

tert-butyl (2R,6S,13aS,14aR,16aS,Z)-14a-(cyclopropylsulfonylcarbamoyl)-2-(3-ethyl-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

Example 121a

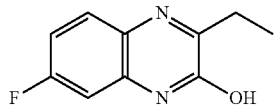

3-ethyl-7-fluoroquinoxalin-2-ol

The title compound 121a was prepared according to the procedures used for Examples 20a, Example 20b and Example 20c, replacing ethyl 2-aminopropanoate with methyl 2-aminobutanoate.

Example 121

The title compound 121 was prepared similarly to the procedures used for Example 20, replacing the product of Example 20c with the product of Example 121a. MS (ESI): m/z=743.1 [M+H]. Example 121 provided an $EC_{50}$ of between 3-20 nM in a transient replicon assay with a D168E mutation in a 1a-H77 background, an $EC_{50}$ of between 50-250 nM in a transient replicon assay with a D168V mutation in a 1a-H77 background, and an $EC_{50}$ of between 1-10 nM in a transient replicon assay with a R155K mutation in a 1a-H77 background.

Example 122

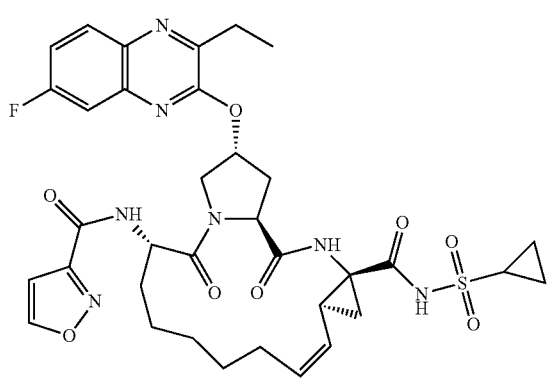 [SMILES: CCc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)c3ccon3)C(=O)N2C1]

N-((2R,6S,13aS,14aR,16aS,Z)-14a-(cyclopropylsulfonylcarbamoyl)-2-(3-ethyl-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 122 was prepared similarly to the procedures used for Example 3, replacing the product of Example 1 with the product of Example 121. MS (ESI): m/z=738.8 [M+H].

Example 122 provided an $EC_{50}$ of between 20-50 nM in a transient replicon assay with a D168E mutation in a 1a-H77 background, an $EC_{50}$ of between 250-1000 nM in a transient replicon assay with a D168V mutation in a 1a-H77 background, and an $EC_{50}$ of between 1-10 nM in a transient replicon assay with a R155K mutation in a 1a-H77 background.

Example 123

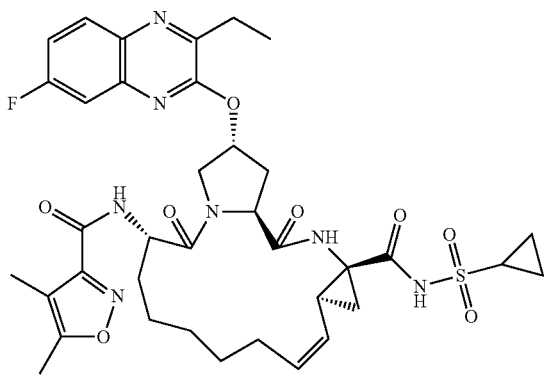 [SMILES: CCc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)c3noc(C)c3C)C(=O)N2C1]

N-((2R,6S,13aS,14aR,16aS,Z)-14a-(cyclopropylsulfonylcarbamoyl)-2-(3-ethyl-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole-3-carboxamide The title compound 123 was prepared according to the procedures used for Example 122, replacing isoxazole-3-carboxylic acid with 4,5-methylisoxazole-3-carboxylic acid. MS (ESI): m/z=766.6 [M+H].

Example 123 provided an $EC_{50}$ of between 3-20 nM in a transient replicon assay with a D168E mutation in a 1a-H77 background, an $EC_{50}$ of between 50-250 nM in a transient replicon assay with a D168V mutation in a 1a-H77 background, and an $EC_{50}$ of between 1-10 nM in a transient replicon assay with a R155K mutation in a 1a-H77 background.

Example 124

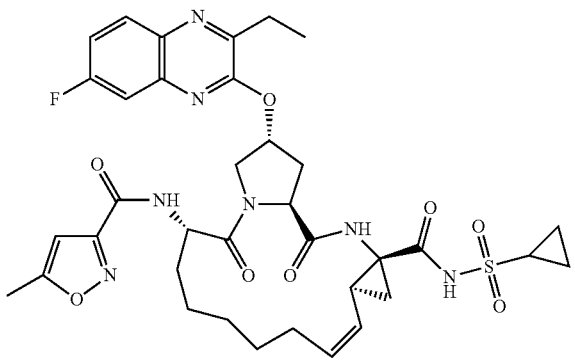 [SMILES: CCc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)c3cc(C)on3)C(=O)N2C1]

N-((2R,6S,13aS,14aR,16aS,Z)-14a-(cyclopropylsulfonylcarbamoyl)-2-(3-ethyl-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide The title compound 124 was prepared according to the procedures used for Example 122, replacing isoxazole-3-carboxylic acid with 5-methylisoxazole-3-carboxylic acid. MS (ESI): m/z=752.9 [M+H].

Example 124 provided an $EC_{50}$ of between 20-50 nM in a transient replicon assay with a D168E mutation in a 1a-H77 background, an $EC_{50}$ of between 50-250 nM in a transient replicon assay with a D168V mutation in a 1a-H77 background, and an $EC_{50}$ of between 1-10 nM in a transient replicon assay with a R155K mutation in a 1a-H77 background.

Example 125

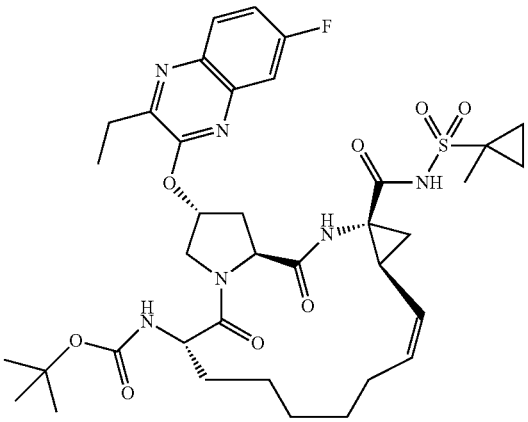 [SMILES: CCc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](NC(=O)OC(C)(C)C)C(=O)N2C1]

tert-butyl (2R,6S,13aS,14aR,16aS,Z)-2-(3-ethyl-7-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate The title compound 125 was prepared according to the procedures used for Example 121, replacing cyclopropanesulfonamide with 1-methylcyclopropane-1-sulfonamide. MS (ESI): m/z=757.1 [M+H].

Example 125 provided an $EC_{50}$ of between 3-20 nM in a transient replicon assay with a D168E mutation in a 1a-H77 background, an $EC_{50}$ of between 25-50 nM in a transient replicon assay with a D168V mutation in a 1a-H77 background, and an $EC_{50}$ of <1 nM in a transient replicon assay with a R155K mutation in a 1a-H77 background.

Example 126

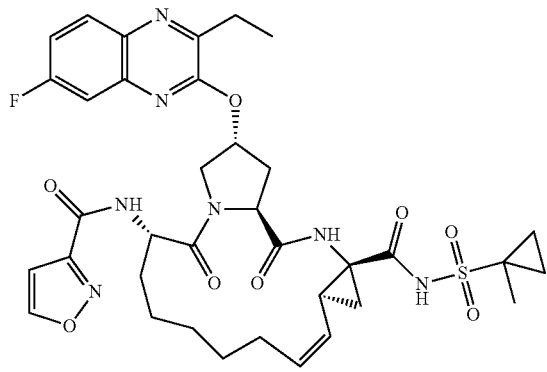 [SMILES: CCc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](NC(=O)c3ccon3)C(=O)N2C1]

N-((2R,6S,13aS,14aR,16aS,Z)-2-(3-ethyl-7-fluoro-quinoxalin-2-yloxy)-14a-(1-methylcyclopropylsulfo-nylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 126 was prepared similarly to the procedures used for Example 3, replacing the product of Example 1 with the product of Example 125. MS (ESI): m/z=752.2 [M+H].

Example 127

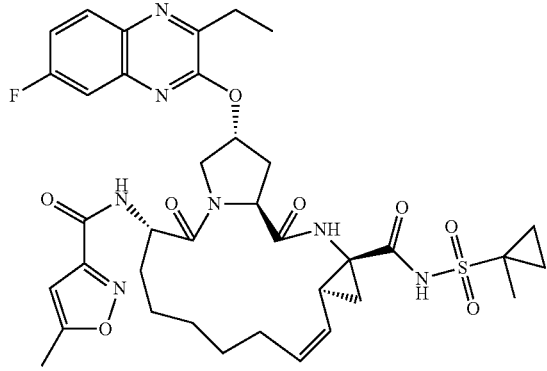 [SMILES: CCc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](NC(=O)c3cc(C)on3)C(=O)N2C1]

N-((2R,6S,13aS,14aR,16aS,Z)-2-(3-ethyl-7-fluoro-quinoxalin-2-yloxy)-14a-(1-methylcyclopropylsulfo-nylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide The title compound 127 was prepared according to the procedures used for Example 126, replacing isoxazole-3-carboxylic acid with 5-methylisoxazole-3-carboxylic acid. MS (ESI): m/z=766.2 [M+H].

Example 128

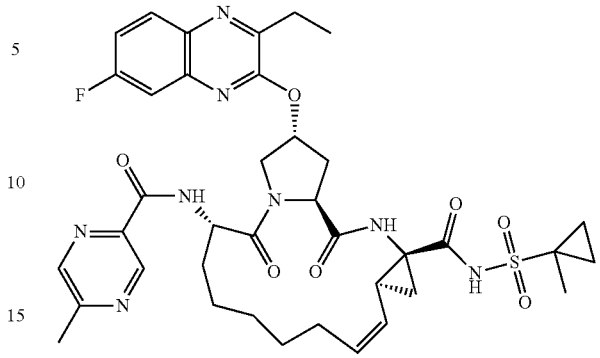

(2R,6S,13aS,14aR,16aS,Z)-2-(3-ethyl-7-fluoroqui-noxalin-2-yloxy)-N-(1-methylcyclopropylsulfonyl)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 128 was prepared according to the procedures used for Example 126, replacing isoxazole-3-carboxylic acid with 5-methylpyrazine-2-carboxylic acid. MS (ESI): m/z=777.2 [M+H].

Example 129-146

Example 129a

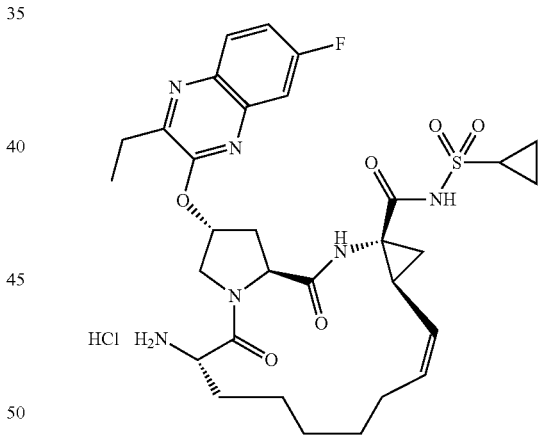

(2R,6S,13aS,14aR,16aS,Z)-6-amino-N-(cyclopro-pylsulfonyl)-2-(3-ethyl-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide, Hydrochloric Acid The title compound 129a was prepared according to the procedure used for Example 2a, replacing the product of Example 1 with the product of Example 121.

General Procedures for Example 129-146

To a solution of 129a (14 mg, 0.02 mmol) in DMA in a 4 ml vial was added the acid monomer (0.025 mmol)

dissolved in DMA followed by a solution of HATU (0.025 mmol) in DMA and then triethylamine (0.4 mmol) neat. The vial was capped and microwaved at 150° C. for 30 minutes. The reaction was checked by LC/MS and concentrated to dryness. The residue was dissolved in MeOH:DMSO (1:1 v:v, 1.5 ml) and purified by reverse phase HPLC.

HPLC condition: Samples were purified by preparative HPLC on a Phenomenex Luna C8(2) 5 um 100 Å AXIA column (30 mm×75 mm). A gradient of methanol (A) and 0.1% trifluoroacetic acid in water (B) was used, at a flow rate of 50 mL/min (0-0.5 min 20% A, 0.5-6.0 min linear gradient 20-100% A, 6.0-7.0 min 100% A, 7.0-8.0 min linear gradient 100-10% A).

Example 129

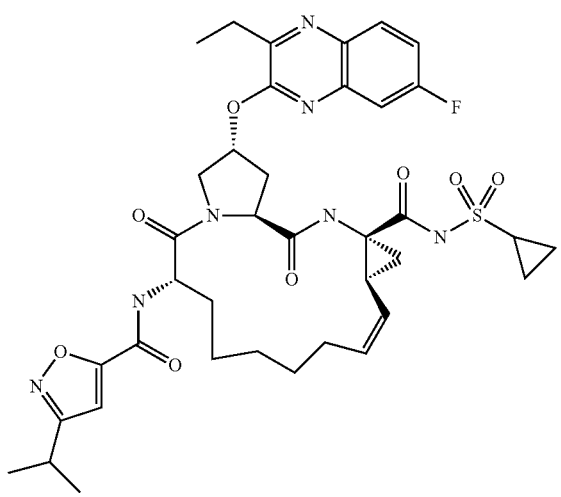 [SMILES: CCc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)c3cc(C(C)C)no3)C(=O)N2C1]

N-((2R,6S,13aS,14aR,16aS,Z)-14a-(cyclopropylsulfonylcarbamoyl)-2-(3-ethyl-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-3-isopropylisoxazole-5-carboxamide The title compound 129 was prepared according to the general procedure used for Example 129-146 using 3-isopropylisoxazole-5-carboxylic acid as the acid monomer. MS (ESI): m/z=780.6 [M+H].

Example 130

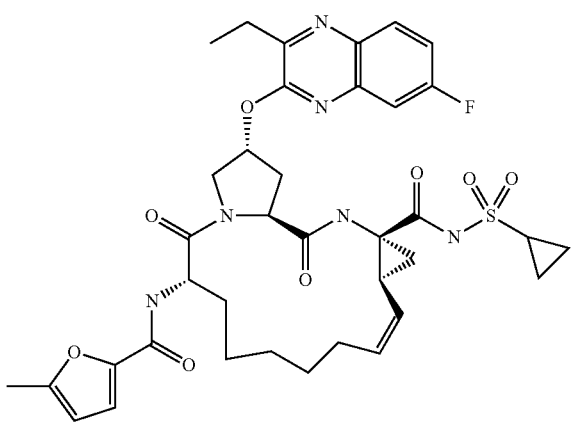

(2R,6S,13aS,14aR,16aS,Z)—N-(cyclopropylsulfonyl)-2-(3-ethyl-7-fluoroquinoxalin-2-yloxy)-6-(5-methylfuran-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 130 was prepared according to the general procedure used for Example 129-146, using 5-methylfuran-2-carboxylic acid as the acid monomer. MS (ESI): m/z=751.2 [M+H].

Example 131

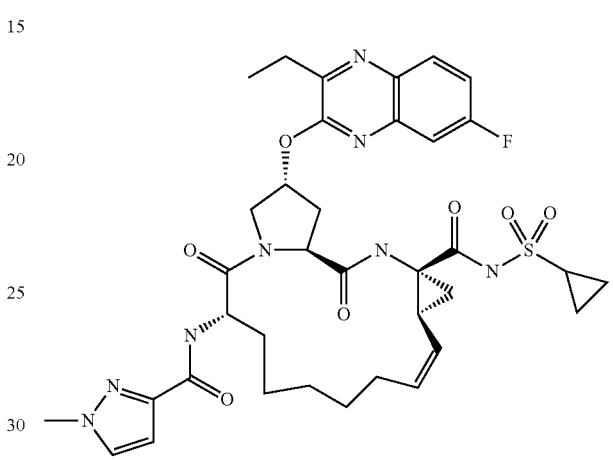

(2R,6S,13aS,14aR,16aS,Z)—N-(cyclopropylsulfonyl)-2-(3-ethyl-7-fluoroquinoxalin-2-yloxy)-6-(1-methyl-1H-pyrazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 131 was prepared according to the general procedure used for Example 129-146, using 1-methyl-1H-pyrazole-3-carboxylic acid as the acid monomer. MS (ESI): m/z=751.2 [M+H].

Example 132

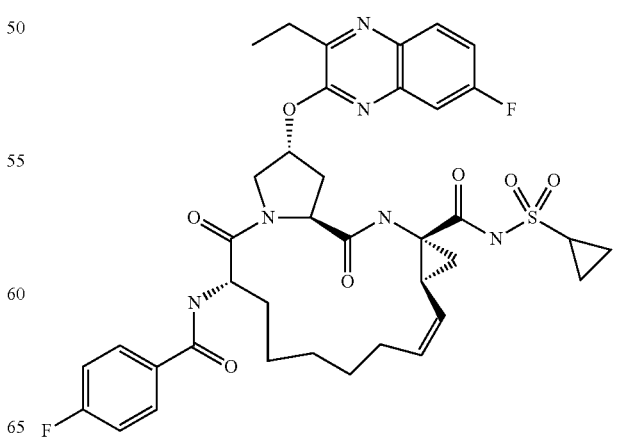

(2R,6S,13aS,14aR,16aS,Z)—N-(cyclopropylsulfonyl)-2-(3-ethyl-7-fluoroquinoxalin-2-yloxy)-6-(4-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 132 was prepared according to the general procedure used for Example 129-146, using 4-fluorobenzoic acid as the acid monomer. MS (ESI): m/z=765.2 [M+H].

Example 133

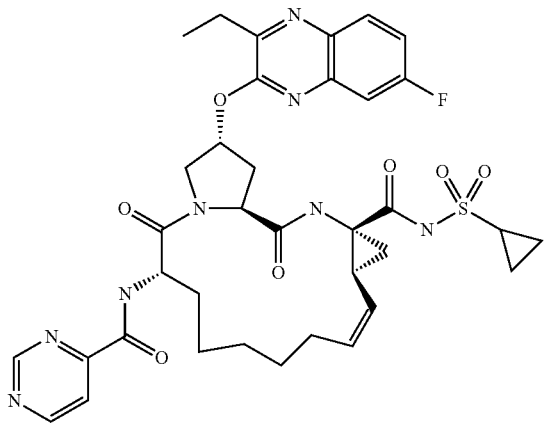 [SMILES: CCc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)c3ccncn3)C(=O)N2C1]

(2R,6S,13aS,14aR,16aS,Z)—N-(cyclopropylsulfonyl)-2-(3-ethyl-7-fluoroquinoxalin-2-yloxy)-5,16-dioxo-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 133 was prepared according to the general procedure used for Example 129-146, using pyrimidine-4-carboxylic acid as the acid monomer. MS (ESI): m/z=749.2 [M+H].

Example 134

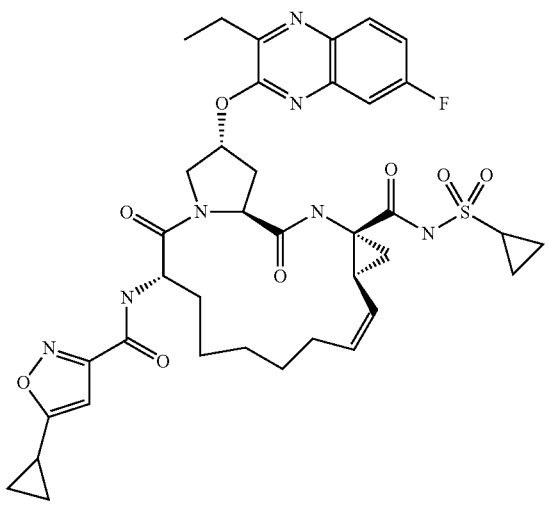 [SMILES: CCc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)c3cc(C4CC4)on3)C(=O)N2C1]

5-cyclopropyl-N-((2R,6S,13aS,14aR,16aS,Z)-14a-(cyclopropylsulfonylcarbamoyl)-2-(3-ethyl-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 134 was prepared according to the general procedure used for Example 129-146, using 5-cyclopropylisoxazole-3-carboxylic acid as the acid monomer. MS (ESI): m/z=778.2 [M+H].

Example 135

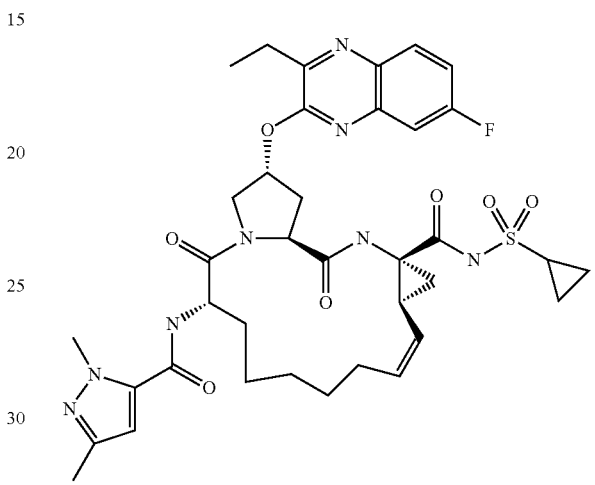

(2R,6S,13aS,14aR,16aS,Z)—N-(cyclopropylsulfonyl)-6-(1,3-dimethyl-1H-pyrazole-5-carboxamido)-2-(3-ethyl-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 135 was prepared according to the general procedure used for Example 129-146, using 1,3-dimethyl-1H-pyrazole-5-carboxylic acid as the acid monomer. MS (ESI): m/z=765.2 [M+H].

Example 136

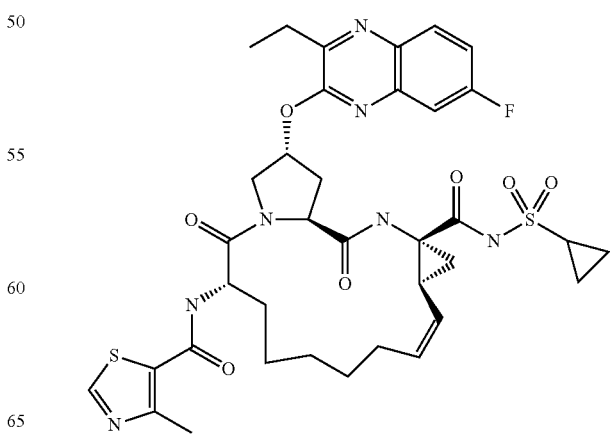

N-((2R,6S,13aS,14aR,16aS,Z)-14a-(cyclopropylsulfonylcarbamoyl)-2-(3-ethyl-7-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4-methylthiazole-5-carboxamide The title compound 136 was prepared according to the general procedure used for Example 129-146, using 4-methylthiazole-5-carboxylic acid as the acid monomer. MS (ESI): m/z=768.2 [M+H].

Example 137

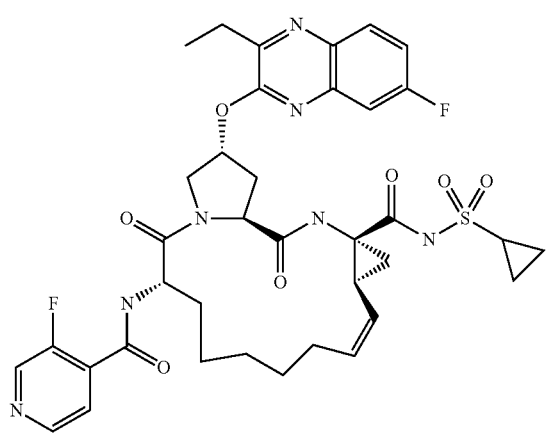 [SMILES: CCc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)c3ccncc3F)C(=O)N2C1]

(2R,6S,13aS,14aR,16aS,Z)—N-(cyclopropylsulfonyl)-2-(3-ethyl-7-fluoroquinoxalin-2-yloxy)-6-(3-fluoroisonicotinamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 137 was prepared according to the general procedure used for Example 129-146, using 3-fluoroisonicotinic acid as the acid monomer. MS (ESI): m/z=766.2 [M+H].

Example 138

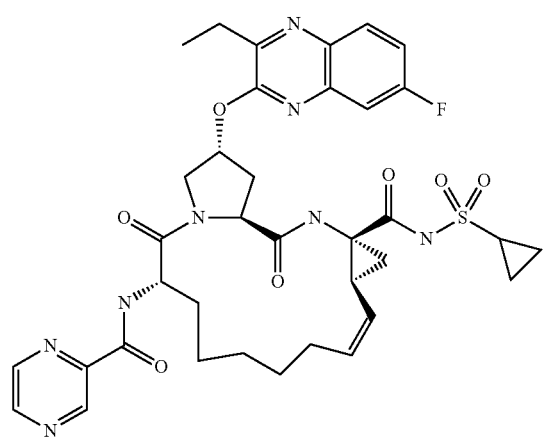 [SMILES: CCc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)c3cnccn3)C(=O)N2C1]

(2R,6S,13aS,14aR,16aS,Z)—N-(cyclopropylsulfonyl)-2-(3-ethyl-7-fluoroquinoxalin-2-yloxy)-5,16-dioxo-6-(pyrazine-2-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 138 was prepared according to the general procedure used for Example 129-146, using pyrazine-2-carboxylic acid as the acid monomer. MS (ESI): m/z=749.2 [M+H].

Example 139

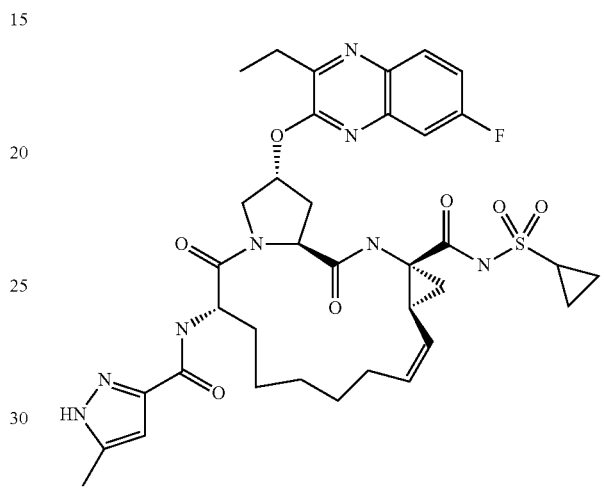

(2R,6S,13aS,14aR,16aS,Z)—N-(cyclopropylsulfonyl)-2-(3-ethyl-7-fluoroquinoxalin-2-yloxy)-6-(5-methyl-1H-pyrazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 139 was prepared according to the general procedure used for Example 129-146, using 5-methyl-1H-pyrazole-3-carboxylic acid as the acid monomer. MS (ESI): m/z=751.3 [M+H].

Example 140

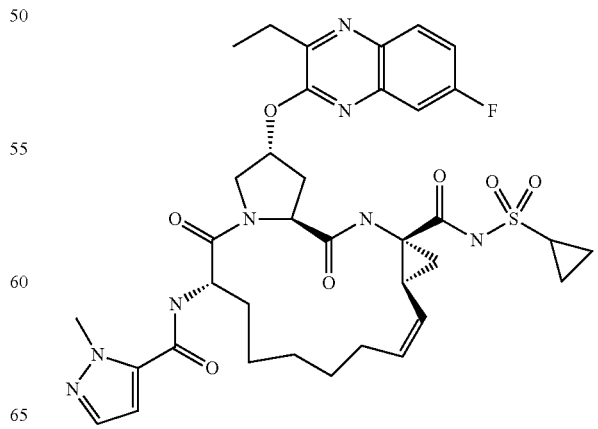

(2R,6S,13aS,14aR,16aS,Z)—N-(cyclopropylsulfonyl)-2-(3-ethyl-7-fluoroquinoxalin-2-yloxy)-6-(1-methyl-1H-pyrazole-5-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 140 was prepared according to the general procedure used for Example 129-146, using 1-methyl-1H-pyrazole-5-carboxylic acid as the acid monomer. MS (ESI): m/z=751.2 [M+H].

Example 141

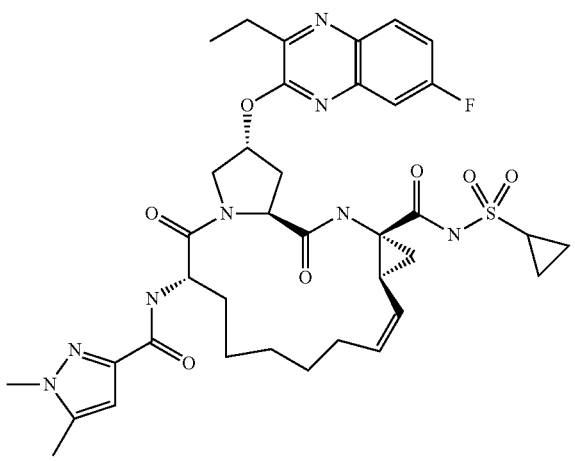 [SMILES: CCc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)c3cc(C)n(C)n3)C(=O)N2C1]

(2R,6S,13aS,14aR,16aS,Z)-6-(1,5-dimethyl-1H-pyrazole-3-carboxamido)-2-(3-ethyl-7-fluoroquinoxalin-2-yloxy)-N-(cyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 141 was prepared according to the general procedure used for Example 129-146, using 1,5-dimethyl-1H-pyrazole-3-carboxylic acid as the acid monomer. MS (ESI): m/z=765.2 [M+H].

Example 142

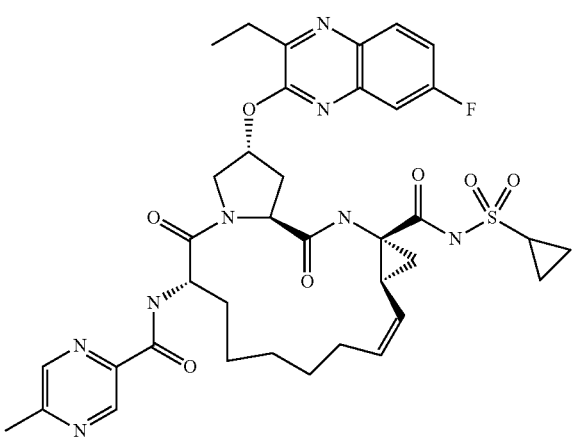 [SMILES: CCc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)c3cnc(C)cn3)C(=O)N2C1]

(2R,6S,13aS,14aR,16aS,Z)—N-(cyclopropylsulfonyl)-2-(3-ethyl-7-fluoroquinoxalin-2-yloxy)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 142 was prepared according to the general procedure used for Example 129-146, using 5-methylpyrazine-2-carboxylic acid as the acid monomer. MS (ESI): m/z=763.2 [M+H].

Example 143

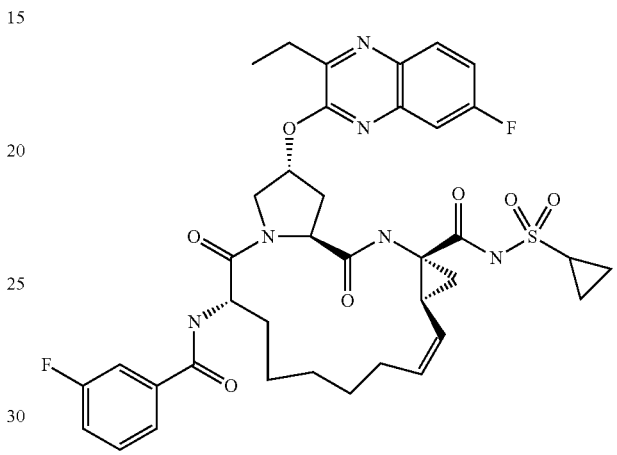

(2R,6S,13aS,14aR,16aS,Z)—N-(cyclopropylsulfonyl)-2-(3-ethyl-7-fluoroquinoxalin-2-yloxy)-6-(3-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 143 was prepared according to the general procedure used for Example 129-146, using 3-fluorobenzoic acid as the acid monomer. MS (ESI): m/z=765.2 [M+H].

Example 144

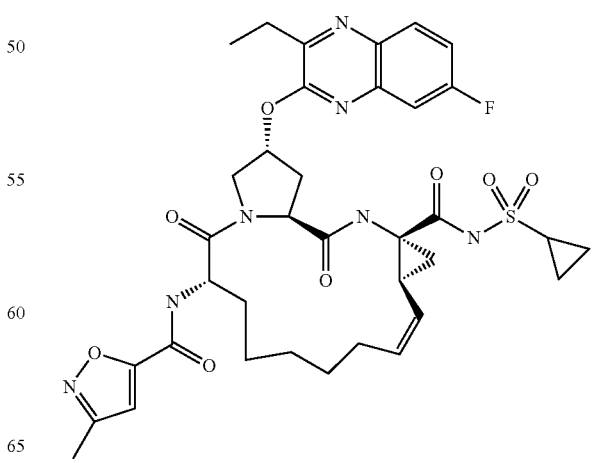

N-((2R,6S,13aS,14aR,16aS,Z)-2-(3-ethyl-7-fluoro-quinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-3-methylisoxazole-5-carboxamide The title compound 144 was prepared according to the general procedure used for Example 129-146, using 3-methylisoxazole-5-carboxylic acid as the acid monomer. MS (ESI): m/z=752.2 [M+H].

Example 145

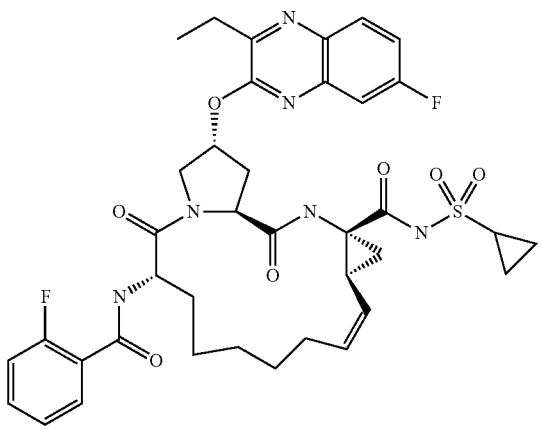 [SMILES: CCc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)c3ccccc3F)C(=O)N2C1]

(2R,6S,13aS,14aR,16aS,Z)—N-(cyclopropylsulfonyl)-2-(3-ethyl-7-fluoroquinoxalin-2-yloxy)-6-(2-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 145 was prepared according to the general procedure used for Example 129-146, using 2-fluorobenzoic acid as the acid monomer. MS (ESI): m/z=765.2 [M+H].

Example 146

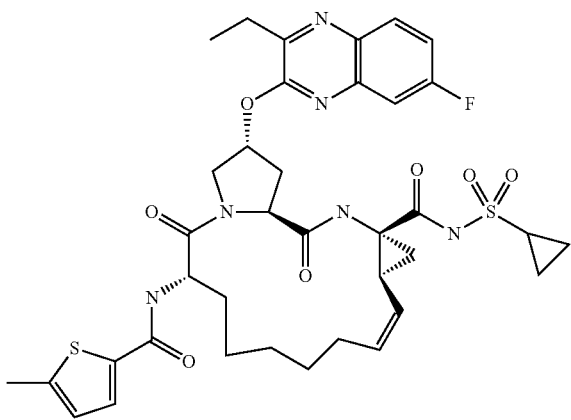 [SMILES: CCc1nc2ccc(F)cc2nc1O[C@@H]1C[C@H]2C(=O)N[C@]3(C(=O)NS(=O)(=O)C4CC4)C[C@H]3/C=C\CCCCC[C@H](NC(=O)c3ccc(C)s3)C(=O)N2C1]

(2R,6S,13aS,14aR,16aS,Z)-2-(3-ethyl-7-fluoroquinoxalin-2-yloxy)-N-(cyclopropylsulfonyl)-6-(5-methylthiophene-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 146 was prepared according to the general procedure used for Example 129-146, using 5-methylthiophene-2-carboxylic acid as the acid monomer. MS (ESI): m/z=767.2 [M+H].

Example 147-159

Example 147a

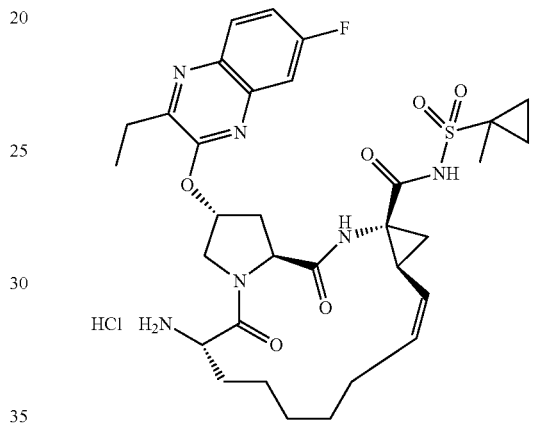

(2R,6S,13aS,14aR,16aS,Z)-6-amino-2-(3-ethyl-7-fluoroquinoxalin-2-yloxy)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide, Hydrochloric Acid The title compound 147a was prepared according to the procedure used for Example 129a, replacing the product of Example 121 with the product of Example 125.

General Procedures for Example 147-159

To a solution of 147a (13 mg, 0.02 mmol) in DMA in a 4 ml vial was added the acid monomer (0.025 mmol) dissolved in DMA followed by a solution of HATU (0.025 mmol) in DMA and then triethylamine (0.4 mmol) neat. The vial was capped and microwaved at 150° C. for 30 minutes. The reaction was checked by LC/MS and concentrated to dryness. The residue was dissolved in MeOH:DMSO (1:1 v:v, 1.5 ml) and purified by reverse phase HPLC.

HPLC condition: Samples were purified by preparative HPLC on a Phenomenex Luna C8(2) 5 um 100 Å AXIA column (30 mm×75 mm). A gradient of methanol (A) and 0.1% trifluoroacetic acid in water (B) was used, at a flow rate of 50 mL/min (0-0.5 min 20% A, 0.5-6.0 min linear gradient 20-100% A, 6.0-7.0 min 100% A, 7.0-8.0 min linear gradient 100-10% A).

Example 147

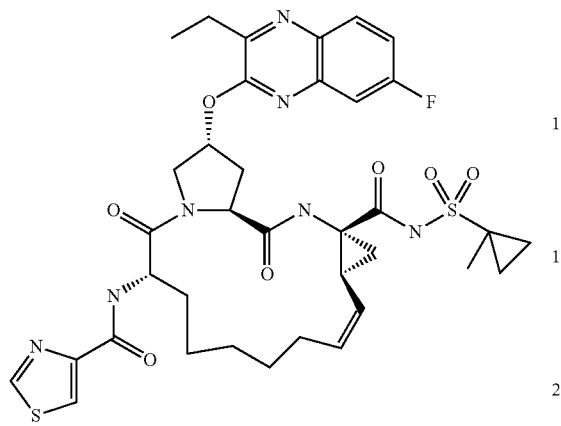

N-((2R,6S,13aS,14aR,16aS,Z)-2-(3-ethyl-7-fluoro-
quinoxalin-2-yloxy)-14a-(1-methylcyclopropylsulfo-
nylcarbamoyl)-5,16-dioxo-1,2,3,5,6,7,8,9,10,11,13a,
14,14a,15,16,16a-hexadecahydrocyclopropa[e]
pyrrolo[1,2-a][1,4]diazacyclopentadecin-6-yl)
thiazole-4-carboxamide The title compound 147 was prepared according to the general procedure used for Example 147-159, using thiazole-4-carboxylic acid as the acid monomer. MS (ESI): m/z=768.2 [M+H].

Example 148

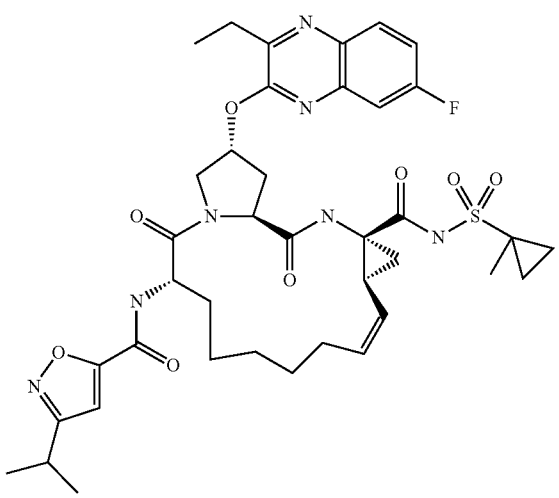 [SMILES: CCc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](NC(=O)c3cc(C(C)C)no3)C(=O)N2C1]

N-((2R,6S,13aS,14aR,16aS,Z)-2-(3-ethyl-7-fluoro-
quinoxalin-2-yloxy)-14a-(1-methylcyclopropylsulfo-
nylcarbamoyl)-5,16-dioxo-1,2,3,5,6,7,8,9,10,11,13a,
14,14a,15,16,16a-hexadecahydrocyclopropa[e]
pyrrolo[1,2-a][1,4]diazacyclopentadecin-6-yl)-3-
isopropylisoxazole-5-carboxamide The title compound 148 was prepared according to the general procedure used for Example 147-159, using 3-isopropylisoxazole-5-carboxylic acid as the acid monomer. MS (ESI): m/z=794.2 [M+H].

Example 149

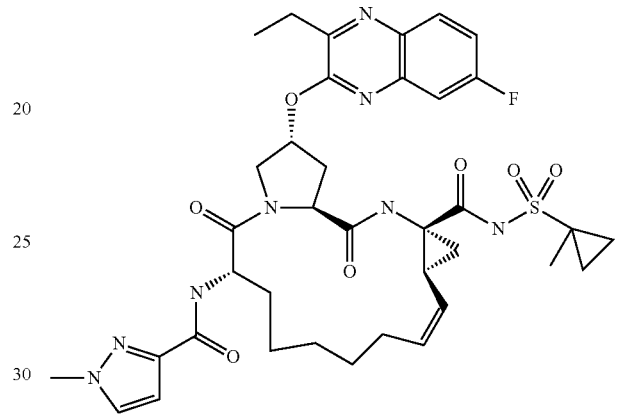

(2R,6S,13aS,14aR,16aS,Z)-2-(3-ethyl-7-fluoroqui-
noxalin-2-yloxy)-6-(1-methyl-1H-pyrazole-3-car-
boxamido)-N-(1-methylcyclopropylsulfonyl)-5,16-
dioxo-1,2,3,5,6,7,8,9,10,11,13a,14,14a,15,16,16a-
hexadecahydrocyclopropa[e]pyrrolo[1,2-a][1,4]
diazacyclopentadecine-14a-carboxamide The title compound 149w as prepared according to the general procedure used for Example 147-159, using 1-methyl-1H-pyrazole-3-carboxylic acid as the acid monomer. MS (ESI): m/z=765.2 [M+H].

Example 150

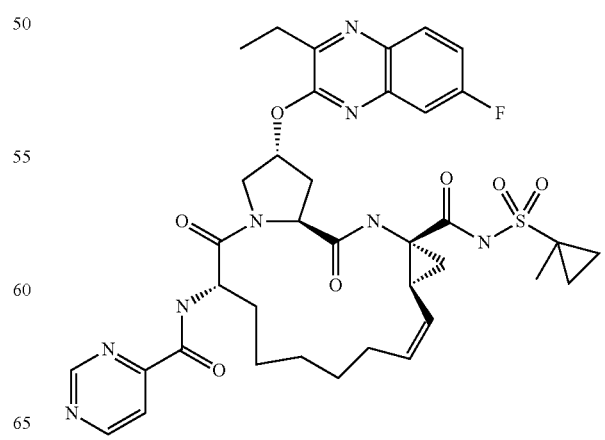

(2R,6S,13aS,14aR,16aS,Z)-2-(3-ethyl-7-fluoroqui-
noxalin-2-yloxy)-N-(1-methylcyclopropylsulfonyl)-
5,16-dioxo-6-(pyrimidine-4-carboxamido)-1,2,3,5,6,
7,8,9,10,11,13a,14,14a,15,16,16a-
hexadecahydrocyclopropa[e]pyrrolo[1,2-a][1,4]
diazacyclopentadecine-14a-carboxamide The title compound 150 was prepared according to the general procedure used for Example 147-159, using pyrimidine-4-carboxylic acid as the acid monomer. MS (ESI): m/z=763.3 [M+H].

Example 151

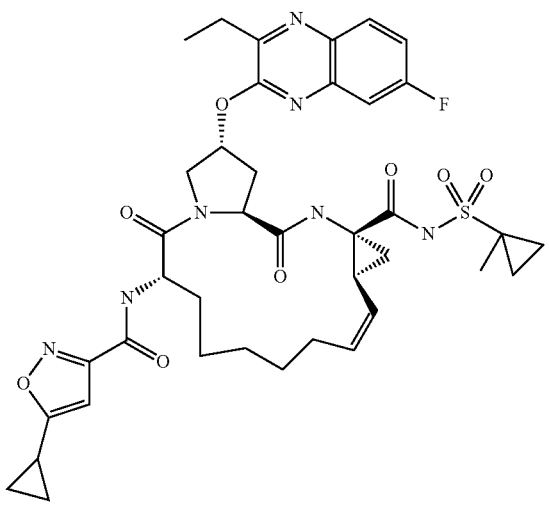 [SMILES: CCc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](NC(=O)c3cc(C4CC4)on3)C(=O)N2C1]

5-cyclopropyl-N-((2R,6S,13aS,14aR,16aS,Z)-2-(3-
ethyl-7-fluoroquinoxalin-2-yloxy)-14a-(1-methylcy-
clopropylsulfonylcarbamoyl)-5,16-dioxo-1,2,3,5,6,7,
8,9,10,11,13a,14,14a,15,16,16a-
hexadecahydrocyclopropa[e]pyrrolo[1,2-a][1,4]
diazacyclopentadecin-6-yl)isoxazole-3-carboxamide The title compound 151 was prepared according to the general procedure used for Example 147-159, using 5-cyclopropylisoxazole-3-carboxylic acid as the acid monomer. MS (ESI): m/z=792.2 [M+H].

Example 151 provided an $EC_{50}$ of between 3-20 nM in a transient replicon assay with a D168E mutation in a 1a-H77 background, an $EC_{50}$ of <25 nM in a transient replicon assay with a D168V mutation in a 1a-H77 background, and an $EC_{50}$ of between 1-10 nM in a transient replicon assay with a R155K mutation in a 1a-H77 background.

Example 152

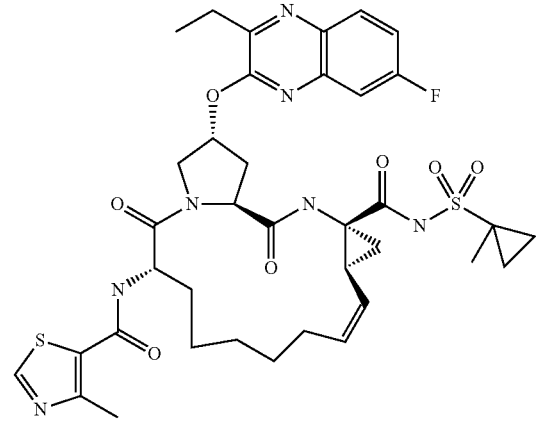 [SMILES: CCc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](NC(=O)c3scnc3C)C(=O)N2C1]

N-((2R,6S,13aS,14aR,16aS,Z)-2-(3-ethyl-7-fluoro-
quinoxalin-2-yloxy)-14a-(1-methylcyclopropylsulfo-
nylcarbamoyl)-5,16-dioxo-1,2,3,5,6,7,8,9,10,11,13a,
14,14a,15,16,16a-hexadecahydrocyclopropa[e]
pyrrolo[1,2-a][1,4]diazacyclopentadecin-6-yl)-4-
methylthiazole-5-carboxamide The title compound 152 was prepared according to the general procedure used for Example 147-159, using 4-methylthiazole-5-carboxylic acid as the acid monomer. MS (ESI): m/z=782.2 [M+H].

Example 153

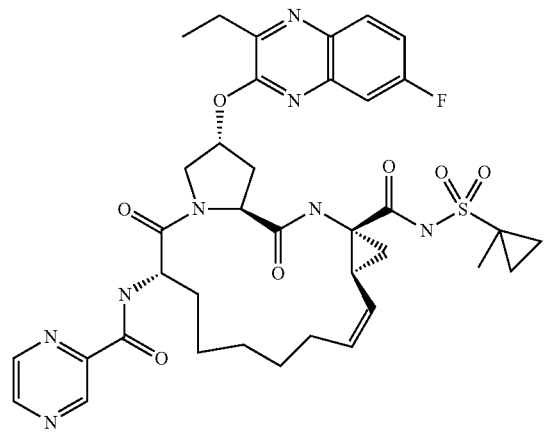

(2R,6S,13aS,14aR,16aS,Z)-2-(3-ethyl-7-fluoroqui-
noxalin-2-yloxy)-N-(1-methylcyclopropylsulfonyl)-
5,16-dioxo-6-(pyrazine-2-carboxamido)-1,2,3,5,6,7,
8,9,10,11,13a,14,14a,15,16,16a-
hexadecahydrocyclopropa[e]pyrrolo[1,2-a][1,4]
diazacyclopentadecine-14a-carboxamide The title compound 153 was prepared according to the general procedure used for Example 147-159, using pyrazine-2-carboxylic acid as the acid monomer. MS (ESI): m/z=763.2 [M+H].

Example 154

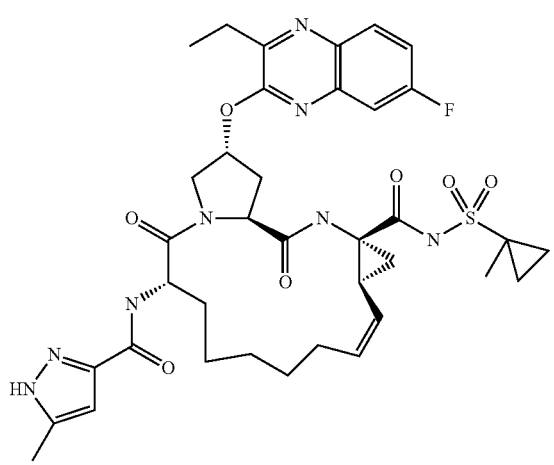 [SMILES: CCc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](NC(=O)c3cc(C)[nH]n3)C(=O)N2C1]

(2R,6S,13aS,14aR,16aS,Z)-2-(3-ethyl-7-fluoroquinoxalin-2-yloxy)-6-(5-methyl-H-pyrazole-3-carboxamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 154 was prepared according to the general procedure used for Example 147-159, using 5-methyl-1H-pyrazole-3-carboxylic acid as the acid monomer. MS (ESI): m/z=765.2 [M+H].

Example 155

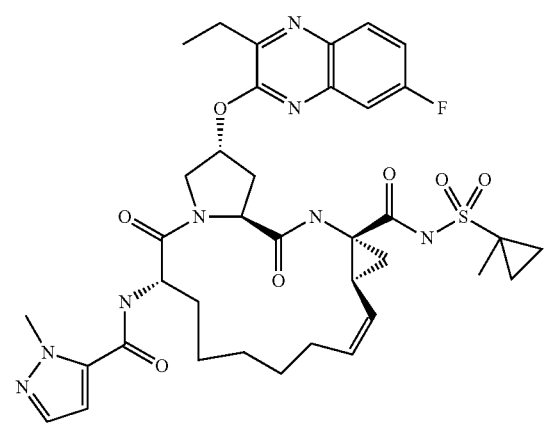 [SMILES: CCc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](NC(=O)c3ccnn3C)C(=O)N2C1]

(2R,6S,13aS,14aR,16aS,Z)-2-(3-ethyl-7-fluoroquinoxalin-2-yloxy)-6-(1-methyl-1H-pyrazole-5-carboxamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 155 was prepared according to the general procedure used for Example 147-159, using 1-methyl-1H-pyrazole-5-carboxylic acid as the acid monomer. MS (ESI): m/z=765.2 [M+H].

Example 156

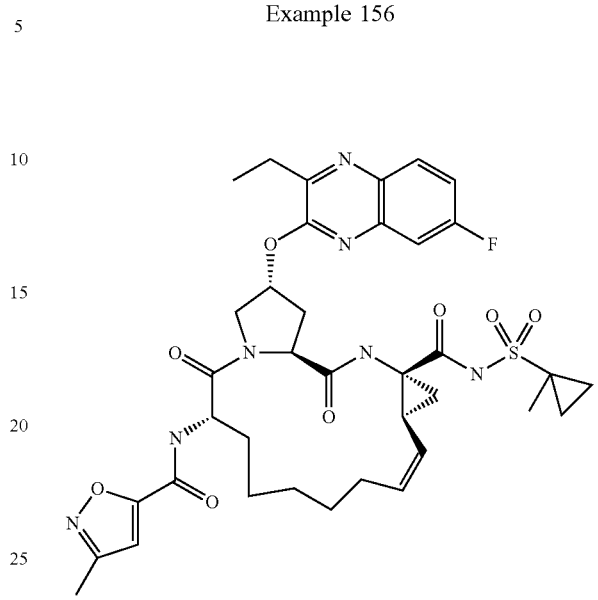

N-((2R,6S,13aS,14aR,16aS,Z)-2-(3-ethyl-7-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-3-methylisoxazole-5-carboxamide The title compound 156 was prepared according to the general procedure used for Example 147-159, using 3-methylisoxazole-5-carboxylic acid as the acid monomer. MS (ESI): m/z=766.2 [M+H].

Example 157

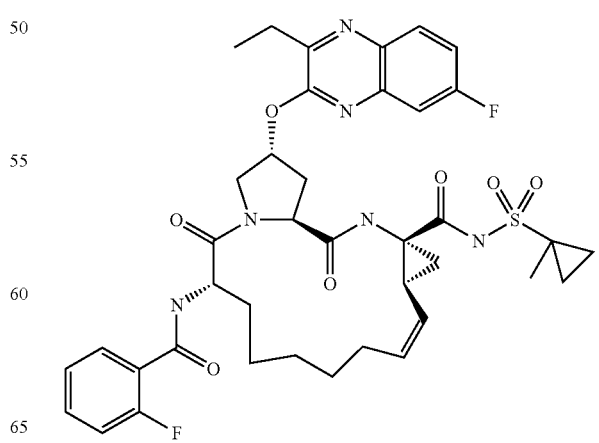

(2R,6S,13aS,14aR,16aS,Z)-2-(3-ethyl-7-fluoroqui-
noxalin-2-yloxy)-6-(2-fluorobenzamido)-N-(1-meth-
ylcyclopropylsulfonyl)-5,16-dioxo-1,2,3,5,6,7,8,9,
10,11,13a,14,14a,15,16,16a-
hexadecahydrocyclopropa[e]pyrrolo[1,2-a][1,4]
diazacyclopentadecine-14a-carboxamide The title compound 157 was prepared according to the general procedure used for Example 147-159, using 2-fluorobenzoic acid as the acid monomer. MS (ESI): m/z=779.2 [M+H].

Example 158

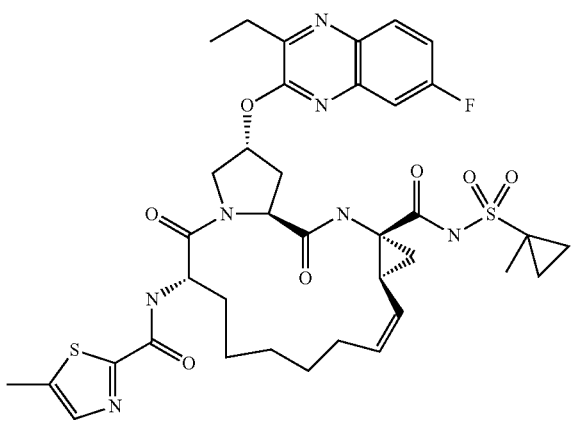 [SMILES: CCc1nc2ccc(F)cc2nc1O[C@@H]1C[C@H]2C(=O)N[C@]3(C(=O)NS(=O)(=O)C4(C)CC4)C[C@H]3/C=C\CCCCC[C@H](NC(=O)c3ncc(C)s3)C(=O)N2C1]

N-((2R,6S,13aS,14aR,16aS,Z)-2-(3-ethyl-7-fluoro-
quinoxalin-2-yloxy)-14a-(1-methylcyclopropylsulfo-
nylcarbamoyl)-5,16-dioxo-1,2,3,5,6,7,8,9,10,11,13a,
14,14a,15,16,16a-hexadecahydrocyclopropa[e]
pyrrolo[1,2-a][1,4]diazacyclopentadecin-6-yl)-5-
methylthiazole-2-carboxamide The title compound 158 was prepared according to the general procedure used for Example 147-159, using 5-methylthiazole-2-carboxylic acid as the acid monomer. MS (ESI): m/z=782.2 [M+H].

Example 159

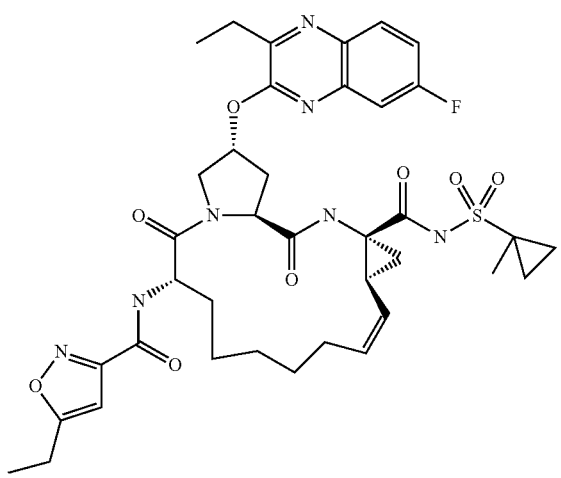 [SMILES: CCc1cc(C(=O)N[C@H]2CCCCC/C=C\[C@@H]3C[C@@]3(C(=O)NS(=O)(=O)C3(C)CC3)NC(=O)[C@@H]3C[C@@H](Oc4nc5cc(F)ccc5nc4CC)CN3C2=O)no1]

5-ethyl-N-((2R,6S,13aS,14aR,16aS,Z)-2-(3-ethyl-7-
fluoroquinoxalin-2-yloxy)-14a-(1-methylcyclopro-
pylsulfonylcarbamoyl)-5,16-dioxo-1,2,3,5,6,7,8,9,
10,11,13a,14,14a,15,16,16a-
hexadecahydrocyclopropa[e]pyrrolo[1,2-a][1,4]
diazacyclopentadecin-6-yl)isoxazole-3-carboxamide The title compound 159 was prepared according to the general procedure used for Example 147-159, using 5-ethylisoxazole-3-carboxylic acid as the acid monomer. MS (ESI): m/z=780.2 [M+H].

Example 160

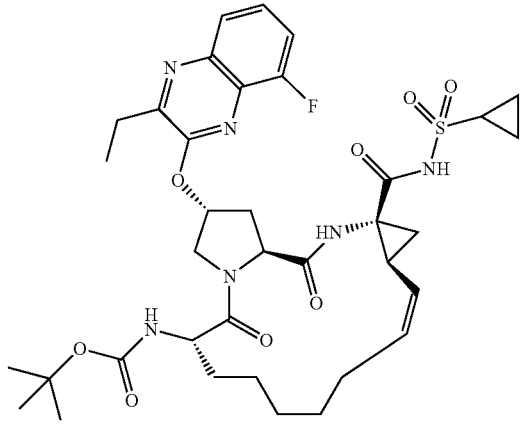 [SMILES: CCc1nc2cccc(F)c2nc1O[C@@H]1C[C@H]2C(=O)N[C@]3(C(=O)NS(=O)(=O)C4CC4)C[C@H]3/C=C\CCCCC[C@H](NC(=O)OC(C)(C)C)C(=O)N2C1]

tert-butyl (2R,6S,13aS,14aR,16aS,Z)-14a-(cyclopro-
pylsulfonylcarbamoyl)-2-(3-ethyl-8-fluoroquinoxa-
lin-2-yloxy)-5,16-dioxo-1,2,3,5,6,7,8,9,10,11,13a,14,
14a,15,16,16a-hexadecahydrocyclopropa[e]pyrrolo
[1,2-a][1,4]diazacyclopentadecin-6-ylcarbamate Example 160a

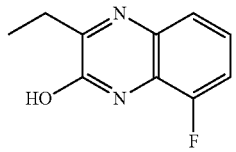

3-ethyl-8-fluoroquinoxalin-2-ol

The title compound 160a was prepared according to the procedures used for Examples 121a, replacing 1,3-difluoro-2-nitrobenzene with 1,2-difluoro-3-nitrobenzene.

Example 160

The title compound 160 was prepared according to the procedures used for Example 121, replacing the product of Example 121a with the product of Example 160a. MS (ESI): m/z=760.0 [M+NH4].

Example 160 provided an $EC_{50}$ of between 20-50 nM in a transient replicon assay with a D168E mutation in a 1a-H77 background, an $EC_{50}$ of between 50-250 nM in a transient replicon assay with a D168V mutation in a 1a-H77 background, and an $EC_{50}$ of between 1-10 nM in a transient replicon assay with a R155K mutation in a 1a-H77 background.

Example 161

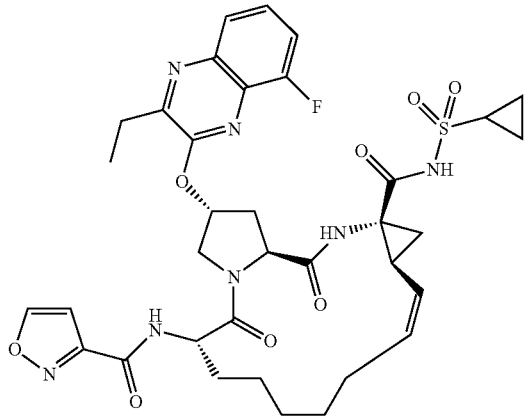 [SMILES: CCc1nc2cccc(F)c2nc1O[C@@H]1C[C@H]2C(=O)N[C@]3(C(=O)NS(=O)(=O)C4CC4)C[C@H]3/C=C\CCCCC[C@H](NC(=O)c3ccon3)C(=O)N2C1]

N-((2R,6S,13aS,14aR,16aS,Z)-14a-(cyclopropylsulfonylcarbamoyl)-2-(3-ethyl-8-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 161 was prepared according to the procedures used for Example 122, replacing the product of Example 121 with the product of Example 160. MS (ESI): m/z=738.2 [M+H].

Example 161 provided an $EC_{50}$ of between 3-20 nM in a transient replicon assay with a D168E mutation in a 1a-H77 background, an $EC_{50}$ of between 50-250 nM in a transient replicon assay with a D168V mutation in a 1a-H77 background, and an $EC_{50}$ of between 1-10 nM in a transient replicon assay with a R155K mutation in a 1a-H77 background.

Example 162

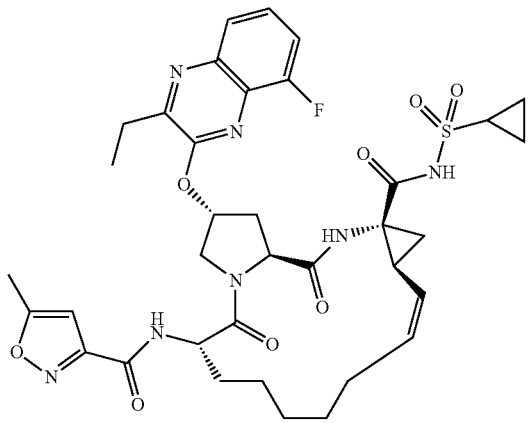 [SMILES: CCc1nc2cccc(F)c2nc1O[C@@H]1C[C@H]2C(=O)N[C@]3(C(=O)NS(=O)(=O)C4CC4)C[C@H]3/C=C\CCCCC[C@H](NC(=O)c3cc(C)on3)C(=O)N2C1]

N-((2R,6S,13aS,14aR,16aS,Z)-14a-(cyclopropylsulfonylcarbamoyl)-2-(3-ethyl-8-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide The title compound 162 was prepared according to the procedures used for Example 161, replacing isoxazole-3-carboxylic acid with 5-methylisoxazole-3-carboxylic acid. MS (ESI): m/z=752.2 [M+H].

Example 162 provided an $EC_{50}$ of between 3-20 nM in a transient replicon assay with a D168E mutation in a 1a-H77 background, an $EC_{50}$ of between 50-250 nM in a transient replicon assay with a D168V mutation in a 1a-H77 background, and an $EC_{50}$ of between 1-10 nM in a transient replicon assay with a R155K mutation in a 1a-H77 background.

Example 163

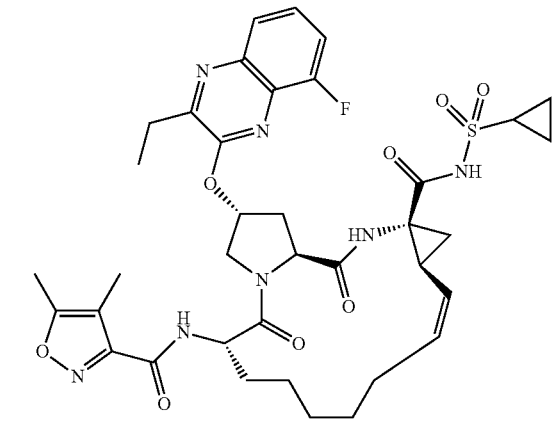 [SMILES: CCc1nc2cccc(F)c2nc1O[C@@H]1C[C@H]2C(=O)N[C@]3(C(=O)NS(=O)(=O)C4CC4)C[C@H]3/C=C\CCCCC[C@H](NC(=O)c3noc(C)c3C)C(=O)N2C1]

N-((2R,6S,13aS,14aR,16aS,Z)-14a-(cyclopropylsulfonylcarbamoyl)-2-(3-ethyl-8-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4,5-dimethylisoxazole isoxazole-3-carboxamide The title compound 163 was prepared according to the procedures used for Example 161, replacing isoxazole-3-carboxylic acid with 4,5-dimethylisoxazole-3-carboxylic acid. MS (ESI): m/z=766.2 [M+H].

Example 163 provided an $EC_{50}$ of <3 nM in a transient replicon assay with a D168E mutation in a 1a-H77 background, an $EC_{50}$ of between 25-50 nM in a transient replicon assay with a D168V mutation in a 1a-H77 background, and an $EC_{50}$ of <1 nM in a transient replicon assay with a R155K mutation in a 1a-H77 background.

Example 164

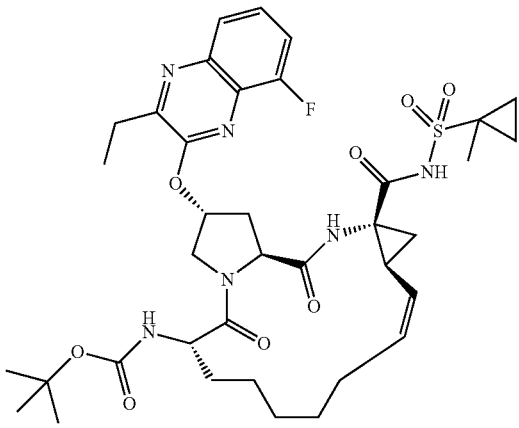 [SMILES: CCc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)OC(C)(C)C)C(=O)N2C1]

tert-butyl (2R,6S,13aS,14aR,16aS,Z)-2-(3-ethyl-8-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate The title compound 164 was prepared according to the procedures used for Example 160, replacing cyclopropanesulfonamide with 1-methylcyclopropane-1-sulfonamide. MS (ESI): m/z=774.1 [M+NH4].

Example 164 provided an $EC_{50}$ of between 20-50 nM in a transient replicon assay with a D168E mutation in a 1a-H77 background, an $EC_{50}$ of between 50-250 nM in a transient replicon assay with a D168V mutation in a 1a-H77 background, and an $EC_{50}$ of between 1-10 nM in a transient replicon assay with a R155K mutation in a 1b-N background.

Example 165-167

Example 165a

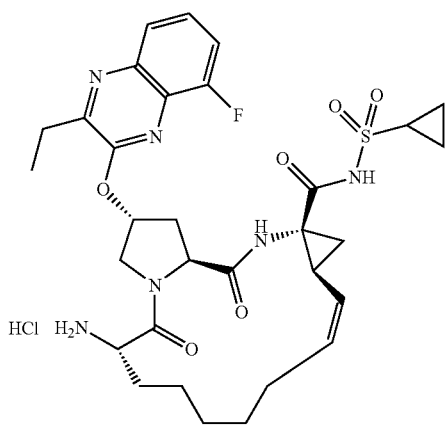

(2R,6S,13aS,14aR,16aS,Z)-6-amino-N-(cyclopropylsulfonyl)-2-(3-ethyl-8-fluoroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide, Hydrochloric Acid The title compound 165a was prepared according to the procedure used for Example 2a, replacing the product of Example 1 with the product of Example 160.

General Procedures for Example 165-167

To a solution of 165a (13 mg, 0.02 mmol) in DMA in a 4 ml vial was added the acid monomer (0.025 mmol) dissolved in DMA followed by a solution of HATU (0.025 mmol) in DMA and then triethylamine (0.4 mmol) neat. The vial was capped and microwaved at 150° C. for 30 minutes. The reaction was checked by LC/MS and concentrated to dryness. The residue was dissolved in MeOH:DMSO (1:1 v:v, 1.5 ml) and purified by reverse phase HPLC.

HPLC condition: Samples were purified by preparative HPLC on a Phenomenex Luna C8(2) 5 um 100 Å AXIA column (30 mm×75 mm). A gradient of methanol (A) and 0.1% trifluoroacetic acid in water (B) was used, at a flow rate of 50 mL/min (0-0.5 min 20% A, 0.5-6.0 min linear gradient 20-100% A, 6.0-7.0 min 100% A, 7.0-8.0 min linear gradient 100-10% A).

Example 165

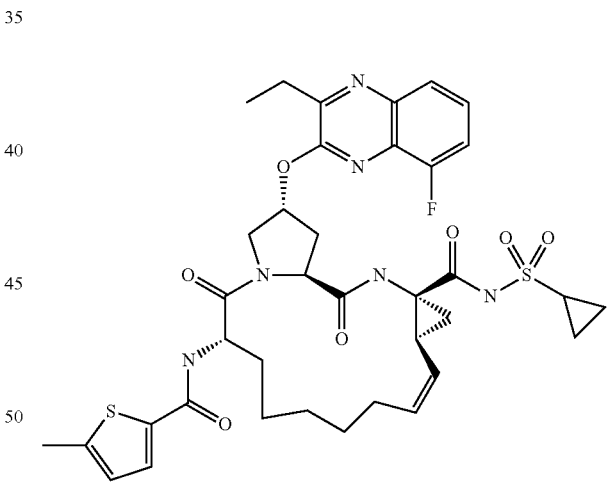

(2R,6S,13aS,14aR,16aS,Z)—N-(cyclopropylsulfonyl)-2-(3-ethyl-8-fluoroquinoxalin-2-yloxy)-6-(5-methylthiophene-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 165 was prepared according to the general procedure used for Example 165-167, using 5-methylthiophene-2-carboxylic acid as the acid monomer. MS (ESI): m/z=767.2 [M+H].

Example 166

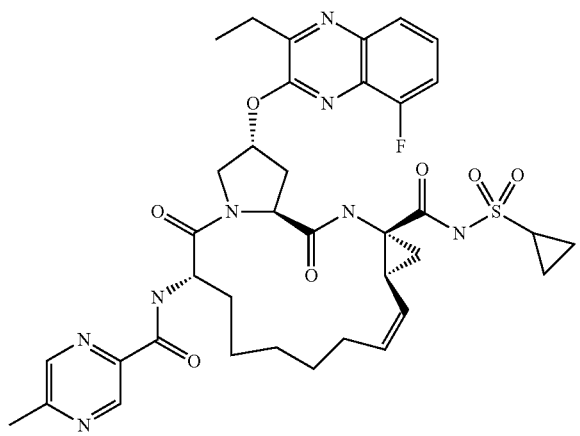 [SMILES: CCc1nc2cccc(F)c2nc1O[C@@H]1C[C@H]2C(=O)N[C@]3(C(=O)NS(=O)(=O)C4CC4)C[C@H]3/C=C\CCCCC[C@H](NC(=O)c3cnc(C)cn3)C(=O)N2C1]

(2R,6S,13aS,14aR,16aS,Z)—N-(cyclopropylsulfo-
nyl)-2-(3-ethyl-8-fluoroquinoxalin-2-yloxy)-6-(5-
methylpyrazine-2-carboxamido)-5,16-dioxo-1,2,3,5,
6,7,8,9,10,11,13a,14,14a,15,16,16a-
hexadecahydrocyclopropa[e]pyrrolo[1,2-a][1,4]
diazacyclopentadecine-14a-carboxamide The title compound 166 was prepared according to the general procedure used for Example 165-167, using 5-methylpyrazine-2-carboxylic acid as the acid monomer. MS (ESI): m/z=763.2 [M+H].

Example 167

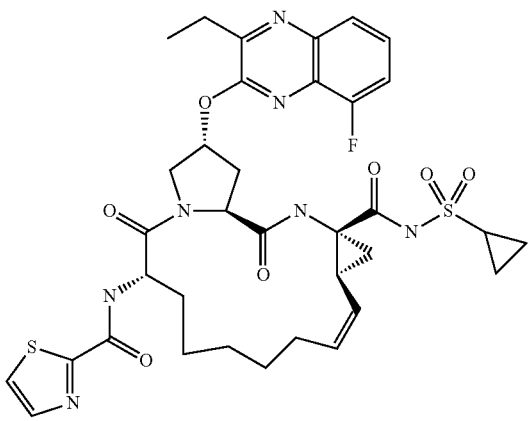 [SMILES: CCc1nc2cccc(F)c2nc1O[C@@H]1C[C@H]2C(=O)N[C@]3(C(=O)NS(=O)(=O)C4CC4)C[C@H]3/C=C\CCCCC[C@H](NC(=O)c3nccs3)C(=O)N2C1]

N-((2R,6S,13aS,14aR,16aS,Z)-14a-(cyclopropylsul-
fonylcarbamoyl)-2-(3-ethyl-8-fluoroquinoxalin-2-
yloxy)-5,16-dioxo-1,2,3,5,6,7,8,9,10,11,13a,14,14a,
15,16,16a-hexadecahydrocyclopropa[e]pyrrolo[1,2-
a][1,4]diazacyclopentadecin-6-yl)thiazole-2-
carboxamide The title compound 167 was prepared according to the general procedure used for Example 165-167, using thiazole-2-carboxylic acid as the acid monomer. MS (ESI): m/z=755.3 [M+H].

Example 168-185

Example 168a

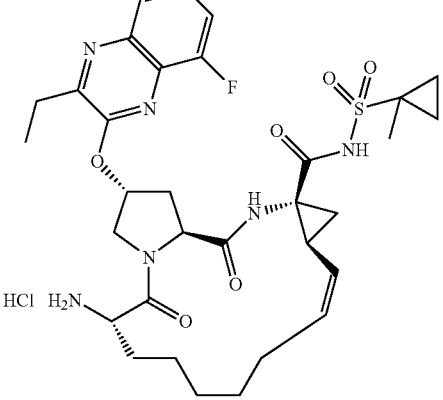

(2R,6S,13aS,14aR,16aS,Z)-6-amino-2-(3-ethyl-8-
fluoroquinoxalin-2-yloxy)-N-(1-methylcyclopropyl-
sulfonyl)-5,16-dioxo-1,2,3,5,6,7,8,9,10,11,13a,14,
14a,15,16,16a-hexadecahydrocyclopropa[e]pyrrolo
[1,2-a][1,4]diazacyclopentadecine-14a-carboxamide,
Hydrochloric Acid The title compound 168a was prepared according to the procedure used for Example 165a, replacing the product of Example 160 with the product of Example 164.

General Procedures for Example 168-185

To a solution of 168a (13 mg, 0.02 mmol) in DMA in a 4 ml vial was added the acid monomer (0.025 mmol) dissolved in DMA followed by a solution of HATU (0.025 mmol) in DMA and then triethylamine (0.4 mmol) neat. The vial was capped and microwaved at 150° C. for 30 minutes. The reaction was checked by LC/MS and concentrated to dryness. The residue was dissolved in MeOH:DMSO (1:1 v:v, 1.5 ml) and purified by reverse phase HPLC.

HPLC condition: Samples were purified by preparative HPLC on a Phenomenex Luna C8(2) 5 um 100 Å AXIA column (30 mm×75 mm). A gradient of methanol (A) and 0.1% trifluoroacetic acid in water (B) was used, at a flow rate of 50 mL/min (0-0.5 min 20% A, 0.5-6.0 min linear gradient 20-100% A, 6.0-7.0 min 100% A, 7.0-8.0 min linear gradient 100-10% A).

Example 168

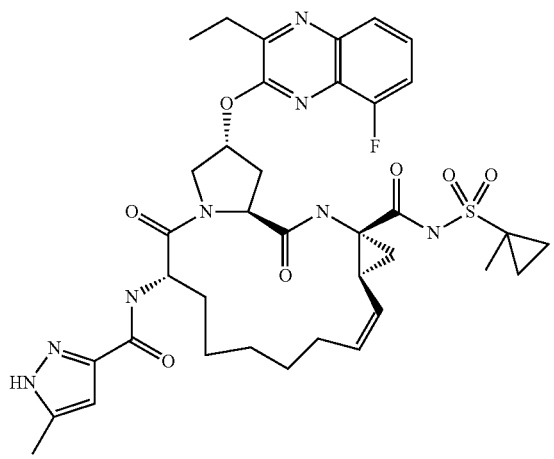 [SMILES: CCc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3cc(C)[nH]n3)C(=O)N2C1]

(2R,6S,13aS,14aR,16aS,Z)-2-(3-ethyl-8-fluoroquinoxalin-2-yloxy)-6-(5-methyl-1H-pyrazole-3-carboxamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 168 was prepared according to the general procedure used for Example 168-185 using 5-methyl-1H-pyrazole-3-carboxylic acid as the acid monomer. MS (ESI): m/z=765.3 [M+H].

Example 169

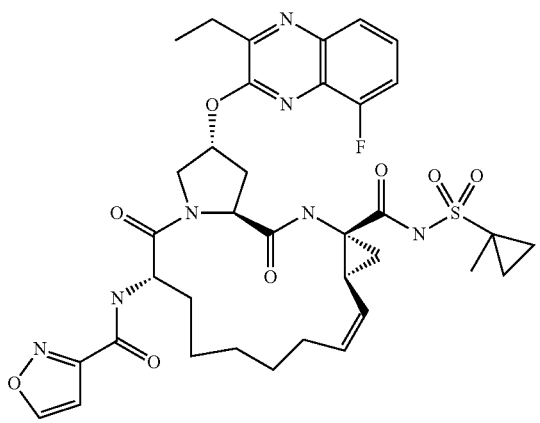 [SMILES: CCc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3ccon3)C(=O)N2C1]

N-((2R,6S,13aS,14aR,16aS,Z)-2-(3-ethyl-8-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 169 was prepared according to the general procedure used for Example 168-185 using isoxazole-3-carboxylic acid as the acid monomer. MS (ESI): m/z=752.2 [M+H].

Example 170

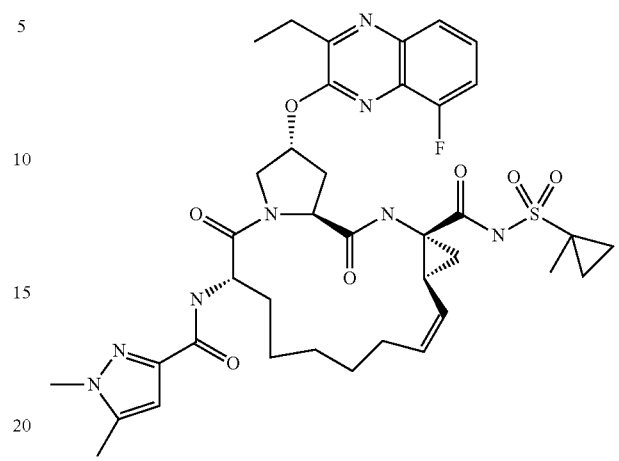

(2R,6S,13aS,14aR,16aS,Z)-6-(1,5-dimethyl-1H-pyrazole-3-carboxamido)-2-(3-ethyl-8-fluoroquinoxalin-2-yloxy)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 170 was prepared according to the general procedure used for Example 168-185 using 1,5-dimethyl-1H-pyrazole-3-carboxylic acid as the acid monomer. MS (ESI): m/z=779.2 [M+H].

Example 171

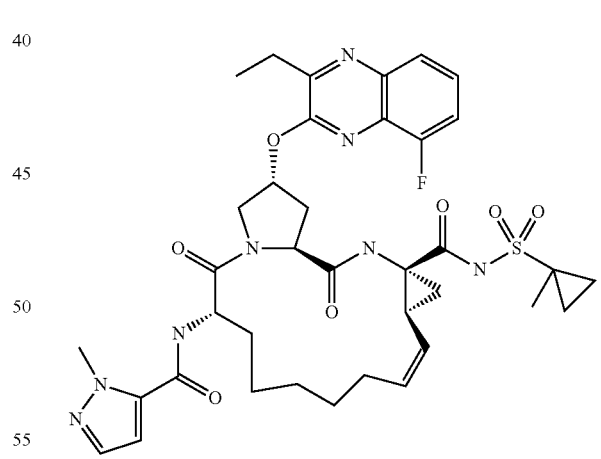

(2R,6S,13aS,14aR,16aS,Z)-2-(3-ethyl-8-fluoroquinoxalin-2-yloxy)-6-(1-methyl-1H-pyrazole-5-carboxamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 171 was prepared according to the general procedure used for Example 168-185 using 1-methyl-1H-pyrazole-5-carboxylic acid as the acid monomer. MS (ESI): m/z=765.2 [M+H].

Example 172

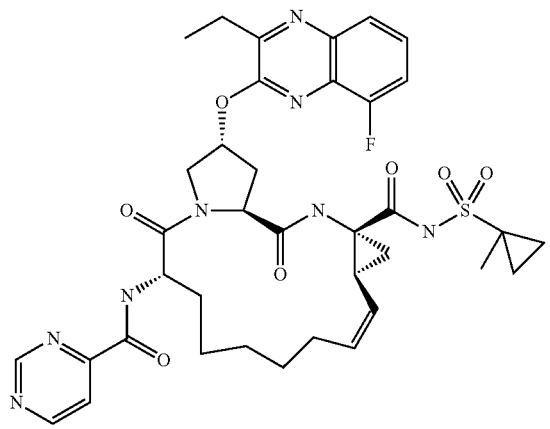 [SMILES: CCc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3ccncn3)C(=O)N2C1]

(2R,6S,13aS,14aR,16aS,Z)-2-(3-ethyl-8-fluoroquinoxalin-2-yloxy)-N-(1-methylcyclopropylsulfonyl)-5,16-dioxo-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 172 was prepared according to the general procedure used for Example 168-185 using pyrimidine-4-carboxylic acid as the acid monomer. MS (ESI): m/z=763.2 [M+H].

Example 173

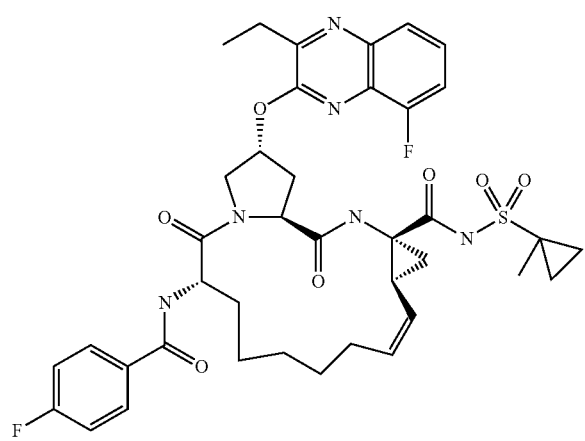 [SMILES: CCc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3ccc(F)cc3)C(=O)N2C1]

(2R,6S,13aS,14aR,16aS,Z)-2-(3-ethyl-8-fluoroquinoxalin-2-yloxy)-6-(4-fluorobenzamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 173 was prepared according to the general procedure used for Example 168-185 using 4-fluorobenzoic acid as the acid monomer. MS (ESI): m/z=779.2 [M+H].

Example 174

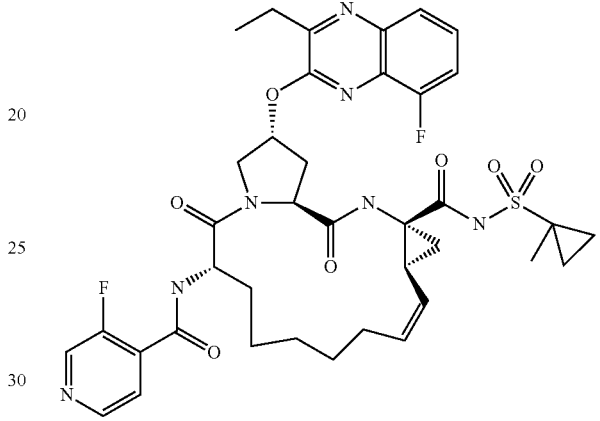

(2R,6S,13aS,14aR,16aS,Z)-2-(3-ethyl-8-fluoroquinoxalin-2-yloxy)-6-(3-fluoroisonicotinamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 174 was prepared according to the general procedure used for Example 168-185 using 3-fluoroisonicotinic acid as the acid monomer. MS (ESI): m/z=780.2 [M+H].

Example 175

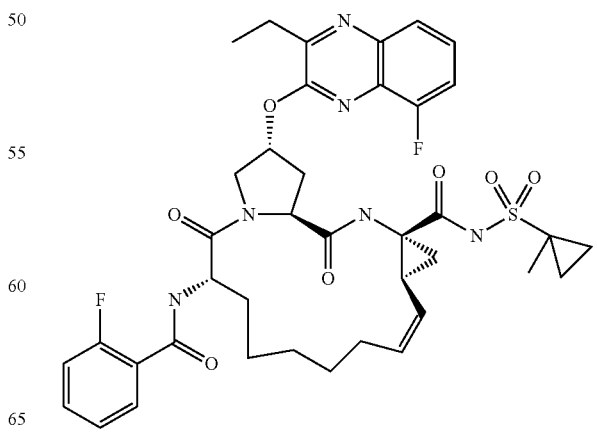

(2R,6S,13aS,14aR,16aS,Z)-2-(3-ethyl-8-fluoroqui-
noxalin-2-yloxy)-6-(2-fluorobenzamido)-N-(1-meth-
ylcyclopropylsulfonyl)-5,16-dioxo-1,2,3,5,6,7,8,9,
10,11,13a,14,14a,15,16,16a-
hexadecahydrocyclopropa[e]pyrrolo[1,2-a][1,4]
diazacyclopentadecine-14a-carboxamide The title compound 175 was prepared according to the general procedure used for Example 168-185 using 2-fluorobenzoic acid as the acid monomer. MS (ESI): m/z=779.2 [M+H].

Example 176

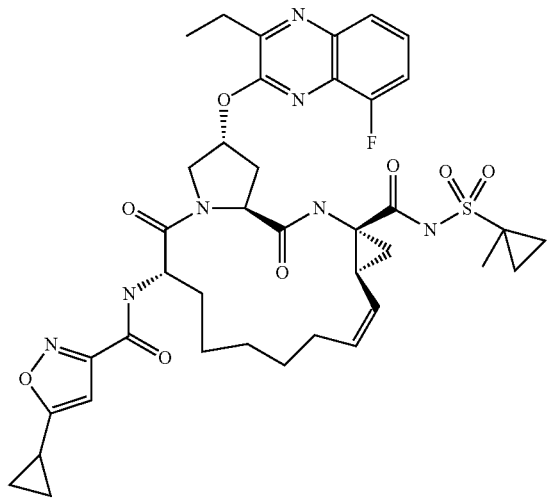 [SMILES: CCc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3cc(C4CC4)on3)C(=O)N2C1]

5-cyclopropyl-N-((2R,6S,13aS,14aR,16aS,Z)-2-(3-
ethyl-8-fluoroquinoxalin-2-yloxy)-14a-(1-methylcy-
clopropylsulfonylcarbamoyl)-5,16-dioxo-1,2,3,5,6,7,
8,9,10,11,13a,14,14a,15,16,16a-
hexadecahydrocyclopropa[e]pyrrolo[1,2-a][1,4]
diazacyclopentadecin-6-yl)isoxazole-3-carboxamide The title compound 176 was prepared according to the general procedure used for Example 168-185 using 5-cyclopropylisoxazole-3-carboxylic acid as the acid monomer. MS (ESI): m/z=792.2 [M+H].

Example 177

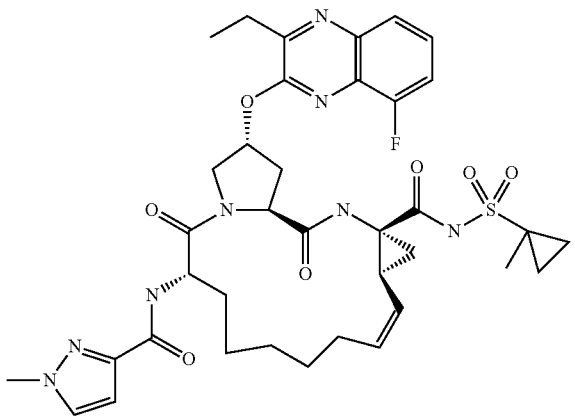 [SMILES: CCc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3ccn(C)n3)C(=O)N2C1]

(2R,6S,13aS,14aR,16aS,Z)-2-(3-ethyl-8-fluoroqui-
noxalin-2-yloxy)-6-(1-methyl-1H-pyrazole-3-car-
boxamido)-N-(1-methylcyclopropylsulfonyl)-5,16-
dioxo-1,2,3,5,6,7,8,9,10,11,13a,14,14a,15,16,16a-
hexadecahydrocyclopropa[e]pyrrolo[1,2-a][1,4]
diazacyclopentadecine-14a-carboxamide The title compound 177 was prepared according to the general procedure used for Example 168-185 using 1-methyl-1H-pyrazole-3-carboxylic acid as the acid monomer. MS (ESI): m/z=765.2 [M+H].

Example 178

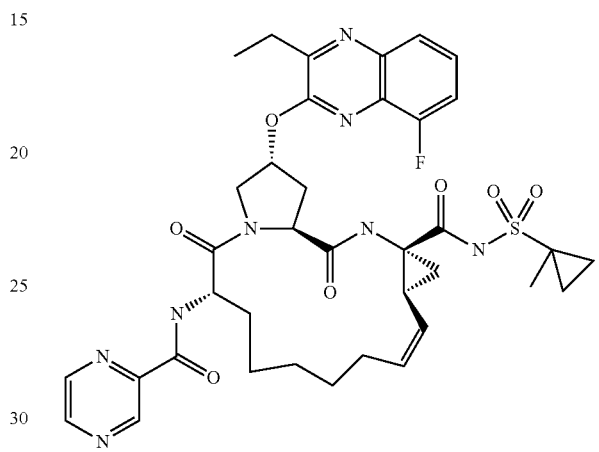

(2R,6S,13aS,14aR,16aS,Z)-2-(3-ethyl-8-fluoroqui-
noxalin-2-yloxy)-N-(1-methylcyclopropylsulfonyl)-
5,16-dioxo-6-(pyrazine-2-carboxamido)-1,2,3,5,6,7,
8,9,10,11,13a,14,14a,15,16,16a-
hexadecahydrocyclopropa[e]pyrrolo[1,2-a][1,4]
diazacyclopentadecine-14a-carboxamide The title compound 178 was prepared according to the general procedure used for Example 168-185 using pyrazine-2-carboxylic acid as the acid monomer. MS (ESI): m/z=763.2 [M+H].

Example 179

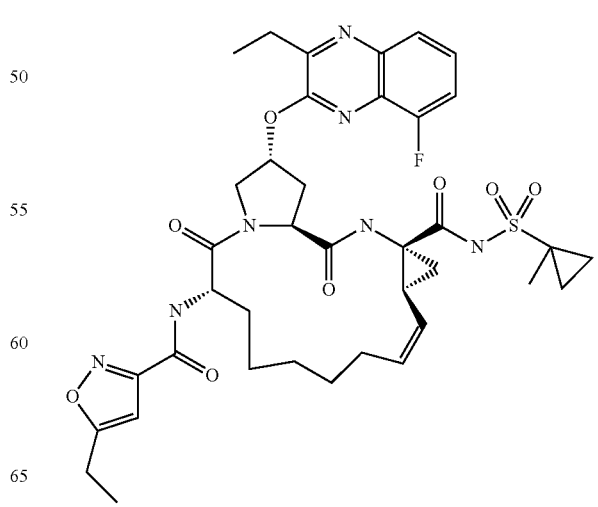

181

5-ethyl-N-((2R,6S,13aS,14aR,16aS,Z)-2-(3-ethyl-8-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-3-carboxamide The title compound 179 was prepared according to the general procedure used for Example 168-185 using 5-ethylisoxazole-3-carboxylic acid as the acid monomer. MS (ESI): m/z=780.2 [M+H].

Example 180

182

N-((2R,6S,13aS,14aR,16aS,Z)-2-(3-ethyl-8-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-4-methylthiazole-5-carboxamide The title compound 181 was prepared according to the general procedure used for Example 168-185 using 4-methylthiazole-5-carboxylic acid as the acid monomer. MS (ESI): m/z=782.2 [M+H].

Example 182

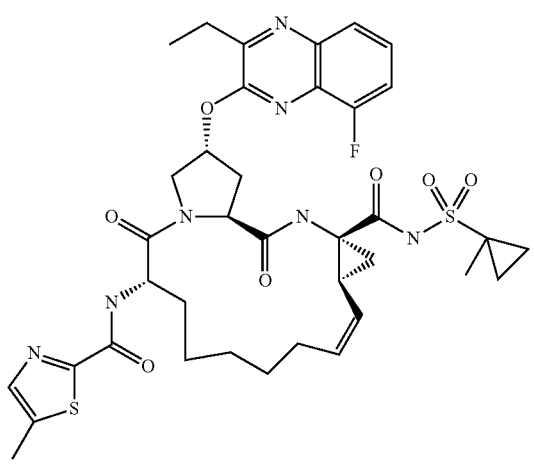 [SMILES: CCc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3ncc(C)s3)C(=O)N2C1]

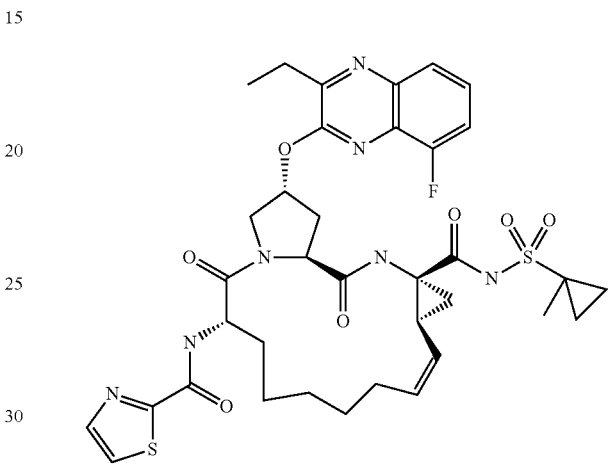

N-((2R,6S,13aS,14aR,16aS,Z)-2-(3-ethyl-8-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylthiazole-2-carboxamide The title compound 180 was prepared according to the general procedure used for Example 168-185 using 5-methylthiazole-2-carboxylic acid as the acid monomer. MS (ESI): m/z=782.2 [M+H].

Example 181

N-((2R,6S,13aS,14aR,16aS,Z)-2-(3-ethyl-8-fluoroquinoxalin-2-yloxy)-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-2-carboxamide The title compound 182 was prepared according to the general procedure used for Example 168-185 using thiazole-2-carboxylic acid as the acid monomer. MS (ESI): m/z=768.2 [M+H].

Example 183

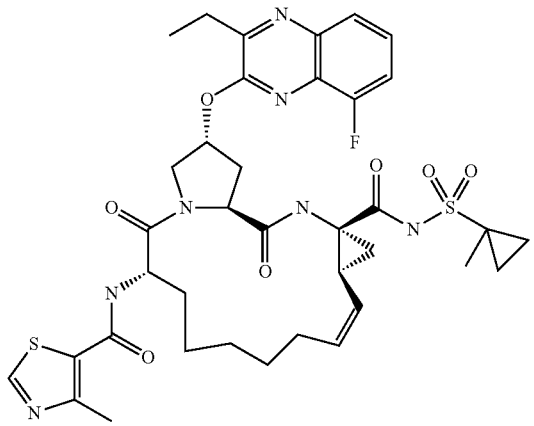 [SMILES: CCc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3scnc3C)C(=O)N2C1]

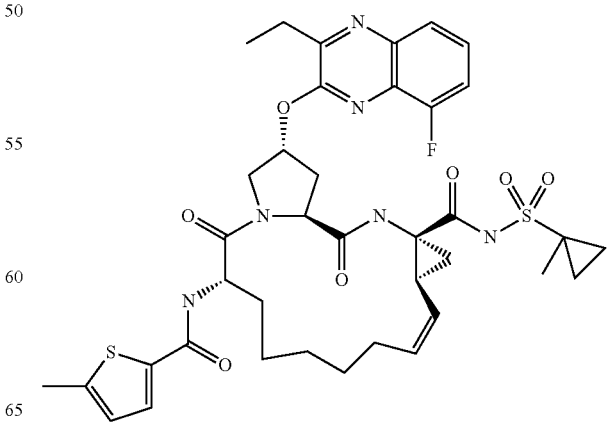

183

(2R,6S,13aS,14aR,16aS,Z)-2-(3-ethyl-8-fluoroquinoxalin-2-yloxy)-N-(1-methylcyclopropylsulfonyl)-6-(5-methylthiophene-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 183 was prepared according to the general procedure used for Example 168-185 using 5-methylthiophene-2-carboxylic acid as the acid monomer. MS (ESI): m/z=781.2 [M+H].

Example 184

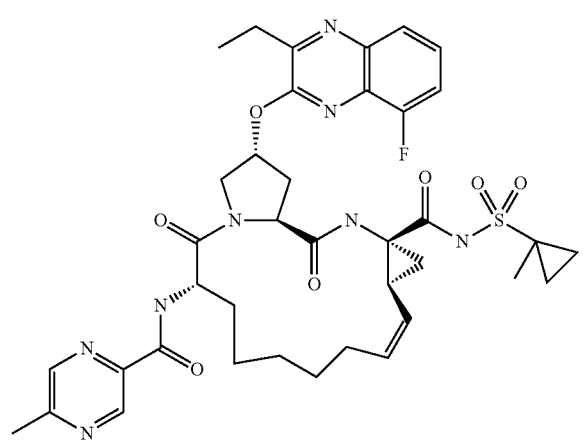 [SMILES: CCc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3cnc(C)cn3)C(=O)N2C1]

(2R,6S,13aS,14aR,16aS,Z)-2-(3-ethyl-8-fluoroquinoxalin-2-yloxy)-N-(1-methylcyclopropylsulfonyl)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 184 was prepared according to the general procedure used for Example 168-185 using 5-methylpyrazine-2-carboxylic acid as the acid monomer. MS (ESI): m/z=777.2 [M+H].

Example 185

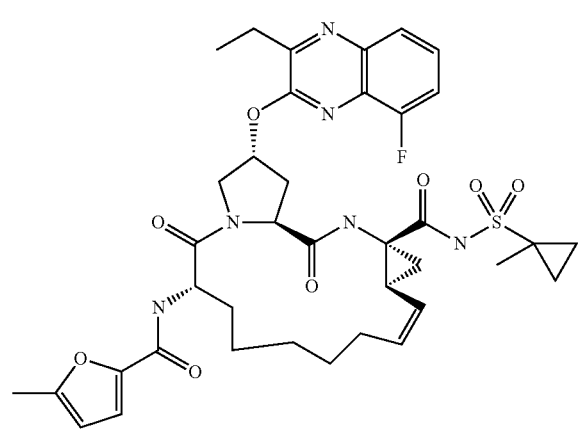 [SMILES: CCc1nc2cccc(F)c2nc1O[C@@H]1C[C@H]2C(=O)N[C@]3(C(=O)NS(=O)(=O)C4(C)CC4)C[C@H]3/C=C\CCCCC[C@H](NC(=O)c3ccc(C)o3)C(=O)N2C1]

184

(2R,6S,13aS,14aR,16aS,Z)-2-(3-ethyl-8-fluoroquinoxalin-2-yloxy)-N-(1-methylcyclopropylsulfonyl)-6-(5-methylfuran-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide The title compound 185 was prepared according to the general procedure used for Example 168-185 using 5-methylfuran-2-carboxylic acid as the acid monomer. MS (ESI): m/z=765.2 [M+H].

Example 186

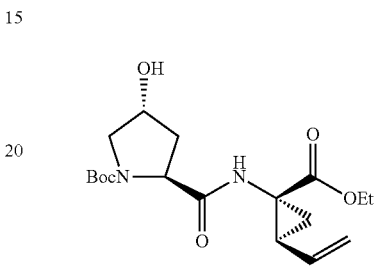

(2S,4R)-tert-butyl 2-((1R,2S)-1-(ethoxycarbonyl)-2-vinylcyclopropylcarbamoyl)-4-hydroxypyrrolidine-1-carboxylate To a stirring slurry of N-Boc-hydroxy proline (78 g), HATU (128 g), and EtOAc (558 g), at 0° C., was added diisopropylethylamine (65 g). After 45 min, a solution containing vinylcyclopropylammonium tosylate (100 g), diisopropylethylamine (65.0 g), and EtOAc (366 g) was added to the activated ester solution. After 3 h at 10° C., the reaction slurry was filtered and the resulting cake was rinsed with EtOAc (1.8 kg). The resulting filtrate was washed with a 10% aqueous solution of NaCl (5×770 g). The product-containing organic layer was filtered, concentrated under reduced pressure, diluted with EtOAc (450 g), and then filtered again. The assay yield of the final product-containing solution was determined to be 85%.

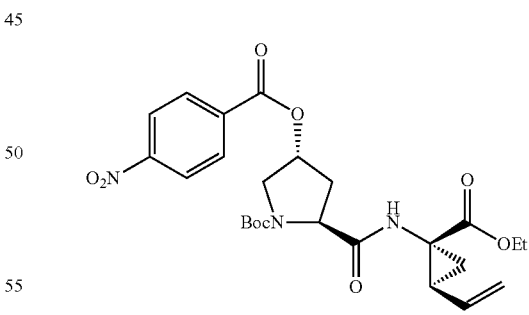

(2S,4R)-tert-butyl 2-((1R,2S)-1-(ethoxycarbonyl)-2-vinylcyclopropylcarbamoyl)-4-(4-nitrobenzoyloxy)pyrrolidine-1-carboxylate To a stirring slurry of (2S,4R)-tert-butyl 2-((1R,2S)-1-(ethoxycarbonyl)-2-vinylcyclopropylcarbamoyl)-4-hydroxypyrrolidine-1-carboxylate (1.69 kg), 4-dimethylaminopyridine (28.0 g), diisopropylethylamine (946 g) and EtOAc (4.82 kg), at 10° C., was added p-nitrobenzoyl chloride (1.06 kg) as a solution in EtOAc (3.48 kg). After 2.5 h at 10° C., the reaction was cooled to 5° C. and quench by the addition of water (1.85 kg). The resulting layers were separated and the organic layer was washed with a 1.0 N aqueous solution of HCl (3.75 kg), 10% aqueous solution of KHCO$_3$ (2×2.8 kg), water (3.1 kg), and a 10% aqueous solution of NaCl (3.1 kg). The organic layer was washed again with a 1.0 N aqueous solution of HCl (1.88 kg), 10% aqueous solution of KHCO$_3$ (4.2 kg), H$_2$O (1.5 kg), and a 10% aqueous solution of NaCl (2×755 g). The organic layer was concentrated under reduced pressure, diluted with EtOAc (5.6 kg), and then concentrated again. The resulting oil was diluted with EtOAc (10.0 kg), filtered, and then concentrated. EtOAc (10.0 kg) was added and then the resulting solution was concentrated to a mass of 7.9 kg. The assay yield was determined on the product-containing solution to be 98%.

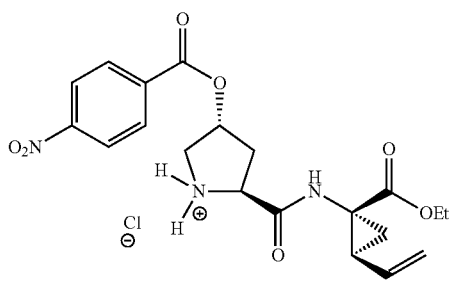 [SMILES: C=C[C@@H]1C[C@]1(NC(=O)[C@@H]1C[C@@H](OC(=O)c2ccc([N+](=O)[O-])cc2)C[NH2+]1)C(=O)OCC ; [Cl-]]

(2S,4R)-2-((1R,2S)-1-(ethoxycarbonyl)-2-vinylcyclopropylcarbamoyl)-4-(4-nitrobenzoyloxy)pyrrolidinium chloride To a stirring solution of ethanol at 0° C., was added acetyl chloride (1.77 kg). The resulting solution was aged for 30 min. (2S,4R)-tert-Butyl 2-((1R,2S)-1-(ethoxycarbonyl)-2-vinylcyclopropylcarbamoyl)-4-(4-nitrobenzoyloxy)pyrrolidine-1-carboxylate (2.34 kg) was then added as a solution in EtOAc (8.36 kg) to the acidic ethanol slurry solution at 10° C. The reaction was allowed to proceed for 1 h at 10° C., warmed to 15° C., held at that temperature for 1 h and then warmed to 20° C. After 18 h, EtOAc (8.35 kg) was added to the reactor and the resulting slurry was filtered. The cake was rinsed with EtOAc (8.35 kg) that had been cooled to 0° C. The title compound was placed in a vacuum oven, at 40° C., to remove residual solvent (2.1 kg, 100% yield).

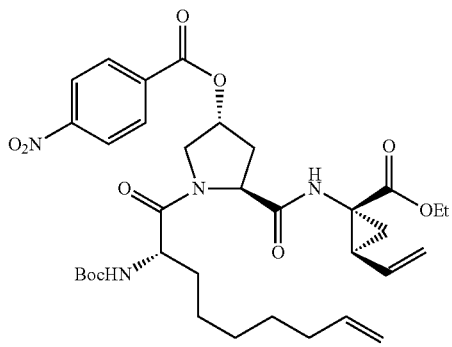 [SMILES: C=CCCCCC[C@H](NC(=O)OC(C)(C)C)C(=O)N1C[C@H](OC(=O)c2ccc([N+](=O)[O-])cc2)C[C@H]1C(=O)N[C@]1(C(=O)OCC)C[C@H]1C=C]

(3R,5S)-1-((S)-2-(tert-butoxycarbonylamino)non-8-enoyl)-5-((1R,2S)-1-(ethoxycarbonyl)-2-vinylcyclopropylcarbamoyl)pyrrolidin-3-yl 4-nitrobenzoate To a slurry of (2S,4R)-2-((1R,2S)-1-(ethoxycarbonyl)-2-vinylcyclopropylcarbamoyl)-4-(4-nitrobenzoyloxy)pyrrolidinium chloride (2.05 kg), (S)-2-(tertbutoxycarbonylamino)non-8-enoic acid (1.42 kg), EtOAc (5.93 kg), and NMP (4.1 kg) at 0° C. was added diisopropylethylamine (2.10 kg). Propanephosphonic acid anhydride (1.72 kg) was charged as a solution in EtOAc (3.83 kg) to the reaction mixture. The temperature of the reaction solution was adjusted to 5° C., held for 30 min, and then adjusted to 20° C. After 45 min, the reaction was diluted with EtOAc (20.5 kg) and then quenched with water (20.5 kg). The resulting layers were separated and the organic layer was washed with a 0.2 N aqueous solution of HCl (20.5 kg). The layers were separated and the organic layer was washed with a 5% aqueous solution of NaHCO$_3$ (31.0 kg), a 5% aqueous solution of NaCl (2×10.5 kg), and then concentrated under reduced pressure. The resulting oil was diluted with EtOAc (10.0 kg) and then filtered. The filtrate was concentrated under reduced pressure, and then diluted with toluene (5.0 kg). The solution was concentrated to an oil, diluted with toluene (5.0 kg), and then concentrated again. The oil was diluted with toluene (7.2 kg) and filtered to provide the title compound (2.87 kg, 94.9% yield) as a solution in toluene.

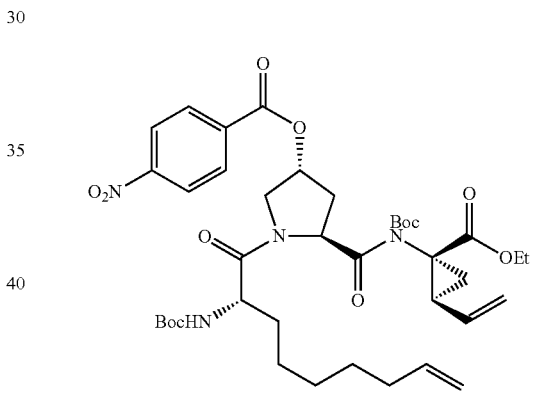

(3R,5S)-5-(tert-butoxycarbonyl((1R)-1-(ethoxycarbonyl)-2-vinylcyclopropyl)carbamoyl)-1-((S)-2-(tert-butoxycarbonylamino)non-8-enoyl)pyrrolidin-3-yl 4-nitrobenzoate To a solution of (3R,5S)-1-((S)-2-(tert-butoxycarbonylamino)non-8-enoyl)-5-((1R)-1-(ethoxycarbonyl)-2-vinylcyclopropylcarbamoyl)pyrrolidin-3-yl4-nitrobenzoate in toluene (26.7% w/w, 38.0 g solution, 10.2 g substrate) was charged toluene (7.7 mL) and 4-dimethylaminopyridine (370 mg). A mixture of di-tert-butyl dicarbonate (4.95 g) and toluene (10 mL) was then added over a period of 5 minutes, and the mixture was heated to 40° C. The reaction was stirred for 2 hours at 40° C. at which time the mixture was cooled to room temperature and diluted with toluene (30 mL). The organic mixture was extracted twice with 10% aq. KH$_2$PO$_4$ (50 mL) followed by water (50 mL). The organic layer was used as is in the next step, but was analyzed by HPLC (11.4 g, 98% yield).

187

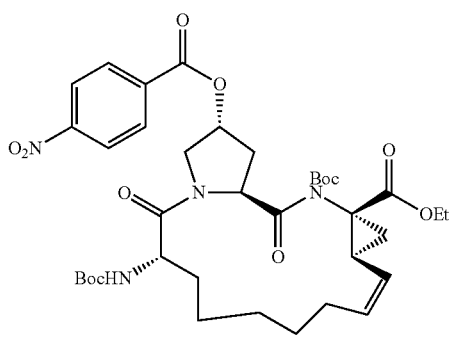 [SMILES: CCOC(=O)[C@@]12C[C@H]1/C=C\CCCCC[C@H](NC(=O)OC(C)(C)C)C(=O)N1C[C@H](OC(=O)c3ccc([N+](=O)[O-])cc3)C[C@H]1C(=O)N2C(=O)OC(C)(C)C]

(2R,6S,14aR,16aS,Z)-15-tert-butyl 14a-ethyl 6-(tert-butoxycarbonylamino)-2-(4-nitrobenzoyloxy)-5,16-dioxo-2,3,5,6,7,8,9,10,11,13a,14,14a,16,16a-tetradecahydrocyclopropa[e]pyrrolo[1,2-a][1,4]diazacyclopentadecine-14a,15(1H)-dicarboxylate A 100 L 3-neck flask containing two condensers, a nitrogen inlet tube, temperature probe and a stir bar was charged with toluene (37.6 kg) and warmed to 60° C. A solution of (1,3-dimesitylimidazolidin-2-ylidene)(5-(N,N-dimethylsulfamoyl)-2-isopropoxybenzylidene)ruthenium(VI) chloride (15 g) in toluene (4 kg) was added over 4 h. At the same time, a solution of (3R,5S)-5-(tert-butoxycarbonyl((1R)-1-(ethoxycarbonyl)-2-vinylcyclopropyl)carbamoyl)-1-((S)-2-(tertbutoxycarbonylamino)non-8-enoyl)pyrrolidin-3-yl 4-nitrobenzoate (1 kg) in toluene (4 kg) was added over 4 h. Both solutions were charged while maintaining the temperature at 60° C. Another charge of catalyst (3 g) in toluene (1 kg) was added over 30 minutes. Filterol (540 g) and imidazole (54 g) were then charged to the reaction mixture and the reaction was allowed to cool to ambient temperature for 12 h. The mixture was filtered to remove the solids and passed over an AKS-6 carbon pad. The pad was rinsed with toluene (2 kg). The solvent was evaporated under reduced pressure to a volume of 5 L. The solution was distilled at a constant volume while charging isopropanol (36 kg) and then diluted out to 100 L with isopropanol. The slurry was heated to 60° C. to dissolve the solids and then cooled to 55° C. The solution was seeded at 55° C. and allowed to cool at a rate of 2° C./hour down to 35° C. and then cooled at a rate of 5° C./hour down to 20° C. The slurry was allowed to stir for an additional 12 hours at 20° C., then filtered and washed with cold IPA (2 L). The solids were dried in the oven overnight at 50° C. (1.83 kg, 99% pure, 61% yield).

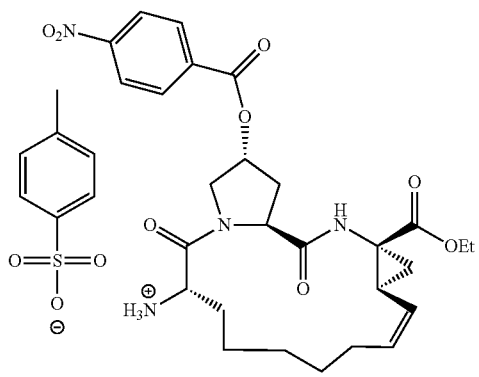 [SMILES: Cc1ccc(S(=O)(=O)[O-])cc1 ; CCOC(=O)[C@@]12C[C@H]1/C=C\CCCCC[C@H]([NH3+])C(=O)N1C[C@H](OC(=O)c3ccc([N+](=O)[O-])cc3)C[C@H]1C(=O)N2]

188

(2R,6S,13aS,14aR,16aS,Z)-14a-(ethoxycarbonyl)-2-(4-nitrobenzoyloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-aminium 4-methylbenzenesulfonate To a solution of (2R,6S,13aS,14aR,16aS,Z)-15-tert-butyl 14a-ethyl 6-(tert-butoxycarbonylamino)-2-(4-nitrobenzoyloxy)-5,16-dioxo-2,3,5,6,7,8,9,10,11,13a,14,14a,16,16a-tetradecahydrocyclopropa[e]pyrrolo[1,2-a][1,4]diazacyclopentadecine-14a,15(1H)-dicarboxylate (1768 g) dissolved in dichloromethane (10.6 L) was added trifluoroacetic acid (5400 g). The solution was warmed to 40° C. for 6 hours, then concentrated by distillation under vacuum. 2-Methyltetrahydrofuran (9 L) was added and removed by distillation (repeated two more times). A mixture of 2-methyltetrahydrofuran (13.3 L) and methyl-t-butyl ether (13.3 L) was charged and the resulting solution was extracted with 20% aqueous solution of potassium phosphate dibasic (35.4 L). After separation the organic layer was extracted with water (8.9 L). The solvent was changed to 2-methyltetrahydrofuran by distillation under vacuum. The final solvent level was 11.9 L. This solution was charged to a mixture p-toluenesulfonic acid monohydrate (461 g) and acetonitrile (24.7 L) over 6 h. The product was isolated by filtration and the cake was washed with acetonitrile and the dried under vacuum at 50° C. (1582 g, 90% yield).

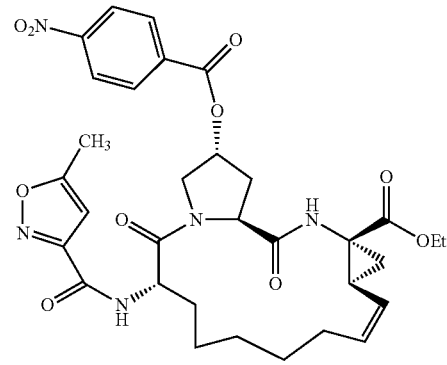 [SMILES: CCOC(=O)[C@@]12C[C@H]1/C=C\CCCCC[C@H](NC(=O)c1cc(C)on1)C(=O)N1C[C@H](OC(=O)c3ccc([N+](=O)[O-])cc3)C[C@H]1C(=O)N2]

(2R,6S,13aS,14aR,16aS,Z)-ethyl 6-(5-methylisoxazole-3-carboxamido)-2-(4-nitrobenzoyloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate To a solution of (2R,6S,13aS,14aR,16aS,Z)-14a-(ethoxycarbonyl)-2-(4-nitrobenzoyloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-aminium 4-methylbenzenesulfonate (1.53 kg), 5-methylisoxazole-3-carboxylic acid (327 g), and NMP (4.74 kg) at 5° C. was added diisopropylethylamine (996 g). Propanephosphonic acid anhydride (817 g) was charged as a solution in EtOAc (817 g) and NMP (3.16 kg) to the reaction mixture. The reaction was allowed to proceed for 30 min at 5° C., then warmed to 20° C. and aged for an additional hour. The reaction solution was diluted with IPAc (10.5 kg) and 2-methyltetrahydrofuran (10.5 kg). The diluted reaction solution was washed with water (23.7 kg), a 1.0 M aqueous solution of $H_3PO_4$ (2×7.5 kg), water (7.9 kg), a 5% aqueous solution of $NaHCO_3$ (7.5 kg), and then a 10% aqueous solution of NaCl (2×7.5 kg). The organic solution was concentrated under reduced pressure, diluted with THF (12 kg), and then filtered. Concentration of the organic solution to a volume of 5 L was followed by co-distillation with THF (30 kg) to a final volume of 5 L. The solution was diluted with THF (2.5 kg). The assay yield was determined on the product-containing solution to be 96.5% (1.35 kg).

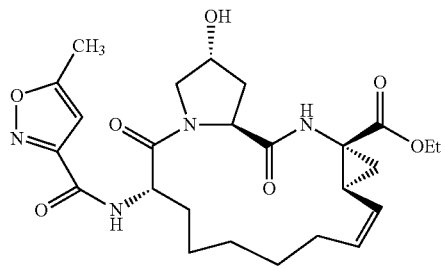 [SMILES: CCOC(=O)[C@@]12C[C@H]1/C=C\CCCCC[C@H](NC(=O)c1cc(C)on1)C(=O)N1C[C@H](O)C[C@H]1C(=O)N2]

(2R,6S,14aR,16aS,Z)-ethyl 2-hydroxy-6-(5-methylisoxazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate To a solution of (2R,6S,14aR,16aS,Z)-ethyl 6-(5-methylisoxazole-3-carboxamido)-2-(4-nitrobenzoyloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (64.6 g solution, 15.5% w/w solution in THF, 10 g starting material) was added THF (34 mL). The solution was then cooled to 0° C. and a solution of 0.5M LiOH (33.8 mL) was added dropwise keeping the temperature below 5° C. After 1 hour, the reaction was diluted with dichloromethane (150 mL) and neutralized with 1N HCl (50 mL). The organic layer was extracted and washed with 5% NaHCO₃ (50 mL) twice and once with a 5% aq. NaCl solution (50 mL). The dichloromethane layer was evaporated under reduced pressure and diluted with THF (41 g) to give a solution. Analysis by HPLC indicated a yield of 7.8 g of the title compound (100%).

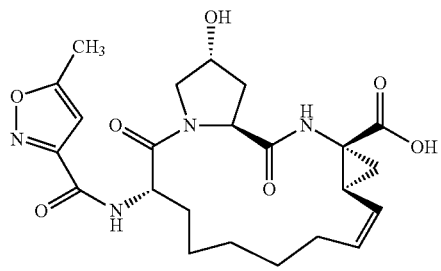 [SMILES: Cc1cc(C(=O)N[C@H]2CCCCC/C=C\[C@@H]3C[C@@]3(C(=O)O)NC(=O)[C@@H]3C[C@@H](O)CN3C2=O)no1]

(2R,6S,14aR,16aS,Z)-2-hydroxy-6-(5-methylisoxazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid To a solution of (2R,6S,14aR,16aS,Z)-ethyl 2-hydroxy-6-(5-methylisoxazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate in THF (62.5 grams, 16% w/w, 10 g starting material) and methanol (33 mL) at 0° C. was added 10% aq. LiOH (14.3 g, 3 equiv) keeping the temperature below 10° C. The solution was stirred at 10° C. for 22 h, then diluted with dichloromethane (150 mL). The reaction mixture was extracted with 1N HCl (100 mL) followed by water (100 mL). The solvent was changed to acetonitrile by distillation. The final acetonitrile level was approximately 70 mL. The slurry in acetonitrile was heated to 50° C. for 4 h, then allowed to cool to ambient temperature for 12 h. The slurry was filtered and the cake was washed with acetonitrile (20 mL) then dried in a vacuum at 50° C. (8.5 g, 86% pure, 77% yield of the title compound).

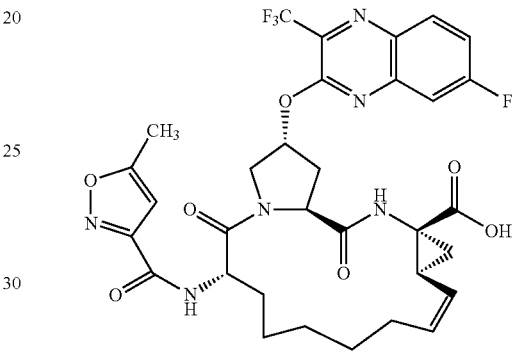

(2R,6S,13aS,14aR,16aS,Z)-2-(7-fluoro-3-(trifluoromethyl)quinoxalin-2-yloxy)-6-(5-methylisoxazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (2R,6S,13aS,14aR,16aS,Z)-2-hydroxy-6-(5-methylisoxazole-3-carboxamido)-5,16-dioxo 1,2,3,5,6,7,8,9,10,11,13a,14,14a,15,16,16a-hexadecahydrocyclopropa[e]pyrrolo[1,2a][1,4]diazacyclopentadecine-14a-carboxylic acid (55.1 g) was dissolved in dimethylsulfoxide (440 mL) and a solution of potassium tert-butoxide in THF (1.0M, 250 mL) was added dropwise, keeping the temperature to less than 30° C. The resulting solution was added to a solution of 3-chloro-6-fluoro-2-(trifluoromethyl)quinoxaline (30.6 g) in dimethylformamide (551 mL) over 30 min while keeping the temperature below 0° C. After stirring for 30 min, the reaction was diluted with 2-methyltetrahydrofuran (1200 mL), quenched with phosphoric acid (102.5 g), and finally diluted with water (1200 mL). The layers were separated and the lower layer was extracted with 2-methyltetrahydrofuran (600 mL). The organic layers were combined and extracted twice with water (1200 mL each time). The organic layer was concentrated, chased with acetonitrile, and the final volume adjusted to about 2.5 L with acetonitrile. The slurry was warmed to 80° C., cooled to room temperature, and filtered. The solid was rinsed with acetonitrile and dried under vacuum at 50° C. (68.7 g, 86% yield).

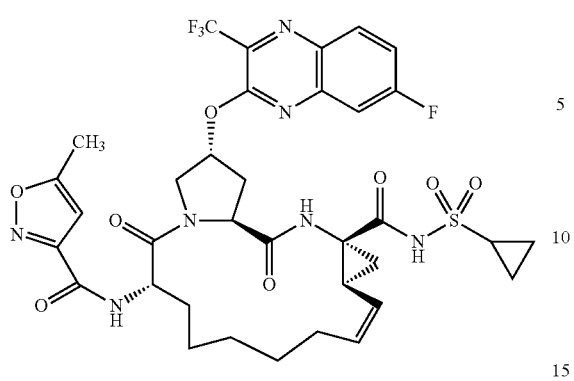

Example 187

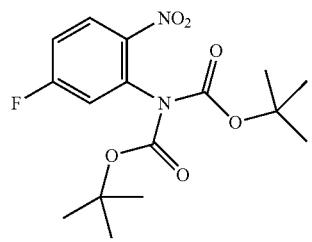 [SMILES: CC(C)(C)OC(=O)N(C(=O)OC(C)(C)C)c1cc(F)ccc1[N+](=O)[O-]]

di-tert-butyl 5-fluoro-2-nitrophenyl dicarbamate

N-((2R,6S,13aS,14aR,16aS,Z)-14a-(cyclopropylsulfonylcarbamoyl)-2-(7-fluoro-3-(trifluoromethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide To a solution of 5-fluoro-2-nitroaniline (10 g) and N,N-dimethylpyridin-4-amine (0.16 g) in 2-Me-THF (140 mL) was added dropwise di-tert-butyl dicarbonate (28.0 g) in 2-Me-THF (60 mL) and the reaction stirred at room temp overnight. Upon completion, the reaction was extracted with water twice (50 mL each). The solution was dried with $MgSO_4$ and concentrated to give a bright yellow solid (22.8 g, 100% yield).

To a stirring solution of (2R,6S,13aS,14aR,16aS,Z)-2-(7-fluoro-3-(trifluoromethyl)quinoxalin-2-yloxy)-6-(5-methylisoxazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (5.13 g) and NMP (12.9 g) was added carbonyl diimidazole (1.83 g) as a solution in NMP (7.7 g). After 30 min, cyclopropylsulfonamide (1.81 g) was added to the reaction mixture as a solution in NMP (5.13 g). The solution was cooled to 5° C. and then DBU (4.0 g) was charged to the reaction mixture. The reaction was allowed to proceed for 15 h and then diluted with isopropyl acetate (IPAc) (33.5 g) and 2-methyltetrahydrofuran (33.5 g). The organic solution was washed with a 2.0 M aqueous solution of $H_3PO_4$ (51.3 g), a 5:3:1 solution of 2.0 M $H_3PO_4$, $H_2O$, 10% aqueous solution of NaCl (total volume of 50 mL), water (5×25 g), and then concentrated to 25 mL by distillation. The organic solution was diluted with IPAc (25.0 g) and then concentrated back to 25 mL by distillation. This process was repeated three times. The concentrated product-containing solution was diluted with IPAc (108 g), filtered, and then concentrated again to 25 mL. The product-containing solution was distilled, maintaining a constant volume by the addition of ethanol (106 g). Ethanol (35 mL) was then added. Water (3.0 g) was then added to the product solution and the mixture was heated to 80° C. and then cooled to 20° C. over 12 h. The slurry was filtered and the cake was rinsed with ethanol (10 mL). The cake was dried under vacuum to provide the product (4.64 g, 79% yield) as a white, crystalline solid: $^1$H NMR (400 MHz, DMSO-D6) δ ppm 11.14 (s, 1H), 9.02 (s, 1H), 8.69 (d, J=6.7 Hz, 1H), 8.27 (dd, J=9.1, 5.9 Hz, 1H), 7.79 (dd, J=9.6, 2.3 Hz, 1H), 7.72 (td, J=8.7, 2.3 Hz, 1H), 6.09 (s, 1H), 5.95 (br s, 1H), 5.61 (q, J=8.5 Hz, 1H), 5.12 (t, J=9.5 Hz, 1H), 4.65 (d, J=11.7 Hz, 1H), 4.50 (t, J=8.2 Hz, 1H), 4.38-4.28 (m, 1H), 3.96 (dd, J=11.3, 2.4 Hz, 1H), 2.96-2.88 (m, 1H), 2.69-2.55 (m, 2H), 2.52-2.44 (m, 1H), 2.42 (s, 3H), 2.31 (q, J=8.7 Hz, 1H), 1.96 (q, J=11.4 Hz, 1H), 1.77-1.66 (m, 1H), 1.63-1.56 (m, 2H), 1.45-1.28 (m, 5H), 1.27-1.16 (m, 2H), 1.15-0.95 (m, 4H). LC-MS (ESI): m/z=792.2 [M+H].

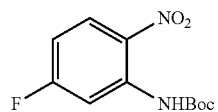

tert-butyl 5-fluoro-2-nitrophenylcarbamate

To di-tert-butyl 5-fluoro-2-nitrophenyl dicarbamate (10 g) in DCM (100 mL) was added trifluoroacetic acid (3.2 mL). The reaction mixture stirred for 1.5 h, and then the reaction mixture was extracted with saturated aq. $NaHCO_3$ (50 mL) twice. The organic layer was then extracted with brine (50 mL). The organic layer was evaporated to dryness and chased with THF to give the product (7.2 g, 100% yield)

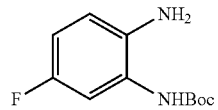

tert-butyl 2-amino-5-fluorophenylcarbamate

A slurry of Raney nickel (W. R. Grace 2800, 30.6 g calc. dry weight) was added to a 2-gallon Parr stirred pressure reactor containing THF (3 L). tert-Butyl 5-fluoro-2-nitrophenylcarbamate (102 g) was added. The vessel was sealed, purged, and pressurized to about 30 psig with hydrogen. The mixture was vigorously stirred at ambient temperature (20° C.) while hydrogen was supplied on-demand at 30 psig. After stirring for 16 h, the vessel was vented and purged with nitrogen. The product mixture was filtered to remove the catalyst using THF (1 L) to rinse the reactor and catalyst cake. The solvent was removed under vacuum. Heptane (510 mL) was added and the mixture was heated to 50° C. for 1 h, then cooled slowly to 0° C. The solids were filtered and washed with cold heptanes (100 mL) and dried under vacuum at 50° C. (76.7 g of product isolated, 87% pure, 73% yield).

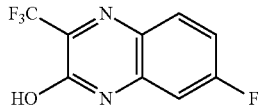 [SMILES: Oc1nc2cc(F)ccc2nc1C(F)(F)F]

7-fluoro-3-(trifluoromethyl)quinoxalin-2-ol tert-Butyl 2-amino-5-fluorophenylcarbamate (30.5 g), toluene (300 mL), triethylamine (34.1 g) and ethyl 3,3,3-trifluoro-2-oxopropanoate (69.5 g) were charged into a reactor and warmed to 63° C. for 14 h, then cooled to ambient temperature. A 5% aq. NaOH solution (390 mL) was added, stirred, settled, and then the lower layer was separated. The organic layer extracted with another charge of 5% aq. NaOH solution (130 mL). To the combined aq. NaOH layers was charged 2-methyl-THF (390 mL) and concentrated HCl (77.9 g), keeping the temperature below 25° C. The layers were mixed, settled and separated. The acidic aq. layer was separated, and the organic layer was extracted with water (260 mL). The layers were separated and the organic layer was filtered to remove insoluble material. The product was isolated by switching the solvent to toluene by distillation (a total of 1.1 L toluene used). The final slurry was briefly warmed to 80° C. and then cooled −10° C. and filtered. The cake was washed with toluene (128 mL), then dried under vacuum at 60° C. To the crude solid was added ethanol (350 mL) and warmed to reflux to dissolve the solids. The solution was cooled to room temperature and concentrated to approximately 270 mL total volume by distillation. Water (250 g) was then added over 30 min. The slurry was filtered and washed with cold (1:1) ethanol: water (2×60 mL). The solid was dried under vacuum at 60° C. (26.1 g, 83% yield).

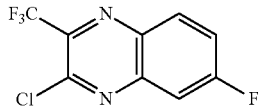

3-chloro-6-fluoro-2-(trifluoromethyl)quinoxaline

7-Fluoro-3-(trifluoromethyl)quinoxalin-2-ol (24.1 g) and POCl₃ (158.1 g) were combined and warmed to 100° C. for 12 h. The reaction mixture was cooled to room temperature and diluted with acetonitrile (104 mL). To a separate vessel was charged water (320 g) and acetonitrile (124 g), then cooled to 10° C. The reaction mixture was added to the acetonitrile/water mixture over 1 hour. The slurry was cooled to 10° C. for 30 min, then it was filtered and the cake was washed with 2:1 (v/v) water:acetonitrile (3×65 mL). The solid was dried under vacuum at 50° C. for 14 h (24.7 g, 95% yield).

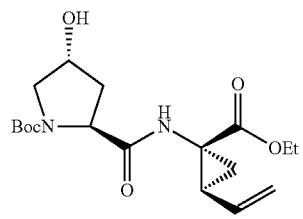 [SMILES: C=C[C@@H]1C[C@]1(NC(=O)[C@@H]1C[C@@H](O)CN1C(=O)OC(C)(C)C)C(=O)OCC]

(2S,4R)-tert-butyl 2-((1R,2S)-1-(ethoxycarbonyl)-2-vinylcyclopropylcarbamoyl)-4-hydroxypyrrolidine-1-carboxylate To a stirring slurry of N-Boc-hydroxy proline (78 g), HATU (128 g), and EtOAc (558 g), at 0° C., was added diisopropylethylamine (65 g). After 45 min, a solution containing vinylcyclopropylammonium tosylate (100 g), diisopropylethylamine (65.0 g), and EtOAc (366 g) was added to the activated ester solution. After 3 h at 10° C., the reaction slurry was filtered and the resulting cake was rinsed with EtOAc (2 L). The resulting filtrate was washed with a 10% aqueous solution of NaCl (5×770 g). The product-containing organic layer was filtered, concentrated under reduced pressure to an oil (85% yield).

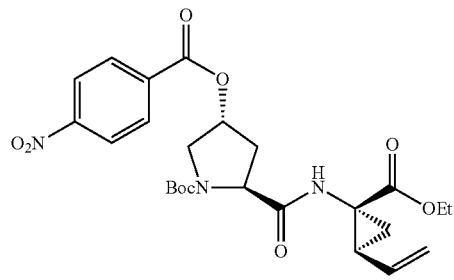 [SMILES: C=C[C@@H]1C[C@]1(NC(=O)[C@@H]1C[C@@H](OC(=O)c2ccc([N+](=O)[O-])cc2)CN1C(=O)OC(C)(C)C)C(=O)OCC]

(2S,4R)-tert-butyl 2-((1R,2S)-1-(ethoxycarbonyl)-2-vinylcyclopropylcarbamoyl)-4-(4-nitrobenzoyloxy)pyrrolidine-1-carboxylate To a mixture of (2S,4R)-tert-butyl 2-((1R,2S)-1-(ethoxycarbonyl)-2-vinylcyclopropylcarbamoyl)-4-hydroxypyrrolidine-1-carboxylate (90.0 g), 4-dimethylaminopyridine (1.5 g), diisopropylethylamine (39.5 g) and EtOAc (180 mL), at 5° C., was added p-nitrobenzoyl chloride (49.9 g) as a solution in EtOAc (310 mL). After 1 h at 5° C., the reaction was warmed to rt. After 15 h, the reaction was cooled to rt and additional p-nitrobenzoyl chloride (8.6 g), diisopropylethylamine (11.0 g), and EtOAc (70 mL) were added to the reaction solution. After 4.5 h at 5° C., the reaction was quenched by the addition of water (90 mL). The resulting layers were separated and the organic layer was washed with a 1.0 N aqueous solution of HCl (180 mL), 10% aqueous solution of KHCO₃ (2×135 g), water (150 mL), and a 10% aqueous solution of NaCl. The product-containing organic layer was concentrated to an oil (99% yield).

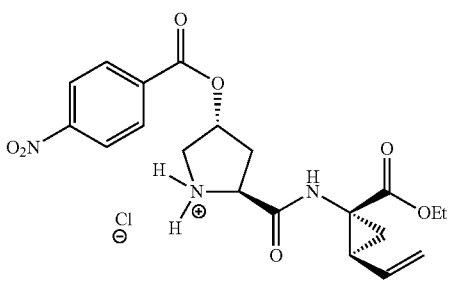 [SMILES: C=C[C@@H]1C[C@]1(NC(=O)[C@@H]1C[C@@H](OC(=O)c2ccc([N+](=O)[O-])cc2)C[NH2+]1)C(=O)OCC ; [Cl-]]

(2S,4R)-2-((1R,2S)-1-(ethoxycarbonyl)-2-vinylcyclopropylcarbamoyl)-4-(4-nitrobenzoyloxy)pyrrolidinium chloride To a stirring solution of ethanol at 0° C., was added acetyl chloride (5.7 g). The resulting solution was aged for 30 min. (2S,4R)-tert-Butyl 2-((1R,2S)-1-(ethoxycarbonyl)-2-vinylcyclopropylcarbamoyl)-4-(4-nitrobenzoyloxy)pyrrolidine-1-carboxylate (7.5 g) was then added as a solution in EtOAc (30 mL) to the acidic ethanol slurry solution at 10° C. The reaction was allowed to proceed for 1 h at 10° C., warmed to 15° C. for 1 h and then warmed to 20° C. After 16 h, EtOAc (30 mL) was added to the slurry and the resulting slurry was filtered. The cake was rinsed with EtOAc (30 mL) that had been cooled to 0° C. The title compound was placed in a vacuum oven, at 43° C., to remove residual solvent (6.9 g, 100% yield).

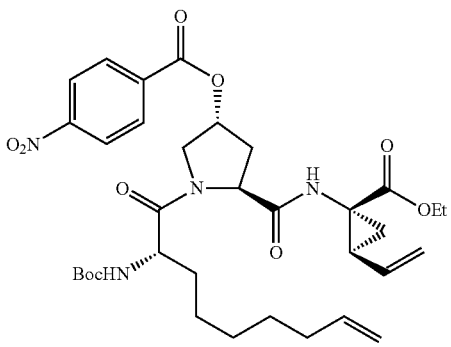 [SMILES: C=CCCCCC[C@H](NC(=O)OC(C)(C)C)C(=O)N1C[C@H](OC(=O)c2ccc([N+](=O)[O-])cc2)C[C@H]1C(=O)N[C@]1(C(=O)OCC)C[C@H]1C=C]

(3R,5S)-1-((S)-2-(tert-butoxycarbonylamino)non-8-enoyl)-5-((1R,2S)-1-(ethoxycarbonyl)-2-vinylcyclopropylcarbamoyl)pyrrolidin-3-yl 4-nitrobenzoate To a slurry of (2S,4R)-2-((1R,2S)-1-(ethoxycarbonyl)vinylcyclopropylcarbamoyl)-4-(4-nitrobenzoyloxy)pyrrolidinium chloride (34 g), (S)-2-(tert-butoxycarbonylamino) non-8-enoic acid (21.2 g), EtOAc (66 mL), and NMP (66 mL) at 0° C. was added diisopropylethylamine (34 g). Propanephosphonic acid anhydride (37.2 g) was charged as a solution in EtOAc (40 mL) to the reaction mixture. The temperature of the reaction solution was adjusted to 4° C., held for 30 min, and then warmed to 20° C. After 14 h, the reaction was diluted with EtOAc (250 mL) and then quenched with water (170 mL). The resulting layers were separated and the organic layer was washed with a 0.2 N aqueous solution of HCl (330 mL). The layers were separated and the organic layer was washed with a 8% aqueous solution of NaHCO₃ (330 mL). The phases were separated and then the wet organic solution was filtered over celite, extracted with a 5% aqueous solution of brine twice (330 g each time), and then concentrated under reduced pressure. The resulting oil was diluted with EtOAc (500 mL) and then filtered. The filtrate was concentrated under reduced pressure to an oil (49.1 g, 100% yield).

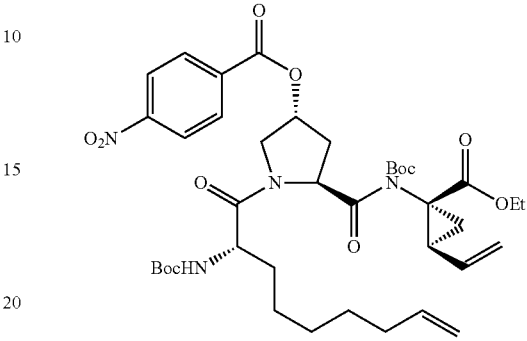

(3R,5S)-5-(tert-butoxycarbonyl((1R)-1-(ethoxycarbonyl)-2-vinylcyclopropyl)carbamoyl)-1-((S)-2-(tert-butoxycarbonylamino)non-8-enoyl)pyrrolidin-3-yl 4-nitrobenzoate To a solution of (3R,5S)-1-((S)-2-(tert-butoxycarbonylamino)non-8-enoyl)-5-((1R)-1-(ethoxycarbonyl)-2-vinylcyclopropylcarbamoyl)pyrrolidin-3-yl 4-nitrobenzoate (10.2 g) in toluene (34 g) was charged 4-dimethylaminopyridine (370 mg). A mixture of di-tert-butyl dicarbonate (4.95 g) and toluene (10 mL) was then added over a period of 5 minutes, and the mixture was heated to 40° C. The reaction was stirred for 2 h at 40° C. at which time the mixture was cooled to room temperature and diluted with toluene (30 mL). The organic mixture was extracted twice with 10% aq. KH₂PO₄ (50 mL each) followed by water (50 mL). The organic layer was evaporated to an oil (11.4 g, 98% yield).

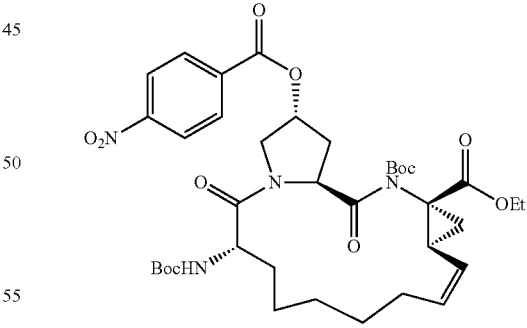

(2R,6S,14aR,16aS,Z)-15-tert-butyl 14a-ethyl 6-(tert-butoxycarbonylamino)-2-(4-nitrobenzoyloxy)-5,16-dioxo-2,3,5,6,7,8,9,10,11,13a,14,14a,16,16a-tetradecahydrocyclopropa[e]pyrrolo[1,2-a][1,4]diazacyclopentadecine-14a,15(1H)-dicarboxylate A flask containing toluene (140 mL) was warmed to 60° C. A solution of (1,3-dimesitylimidazolidin-2-ylidene)(5-(N, N-dimethylsulfamoyl)-2-isopropoxybenzylidene)ruthenium (VI) chloride (41 mg) in toluene (15 mL) and a solution of (3R,5S)-5-(tert-butoxycarbonyl((1R)-1-(ethoxycarbonyl)-2-vinylcyclopropyl)carbamoyl)-1-((S)-2-(tert-butoxycarbonylamino)non-8-enoyl)pyrrolidin-3-yl 4-nitrobenzoate (10 g) in toluene (46 mL) were added over 4 h. After 4 h, filterol (1.7 g) and imidazole (170 mg) were charged and the reaction was allowed to cool to room temperature overnight. The mixture was filtered and the filtrate was evaporated under vacuum. The product was crystallized from toluene/heptanes (1/5 v/v) to give a solid (9.3 g, 93% yield) after drying.

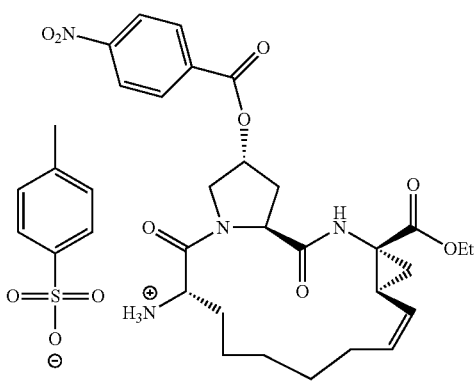 [SMILES: Cc1ccc(S(=O)(=O)[O-])cc1 ; CCOC(=O)[C@@]12C[C@H]1/C=C\CCCCC[C@H]([NH3+])C(=O)N1C[C@H](OC(=O)c3ccc([N+](=O)[O-])cc3)C[C@H]1C(=O)N2]

(2R,6S,13aS,14aR,16aS,Z)-14a-(ethoxycarbonyl)-2-(4-nitrobenzoyloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-aminium 4-methylbenzenesulfonate To a solution of (2R,6S,13aS,14aR,16aS,Z)-15-tert-butyl 14a-ethyl 6-(tert-butoxycarbonylamino)-2-(4-nitrobenzoyloxy)-5,16-dioxo-2,3,5,6,7,8,9,10,11,13a,14,14a,16,16a-tetradecahydrocyclopropa[e]pyrrolo[1,2-a][1,4]diazacyclopentadecine-14a, 15(1H)-dicarboxylate (25.6 g) dissolved in dichloromethane (150 mL) was added trifluoroacetic acid (71.6 g). The solution was warmed to 40° C. for 6 h, then concentrated by distillation under vacuum. Methyl-t-butyl ether and 2-methyltetrahydrofuran (130 mL each) were added and evaporated by distillation. A mixture of 2-methyltetrahydrofuran (190 mL) and methyl-t-butyl ether (190 mL) was charged and the resulting solution was extracted with 20% aq. solution of potassium phosphate dibasic (460 mL). After separation the organic layer was extracted with water (120 mL). The solvent was changed to 2-methyltetrahydrofuran by distillation under vacuum and replacing with 2-methyltetrahydrofuran. The final solvent level was about 160 mL. This solution was charged to a mixture p-toluenesulfonic acid monohydrate (6.0 g) and acetonitrile (320 mL.) The product was isolated by filtration and the cake was washed with acetonitrile and then dried under vacuum at 50° C. (20.3 g, 89% yield).

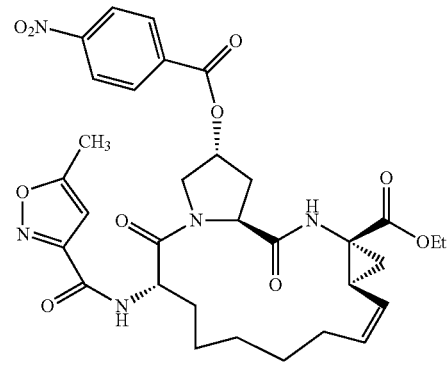 [SMILES: CCOC(=O)[C@@]12C[C@H]1/C=C\CCCCC[C@H](NC(=O)c1cc(C)on1)C(=O)N1C[C@H](OC(=O)c3ccc([N+](=O)[O-])cc3)C[C@H]1C(=O)N2]

(2R,6S,13aS,14aR,16aS,Z)-ethyl 6-(5-methylisoxazole-3-carboxamido)-2-(4-nitrobenzoyloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate To a solution of (2R,6S,13aS,14aR,16aS,Z)-14a-(ethoxycarbonyl)-2-(4-nitrobenzoyloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-aminium 4-methylbenzenesulfonate (9.95 g), 5-methylisoxazole-3-carboxylic acid (2.12 g), and NMP (30.0 g) at 5° C. was added diisopropylethylamine (6.5 g). Propanephosphonic acid anhydride (5.3 g) was charged as a solution in EtOAc (5.3 g) and NMP (10 mL) to the reaction mixture. The reaction was warmed to rt over 14 h. The reaction solution was diluted with 2-Me-THF (150 mL). The diluted reaction solution was washed with water (150 mL), a 1.0 M aqueous solution of $H_3PO_4$ (2×50 mL), water (50 mL), a 5% aqueous solution of $NaHCO_3$ (50 mL), and then a 10% aqueous solution of NaCl (2×50 mL). The organic solution was dried over $MgSO_4$, filtered, and then concentrated under reduced pressure, and then co-distilled with THF (200 mL). THF was added and the product-containing solution was filtered and evaporated to an oil (8.5 g, 93% yield).

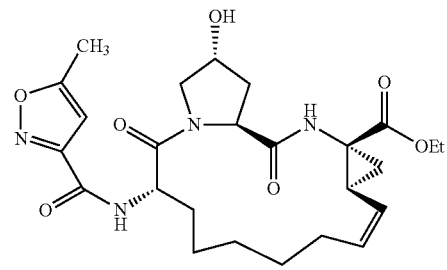 [SMILES: CCOC(=O)[C@@]12C[C@H]1/C=C\CCCCC[C@H](NC(=O)c1cc(C)on1)C(=O)N1C[C@H](O)C[C@H]1C(=O)N2]

(2R,6S,14aR,16aS,Z)-ethyl 2-hydroxy-6-(5-methylisoxazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate To a solution of (2R,6S,14aR,16aS,Z)-ethyl 6-(5-methylisoxazole-3-carboxamido)-2-(4-nitrobenzoyloxy)-5,16-dioxo-1,2,3,5,6,7,8,9,10,11,13a,14,14a,15,16,16a-hexadecahydrocyclopropa[e]pyrrolo[1,2-a][1,4]

diazacyclopentadecine-14a-carboxylate (10 g) in THF (110 mL) at 0° C. was added a solution of 0.5 M LiOH (33.8 mL). After 1 h, the reaction was diluted with dichloromethane (150 mL) and neutralized with 1N HCl (50 mL). The organic layer was extracted and washed with 5% NaHCO₃ (50 mL) twice and once with a 5% aq. NaCl solution (50 mL). The dichloromethane layer was evaporated under reduced pressure to an oil (8.0 g, 100% yield).

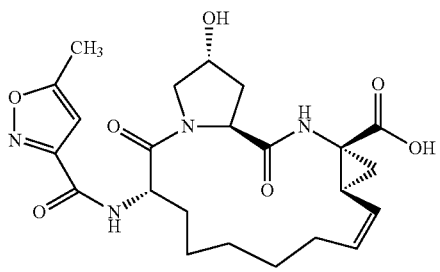 [SMILES: Cc1cc(C(=O)N[C@H]2CCCCC/C=C\[C@@H]3C[C@@]3(C(=O)O)NC(=O)[C@@H]3C[C@@H](O)CN3C2=O)no1]

(2R,6S,14aR,16aS,Z)-2-hydroxy-6-(5-methylisoxazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid To a solution of (2R,6S,14aR,16aS,Z)-ethyl 2-hydroxy-6-(5-methylisoxazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (10 g) in THF (52 g) and methanol (33 mL) at 0° C. was added 10% aq. LiOH (14.3 g). The solution was stirred at 10° C. for 22 h, then diluted with dichloromethane (150 mL). The reaction mixture was extracted with 1N HCl (100 mL) followed by water (100 mL). The solvent was changed to acetonitrile by distillation and the product crystallized. The final acetonitrile level was approximately 70 mL. The slurry was heated to 50° C. for 4 h, then allowed to cool to ambient temperature for 12 h. The slurry was filtered and the cake was washed with acetonitrile (20 mL) then dried under vacuum at 50° C. (8.5 g, 86% pure, 77% yield).

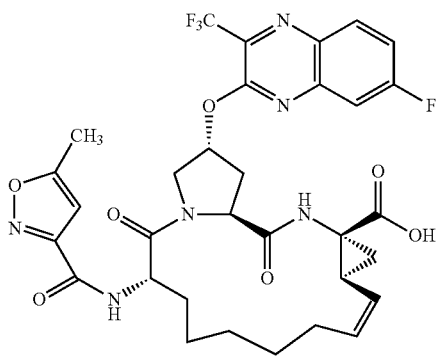 [SMILES: Cc1cc(C(=O)N[C@H]2CCCCC/C=C\[C@@H]3C[C@@]3(C(=O)O)NC(=O)[C@@H]3C[C@@H](Oc4nc5cc(F)ccc5nc4C(F)(F)F)CN3C2=O)no1]

(2R,6S,13aS,14aR,16aS,Z)-2-(7-fluoro-3-(trifluoromethyl)quinoxalin-2-yloxy)-6-(5-methylisoxazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (2R,6S,13aS,14aR,16aS,Z)-2-hydroxy-6-(5-methylisoxazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (15.2 g) was dissolved in dimethylsulfoxide (122 mL) and a solution of potassium tert-butoxide in THF (1.0M, 68.8 mL) was added dropwise, keeping the temperature to less than 30° C. The resulting solution was added to a solution of 3-chloro-6-fluoro-2-(trifluoromethyl)quinoxaline (8.3 g) in dimethylformamide (152 mL) over 30 min while at 0° C. After stirring for 30 min, the reaction was diluted with 2-methyltetrahydrofuran (330 mL), quenched with phosphoric acid (29.1 g), and finally diluted with water (441 mL). The layers were separated and the lower layer was extracted with 2-methyltetrahydrofuran (165 mL). The organic layers were combined and extracted twice with water (330 mL each time). The organic layer was concentrated, chased with acetonitrile, and the final volume adjusted to about 900 mL with acetonitrile. The slurry was warmed to 80° C., cooled to 0° C., and filtered. The solid was rinsed with acetonitrile (100 mL) and dried under vacuum at 50° C. (19.5 g, 84% yield)

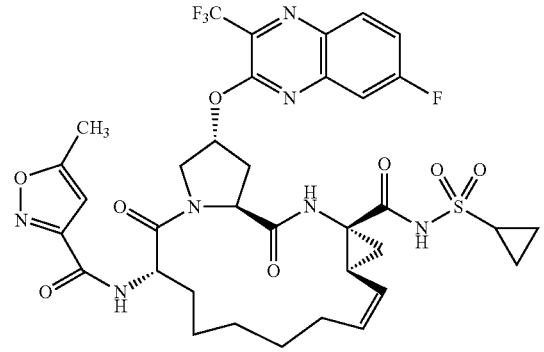 [SMILES: Cc1cc(C(=O)N[C@H]2CCCCC/C=C\[C@@H]3C[C@@]3(C(=O)NS(=O)(=O)C3CC3)NC(=O)[C@@H]3C[C@@H](Oc4nc5cc(F)ccc5nc4C(F)(F)F)CN3C2=O)no1]

N-((2R,6S,13aS,14aR,16aS,Z)-14a-(cyclopropylsulfonylcarbamoyl)-2-(7-fluoro-3-(trifluoromethyl)quinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide To a stirring solution of (2R,6S,13aS,14aR,16aS,Z)-2-(7-fluoro-3-(trifluoromethyl)quinoxalin-2-yloxy)-6-(5-methylisoxazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (5.13 g) and NMP (12.9 g) was added carbonyl diimidazole (1.83 g) as a solution in NMP (7.7 g). After 30 min, cyclopropylsulfonamide (1.81 g) was added to the reaction mixture as a solution in NMP (5.13 g). The solution was cooled to 5° C. and then DBU (4.0 g) was charged to the reaction mixture. The reaction was allowed to proceed for 15 h and then diluted with isopropyl acetate (IPAc) (33.5 g) and 2-methyltetrahydrofuran (33.5 g). The organic solution was washed with a 2.0 M aqueous solution of H₃PO₄ (51.3 g), a 5:3:1 solution of 2.0 M H₃PO₄, H₂O, 10% aqueous solution of NaCl (total volume of 50 mL), water (5×25 g), and then concentrated to 25 mL by distillation. The organic solution was diluted with IPAc (25.0 g) and then concentrated back to 25 mL by distillation. This process was repeated three times. The concentrated product-containing solution was diluted with IPAc (108 g), filtered, and then concentrated again to 25 mL. The product-containing solution was distilled, maintaining a constant volume by the addition of ethanol (106 g). Ethanol (35 mL) was then added. Water (3.0 g) was then added to the product solution and the mixture was heated to 80° C. and then cooled to 20° C. over 12 h. The slurry was filtered and the cake was rinsed with ethanol (10 mL). The cake was dried under vacuum to provide the product (4.64 g, 79% yield) as a white, crystalline solid: $^1$H NMR (400 MHz, DMSO-D6) ☐ ppm 11.14 (s, 1H), 9.02 (s, 1H), 8.69 (d, J=6.7 Hz, 1H), 8.27 (dd, J=9.1, 5.9 Hz, 1H), 7.79 (dd, J=9.6, 2.3 Hz, 1H), 7.72 (td, J=8.7, 2.3 Hz, 1H), 6.09 (s, 1H), 5.95 (br s, 1H), 5.61 (q, J=8.5 Hz, 1H), 5.12 (t, J=9.5 Hz, 1H), 4.65 (d, J=11.7 Hz, 1H), 4.50 (t, J=8.2 Hz, 1H), 4.38-4.28 (m, 1H), 3.96 (dd, J=11.3, 2.4 Hz, 1H), 2.96-2.88 (m, 1H), 2.69-2.55 (m, 2H), 2.52-2.44 (m, 1H), 2.42 (s, 3H), 2.31 (q, J=8.7 Hz, 1H), 1.96 (q, J=11.4 Hz, 1H), 1.77-1.66 (m, 1H), 1.63-1.56 (m, 2H), 1.45-1.28 (m, 5H), 1.27-1.16 (m, 2H), 1.15-0.95 (m, 4H). LC-MS (ESI): m/z=792.2 [M+H].

Example 188

(1aR,3aS,5R,9S,16aS,Z)-9-(tert-butoxycarbonylamino)-5-(6,7-dichloro-3-(thiophen-2-yl)quinoxalin-2-yloxy)-3,8-dioxo-1,1a,2,3,3a,4,5,6,8,9,10,11,12,13,14,16a-hexadecahydrocyclopropa[e]pyrrolo[1,2-a][1,4]diazacyclopentadecine-1a-carboxylic acid Step A 6,7-dichloro-3-(thiophen-2-yl)quinoxalin-2(1H)-one 6,7-dichloro-3-(thiophen-2-yl)quinoxalin-2(1H)-one A mixture of 4,5-dichlorobenzene-1,2-diamine (1.0 g, 5.65 mmol), ethyl 2-oxo-2-(thiophen-2-yl)acetate (1.056 g, 5.73 mmol) and ethanol (8 ml) was stirred at 70° C. for 11 h, cooled to room temperature, filtered and washed with cold ethanol. The collected pale yellow solid was dried further (1.07 g) and used directly in next step.

Step B (1aR,3aS,5R,9S,16aS,Z)-ethyl 9-(tert-butoxycarbonylamino)-5-(6,7-dichloro-3-(thiophen-2-yl)quinoxalin-2-yloxy)-3,8-dioxo-1,1a,2,3,3a,4,5,6,8,9,10,11,12,13,14,16a-hexadecahydrocyclopropa[e]pyrrolo[1,2-a][1,4]diazacyclopentadecine-1a-carboxylate

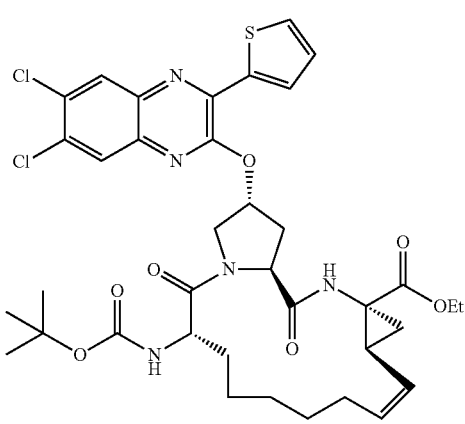

To a mixture of (1aR,3aS,5S,9S,16aS,Z)-ethyl 9-(tert-butoxycarbonylamino)-5-hydroxy-3,8-dioxo-1,1a,2,3,3a,4,5,6,8,9,10,11,12,13,14,16a-hexadecahydrocyclopropa[e]pyrrolo[1,2-a][1,4]diazacyclopentadecine-1a-carboxylate (WO2008/002924, 122 mg, 0.24 mmol), 6,7-dichloro-3-(thiophen-2-yl)quinoxalin-2(1H)-one (82 mg, 0.276 mmol), triphenylphosphine (90 mg, 0.34 mmol) and THF (5 ml) at room temperature was added dropwise DIAD (0.08 ml, 0.41 mmol). The resulting mixture was stirred at room temperature over 24 h, concentrated, and purified by flash chromatography (Ethyl acetate/hexanes 1:5 to 1:2) to give the title compound as an off-white solid (58 mg).

Step C

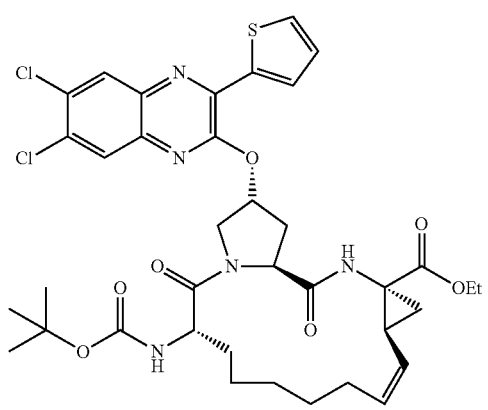

→

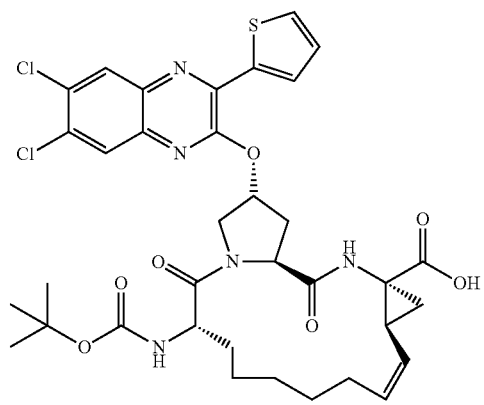

To a solution of (1aR,3aS,5R,9S,16aS,Z)-ethyl 9-(tert-butoxycarbonylamino)-5-(6,7-dichloro-3-(thiophen-2-yl)quinoxalin-2-yloxy)-3,8-dioxo-1,1a,2,3,3a,4,5,6,8,9,10,11,12,13,14,16a-hexadecahydrocyclopropa[e]pyrrolo[1,2-a][1,4]diazacyclopentadecine-1a-carboxylate (58 mg, 0.075 mmol) in THF (3.2 ml) and MeOH (1.6 ml) at room temperature was added aqueous lithium hydroxide (1M, 2 ml). The resulting mixture was stirred at room temperature for 24 h, diluted with EtOAc, acidified with 1N HCl to pH 4-5, extracted with EtOAc (3×). The combined organic layers was washed with brine, dried over sodium sulfate and concentrated to give the title compound. MS (ESI): m/z 744.11 (M+H)

Example 189

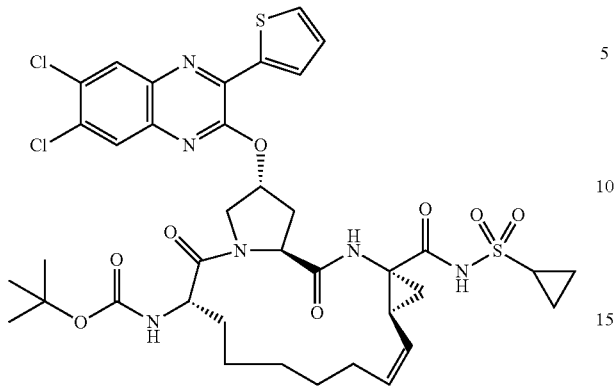

tert-butyl (1aR,3aS,5R,9S,16aS,Z)-1a-(cyclopropyl-sulfonylcarbamoyl)-5-(6,7-dichloro-3-(thiophen-2-yl)quinoxalin-2-yloxy)-3,8-dioxo-1,1a,2,3,3a,4,5,6,8,9,10,11,12,13,14,16a-hexadecahydrocyclopropa[e]pyrrolo[1,2-a][1,4]diazacyclopentadecin-9-ylcarbamate To a solution of (1aR,3aS,5R,9S,16aS,Z)-9-(tert-butoxycarbonylamino)-5-(6,7-dichloro-3-(thiophen-2-yl)quinoxalin-2-yloxy)-3,8-dioxo-1,1a,2,3,3a,4,5,6,8,9,10,11,12,13,14,16a-hexadecahydrocyclopropa[e]pyrrolo[1,2-a][1,4]diazacyclopentadecine-1a-carboxylic acid (0.07 mmol) in dichloromethane (4 ml) was added CDI (24 mg, 0.14 mmol). The resulting mixture was stirred at 45° C. for 1 h. To this were added cyclopropylsulfonamide (12 mg, 0.1 mmol) and DBU (0.1 mmol). The resulting mixture was stirred at 45° C. for 20 h. Purification by preparative HPLC gave the title compound as a pale yellow solid. MS (ESI): m/z 847.38 (M+H)

Example 190

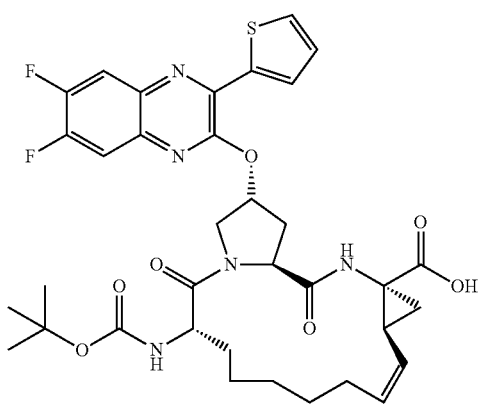

(1aR,3aS,5R,9S,16aS,Z)-9-(tert-butoxycarbonylamino)-5-(6,7-difluoro-3-(thiophen-2-yl)quinoxalin-2-yloxy)-3,8-dioxo-1,1a,2,3,3a,4,5,6,8,9,10,11,12,13,14,16a-hexadecahydrocyclopropa[e]pyrrolo[1,2-a][1,4]diazacyclopentadecine-1a-carboxylic acid The title compound was prepared from 4,5-difluorobenzene-1,2-diamine following the same procedures as described above. MS (ESI): m/z 712.38 (M+H).

Example 191

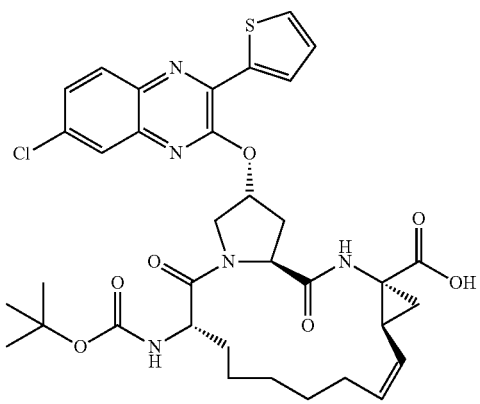

(1aR,3aS,5R,9S,16aS,Z)-9-(tert-butoxycarbonylamino)-5-(7-chloro-3-(thiophen-2-yl)quinoxalin-2-yloxy)-3,8-dioxo-1,1a,2,3,3a,4,5,6,8,9,10,11,12,13,14,16a-hexadecahydrocyclopropa[e]pyrrolo[1,2-a][1,4]diazacyclopentadecine-1a-carboxylic acid The title compound was prepared from 4-chlorobenzene-1,2-diamine following the same procedures as described above. MS (ESI): m/z 710.09 (M+H).

Example 192

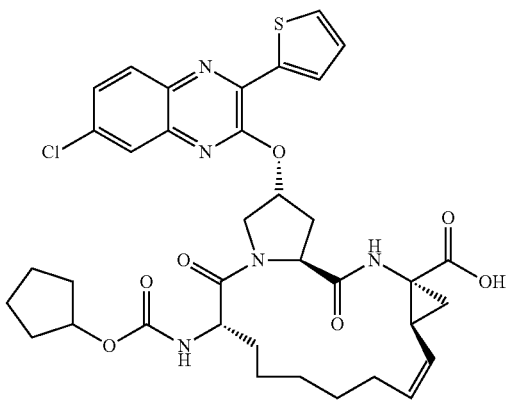

(1aR,3aS,5R,9S,16aS,Z)-5-(7-chloro-3-(thiophen-2-yl)quinoxalin-2-yloxy)-9-(cyclopentyloxycarbonylamino)-3,8-dioxo-1,1a,2,3,3a,4,5,6,8,9,10,11,12,13,14,16a-hexadecahydrocyclopropa[e]pyrrolo[1,2-a][1,4]diazacyclopentadecine-1a-carboxylic acid The title compound was prepared from 4-chlorobenzene-1,2-diamine following the similar procedures as described above. MS (ESI): m/z 722.25 (M+H).

Example 193

Synthesis of the Cyclic Peptide Precursor

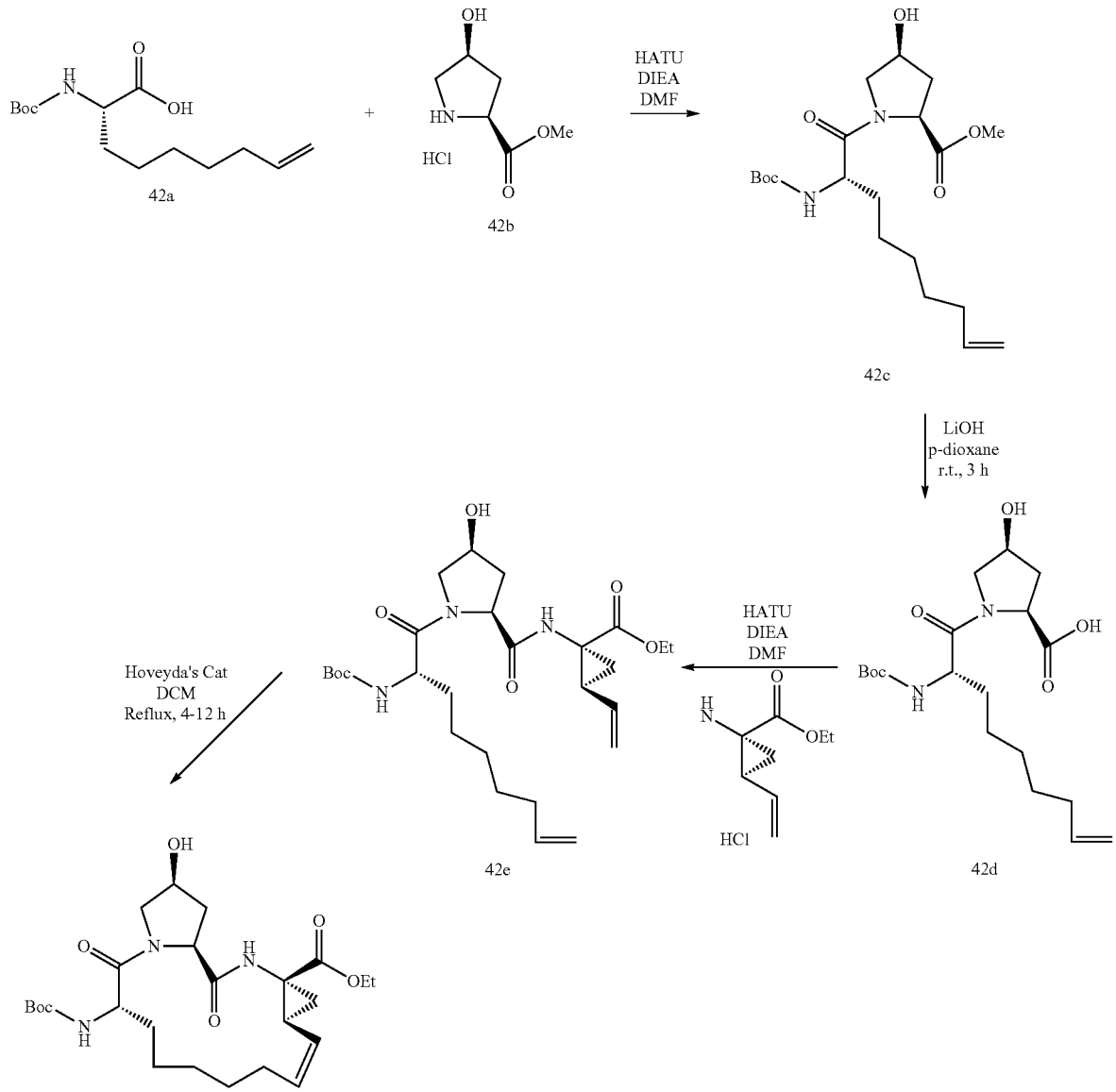

To a solution of Boc-L-2-amino-8-nonenoic acid 42a (1.36 g, 5 mol) and the commercially available cis-L-hydroxyproline methyl ester 42b (1.09 g, 6 mmol) in 15 ml DMF, was added DIEA (4 ml, 4 eq.) and HATU (4 g, 2 eq). The coupling was carried out at 0° C. over a period of 1 hour. The reaction mixture was diluted with 100 mL EtOAc, and followed by washing with 5% citric acid 2×20 ml, water 2×20 ml, 1M NaHCO$_3$ 4×20 ml and brine 2×10 ml, respectively. The organic phase was dried over anhydrous Na$_2$SO$_4$ and then was evaporated, affording the dipeptide 42c (1.91 g, 95.8%) that was identified by HPLC (Retention time=8.9 min, 30-70%, 90% B), and MS (found 421.37, M+Na$^+$).

The dipeptide 42c (1.91 g) was dissolved in 15 mL of dioxane and 15 mL of 1 N LiOH aqueous solution and the hydrolysis reaction was carried out at room temperature for 4 hours. The reaction mixture was acidified by 5% citric acid and extracted with 100 mL EtOAc, and followed by washing with water 2×20 ml, and brine 2×20 ml, respectively. The organic phase was dried over anhydrous Na$_2$SO$_4$ and then removed in vacuum, yielding the free carboxylic acid compound 42d (1.79 g, 97%), which was used for next step synthesis without need for further purification.

To a solution of the free acid obtained above (1.77, 4.64 mmol) in 5 ml DMF, D-β-vinyl cyclopropane amino acid ethyl ester (0.95 g, 5 mmol), DIEA (4 ml, 4 eq.) and HATU (4 g, 2 eq) were added. The coupling was carried out at 0° C. over a period of 5 hours. The reaction mixture was diluted with 80 mL EtOAc, and followed by washing with 5% citric acid 2×20 ml, water 2×20 ml, 1M NaHCO$_3$ 4×20 ml and brine 2×10 ml, respectively. The organic phase was dried over anhydrous Na$_2$SO$_4$ and then evaporated. The residue was purified by silica gel flash chromatography using different ratios of hexanes:EtOAc as elution phase (5:1→3:1→1:1→1:2→1:5). The linear tripeptide 42e was isolated as an oil after removal of the elution solvents (1.59 g, 65.4%), identified by HPLC (Retention time=11.43 min) and MS (found 544.84, M+Na$^+$).

A solution of the linear tripeptide 42e (1.51 g, 2.89 mmol) in 200 ml dry DCM was deoxygenated by bubbling N$_2$. Hoveyda's 1$^{st}$ generation catalyst (5 mol % eq.) was then added as solid. The reaction was refluxed under N$_2$ atmosphere 12 hours. The solvent was evaporated and the residue was purified by silica gel flash chromatography using different ratios of hexanes:EtOAc as elution phase (9:1→5:1→3:1→1:1→1:2→1:5). The cyclic peptide precursor was isolated as a white powder after removal of the elution solvents (1.24 g, 87%), identified by HPLC (Retention time=7.84 min, 30-70%, 90% B), and MS (found 516.28, M+Na$^+$).

(2S,6S,13aS,14aR,16aS,Z)-ethyl 2-(4-bromophenyl-sulfonyloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate

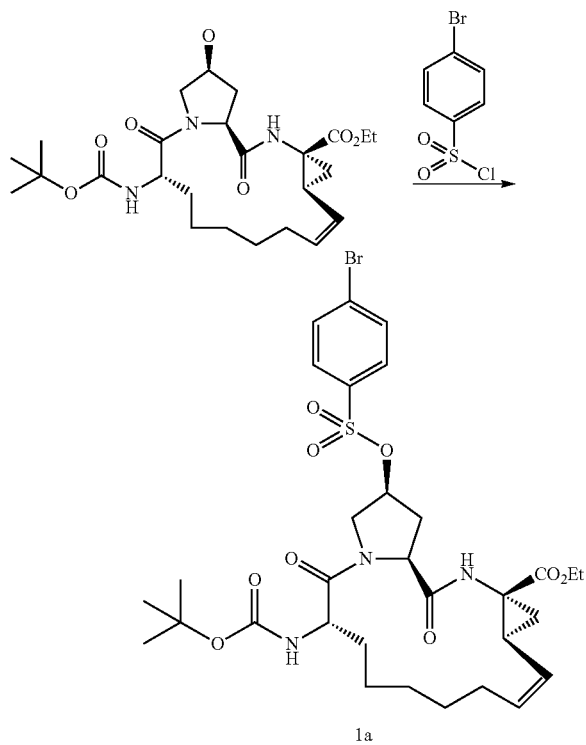

1a

A solution of (2S,6S,13aS,14aR,16aS,Z)-ethyl 6-(tert-butoxycarbonylamino)-2-hydroxy-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (22.1 g, 44.8 mmol) and DABCO (8.5 g, 76.7 mmol) in toluene (88 mL) was stirred at room temperature. To this solution was added a solution of 4-bromobenzene-1-sulfonyl chloride 17.2 g, 67.2 mmol) in toluene (44 mL). After the addition was complete the reaction mixture was quenched with 10% aqueous sodium carbonate (110 mL) and the mixture stirred for 15 min. Tetrahydrofuran (44 mL) was added and the mixture was washed with 0.5 M HCl, water, and then saturated aqueous sodium chloride. The organic layer was dried over anhydrous magnesium sulfate, filtered, and evaporated under reduced pressure and dried to provide the title compound (27.7 g, 87% yield), which was used without further purification.}

Example 194

Measurement of Potency of Inhibition with Purified NS3 Protease Enzyme

The activity of recombinant HCV NS3 proteases derived from isolates representing genotypes 1, 2, 3 or 4 is measured by cleavage of the following peptide substrate:

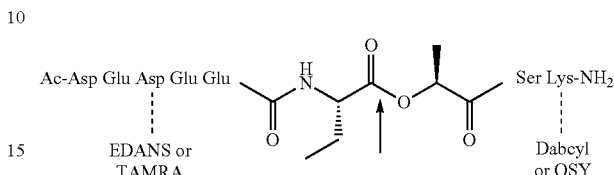

The substrate is labeled with a fluor and a fluorescence quencher. Cleavage results in release of the quencher and an increase in fluorescence. NS3 protease is incubated with a dilution series of inhibitor in 150 mM NaCl, 10% Glycerol, 5 mM DTT, with or without 0.01% dodecyl maltoside for either 30 minutes or 300 minutes. Substrate is added at a concentration of 5 uM to initiate the reaction, and fluorescence is measured at 2 minute intervals for 30 minutes. Enzyme concentrations range from 10 to 100 nM in the absence of detergent, or 10-fold lower in the presence of detergent. Substrate peptides are labeled with either EDANS and DABCYL (excitation 355 nm, emission 485 nm) or TAMRA and QSY (excitation 544 nm, emission 590 nm). For routine IC50 determination, 3-fold serial dilutions starting with initial concentrations of 100 μM, 200 μM, or 2 mM are used. For compounds with K$_i$ values approaching or lower than the enzyme concentration, a tight-binding calculation format is used, with 24 dilutions of inhibitor covering a range of 0 to 100 nM inhibitor. K$_i$ values are calculated using the tight binding assay format, according to the following equation:

$$V=A\{[(K+I-E)^2+4KE])^{1/2}-(K+I-E)\},$$

where I=total inhibitor concentration, E=active enzyme concentration, K=apparent K$_i$ value and A=[k$_{cat}$)S/2][K$_m$=(S)].

Replicon Cell Lines

Two subgenomic replicon cell lines can be used for compound characterization in cell culture: one derived from genotype 1a and one derived from genotype 1b. Both replicon constructs are bicistronic subgenomic replicons essentially similar to those described by Bartenschlager and coworkers (Lohmann et al., *Science* (1999) 285(5424):110-113). The genotype 1a replicon construct contains the NS3-NS5B coding region derived from the H77 strain of HCV (1a-H77) (Blight et al., *J Virol* (2003) 77(5):3181-3190). The first cistron of the construct consists of the first 36 nucleotides of the HCV 1a-H77 core gene fused to a firefly luciferase reporter and a neomycin phosphotransferase (Neo) selectable marker. The luciferase and Neo coding regions are separated by the FMDV 2a protease. The second cistron contains the NS3-NS5B coding region derived from 1a-H77 with the addition of adaptive mutations E1202G in NS3, K1691R in NS4A, and K2040R and S2204I in NS5A. The 1b-Con-1 replicon construct is identical to the 1a-H77 replicon, except that the 5' and 3' NTRs and the NS3-NS5B coding region can be derived from the 1b-Con-1 strain (Blight et al., *Science* (2000) 290(5498):1972-1974), and the adaptive mutations are E1202G and T1280I in NS3 and S2204I in NS5A.

Replicon Compound Testing

Replicon cell lines can be maintained in Dulbecco's modified Eagles medium (DMEM) containing 100 IU/ml penicillin, 100 mg/ml streptomycin (Invitrogen), 200 mg/ml G418 (Invitrogen) and 10% (v/v) fetal bovine serum (FBS). Replicon-containing cells can be seeded into 96 well plates at a density of 5000 cells per well in 100 µl DMEM containing 5% FBS. The next day, the compound can be initially diluted in dimethyl sulfoxide (DMSO) to generate a 200× stock of the inhibitor in a series of 8 half-log dilutions. The dilution series can then be diluted 100-fold in the medium containing 5% FBS. One hundred microliters of medium with the inhibitor can be added to each well of the overnight cell culture plate already containing 100 µl of DMEM with 5% FBS. In assays where the protein binding effect on inhibitor potency is assessed, the medium from the overnight cell culture plates can be replaced with 200 µl DMEM containing 40% human plasma (Innovative Research) plus 5% FBS as well as compound. The cells can be grown for 4 days in tissue culture incubators. The inhibitory effects of compounds against the replicons can be determined by measuring either the level of luciferase or HCV RNA. The luciferase assay can be conducted using a Luciferase Assay System kit (Promega) following the manufacturer's instructions. Briefly, the cell culture medium is removed and wells are washed with 200 µl of phosphate-buffered saline. To each well Passive Lysis buffer (Promega, Wis.) is added and the plates are incubated for 30 min with rocking to lyse the cells. Luciferin solution (50 µl, Promega) is added, and luciferase activity is measured with a Victor II luminometer (Perkin-Elmer). To determine HCV RNA levels, RNA extractions can be performed using the CellsDirect kit (Invitrogen), and the HCV RNA copy number can be measured using the SuperScript III Platinum One-Step qRT-PCR system (Invitrogen) and primers specific to the HCV 5' nontranslated region. Cytotoxicity can be determined by the 3-[4,5-dimethylhiazol-2-yl]-2,5-diphenyltetrazolium bromide (MTT) colorimetric assay as follows. Replicon cells is plated in 96-well plates (4000 cells per well), the next day compound dilutions are added as in the activity assay, and the cells are grown in the presence of the inhibitors for 4 days. The MTT solution is diluted in DMEM containing 5% FBS and 60 µl of the solution is added to the cells. After 4 hrs, the cells are solubilized by the addition of 30 □µl SDS (20% in 0.02 N HCl). The plates are incubated overnight and the optical density can be measured at 570 nm. To determine compounds' $EC_{50}$ and $TD_{50}$, luciferase, RNA inhibition and MTT data can be analyzed using the GraphPad Prism 4 software (equation: sigmoidal dose-response—variable slope).

Mutants in Transient Replicons

Mutations detected in resistance selection studies can be introduced into wild type transient replicon constructs based on genotypes 1a-H77 and 1b-N. Both replicons are bicistronic sub-genomic constructs containing a firefly luciferase reporter similar to those described above, but they do not contain a Neo selectable marker and are therefore only suitable for transient replication assays. The 1a-H77 replicon for transient assays further differs from the replicon in the stable cell line in that it contains NS2 through NS5B in the second cistron. The 1b-N strain replicon contains NS3 through NS5B in the second cistron, with adaptive mutations E1202G in NS3 and S2204I in NS5A. Mutagenesis can be performed using the Stratagene QuikChange XL II site-directed mutagenesis kit. Mutants' sequences can be confirmed, plasmids can be linearized with Xba I restriction enzyme and used as template for in vitro transcription reactions to make mutant replicon RNA for transient transfections. In vitro transcription can be performed with the T7 Megascript kit (Ambion).

Transient replicon transfections can be performed essentially as described by Mo et al. (*Antimicrob Agents Chemother* (2005) 49(10):4305-4314) with slight modifications. Fifteen micrograms of template RNA can be used to electroporate $3 \times 10^6$ cells in a 200 µl volume in a 0.2 cm cuvette. The cells used for transient transfections can be Huh7 cells obtained by curing replicon-containing cells with IFN (Mo et al., supra). Electroporation can be done with a Gene Pulser II (Bio-Rad, CA) at 480V and 25 µF, using two manual pulses. Transfected cells can be diluted to $7.5 \times 10^4$ cells/ml and plated in 96 well plates at $7.5 \times 10^3$ cells per well in DMEM with 5% FBS and 100 IU/ml penicillin, 100 mg/ml streptomycin (Invitrogen). Four hours post-transfection, one plate is harvested for luciferase measurement; this plate may provide a measure of the amount of input RNA that can be translated, and thus of transfection efficiency. To the remaining plates, test compound serial dilutions in DMSO can be added (0.5% DMSO final concentration), and plates are incubated for 4 days.

Exemplary compounds of the present invention were tested for their anti-HCV activities. Many of the compounds tested showed unexpected anti-HCV activities, including excellent activities in biochemical assays against HCV proteases representing various HCV genotypes, superior activities in standard HCV replicon assays including activity against 1a-H77 and 1b-con1 HCV strains in the absence or presence of 40% human plasma, and/or excellent activities in transient replicon assays against drug-resistant mutants in a number of different HCV genetic backgrounds.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

Those skilled in the art will recognize, or be able to ascertain using no more than routine experimentation, many equivalents of the specific embodiments of the invention described herein. Such equivalents are intended with be encompassed by the following claims.

What is claimed is:

1. A compound of Formula I:

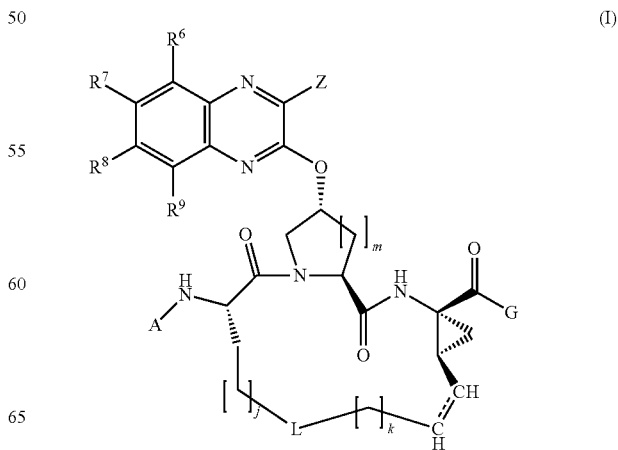

(I)

wherein

A is H, —(C=O)—O—R$^1$, —(C=O)—R$^1$, —(C=O)—N(R$^1$R$^2$), —S(O)$_2$—R$^1$, or —S(O)$_2$—N(R$^1$R$^2$), each R$^1$ is independently selected from the group consisting of:
(i) H, aryl; substituted aryl; heteroaryl; substituted heteroaryl;
(ii) heterocycloalkyl or substituted heterocycloalkyl; and
(iii) —C$_1$-C$_8$ alkyl, —C$_2$-C$_8$ alkenyl or —C$_2$-C$_8$ alkynyl, each containing 0, 1, 2, or 3 heteroatoms independently selected from O, S, and N; substituted —C$_1$-C$_8$ alkyl, substituted —C$_2$-C$_8$ alkenyl or substituted —C$_2$-C$_8$ alkynyl, each containing 0, 1, 2, or 3 heteroatoms independently selected from O, S and N; —C$_3$-C$_{12}$ cycloalkyl, substituted —C$_3$-C$_{12}$ cycloalkyl; —C$_3$-C$_{12}$ cycloalkenyl, or substituted —C$_3$-C$_{12}$ cycloalkenyl;

each R$^2$ is independently selected from the group consisting of:
(i) hydrogen;
(ii) aryl; substituted aryl; heteroaryl; substituted heteroaryl;
(iii) heterocycloalkyl or substituted heterocycloalkyl; and
(iv) —C$_1$-C$_8$ alkyl, —C$_2$-C$_8$ alkenyl or —C$_2$-C$_8$ alkynyl, each containing 0, 1, 2, or 3 heteroatoms independently selected from O, S, and N; substituted —C$_1$-C$_8$ alkyl, substituted —C$_2$-C$_8$ alkenyl or substituted —C$_2$-C$_8$ alkynyl, each containing 0, 1, 2, or 3 heteroatoms independently selected from O, S and N; —C$_3$-C$_{12}$ cycloalkyl, substituted —C$_3$-C$_{12}$ cycloalkyl; —C$_3$-C$_{12}$ cycloalkenyl, or substituted —C$_3$-C$_{12}$ cycloalkenyl;

G is —NHS(O)$_2$—R$^3$, —O—R$^4$, or —NH(SO$_2$)NR$_4$R$_5$;

each R$_3$ is independently selected from:
(i) C$_3$-C$_{12}$ cycloalkyl, substituted —C$_3$-C$_{12}$ cycloalkyl, aryl; substituted aryl; heteroaryl; substituted heteroaryl;
(ii) heterocycloalkyl or substituted heterocycloalkyl; and
(iii) —C$_1$-C$_8$ alkyl, —C$_2$-C$_8$ alkenyl or —C$_2$-C$_8$ alkynyl, each containing 0, 1, 2, or 3 heteroatoms independently selected from O, S, and N; substituted —C$_1$-C$_8$ alkyl, substituted —C$_2$-C$_8$ alkenyl or substituted —C$_2$-C$_8$ alkynyl, each containing 0, 1, 2, or 3 heteroatoms independently selected from O, S and N; —C$_3$-C$_{12}$ cycloalkenyl, or substituted —C$_3$-C$_{12}$ cycloalkenyl; and each R$_4$ and R$_5$ is independently selected from:
(i) hydrogen;
(ii) aryl; substituted aryl; heteroaryl; substituted heteroaryl;
(iii) heterocycloalkyl or substituted heterocycloalkyl; and
(iv) —C$_1$-C$_8$ alkyl, —C$_2$-C$_8$ alkenyl or —C$_2$-C$_8$ alkynyl, each containing 0, 1, 2, or 3 heteroatoms independently selected from O, S, and N; substituted —C$_1$-C$_8$ alkyl, substituted —C$_2$-C$_8$ alkenyl or substituted —C$_2$-C$_8$ alkynyl, each containing 0, 1, 2, or 3 heteroatoms independently selected from O, S and N; —C$_3$-C$_{12}$ cycloalkyl, or substituted —C$_3$-C$_{12}$ cycloalkyl; —C$_3$-C$_{12}$ cycloalkenyl, or substituted —C$_3$-C$_{12}$ cycloalkenyl;

L is a C$_2$—O$_5$ saturated or unsaturated chain, optionally containing one to three heteroatoms independently selected from O, N and S(O)$_n$, wherein L is optionally substituted with one or more substituents selected from halogen, hydroxy, mercapto, amino, carboxy, nitro, oxo, phosphonoxy, phosphono, thioxo, cyano, C$_1$-C$_6$alkyl, C$_2$-C$_6$alkenyl and C$_2$-C$_6$alkynyl, wherein each C$_1$-C$_6$alkyl, C$_2$-C$_6$alkenyl and C$_2$-C$_6$alkynyl, group is optionally substituted at each occurrence with one or more substituents selected from halogen, hydroxy, mercapto, amino, carboxy, nitro, oxo, phosphonoxy, phosphono, thioxo, formyl and cyano;

Z is
(i) —C$_1$-C$_8$ alkyl, —C$_2$-C$_8$ alkenyl or —C$_2$-C$_8$ alkynyl, each containing 0, 1, 2, or 3 heteroatoms independently selected from O, S, and N and optionally substituted with one or more halo; or
(ii) heteroaryl or substituted heteroaryl;

j=0, 1, 2, 3, or 4;
k=0, 1, 2, or 3;
m=0, 1, or 2;
n is 0, 1, or 2;

---- denotes a carbon-carbon single or double bond (i.e.,

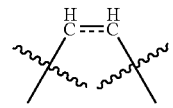

means

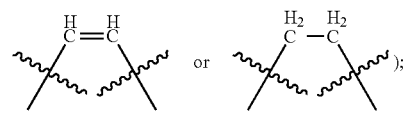

R$^6$ is H or halo;
R$^7$ is H or halo;
R$^8$ is H or halo;
R$^9$ is H or halo;
wherein if each of R$_6$, R$_7$, R$_8$ and R$_9$ is H, then Z is —C$_1$-C$_8$ alkyl, —C$_2$-C$_8$ alkenyl or —C$_2$-C$_8$ alkynyl, each substituted with one or more halo and each containing 0, 1, 2, or 3 heteroatoms independently selected from O, S, and N; and salts, solvates and hydrates thereof.

2. The compound of claim 1, wherein R$^3$ is independently cyclopropyl optionally substituted with C$_1$-C$_6$alkyl, C$_1$-C$_6$alkoxyC$_1$-C$_6$alkyl, —C(O)OH, —C(O)NH$_2$, or —C(O)O—C$_1$-C$_6$alkyl.

3. The compound of claim 1, wherein A is —(C=O)—O—R$^1$.

4. The compound of claim 1, wherein A is —(C=O)—R$^1$.

5. The compound of claim 4, wherein R$^1$ is optionally substituted aryl.

6. The compound of claim 4, wherein R$^1$ is optionally substituted heteroaryl.

7. The compound of claim 5, wherein Z is —C$_1$-C$_8$ alkyl containing 0, 1, 2, or 3 heteroatoms selected from 0, S, or NR$_1$ and substituted with one or more halo.

8. The compound of claim 7 wherein each of R$^6$, R$^7$, R$^8$ and R$^9$ is H.

9. The compound of claim 7 wherein one of R$^6$, R$^7$, R$^8$ and R$^9$ is halo.

10. The compound of claim 7 wherein two of R$^6$, R$^7$, R$^8$ and R$^9$ are halo.

11. The compound of claim 7 wherein one of R$^7$ or R$^8$ is halo.

12. The compound of claim 7 wherein R$^7$ is fluoro.

13. The compound of claim 7 wherein $R^8$ is fluoro.

14. The compound of claim 7 wherein $R^9$ is fluoro.

15. A pharmaceutical composition comprising a therapeutically effective amount of a compound of claim 1 or a pharmaceutically acceptable salt thereof, in combination with a pharmaceutically acceptable carrier or excipient.

16. A method of producing a compound of Formula I, or a pharmaceutically acceptable salt thereof, comprising the step of reacting a compound of Formula (II) with a compound of Formula (III) to provide a compound of Formula (I):

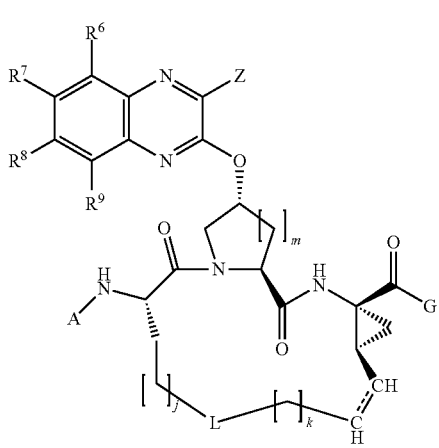

(I)

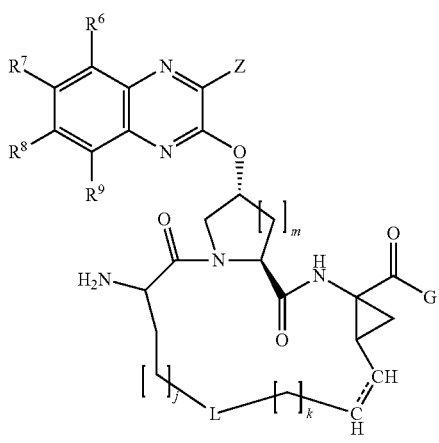

(II)

(III)

wherein for Formulae (I), (II) and (III):

A is —(C=O)—$R^1$, each $R^1$ is independently selected from the group consisting of:
(i) H, aryl; substituted aryl; heteroaryl; substituted heteroaryl;
(ii) heterocycloalkyl or substituted heterocycloalkyl; and
(iii) —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; substituted —$C_1$-$C_8$ alkyl, substituted —$C_2$-$C_8$ alkenyl or substituted —$C_2$-$C_8$ alkynyl, each containing 0, 1, 2, or 3 heteroatoms independently selected from O, S and N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;

G is —NHS(O)$_2$—$R^3$, —O—$R^4$, or —NH(SO$_2$)NR$_4$R$_5$;

each $R_3$ is independently selected from:
(i) $C_3$-$C_{12}$ cycloalkyl, substituted —$C_3$-$C_{12}$ cycloalkyl, aryl; substituted aryl;
heteroaryl; substituted heteroaryl;
(ii) heterocycloalkyl or substituted heterocycloalkyl; and
(iii) —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; substituted —$C_1$-$C_8$ alkyl, substituted —$C_2$-$C_8$ alkenyl or substituted —$C_2$-$C_8$ alkynyl, each containing 0, 1, 2, or 3 heteroatoms independently selected from O, S and N; —$C_3$-$C_{12}$ cycloalkenyl, or substituted —$C_3$-$C_{12}$ cycloalkenyl; and each $R_4$ and $R_5$ is independently selected from:
(i) hydrogen;
(ii) aryl; substituted aryl; heteroaryl; substituted heteroaryl;
(iii) heterocycloalkyl or substituted heterocycloalkyl; and
(iv) —$C_1$-$C_8$ alkyl, —$C_2$-$C_8$ alkenyl or —$C_2$-$C_8$ alkynyl, each containing 0, 1, 2, or 3 heteroatoms independently selected from O, S, and N; substituted —$C_1$-$C_8$ alkyl, substituted —$C_2$-$C_8$ alkenyl or substituted —$C_2$-$C_8$ alkynyl, each containing 0, 1, 2, or 3 heteroatoms independently selected from O, S and N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

L is a $C_2$—$O_5$ saturated or unsaturated chain, optionally containing one to three heteroatoms independently selected from O, N and S(O)$_n$, wherein L is optionally substituted with one or more substituents selected from halogen, hydroxy, mercapto, amino, carboxy, nitro, oxo, phosphonoxy, phosphono, thioxo, cyano, $C_1$-$C_6$alkyl, $C_2$-$C_6$alkenyl and $C_2$-$C_6$alkynyl, wherein each $C_1$-$C_6$alkyl, $C_2$-$C_6$alkenyl and $C_2$-$C_6$alkynyl, group is optionally substituted at each occurrence with one or more substituents selected from halogen, hydroxy, mercapto, amino, carboxy, nitro, oxo, phosphonoxy, phosphono, thioxo, formyl and cyano;

Z is
(i) —$C_1$-$C_8$ alkyl, —$C_2$-$C_8$ alkenyl or —$C_2$-$C_8$ alkynyl, each containing 0, 1, 2, or 3 heteroatoms independently selected from O, S, and N and optionally substituted with one or more halo; or
(ii) heteroaryl or substituted heteroaryl;

j=0, 1, 2, 3, or 4;

k=0, 1, 2, or 3;

m=0, 1, or 2;

n is 0, 1, or 2;

----- denotes a carbon-carbon single or double bond (i.e.,

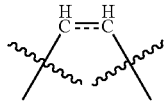

means

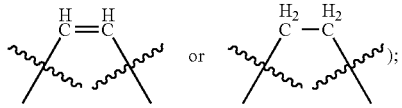
);

R⁶ is H or halo;
R⁷ is H or halo;
R⁸ is H or halo; and
R⁹ is H or halo;
wherein if each of $R_6$, $R_7$, $R_8$ and $R_9$ is H, then Z is —$C_1$-$C_8$ alkyl, —$C_2$-$C_8$ alkenyl or —$C_2$-$C_8$ alkynyl, each substituted with one or more halo and each containing 0, 1, 2, or 3 heteroatoms independently selected from O, S, and N.

17. The compound of claim 6, wherein Z is —$C_1$-$C_8$ alkyl containing 0, 1, 2, or 3 heteroatoms selected from O, S, or $NR_1$ and substituted with one or more halo.

18. The compound of claim 4, wherein $R^1$ is optionally substituted isoxazolyl.

19. The compound of claim 18, wherein A is —(C=O)-(5-methylisoxazol-3-yl).

20. The compound of claim 1, wherein:
A is —(C=O)-(5-methylisoxazol-3-yl);
$R^3$ is cyclopropyl, optionally substituted with $C_1$-$C_6$ alkyl;
L is a $C_4$ alkylene group;
Z is $C_1$-$C_4$ alkyl substituted with one or more halo;
----- denotes a carbon-carbon double bond;
j=0;
k=0;
m=1;
$R^6$, $R^7$ and $R^9$ are each H; and
$R^8$ is H or halo.

21. The compound of claim 1, selected from the group consisting of:

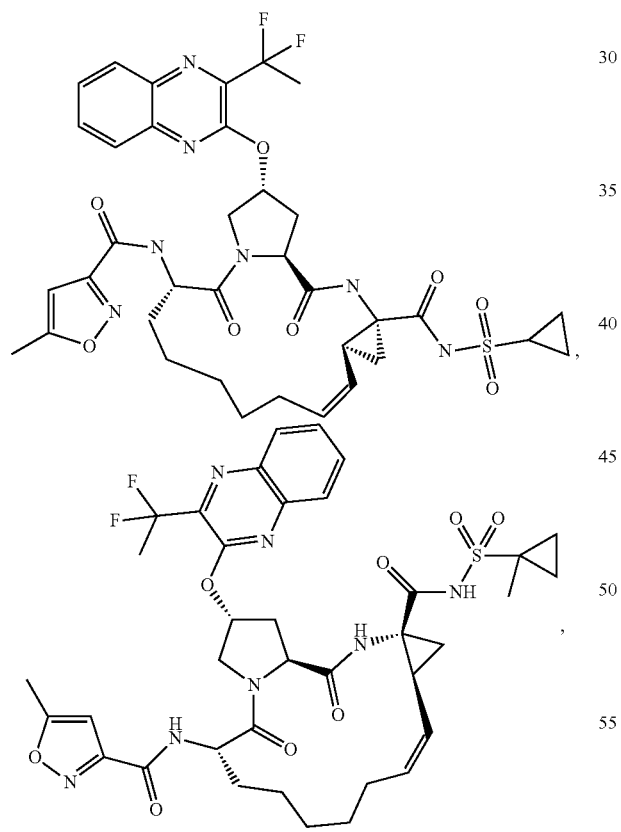

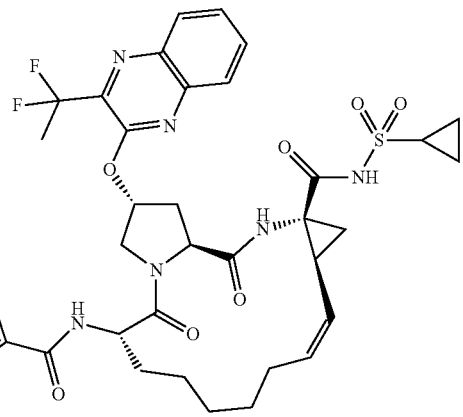

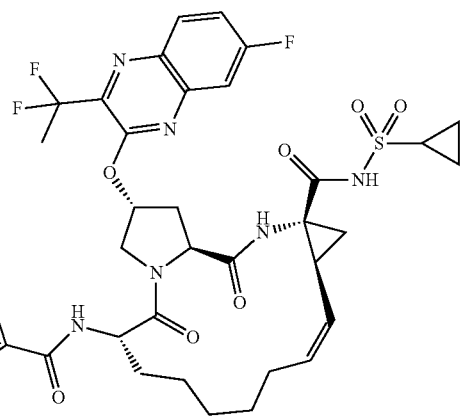

and

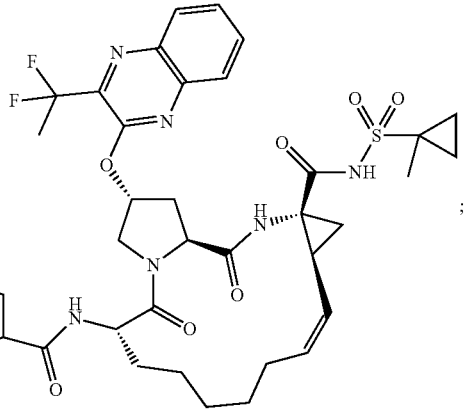

or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 9,493,506 B2 | Page 1 of 1 |
| APPLICATION NO. | : 14/299095 | |
| DATED | : November 15, 2016 | |
| INVENTOR(S) | : Hui-Ju Chen et al. | |

It is certified that error appears in the above-identified patent and that said Letters Patent is hereby corrected as shown below:

On the Title Page

Item number (73), Assignee, replace:
"Enata Pharmacueticals, Inc." with --Enanta Pharmaceuticals, Inc.--.

Signed and Sealed this
Tenth Day of January, 2017

Michelle K. Lee
*Director of the United States Patent and Trademark Office*